US012208287B2

(12) United States Patent
Mckeon et al.

(10) Patent No.: US 12,208,287 B2
(45) Date of Patent: Jan. 28, 2025

(54) INFLAMMATORY BOWEL DISEASE STEM CELLS, AGENTS WHICH TARGET IBD STEM CELLS, AND USES RELATED THERETO

(71) Applicant: UNIVERSITY OF HOUSTON SYSTEM, Houston, TX (US)

(72) Inventors: Frank Mckeon, Sugar Land, TX (US); Matthew Vincent, Amesbury, MA (US)

(73) Assignee: University of Houston System, Houston, TX (US)

( * ) Notice: Subject to any disclaimer, the term of this patent is extended or adjusted under 35 U.S.C. 154(b) by 1323 days.

(21) Appl. No.: 16/611,018

(22) PCT Filed: May 7, 2018

(86) PCT No.: PCT/US2018/031370
§ 371 (c)(1),
(2) Date: Nov. 5, 2019

(87) PCT Pub. No.: WO2018/204913
PCT Pub. Date: Nov. 8, 2018

(65) Prior Publication Data
US 2020/0157495 A1 May 21, 2020

Related U.S. Application Data

(60) Provisional application No. 62/501,878, filed on May 5, 2017.

(51) Int. Cl.
*C12N 5/071* (2010.01)
*C12Q 1/6883* (2018.01)
*G01N 33/50* (2006.01)

(52) U.S. Cl.
CPC ........... *C12N 5/068* (2013.01); *C12Q 1/6883* (2013.01); *G01N 33/5073* (2013.01); *C12N 2501/11* (2013.01); *C12N 2501/115* (2013.01); *C12N 2501/117* (2013.01); *C12N 2501/12* (2013.01); *C12N 2501/13* (2013.01); *C12N 2501/15* (2013.01); *C12N 2501/155* (2013.01); *C12N 2501/999* (2013.01); *C12N 2503/02* (2013.01); *C12Q 2600/154* (2013.01); *C12Q 2600/156* (2013.01)

(58) Field of Classification Search
CPC ................ C12N 5/068; C12N 2501/11; C12N 2501/115; C12N 2501/117; C12N 2501/12; C12N 2501/13; C12N 2501/15; C12N 2501/155; C12N 2501/999; C12N 2503/02; A61K 47/6803; C12Q 1/6883; C12Q 2600/154; C12Q 2600/156; G01N 33/5073
See application file for complete search history.

(56) References Cited

U.S. PATENT DOCUMENTS

| 2007/0140966 A1 | 6/2007 | Chang et al. |
| 2015/0044135 A1 | 2/2015 | Xian et al. |
| 2016/0060594 A1 | 3/2016 | Xian |
| 2016/0061817 A1 | 3/2016 | Xian |
| 2016/0237400 A1 | 8/2016 | Xian |

OTHER PUBLICATIONS

Communication pursuant to Article 94(3) EPC for EP Application No. 18794115.8-1118 dated Mar. 13, 2023, 8 pages.
Barrett et al., "Genome-wide association defines more than 30 distinct susceptibility loci for Crohn's disease," *Nat Genet.*, 40:955-962, 2008.
Chen et al., "Estimation and partitioning of (co)heritability of inflammatory bowel disease from GWAS and immunochip data," *Hum Mol Genet.*, 23:4710-4720, 2014.
Cleynen et al., "Inherited determinants of Crohn's disease and ulcerative colitis phenotypes: a genetic association study," *Lancet*, 387:156-167, 2016.
Dotti et al., "Alterations in the epithelial stem cell compartment could contribute to permanent changes in the mucosa of patients with ulcerative colitis," *Gut*, 66(12):2069-2079, 2017.
Extended European Search Report issued in European Application No. 18794115.8, mailed Apr. 19, 2021.
Franke et al., "Genome-wide meta-analysis increases to 71 the number of confirmed Crohn's disease susceptibility loci," *Nat Genet.*, 42:1118-1125, 2010.
Fransen et al., "Analysis of SNPs with an effect on gene expression identifies UBE2L3 and BCL3 as potential new risk genes for Crohn's disease," *Hum Mol Genet.*, 19:3482-3488, 2010.
Haberman et al., "Pediatric Crohn disease patients exhibit specific ileal transcriptome and microbiome signature," *J Clin Invest.*, 124:3617-3633, 2014.
Hampe et al., "A genome-wide association scan of non-synonymous SNPs identifies a susceptibility variant for Crohn disease in ATG16L1," *Nat Genet.*, 39:207-211, 2007.
Liu et al., "Association analyses identify 38 susceptibility loci for inflammatory bowel disease and highlight shared genetic risk across populations," *Nat Genet.*, 47:979-986, 2015.

(Continued)

*Primary Examiner* — Mark Halvorson
*Assistant Examiner* — Dennis J Sullivan
(74) *Attorney, Agent, or Firm* — Parker Highlander PLLC

(57) ABSTRACT

The present invention addresses IBD from the standpoint of mucosal stem cells cloned from defined regions of the gastrointestinal tract. In the case of pediatric Crohn's disease, for example, isolation of those stem cells according to the methods of the present invention reveals a pattern of inflammatory gene expression in stem cells from the terminal ileum and colon that is epigenetically maintained despite months of continuous cultivation in the absence of immune or stromal cells, or of intestinal microbes. Superimposed on this distributed inflammatory phenotype is a differentiation defect that profoundly and specifically alters the mucosal barrier properties of the terminal ileum. The co-existence of diseased and normal stem cells within the same endoscopic biopsies of Crohn's disease patients implicates an epigenetically enforced heterogeneity among mucosal stem cells in the dynamics of this condition.

4 Claims, 48 Drawing Sheets
Specification includes a Sequence Listing.

(56) References Cited

OTHER PUBLICATIONS

McLean et al., "Integrin antagonists as potential therapeutic options for the treatment of Crohn's disease," *Expert Opinion on Investigational Drugs*, 25(3):263-273, 2016.

Partial Supplementary European Search Report issued in European Application No. 18794115.8, mailed Jan. 13, 2021.

PCT International Search Report and Written Opinion issued in International Application No. PCT/US2018/031370, mailed Sep. 25, 2018.

Rioux et al., "Genome-wide association study identifies new susceptibility loci for Crohn disease and implicates autophagy in disease pathogenesis," *Nat Genet.*, 39:596-604, 2007.

Wang et al., "Cloning and variation of ground state intestinal stem cells," *Nature*, 522(7555):173-178, 2015.

Wang et al., "Comparative genetic analysis of inflammatory bowel disease and type 1 diabetes implicates multiple loci with opposite effects," *Hum Mol Genet.*, 19:2059-2067, 2010.

Yamamoto et al., "Mutational spectrum of Barrett's stem cells suggests paths to initiation of a precancerous lesion," *Nature Communications*, 7(10380):1-10, 2016.

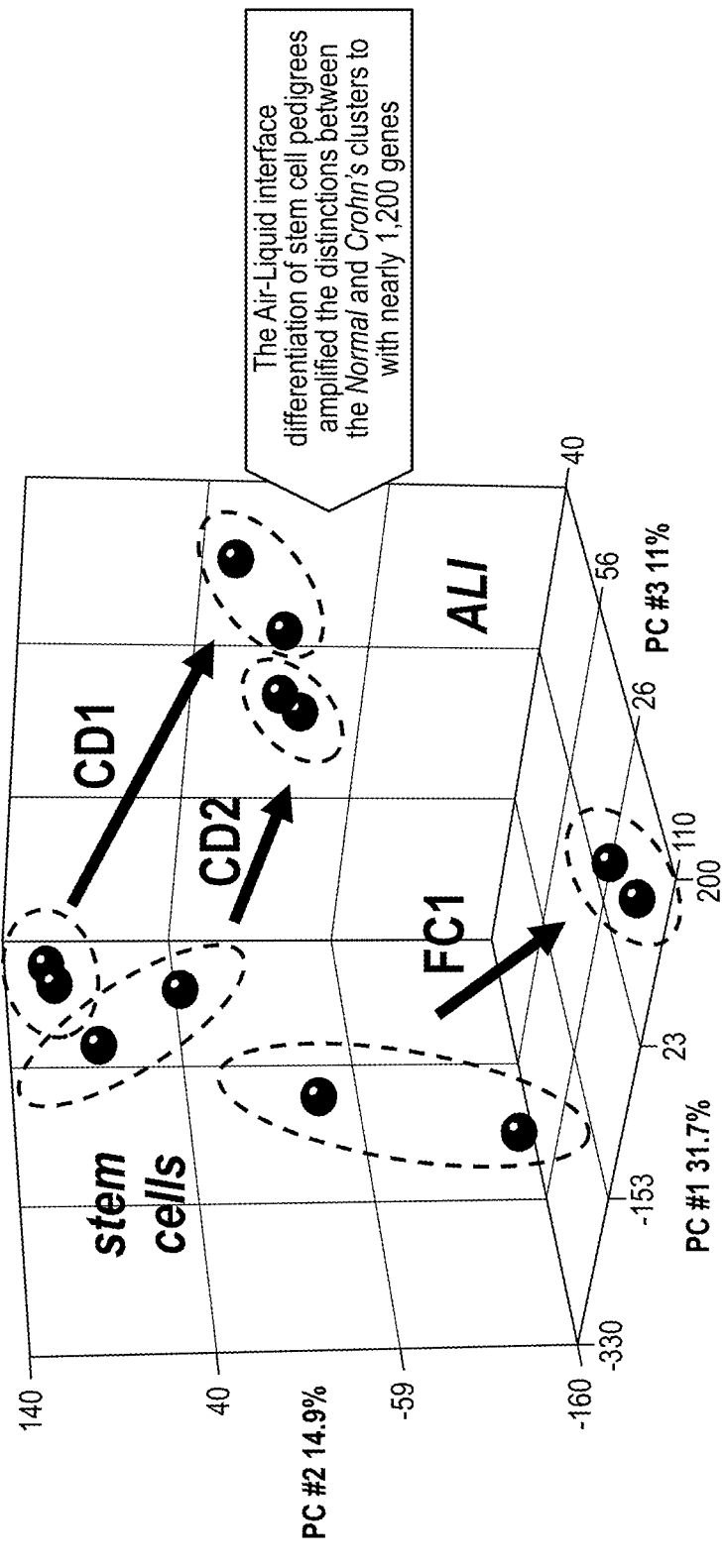

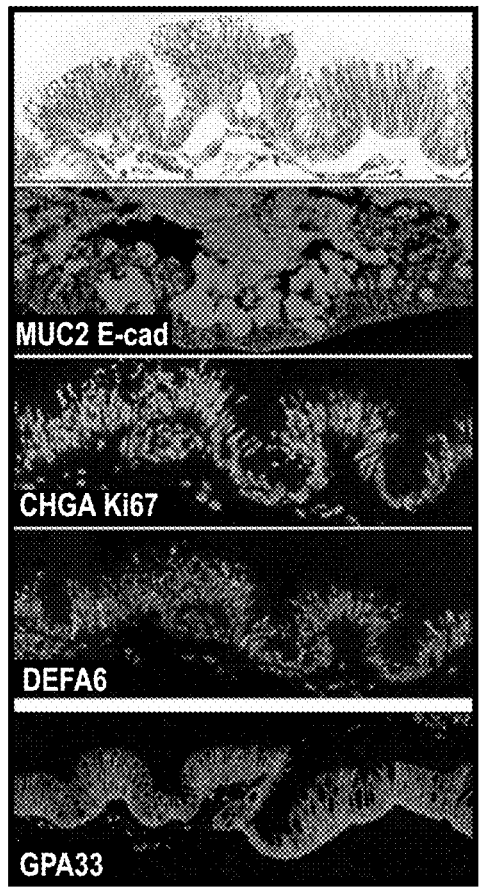
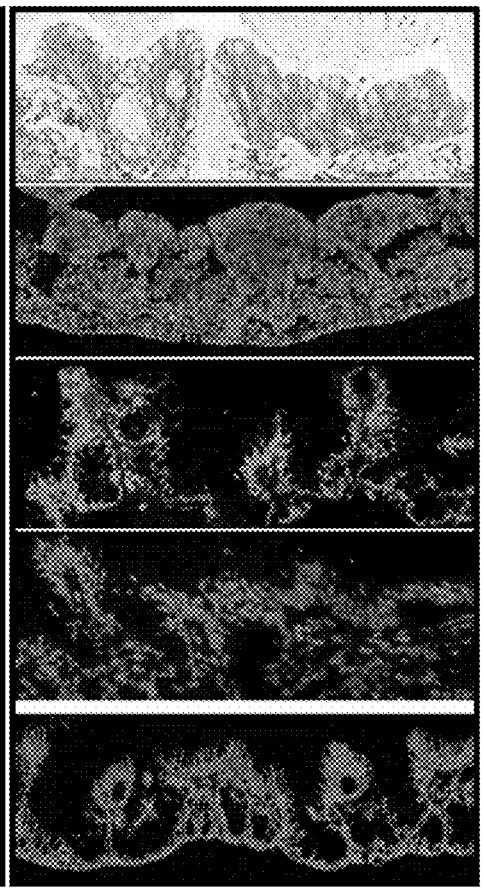
Fig. 3D Normal Right Colon
Fig. 3E Crohn's Right Colon

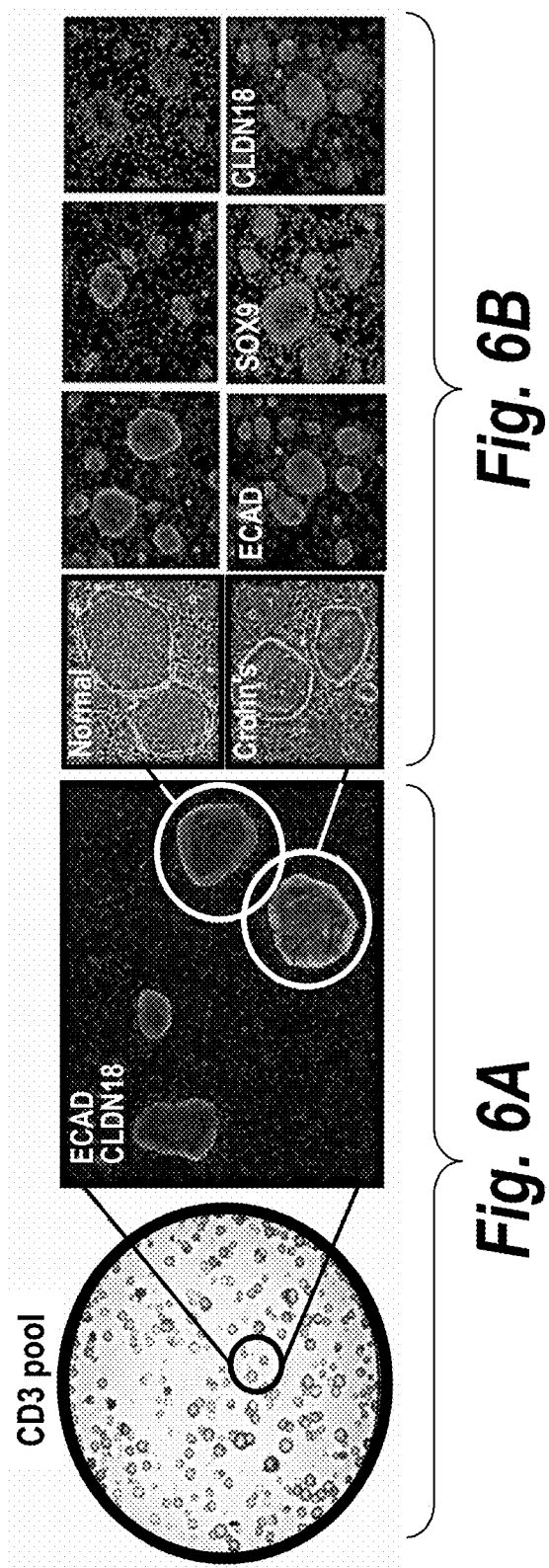

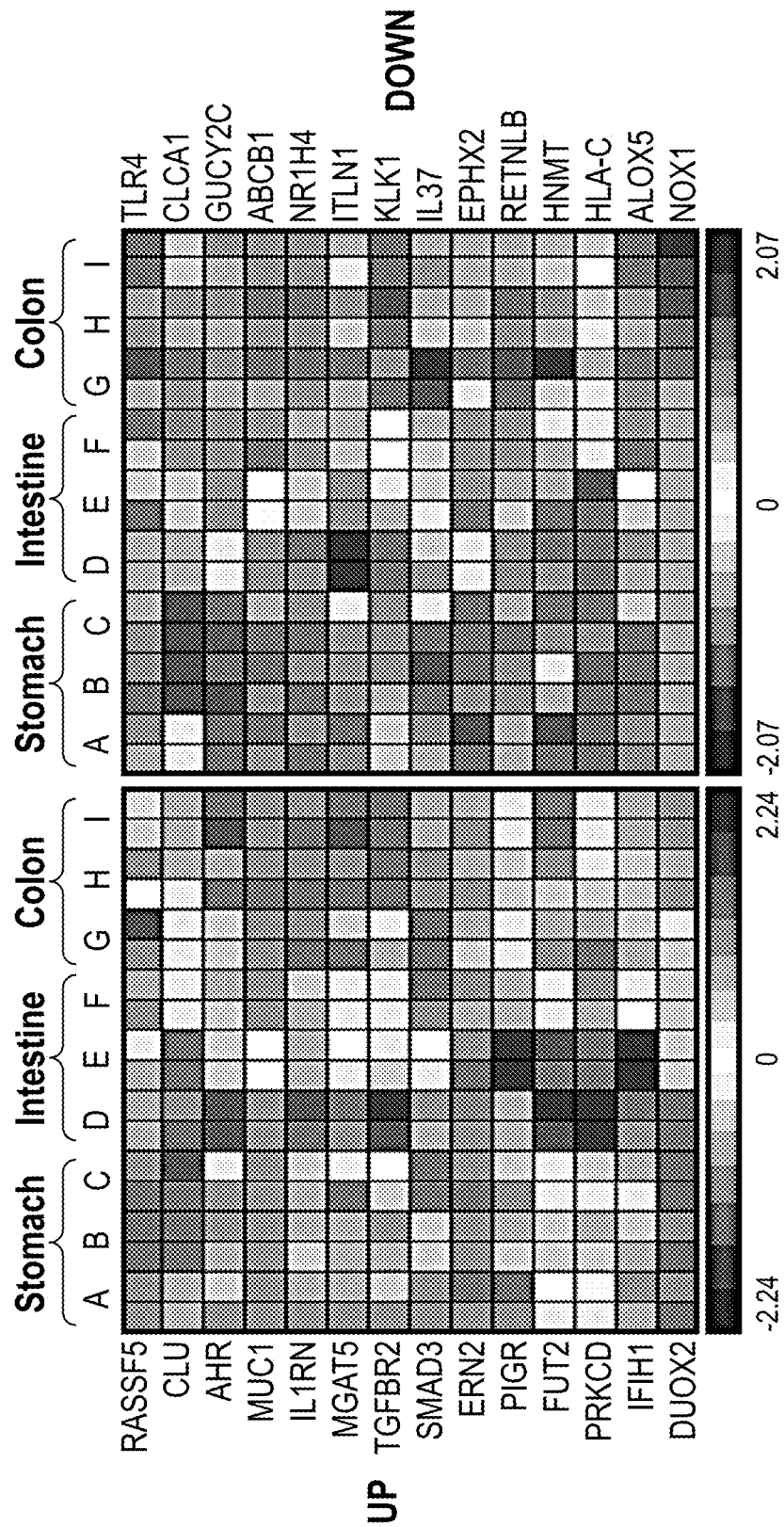

Fig. 15A
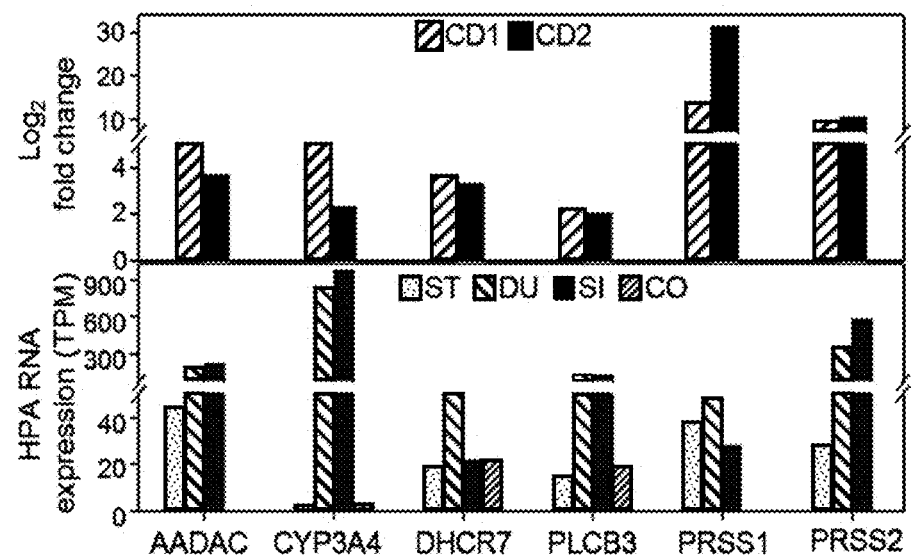
Fig. 15B
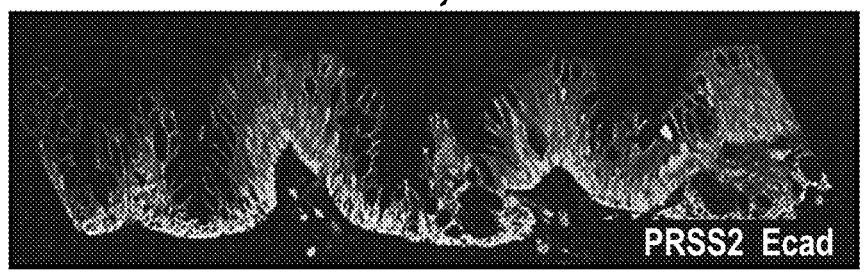
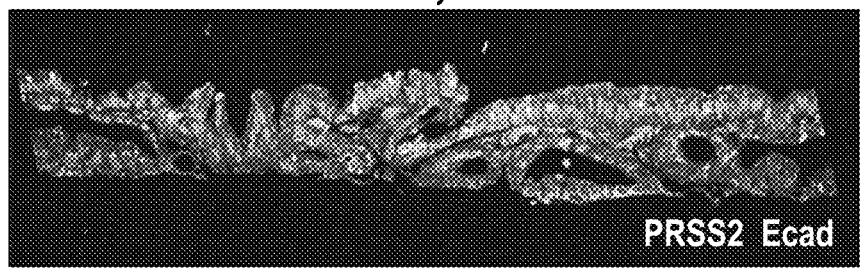

Using whole-genome analyses of epigenetic histone marks, we identified multiple alterations in the epigenetic profiles of the HOX loci of stem cells of the Crohn's cluster compared to those of the Normal cluster Among these genes are a host of transcription factors including CDX2 and GATA5, whose respective roles distal and proximal gastrointestinal tract differentiation are well established

Fig. 22
| CDP11 TI #2: normal 4 WEEKS (20X) | CDP45 TI #1: Crohn's 4 WEEKS (20X) |
|---|---|
| 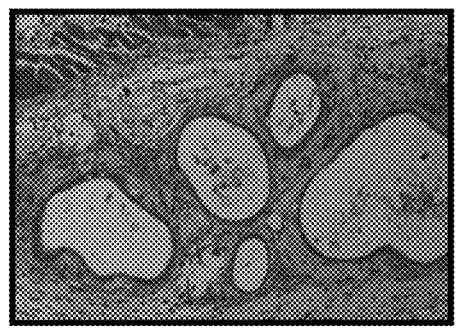 | 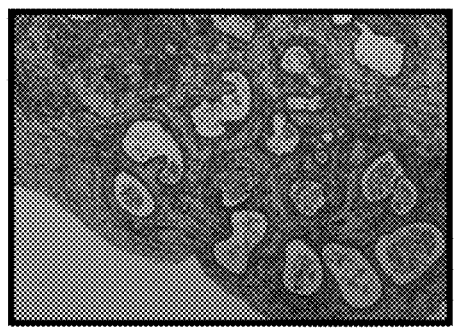 |
| 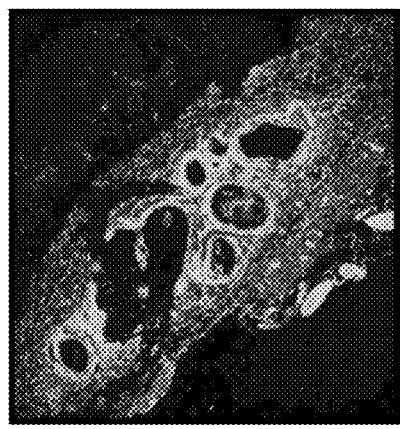 | 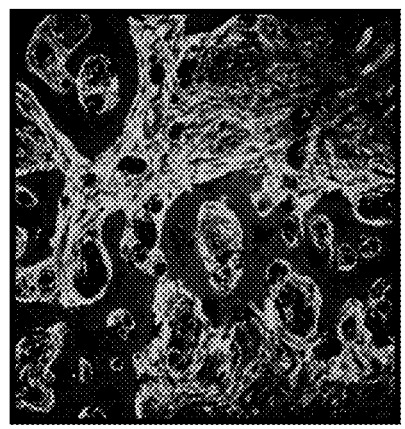 |

SEQUENCE LISTING

```
<160> NUMBER OF SEQ ID NOS: 41

<210> SEQ ID NO 1
<211> LENGTH: 232
<212> TYPE: PRT
<213> ORGANISM: Homo sapiens

<400> SEQUENCE: 1

Met Glu Arg Cys Pro Ser Leu Gly Val Thr Leu Tyr Ala Leu Val Val
1               5                   10                  15

Val Leu Gly Leu Arg Ala Thr Pro Ala Gly Gly Gln His Tyr Leu His
            20                  25                  30

Ile Arg Pro Ala Pro Ser Asp Asn Leu Pro Leu Val Asp Leu Ile Glu
        35                  40                  45

His Pro Asp Pro Ile Phe Asp Pro Lys Glu Lys Asp Leu Asn Glu Thr
    50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly
                85                  90                  95

Gly Ala Glu Asp Leu Ala Glu Leu Asp Gln Leu Leu Arg Gln Arg Pro
                100                 105                 110

Ser Gly Ala Met Pro Ser Glu Ile Lys Gly Leu Glu Phe Ser Glu Gly
            115                 120                 125

Leu Ala Gln Gly Lys Lys Gln Arg Leu Ser Lys Lys Leu Arg Arg Lys
        130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
            180                 185                 190

Lys Pro Ser Lys Ser Val His Leu Thr Val Leu Arg Trp Arg Cys Gln
        195                 200                 205
```

```
Arg Arg Gly Gly Gln Arg Cys Gly Trp Ile Pro Ile Gln Tyr Pro Ile
    210                 215                 220

Ile Ser Glu Cys Lys Cys Ser Cys
225                 230

<210> SEQ ID NO 2
<211> LENGTH: 955
<212> TYPE: PRT
<213> ORGANISM: Homo sapiens

<400> SEQUENCE: 2

Met Pro Ser Leu Pro Ala Pro Ala Pro Leu Leu Leu Gly Leu
1               5                   10                  15

Leu Leu Leu Gly Ser Arg Pro Ala Arg Gly Ala Gly Pro Glu Pro Pro
            20                  25                  30

Val Leu Pro Ile Arg Ser Glu Lys Glu Pro Leu Pro Val Arg Gly Ala
        35                  40                  45

Ala Gly Cys Thr Phe Gly Gly Lys Val Tyr Ala Leu Asp Glu Thr Trp
    50                  55                  60

His Pro Asp Leu Gly Glu Pro Phe Gly Val Met Arg Cys Val Leu Cys
65                  70                  75                  80

Ala Cys Glu Ala Pro Gln Trp Gly Arg Arg Thr Arg Gly Pro Gly Arg
                85                  90                  95

Val Ser Cys Lys Asn Ile Lys Pro Glu Cys Pro Thr Pro Ala Cys Gly
            100                 105                 110

Gln Pro Arg Gln Leu Pro Gly His Cys Cys Gln Thr Cys Pro Gln Glu
        115                 120                 125

Arg Ser Ser Ser Glu Arg Gln Pro Ser Gly Leu Ser Phe Glu Tyr Pro
    130                 135                 140

Arg Asp Pro Glu His Arg Ser Tyr Ser Asp Arg Gly Glu Pro Gly Ala
145                 150                 155                 160

Glu Glu Arg Ala Arg Gly Asp Gly His Thr Asp Phe Val Ala Leu Leu
                165                 170                 175

Thr Gly Pro Arg Ser Gln Ala Val Ala Arg Ala Arg Val Ser Leu Leu
            180                 185                 190

Arg Ser Ser Leu Arg Phe Ser Ile Ser Tyr Arg Arg Leu Asp Arg Pro
        195                 200                 205

Thr Arg Ile Arg Phe Ser Asp Ser Asn Gly Ser Val Leu Phe Glu His
    210                 215                 220

Pro Ala Ala Pro Thr Gln Asp Gly Leu Val Cys Gly Val Trp Arg Ala
225                 230                 235                 240

Val Pro Arg Leu Ser Leu Arg Leu Leu Arg Ala Glu Gln Leu His Val
                245                 250                 255

Ala Leu Val Thr Leu Thr His Pro Ser Gly Glu Val Trp Gly Pro Leu
            260                 265                 270

Ile Arg His Arg Ala Leu Ala Ala Glu Thr Phe Ser Ala Ile Leu Thr
        275                 280                 285

Leu Glu Gly Pro Pro Gln Gln Gly Val Gly Gly Ile Thr Leu Leu Thr
    290                 295                 300

Leu Ser Asp Thr Glu Asp Ser Leu His Phe Leu Leu Phe Arg Gly
305                 310                 315                 320

Leu Leu Glu Pro Arg Ser Gly Gly Leu Thr Gln Val Pro Leu Arg Leu
                325                 330                 335

Gln Ile Leu His Gln Gly Gln Leu Leu Arg Glu Leu Gln Ala Asn Val
            340                 345                 350
```

```
Ser Ala Gln Glu Pro Gly Phe Ala Glu Val Leu Pro Asn Leu Thr Val
        355                 360                 365

Gln Glu Met Asp Trp Leu Val Leu Gly Glu Leu Gln Met Ala Leu Glu
        370                 375                 380

Trp Ala Gly Arg Pro Gly Leu Arg Ile Ser Gly His Ile Ala Ala Arg
385                 390                 395                 400

Lys Ser Cys Asp Val Leu Gln Ser Val Leu Cys Gly Ala Asp Ala Leu
                405                 410                 415

Ile Pro Val Gln Thr Gly Ala Ala Gly Ser Ala Ser Leu Thr Leu Leu
                420                 425                 430

Gly Asn Gly Ser Leu Ile Tyr Gln Val Gln Val Gly Thr Ser Ser
        435                 440                 445

Glu Val Val Ala Met Thr Leu Glu Thr Lys Pro Gln Arg Arg Asp Gln
        450                 455                 460

Arg Thr Val Leu Cys His Met Ala Gly Leu Gln Pro Gly Gly His Thr
465                 470                 475                 480

Ala Val Gly Ile Cys Pro Gly Leu Gly Ala Arg Gly Ala His Met Leu
                485                 490                 495

Leu Gln Asn Glu Leu Phe Leu Asn Val Gly Thr Lys Asp Phe Pro Asp
            500                 505                 510

Gly Glu Leu Arg Gly His Val Ala Ala Leu Pro Tyr Cys Gly His Ser
        515                 520                 525

Ala Arg His Asp Thr Leu Pro Val Pro Leu Ala Gly Ala Leu Val Leu
        530                 535                 540

Pro Pro Val Lys Ser Gln Ala Ala Gly His Ala Trp Leu Ser Leu Asp
545                 550                 555                 560

Thr His Cys His Leu His Tyr Glu Val Leu Leu Ala Gly Leu Gly Gly
                565                 570                 575

Ser Glu Gln Gly Thr Val Thr Ala His Leu Leu Gly Pro Pro Gly Thr
            580                 585                 590

Pro Gly Pro Arg Arg Leu Leu Lys Gly Phe Tyr Gly Ser Glu Ala Gln
        595                 600                 605

Gly Val Val Lys Asp Leu Glu Pro Glu Leu Leu Arg His Leu Ala Lys
        610                 615                 620

Gly Met Ala Ser Leu Leu Ile Thr Thr Lys Gly Ser Pro Arg Gly Glu
625                 630                 635                 640

Leu Arg Gly Gln Val His Ile Ala Asn Gln Cys Glu Val Gly Gly Leu
                645                 650                 655

Arg Leu Glu Ala Ala Gly Ala Glu Gly Val Arg Ala Leu Gly Ala Pro
            660                 665                 670

Asp Thr Ala Ser Ala Ala Pro Pro Val Val Pro Gly Leu Pro Ala Leu
        675                 680                 685

Ala Pro Ala Lys Pro Gly Gly Pro Gly Arg Pro Arg Asp Pro Asn Thr
        690                 695                 700

Cys Phe Phe Glu Gly Gln Gln Arg Pro His Gly Ala Arg Trp Ala Pro
705                 710                 715                 720

Asn Tyr Asp Pro Leu Cys Ser Leu Cys Thr Cys Gln Arg Arg Thr Val
                725                 730                 735

Ile Cys Asp Pro Val Val Cys Pro Pro Ser Cys Pro His Pro Val
            740                 745                 750

Gln Ala Pro Asp Gln Cys Cys Pro Val Cys Pro Glu Lys Gln Asp Val
        755                 760                 765
```

```
Arg Asp Leu Pro Gly Leu Pro Arg Ser Arg Asp Pro Gly Glu Gly Cys
770                 775                 780

Tyr Phe Asp Gly Asp Arg Ser Trp Arg Ala Ala Gly Thr Arg Trp His
785                 790                 795                 800

Pro Val Val Pro Pro Phe Gly Leu Ile Lys Cys Ala Val Cys Thr Cys
                805                 810                 815

Lys Gly Gly Thr Gly Glu Val His Cys Glu Lys Val Gln Cys Pro Arg
                820                 825                 830

Leu Ala Cys Ala Gln Pro Val Arg Val Asn Pro Thr Asp Cys Cys Lys
                835                 840                 845

Gln Cys Pro Val Gly Ser Gly Ala His Pro Gln Leu Gly Asp Pro Met
850                 855                 860

Gln Ala Asp Gly Pro Arg Gly Cys Arg Phe Ala Gly Gln Trp Phe Pro
865                 870                 875                 880

Glu Ser Gln Ser Trp His Pro Ser Val Pro Phe Gly Glu Met Ser
                885                 890                 895

Cys Ile Thr Cys Arg Cys Gly Ala Gly Val Pro His Cys Glu Arg Asp
                900                 905                 910

Asp Cys Ser Leu Pro Leu Ser Cys Gly Ser Gly Lys Glu Ser Arg Cys
                915                 920                 925

Cys Ser Arg Cys Thr Ala His Arg Arg Pro Ala Pro Glu Thr Arg Thr
930                 935                 940

Asp Pro Glu Leu Glu Lys Glu Ala Glu Gly Ser
945                 950                 955

<210> SEQ ID NO 3
<211> LENGTH: 344
<212> TYPE: PRT
<213> ORGANISM: Homo sapiens

<400> SEQUENCE: 3

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
                100                 105                 110

Lys Pro Arg Cys Val Cys Ala Pro Asp Cys Ser Asn Ile Thr Trp Lys
                115                 120                 125

Gly Pro Val Cys Gly Leu Asp Gly Lys Thr Tyr Arg Asn Glu Cys Ala
                130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
                180                 185                 190
```

```
Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
                260                 265                 270

Leu Cys Pro Asp Ser Lys Ser Asp Glu Pro Val Cys Ala Ser Asp Asn
                275                 280                 285

Ala Thr Tyr Ala Ser Glu Cys Ala Met Lys Glu Ala Ala Cys Ser Ser
290                 295                 300

Gly Val Leu Leu Glu Val Lys His Ser Gly Ser Cys Asn Ser Ile Ser
305                 310                 315                 320

Glu Asp Thr Glu Glu Glu Glu Asp Glu Asp Gln Asp Tyr Ser Phe
                325                 330                 335

Pro Ile Ser Ser Ile Leu Glu Trp
                340

<210> SEQ ID NO 4
<211> LENGTH: 180
<212> TYPE: PRT
<213> ORGANISM: Homo sapiens

<400> SEQUENCE: 4

Met Leu Arg Val Leu Val Gly Ala Val Leu Pro Ala Met Leu Leu Ala
1               5                   10                  15

Ala Pro Pro Pro Ile Asn Lys Leu Ala Leu Phe Pro Asp Lys Ser Ala
                20                  25                  30

Trp Cys Glu Ala Lys Asn Ile Thr Gln Ile Val Gly His Ser Gly Cys
            35                  40                  45

Glu Ala Lys Ser Ile Gln Asn Arg Ala Cys Leu Gly Gln Cys Phe Ser
        50                  55                  60

Tyr Ser Val Pro Asn Thr Phe Pro Gln Ser Thr Glu Ser Leu Val His
65                  70                  75                  80

Cys Asp Ser Cys Met Pro Ala Gln Ser Met Trp Glu Ile Val Thr Leu
                85                  90                  95

Glu Cys Pro Gly His Glu Glu Val Pro Arg Val Asp Lys Leu Val Glu
            100                 105                 110

Lys Ile Leu His Cys Ser Cys Gln Ala Cys Gly Lys Glu Pro Ser His
        115                 120                 125

Glu Gly Leu Ser Val Tyr Val Gln Gly Glu Asp Gly Pro Gly Ser Gln
    130                 135                 140

Pro Gly Thr His Pro His Pro His Pro His Pro Gly Gly Gln
145                 150                 155                 160

Thr Pro Glu Pro Glu Asp Pro Pro Gly Ala Pro His Thr Glu Glu
                165                 170                 175

Gly Ala Glu Asp
            180

<210> SEQ ID NO 5
<211> LENGTH: 267
<212> TYPE: PRT
```

<213> ORGANISM: Homo sapiens

<400> SEQUENCE: 5

```
Met His Leu Leu Leu Phe Gln Leu Leu Val Leu Leu Pro Leu Gly Lys
1               5                   10                  15
Thr Thr Arg His Gln Asp Gly Arg Gln Asn Gln Ser Ser Leu Ser Pro
            20                  25                  30
Val Leu Leu Pro Arg Asn Gln Arg Glu Leu Pro Thr Gly Asn His Glu
        35                  40                  45
Glu Ala Glu Glu Lys Pro Asp Leu Phe Val Ala Val Pro His Leu Val
    50                  55                  60
Ala Thr Ser Pro Ala Gly Glu Gly Gln Arg Gln Arg Glu Lys Met Leu
65                  70                  75                  80
Ser Arg Phe Gly Arg Phe Trp Lys Lys Pro Glu Arg Glu Met His Pro
                85                  90                  95
Ser Arg Asp Ser Asp Ser Glu Pro Phe Pro Pro Gly Thr Gln Ser Leu
            100                 105                 110
Ile Gln Pro Ile Asp Gly Met Lys Met Glu Lys Ser Pro Leu Arg Glu
        115                 120                 125
Glu Ala Lys Lys Phe Trp His His Phe Met Phe Arg Lys Thr Pro Ala
    130                 135                 140
Ser Gln Gly Val Ile Leu Pro Ile Lys Ser His Glu Val His Trp Glu
145                 150                 155                 160
Thr Cys Arg Thr Val Pro Phe Ser Gln Thr Ile Thr His Glu Gly Cys
                165                 170                 175
Glu Lys Val Val Val Gln Asn Asn Leu Cys Phe Gly Lys Cys Gly Ser
            180                 185                 190
Val His Phe Pro Gly Ala Ala Gln His Ser His Thr Ser Cys Ser His
        195                 200                 205
Cys Leu Pro Ala Lys Phe Thr Thr Met His Leu Pro Leu Asn Cys Thr
    210                 215                 220
Glu Leu Ser Ser Val Ile Lys Val Val Met Leu Val Glu Glu Cys Gln
225                 230                 235                 240
Cys Lys Val Lys Thr Glu His Glu Asp Gly His Ile Leu His Ala Gly
                245                 250                 255
Ser Gln Asp Ser Phe Ile Pro Gly Val Ser Ala
            260                 265
```

<210> SEQ ID NO 6
<211> LENGTH: 184
<212> TYPE: PRT
<213> ORGANISM: Homo sapiens

<400> SEQUENCE: 6

```
Met Ser Arg Thr Ala Tyr Thr Val Gly Ala Leu Leu Leu Leu Leu Gly
1               5                   10                  15
Thr Leu Leu Pro Ala Ala Glu Gly Lys Lys Lys Gly Ser Gln Gly Ala
            20                  25                  30
Ile Pro Pro Pro Asp Lys Ala Gln His Asn Asp Ser Glu Gln Thr Gln
        35                  40                  45
Ser Pro Gln Gln Pro Gly Ser Arg Asn Arg Gly Arg Gly Gln Gly Arg
    50                  55                  60
Gly Thr Ala Met Pro Gly Glu Glu Val Leu Glu Ser Ser Gln Glu Ala
65                  70                  75                  80
Leu His Val Thr Glu Arg Lys Tyr Leu Lys Arg Asp Trp Cys Lys Thr
```

```
                   85                  90                  95

Gln Pro Leu Lys Gln Thr Ile His Glu Glu Gly Cys Asn Ser Arg Thr
            100                 105                 110

Ile Ile Asn Arg Phe Cys Tyr Gly Gln Cys Asn Ser Phe Tyr Ile Pro
            115                 120                 125

Arg His Ile Arg Lys Glu Glu Gly Ser Phe Gln Ser Cys Ser Phe Cys
            130                 135                 140

Lys Pro Lys Lys Phe Thr Thr Met Met Val Thr Leu Asn Cys Pro Glu
145                 150                 155                 160

Leu Gln Pro Pro Thr Lys Lys Arg Val Thr Arg Val Lys Gln Cys
            165                 170                 175

Arg Cys Ile Ser Ile Asp Leu Asp
            180
```

```
<210> SEQ ID NO 7
<211> LENGTH: 213
<212> TYPE: PRT
<213> ORGANISM: Homo sapiens

<400> SEQUENCE: 7

Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
                20                  25                  30

Ala Thr Glu Ile Ile Pro Glu Leu Gly Glu Tyr Pro Glu Pro Pro Pro
            35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
            115                 120                 125

Gly Pro Asp Phe Arg Cys Ile Pro Asp Arg Tyr Arg Ala Gln Arg Val
            130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
            195                 200                 205

Leu Glu Asn Ala Tyr
            210
```

```
<210> SEQ ID NO 8
<211> LENGTH: 70
<212> TYPE: PRT
<213> ORGANISM: Homo sapiens

<400> SEQUENCE: 8

Met Lys Ala Thr Ile Ile Leu Leu Leu Leu Ala Gln Val Ser Trp Ala
```

```
1               5                   10                  15
Gly Pro Phe Gln Gln Arg Gly Leu Phe Asp Phe Met Leu Glu Asp Glu
            20                  25                  30

Ala Ser Gly Ile Gly Pro Glu Val Pro Asp Asp Arg Asp Phe Glu Pro
            35                  40                  45

Ser Leu Gly Pro Val Cys Pro Phe Arg Cys Gln Cys His Leu Arg Val
            50                  55                  60

Val Gln Cys Ser Asp Leu
65                  70

<210> SEQ ID NO 9
<211> LENGTH: 1474
<212> TYPE: PRT
<213> ORGANISM: Homo sapiens

<400> SEQUENCE: 9

Met Gly Lys Asn Lys Leu Leu His Pro Ser Leu Val Leu Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
            35                  40                  45

Val Leu Leu Ser Tyr Leu Asn Glu Thr Val Thr Val Ser Ala Ser Leu
            50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
        275                 280                 285

Lys Phe Ser Gly Gln Leu Asn Ser His Gly Cys Phe Tyr Gln Gln Val
        290                 295                 300
```

-continued

```
Lys Thr Lys Val Phe Gln Leu Lys Arg Lys Glu Tyr Glu Met Lys Leu
305                 310                 315                 320

His Thr Glu Ala Gln Ile Gln Glu Glu Gly Thr Val Val Glu Leu Thr
                325                 330                 335

Gly Arg Gln Ser Ser Glu Ile Thr Arg Thr Ile Thr Lys Leu Ser Phe
                340                 345                 350

Val Lys Val Asp Ser His Phe Arg Gln Gly Ile Pro Phe Phe Gly Gln
            355                 360                 365

Val Arg Leu Val Asp Gly Lys Gly Val Pro Ile Pro Asn Lys Val Ile
            370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
                420                 425                 430

Gly Tyr Gln Trp Val Ser Glu Glu His Glu Glu Ala His His Thr Ala
            435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
            500                 505                 510

Leu Leu Val Lys Gln Glu Asp Met Lys Gly His Phe Ser Ile Ser Ile
            515                 520                 525

Pro Val Lys Ser Asp Ile Ala Pro Val Ala Arg Leu Leu Ile Tyr Ala
            530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
            580                 585                 590

Ser Val Cys Ala Leu Arg Ala Val Asp Gln Ser Val Leu Leu Met Lys
            595                 600                 605

Pro Asp Ala Glu Leu Ser Ala Ser Ser Val Tyr Asn Leu Leu Pro Glu
610                 615                 620

Lys Asp Leu Thr Gly Phe Pro Gly Pro Leu Asn Asp Gln Asp Asp Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
            660                 665                 670

Met Gly Leu Lys Ala Phe Thr Asn Ser Lys Ile Arg Lys Pro Lys Met
            675                 680                 685

Cys Pro Gln Leu Gln Gln Tyr Glu Met His Gly Pro Glu Gly Leu Arg
            690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
```

-continued

```
                725                 730                 735
Glu Thr Trp Ile Trp Asp Leu Val Val Asn Ser Ala Gly Val Ala
                740                 745                 750
Glu Val Gly Val Thr Val Pro Asp Thr Ile Thr Glu Trp Lys Ala Gly
                755                 760                 765
Ala Phe Cys Leu Ser Glu Asp Ala Gly Leu Gly Ile Ser Ser Thr Ala
                770                 775                 780
Ser Leu Arg Ala Phe Gln Pro Phe Val Glu Leu Thr Met Pro Tyr
785                 790                 795                 800
Ser Val Ile Arg Gly Glu Ala Phe Thr Leu Lys Ala Thr Val Leu Asn
                805                 810                 815
Tyr Leu Pro Lys Cys Ile Arg Val Ser Val Gln Leu Glu Ala Ser Pro
                820                 825                 830
Ala Phe Leu Ala Val Pro Val Glu Lys Glu Gln Ala Pro His Cys Ile
                835                 840                 845
Cys Ala Asn Gly Arg Gln Thr Val Ser Trp Ala Val Thr Pro Lys Ser
                850                 855                 860
Leu Gly Asn Val Asn Phe Thr Val Ser Ala Glu Ala Leu Glu Ser Gln
865                 870                 875                 880
Glu Leu Cys Gly Thr Glu Val Pro Ser Val Pro Glu His Gly Arg Lys
                885                 890                 895
Asp Thr Val Ile Lys Pro Leu Leu Val Glu Pro Glu Gly Leu Glu Lys
                900                 905                 910
Glu Thr Thr Phe Asn Ser Leu Leu Cys Pro Ser Gly Gly Glu Val Ser
                915                 920                 925
Glu Glu Leu Ser Leu Lys Leu Pro Pro Asn Val Val Glu Glu Ser Ala
930                 935                 940
Arg Ala Ser Val Ser Val Leu Gly Asp Ile Leu Gly Ser Ala Met Gln
945                 950                 955                 960
Asn Thr Gln Asn Leu Leu Gln Met Pro Tyr Gly Cys Gly Glu Gln Asn
                965                 970                 975
Met Val Leu Phe Ala Pro Asn Ile Tyr Val Leu Asp Tyr Leu Asn Glu
                980                 985                 990
Thr Gln Gln Leu Thr Pro Glu Ile Lys Ser Lys Ala Ile Gly Tyr Leu
                995                1000                1005
Asn Thr Gly Tyr Gln Arg Gln Leu Asn Tyr Lys His Tyr Asp Gly
                1010                1015                1020
Ser Tyr Ser Thr Phe Gly Glu Arg Tyr Gly Arg Asn Gln Gly Asn
                1025                1030                1035
Thr Trp Leu Thr Ala Phe Val Leu Lys Thr Phe Ala Gln Ala Arg
                1040                1045                1050
Ala Tyr Ile Phe Ile Asp Glu Ala His Ile Thr Gln Ala Leu Ile
                1055                1060                1065
Trp Leu Ser Gln Arg Gln Lys Asp Asn Gly Cys Phe Arg Ser Ser
                1070                1075                1080
Gly Ser Leu Leu Asn Asn Ala Ile Lys Gly Gly Val Glu Asp Glu
                1085                1090                1095
Val Thr Leu Ser Ala Tyr Ile Thr Ile Ala Leu Leu Glu Ile Pro
                1100                1105                1110
Leu Thr Val Thr His Pro Val Val Arg Asn Ala Leu Phe Cys Leu
                1115                1120                1125
Glu Ser Ala Trp Lys Thr Ala Gln Glu Gly Asp His Gly Ser His
                1130                1135                1140
```

```
Val Tyr Thr Lys Ala Leu Leu Ala Tyr Ala Phe Ala Leu Ala Gly
    1145                1150                1155

Asn Gln Asp Lys Arg Lys Glu Val Leu Lys Ser Leu Asn Glu Glu
    1160                1165                1170

Ala Val Lys Lys Asp Asn Ser Val His Trp Glu Arg Pro Gln Lys
    1175                1180                1185

Pro Lys Ala Pro Val Gly His Phe Tyr Glu Pro Gln Ala Pro Ser
    1190                1195                1200

Ala Glu Val Glu Met Thr Ser Tyr Val Leu Leu Ala Tyr Leu Thr
    1205                1210                1215

Ala Gln Pro Ala Pro Thr Ser Glu Asp Leu Thr Ser Ala Thr Asn
    1220                1225                1230

Ile Val Lys Trp Ile Thr Lys Gln Gln Asn Ala Gln Gly Gly Phe
    1235                1240                1245

Ser Ser Thr Gln Asp Thr Val Val Ala Leu His Ala Leu Ser Lys
    1250                1255                1260

Tyr Gly Ala Ala Thr Phe Thr Arg Thr Gly Lys Ala Ala Gln Val
    1265                1270                1275

Thr Ile Gln Ser Ser Gly Thr Phe Ser Ser Lys Phe Gln Val Asp
    1280                1285                1290

Asn Asn Asn Arg Leu Leu Leu Gln Gln Val Ser Leu Pro Glu Leu
    1295                1300                1305

Pro Gly Glu Tyr Ser Met Lys Val Thr Gly Glu Gly Cys Val Tyr
    1310                1315                1320

Leu Gln Thr Ser Leu Lys Tyr Asn Ile Leu Pro Glu Lys Glu Glu
    1325                1330                1335

Phe Pro Phe Ala Leu Gly Val Gln Thr Leu Pro Gln Thr Cys Asp
    1340                1345                1350

Glu Pro Lys Ala His Thr Ser Phe Gln Ile Ser Leu Ser Val Ser
    1355                1360                1365

Tyr Thr Gly Ser Arg Ser Ala Ser Asn Met Ala Ile Val Asp Val
    1370                1375                1380

Lys Met Val Ser Gly Phe Ile Pro Leu Lys Pro Thr Val Lys Met
    1385                1390                1395

Leu Glu Arg Ser Asn His Val Ser Arg Thr Glu Val Ser Ser Asn
    1400                1405                1410

His Val Leu Ile Tyr Leu Asp Lys Val Ser Asn Gln Thr Leu Ser
    1415                1420                1425

Leu Phe Phe Thr Val Leu Gln Asp Val Pro Val Arg Asp Leu Lys
    1430                1435                1440

Pro Ala Ile Val Lys Val Tyr Asp Tyr Tyr Glu Thr Asp Glu Phe
    1445                1450                1455

Ala Ile Ala Glu Tyr Asn Ala Pro Cys Ser Lys Asp Leu Gly Asn
    1460                1465                1470

Ala

<210> SEQ ID NO 10
<211> LENGTH: 263
<212> TYPE: PRT
<213> ORGANISM: Homo sapiens

<400> SEQUENCE: 10

Met Arg Leu Gly Leu Cys Val Val Ala Leu Val Leu Ser Trp Thr His
1               5                   10                  15
```

```
Leu Thr Ile Ser Ser Arg Gly Ile Lys Gly Lys Arg Gln Arg Ile
            20                  25                  30

Ser Ala Glu Gly Ser Gln Ala Cys Ala Lys Gly Cys Glu Leu Cys
            35                  40                  45

Glu Val Asn Gly Cys Leu Lys Cys Ser Pro Lys Leu Phe Ile Leu Leu
 50                  55                  60

Glu Arg Asn Asp Ile Arg Gln Val Gly Val Cys Leu Pro Ser Cys Pro
 65                  70                  75                  80

Pro Gly Tyr Phe Asp Ala Arg Asn Pro Asp Met Asn Lys Cys Ile Lys
                 85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
            115                 120                 125

Cys Pro Glu Gly Ser Ser Ala Ala Asn Gly Thr Met Glu Cys Ser Ser
 130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
            195                 200                 205

Gly Gln Lys Arg Arg Lys Gly Gly Gln Gly Arg Arg Glu Asn Ala Asn
210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gln Gly Thr Val Gly Pro
                245                 250                 255

Leu Thr Ser Ala Gly Pro Ala
            260

<210> SEQ ID NO 11
<211> LENGTH: 243
<212> TYPE: PRT
<213> ORGANISM: Homo sapiens

<400> SEQUENCE: 11

Met Gln Phe Arg Leu Phe Ser Phe Ala Leu Ile Ile Leu Asn Cys Met
 1               5                  10                  15

Asp Tyr Ser His Cys Gln Gly Asn Arg Trp Arg Arg Ser Lys Arg Ala
                20                  25                  30

Ser Tyr Val Ser Asn Pro Ile Cys Lys Gly Cys Leu Ser Cys Ser Lys
            35                  40                  45

Asp Asn Gly Cys Ser Arg Cys Gln Gln Lys Leu Phe Phe Phe Leu Arg
 50                  55                  60

Arg Glu Gly Met Arg Gln Tyr Gly Glu Cys Leu His Ser Cys Pro Ser
 65                  70                  75                  80

Gly Tyr Tyr Gly His Arg Ala Pro Asp Met Asn Arg Cys Ala Arg Cys
                 85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
```

```
            115                 120                 125
Pro Asp Gly Phe Ala Pro Leu Glu Glu Thr Met Glu Cys Val Glu Gly
            130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
                165                 170                 175

Val Lys Lys Pro Val Lys Asp Thr Ile Leu Cys Pro Thr Ile Ala Glu
            180                 185                 190

Ser Arg Arg Cys Lys Met Thr Met Arg His Cys Pro Gly Gly Lys Arg
            195                 200                 205

Thr Pro Lys Ala Lys Glu Lys Arg Asn Lys Lys Arg Lys Leu
210                 215                 220

Ile Glu Arg Ala Gln Glu Gln His Ser Val Phe Leu Ala Thr Asp Arg
225                 230                 235                 240

Ala Asn Gln

<210> SEQ ID NO 12
<211> LENGTH: 272
<212> TYPE: PRT
<213> ORGANISM: Homo sapiens

<400> SEQUENCE: 12

Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Gln Arg Arg
            20                  25                  30

Met His Pro Asn Val Ser Gln Gly Cys Gln Gly Gly Cys Ala Thr Cys
            35                  40                  45

Ser Asp Tyr Asn Gly Cys Leu Ser Cys Lys Pro Arg Leu Phe Phe Ala
50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
            115                 120                 125

Cys Pro Glu Gly Leu Glu Ala Asn Asn His Thr Met Glu Cys Val Ser
130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
            195                 200                 205

Gly Glu Arg Gly Lys Lys Gly Arg Glu Arg Lys Arg Lys Lys Pro Asn
210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
```

```
                        245                 250                 255
Arg Lys Val Gln Asp Lys Gln Lys Ser Val Ser Val Ser Thr Val His
                    260                 265                 270

<210> SEQ ID NO 13
<211> LENGTH: 234
<212> TYPE: PRT
<213> ORGANISM: Homo sapiens

<400> SEQUENCE: 13

Met Arg Ala Pro Leu Cys Leu Leu Leu Val Ala His Ala Val Asp
1               5                   10                  15

Met Leu Ala Leu Asn Arg Arg Lys Lys Gln Val Gly Thr Gly Leu Gly
                20                  25                  30

Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Arg Glu Gly Ile Arg
        50                  55                  60

Gln Tyr Gly Lys Cys Leu His Asp Cys Pro Pro Gly Tyr Phe Gly Ile
65                  70                  75                  80

Arg Gly Gln Glu Val Asn Arg Cys Lys Lys Cys Gly Ala Thr Cys Glu
                85                  90                  95

Ser Cys Phe Ser Gln Asp Phe Cys Ile Arg Cys Lys Arg Gln Phe Tyr
            100                 105                 110

Leu Tyr Lys Gly Lys Cys Leu Pro Thr Cys Pro Pro Gly Thr Leu Ala
        115                 120                 125

His Gln Asn Thr Arg Glu Cys Gln Gly Glu Cys Glu Leu Gly Pro Trp
    130                 135                 140

Gly Gly Trp Ser Pro Cys Thr His Asn Gly Lys Thr Cys Gly Ser Ala
145                 150                 155                 160

Trp Gly Leu Glu Ser Arg Val Arg Glu Ala Gly Arg Ala Gly His Glu
                165                 170                 175

Glu Ala Ala Thr Cys Gln Val Leu Ser Glu Ser Arg Lys Cys Pro Ile
            180                 185                 190

Gln Arg Pro Cys Pro Gly Glu Arg Ser Pro Gly Gln Lys Gly Arg
        195                 200                 205

Lys Asp Arg Arg Pro Arg Lys Asp Arg Lys Leu Asp Arg Arg Leu Asp
    210                 215                 220

Val Arg Pro Arg Gln Pro Gly Leu Gln Pro
225                 230

<210> SEQ ID NO 14
<211> LENGTH: 172
<212> TYPE: PRT
<213> ORGANISM: Homo sapiens

<400> SEQUENCE: 14

Met Arg Ala Pro Leu Cys Leu Leu Leu Val Ala His Ala Val Asp
1               5                   10                  15

Met Leu Ala Leu Asn Arg Arg Lys Lys Gln Val Gly Thr Gly Leu Gly
                20                  25                  30

Gly Asn Cys Thr Gly Cys Ile Ile Cys Ser Glu Glu Asn Gly Cys Ser
            35                  40                  45

Thr Cys Gln Gln Arg Leu Phe Leu Phe Ile Arg Arg Glu Gly Ile Arg
        50                  55                  60

Gln Tyr Gly Lys Cys Leu His Asp Cys Pro Pro Gly Tyr Phe Gly Ile
```

```
                65                  70                  75                  80
Arg Gly Gln Glu Val Asn Arg Cys Lys Lys Cys Gly Ala Thr Cys Glu
                        85                  90                  95

Ser Cys Phe Ser Gln Asp Phe Cys Ile Arg Cys Lys Arg Gln Phe Tyr
                        100                 105                 110

Leu Tyr Lys Gly Lys Cys Leu Pro Thr Cys Pro Pro Gly Thr Leu Ala
                        115                 120                 125

His Gln Asn Thr Arg Glu Cys Gln Glu Arg Ser Pro Gly Gln Lys Lys
                        130                 135                 140

Gly Arg Lys Asp Arg Arg Pro Arg Lys Asp Lys Leu Asp Arg Arg
145                 150                 155                 160

Leu Asp Val Arg Pro Arg Gln Pro Gly Leu Gln Pro
                        165                 170

<210> SEQ ID NO 15
<211> LENGTH: 133
<212> TYPE: PRT
<213> ORGANISM: Homo sapiens

<400> SEQUENCE: 15

Met Arg Lys His Val Leu Ala Ala Ser Phe Ser Met Leu Ser Leu Leu
1               5                   10                  15

Val Ile Met Gly Asp Thr Asp Ser Lys Thr Asp Ser Ser Phe Ile Met
                20                  25                  30

Asp Ser Asp Pro Arg Arg Cys Met Arg His His Tyr Val Asp Ser Ile
                35                  40                  45

Ser His Pro Leu Tyr Lys Cys Ser Ser Lys Met Val Leu Leu Ala Arg
                50                  55                  60

Cys Glu Gly His Cys Ser Gln Ala Ser Arg Ser Glu Pro Leu Val Ser
65                  70                  75                  80

Phe Ser Thr Val Leu Lys Gln Pro Phe Arg Ser Ser Cys His Cys Cys
                        85                  90                  95

Arg Pro Gln Thr Ser Lys Leu Lys Ala Leu Arg Leu Arg Cys Ser Gly
                        100                 105                 110

Gly Met Arg Leu Thr Ala Thr Tyr Arg Tyr Ile Leu Ser Cys His Cys
                        115                 120                 125

Glu Glu Cys Asn Ser
        130

<210> SEQ ID NO 16
<211> LENGTH: 352
<212> TYPE: PRT
<213> ORGANISM: Homo sapiens

<400> SEQUENCE: 16

Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
                20                  25                  30

Ser Ser Leu Gly Ser Gln Pro Ile Leu Cys Ala Ser Ile Pro Gly Leu
                35                  40                  45

Val Pro Lys Gln Leu Arg Phe Cys Arg Asn Tyr Val Glu Ile Met Pro
                50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
```

```
                 85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Val Thr Arg Ser Cys
            115                 120                 125

Ala Glu Gly Thr Ala Ala Ile Cys Gly Cys Ser Ser Arg His Gln Gly
        130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
            195                 200                 205

Ser Gly Ser Cys Glu Val Lys Thr Cys Trp Trp Ser Gln Pro Asp Phe
    210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
            275                 280                 285

Ser Phe Gly Thr Arg Asp Arg Thr Cys Asn Val Ser Ser His Gly Ile
    290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
            340                 345                 350

<210> SEQ ID NO 17
<211> LENGTH: 338
<212> TYPE: PRT
<213> ORGANISM: Homo sapiens

<400> SEQUENCE: 17

Ala Val Gly Ser Pro Leu Val Met Asp Pro Thr Ser Ile Cys Arg Lys
1               5                   10                  15

Ala Arg Arg Leu Ala Gly Arg Gln Ala Glu Leu Cys Gln Ala Glu Pro
            20                  25                  30

Glu Val Val Ala Glu Leu Ala Arg Gly Ala Arg Leu Gly Val Arg Glu
        35                  40                  45

Cys Gln Phe Gln Phe Arg Phe Arg Arg Trp Asn Cys Ser Ser His Ser
    50                  55                  60

Lys Ala Phe Gly Arg Ile Leu Gln Gln Asp Ile Arg Glu Thr Ala Phe
65                  70                  75                  80

Val Phe Ala Ile Thr Ala Ala Gly Ala Ser His Ala Val Thr Gln Ala
                85                  90                  95

Cys Ser Met Gly Glu Leu Leu Gln Cys Gly Cys Gln Ala Pro Arg Gly
            100                 105                 110
```

```
Arg Ala Pro Pro Arg Pro Ser Gly Leu Pro Gly Thr Pro Gly Pro Pro
            115                 120                 125

Gly Pro Ala Gly Ser Pro Glu Gly Ser Ala Ala Trp Glu Trp Gly Gly
        130                 135                 140

Cys Gly Asp Asp Val Asp Phe Gly Asp Glu Lys Ser Arg Leu Phe Met
145                 150                 155                 160

Asp Ala Arg His Lys Arg Gly Arg Gly Asp Ile Arg Ala Leu Val Gln
                165                 170                 175

Leu His Asn Asn Glu Ala Gly Arg Leu Ala Val Arg Ser His Thr Arg
            180                 185                 190

Thr Glu Cys Lys Cys His Gly Leu Ser Gly Ser Cys Ala Leu Arg Thr
        195                 200                 205

Cys Trp Gln Lys Leu Pro Pro Phe Arg Glu Val Gly Ala Arg Leu Leu
210                 215                 220

Glu Arg Phe His Gly Ala Ser Arg Val Met Gly Thr Asn Asp Gly Lys
225                 230                 235                 240

Ala Leu Leu Pro Ala Val Arg Thr Leu Lys Pro Pro Gly Arg Ala Asp
                245                 250                 255

Leu Leu Tyr Ala Ala Asp Ser Pro Asp Phe Cys Ala Pro Asn Arg Arg
            260                 265                 270

Thr Gly Ser Pro Gly Thr Arg Gly Arg Ala Cys Asn Ser Ser Ala Pro
        275                 280                 285

Asp Leu Ser Gly Cys Asp Leu Leu Cys Cys Gly Arg Gly His Arg Gln
290                 295                 300

Glu Ser Val Gln Leu Glu Glu Asn Cys Leu Cys Arg Phe His Trp Cys
305                 310                 315                 320

Cys Val Val Gln Cys His Arg Cys Arg Val Arg Lys Glu Leu Ser Leu
                325                 330                 335

Cys Leu

<210> SEQ ID NO 18
<211> LENGTH: 288
<212> TYPE: PRT
<213> ORGANISM: Homo sapiens

<400> SEQUENCE: 18

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140
```

-continued

Leu Pro Glu Asp Gly Gly Ser Gly Ala Phe Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
                260                 265                 270

Gly Pro Gly Gln Lys Ala Ile Leu Phe Leu Pro Met Ser Ala Lys Ser
            275                 280                 285

<210> SEQ ID NO 19
<211> LENGTH: 194
<212> TYPE: PRT
<213> ORGANISM: Homo sapiens

<400> SEQUENCE: 19

Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
                180                 185                 190

Ile Thr

<210> SEQ ID NO 20
<211> LENGTH: 208
<212> TYPE: PRT
<213> ORGANISM: Homo sapiens -continued

```
<400> SEQUENCE: 20

Met Trp Lys Trp Ile Leu Thr His Cys Ala Ser Ala Phe Pro His Leu
1               5                   10                  15

Pro Gly Cys Cys Cys Cys Phe Leu Leu Leu Phe Leu Val Ser Ser
            20                  25                  30

Val Pro Val Thr Cys Gln Ala Leu Gly Gln Val Met Val Ser Pro Glu
            35                  40                  45

Ala Thr Asn Ser Ser Ser Ser Phe Ser Ser Pro Ser Ser Ala Gly
    50                  55                  60

Arg His Val Arg Ser Tyr Asn His Leu Gln Gly Asp Val Arg Trp Arg
65                  70                  75                  80

Lys Leu Phe Ser Phe Thr Lys Tyr Phe Leu Lys Ile Glu Lys Asn Gly
                85                  90                  95

Lys Val Ser Gly Thr Lys Lys Glu Asn Cys Pro Tyr Ser Ile Leu Glu
            100                 105                 110

Ile Thr Ser Val Glu Ile Gly Val Val Ala Val Lys Ala Ile Asn Ser
        115                 120                 125

Asn Tyr Tyr Leu Ala Met Asn Lys Lys Gly Lys Leu Tyr Gly Ser Lys
130                 135                 140

Glu Phe Asn Asn Asp Cys Lys Leu Lys Glu Arg Ile Glu Glu Asn Gly
145                 150                 155                 160

Tyr Asn Thr Tyr Ala Ser Phe Asn Trp Gln His Asn Gly Arg Gln Met
                165                 170                 175

Tyr Val Ala Leu Asn Gly Lys Gly Ala Pro Arg Arg Gly Gln Lys Thr
            180                 185                 190

Arg Arg Lys Asn Thr Ser Ala His Phe Leu Pro Met Val Val His Ser
        195                 200                 205

<210> SEQ ID NO 21
<211> LENGTH: 1207
<212> TYPE: PRT
<213> ORGANISM: Homo sapiens

<400> SEQUENCE: 21

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125

Glu Val Ile Trp Ser Asn Gln Gln Glu Gly Ile Ile Thr Val Thr Asp
130                 135                 140

Met Lys Gly Asn Asn Ser His Ile Leu Leu Ser Ala Leu Lys Tyr Pro
145                 150                 155                 160
```

```
Ala Asn Val Ala Val Asp Pro Val Glu Arg Phe Ile Phe Trp Ser Ser
            165                 170                 175
Glu Val Ala Gly Ser Leu Tyr Arg Ala Asp Leu Asp Gly Val Gly Val
        180                 185                 190
Lys Ala Leu Leu Glu Thr Ser Glu Lys Ile Thr Ala Val Ser Leu Asp
        195                 200                 205
Val Leu Asp Lys Arg Leu Phe Trp Ile Gln Tyr Asn Arg Glu Gly Ser
210                 215                 220
Asn Ser Leu Ile Cys Ser Cys Asp Tyr Asp Gly Gly Ser Val His Ile
225                 230                 235                 240
Ser Lys His Pro Thr Gln His Asn Leu Phe Ala Met Ser Leu Phe Gly
            245                 250                 255
Asp Arg Ile Phe Tyr Ser Thr Trp Lys Met Lys Thr Ile Trp Ile Ala
            260                 265                 270
Asn Lys His Thr Gly Lys Asp Met Val Arg Ile Asn Leu His Ser Ser
        275                 280                 285
Phe Val Pro Leu Gly Glu Leu Lys Val Val His Pro Leu Ala Gln Pro
        290                 295                 300
Lys Ala Glu Asp Asp Thr Trp Glu Pro Glu Gln Lys Leu Cys Lys Leu
305                 310                 315                 320
Arg Lys Gly Asn Cys Ser Ser Thr Val Cys Gly Gln Asp Leu Gln Ser
            325                 330                 335
His Leu Cys Met Cys Ala Glu Gly Tyr Ala Leu Ser Arg Asp Arg Lys
            340                 345                 350
Tyr Cys Glu Asp Val Asn Glu Cys Ala Phe Trp Asn His Gly Cys Thr
        355                 360                 365
Leu Gly Cys Lys Asn Thr Pro Gly Ser Tyr Tyr Cys Thr Cys Pro Val
370                 375                 380
Gly Phe Val Leu Leu Pro Asp Gly Lys Arg Cys His Gln Leu Val Ser
385                 390                 395                 400
Cys Pro Arg Asn Val Ser Glu Cys Ser His Asp Cys Val Leu Thr Ser
            405                 410                 415
Glu Gly Pro Leu Cys Phe Cys Pro Glu Gly Ser Val Leu Glu Arg Asp
            420                 425                 430
Gly Lys Thr Cys Ser Gly Cys Ser Ser Pro Asp Asn Gly Gly Cys Ser
        435                 440                 445
Gln Leu Cys Val Pro Leu Ser Pro Val Ser Trp Glu Cys Asp Cys Phe
450                 455                 460
Pro Gly Tyr Asp Leu Gln Leu Asp Glu Lys Ser Cys Ala Ala Ser Gly
465                 470                 475                 480
Pro Gln Pro Phe Leu Leu Phe Ala Asn Ser Gln Asp Ile Arg His Met
            485                 490                 495
His Phe Asp Gly Thr Asp Tyr Gly Thr Leu Leu Ser Gln Gln Met Gly
            500                 505                 510
Met Val Tyr Ala Leu Asp His Asp Pro Val Glu Asn Lys Ile Tyr Phe
        515                 520                 525
Ala His Thr Ala Leu Lys Trp Ile Glu Arg Ala Asn Met Asp Gly Ser
530                 535                 540
Gln Arg Glu Arg Leu Ile Glu Glu Gly Val Asp Val Pro Glu Gly Leu
545                 550                 555                 560
Ala Val Asp Trp Ile Gly Arg Arg Phe Tyr Trp Thr Asp Arg Gly Lys
            565                 570                 575
Ser Leu Ile Gly Arg Ser Asp Leu Asn Gly Lys Arg Ser Lys Ile Ile
```

```
                580             585             590
Thr Lys Glu Asn Ile Ser Gln Pro Arg Gly Ile Ala Val His Pro Met
            595                 600                 605

Ala Lys Arg Leu Phe Trp Thr Asp Thr Gly Ile Asn Pro Arg Ile Glu
610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                645                 650                 655

Tyr Trp Cys Asp Ala Lys Gln Ser Val Ile Glu Met Ala Asn Leu Asp
                660                 665                 670

Gly Ser Lys Arg Arg Leu Thr Gln Asn Asp Val Gly His Pro Phe
            675                 680                 685

Ala Val Ala Val Phe Glu Asp Tyr Val Trp Phe Ser Asp Trp Ala Met
690                 695                 700

Pro Ser Val Met Arg Val Asn Lys Arg Thr Gly Lys Asp Arg Val Arg
705                 710                 715                 720

Leu Gln Gly Ser Met Leu Lys Pro Ser Ser Leu Val Val His Pro
                725                 730                 735

Leu Ala Lys Pro Gly Ala Asp Pro Cys Leu Tyr Gln Asn Gly Gly Cys
                740                 745                 750

Glu His Ile Cys Lys Lys Arg Leu Gly Thr Ala Trp Cys Ser Cys Arg
                755                 760                 765

Glu Gly Phe Met Lys Ala Ser Asp Gly Lys Thr Cys Leu Ala Leu Asp
            770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
                805                 810                 815

Thr Glu Ser Gln His Met Leu Val Ala Glu Ile Met Val Ser Asp Gln
                820                 825                 830

Asp Asp Cys Ala Pro Val Gly Cys Ser Met Tyr Ala Arg Cys Ile Ser
                835                 840                 845

Glu Gly Glu Asp Ala Thr Cys Gln Cys Leu Lys Gly Phe Ala Gly Asp
            850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                885                 890                 895

Cys Arg Cys Ser Glu Gly Tyr Gln Gly Asp Gly Ile His Cys Leu Asp
            900                 905                 910

Ile Asp Glu Cys Gln Leu Gly Glu His Ser Cys Gly Glu Asn Ala Ser
            915                 920                 925

Cys Thr Asn Thr Glu Gly Gly Tyr Thr Cys Met Cys Ala Gly Arg Leu
            930                 935                 940

Ser Glu Pro Gly Leu Ile Cys Pro Asp Ser Thr Pro Pro His Leu
945                 950                 955                 960

Arg Glu Asp Asp His His Tyr Ser Val Arg Asn Ser Asp Ser Glu Cys
                965                 970                 975

Pro Leu Ser His Asp Gly Tyr Cys Leu His Asp Gly Val Cys Met Tyr
                980                 985                 990

Ile Glu Ala Leu Asp Lys Tyr Ala  Cys Asn Cys Val Val  Gly Tyr Ile
            995                 1000                1005
```

Gly Glu Arg Cys Gln Tyr Arg Asp Leu Lys Trp Trp Glu Leu Arg
    1010                1015                1020

His Ala Gly His Gly Gln Gln Gln Lys Val Ile Val Val Ala Val
    1025                1030                1035

Cys Val Val Val Leu Val Met Leu Leu Leu Ser Leu Trp Gly
    1040                1045                1050

Ala His Tyr Tyr Arg Thr Gln Lys Leu Leu Ser Lys Asn Pro Lys
    1055                1060                1065

Asn Pro Tyr Glu Glu Ser Ser Arg Asp Val Arg Ser Arg Arg Pro
    1070                1075                1080

Ala Asp Thr Glu Asp Gly Met Ser Ser Cys Pro Gln Pro Trp Phe
    1085                1090                1095

Val Val Ile Lys Glu His Gln Asp Leu Lys Asn Gly Gly Gln Pro
    1100                1105                1110

Val Ala Gly Glu Asp Gly Gln Ala Ala Asp Gly Ser Met Gln Pro
    1115                1120                1125

Thr Ser Trp Arg Gln Glu Pro Gln Leu Cys Gly Met Gly Thr Glu
    1130                1135                1140

Gln Gly Cys Trp Ile Pro Val Ser Ser Asp Lys Gly Ser Cys Pro
    1145                1150                1155

Gln Val Met Glu Arg Ser Phe His Met Pro Ser Tyr Gly Thr Gln
    1160                1165                1170

Thr Leu Glu Gly Gly Val Glu Lys Pro His Ser Leu Leu Ser Ala
    1175                1180                1185

Asn Pro Leu Trp Gln Gln Arg Ala Leu Asp Pro Pro His Gln Met
    1190                1195                1200

Glu Leu Thr Gln
    1205

<210> SEQ ID NO 22
<211> LENGTH: 160
<212> TYPE: PRT
<213> ORGANISM: Homo sapiens

<400> SEQUENCE: 22

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
                20                  25                  30

Asp Pro Pro Val Ala Ala Val Val Ser His Phe Asn Asp Cys Pro
        35                  40                  45

Asp Ser His Thr Gln Phe Cys Phe His Gly Thr Cys Arg Phe Leu Val
    50                  55                  60

Gln Glu Asp Lys Pro Ala Cys Val Cys His Ser Gly Tyr Val Gly Ala
65                  70                  75                  80

Arg Cys Glu His Ala Asp Leu Leu Ala Val Val Ala Ala Ser Gln Lys
                85                  90                  95

Lys Gln Ala Ile Thr Ala Leu Val Val Val Ser Ile Val Ala Leu Ala
                100                 105                 110

Val Leu Ile Ile Thr Cys Val Leu Ile His Cys Cys Gln Val Arg Lys
                115                 120                 125

His Cys Glu Trp Cys Arg Ala Leu Ile Cys Arg His Glu Lys Pro Ser
        130                 135                 140

Ala Leu Leu Lys Gly Arg Thr Ala Cys Cys His Ser Glu Thr Val Val

| 145 | 150 | 155 | 160 |

<210> SEQ ID NO 23
<211> LENGTH: 159
<212> TYPE: PRT
<213> ORGANISM: Homo sapiens

<400> SEQUENCE: 23

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Asp
                20                  25                  30

Pro Pro Val Ala Ala Val Val Ser His Phe Asn Asp Cys Pro Asp
                35                  40                  45

Ser His Thr Gln Phe Cys Phe His Gly Thr Cys Arg Phe Leu Val Gln
        50                  55                  60

Glu Asp Lys Pro Ala Cys Val Cys His Ser Gly Tyr Val Gly Ala Arg
65                  70                  75                  80

Cys Glu His Ala Asp Leu Leu Ala Val Val Ala Ala Ser Gln Lys Lys
                85                  90                  95

Gln Ala Ile Thr Ala Leu Val Val Val Ser Ile Val Ala Leu Ala Val
                100                 105                 110

Leu Ile Ile Thr Cys Val Leu Ile His Cys Cys Gln Val Arg Lys His
                115                 120                 125

Cys Glu Trp Cys Arg Ala Leu Ile Cys Arg His Glu Lys Pro Ser Ala
            130                 135                 140

Leu Leu Lys Gly Arg Thr Ala Cys Cys His Ser Glu Thr Val Val
145                 150                 155

<210> SEQ ID NO 24
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Val Pro Leu Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Asp
                20                  25                  30

Pro Pro Val Ala Ala Val Val Ser His Phe Asn Asp Cys Pro Asp
                35                  40                  45

Ser His Thr Gln Phe Cys Phe His Gly Thr Cys Arg Phe Leu Val Gln
        50                  55                  60

Glu Asp Lys Pro Ala Cys Val Cys His Ser Gly Tyr Val Gly Ala Arg
65                  70                  75                  80

Cys Glu His Ala Asp Leu Leu Ala Val Val Ala Ala Ser Gln Lys Lys
                85                  90                  95

Gln Ala Ile Thr Ala Leu Val Val Val Ser Ile Val Ala Leu Ala Val
                100                 105                 110

Leu Ile Ile Thr Cys Val Leu Ile His Cys Cys Gln Val Arg Lys His
                115                 120                 125

Cys Glu Trp Cys Arg Ala Leu Ile Cys Arg His Glu Lys Pro Ser Ala
            130                 135                 140

Leu Leu Lys Gly Arg Thr Ala Cys Cys His Ser Glu Thr Val Val Leu 145            150            155            160

<210> SEQ ID NO 25
<211> LENGTH: 50
<212> TYPE: PRT
<213> ORGANISM: Unknown
<220> FEATURE:
<223> OTHER INFORMATION: Description of Unknown:
      TGF alpha sequence

<400> SEQUENCE: 25

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
                20                  25                  30

Val Cys His Ser Gly Tyr Val Gly Ala Arg Cys Glu His Ala Asp Leu
            35                  40                  45

Leu Ala
    50

<210> SEQ ID NO 26
<211> LENGTH: 246
<212> TYPE: PRT
<213> ORGANISM: Homo sapiens

<400> SEQUENCE: 26

Met Thr Ile Leu Phe Leu Thr Met Val Ile Ser Tyr Phe Gly Cys Met
1               5                   10                  15

Lys Ala Ala Pro Met Lys Glu Ala Ile Arg Gly Gln Gly Gly Leu Ala
                20                  25                  30

Tyr Pro Gly Val Arg Thr His Gly Thr Leu Glu Ser Val Asn Gly Pro
            35                  40                  45

Lys Ala Gly Ser Arg Gly Leu Thr Ser Leu Ala Asp Thr Phe Glu His
        50                  55                  60

Val Ile Glu Glu Leu Leu Asp Glu Asp Gln Lys Val Arg Pro Asn Glu
65                  70                  75                  80

Glu Asn Asn Lys Asp Ala Asp Leu Tyr Thr Ser Arg Val Met Leu Ser
                85                  90                  95

Ser Gln Val Pro Leu Glu Pro Pro Leu Leu Phe Leu Leu Glu Glu Tyr
                100                 105                 110

Lys Asn Tyr Leu Asp Ala Ala Asn Met Ser Met Arg Val Arg Arg His
            115                 120                 125

Ser Asp Pro Ala Arg Arg Gly Glu Leu Ser Val Cys Asp Ser Ile Ser
        130                 135                 140

Glu Trp Val Thr Ala Ala Asp Lys Lys Thr Ala Val Asp Met Ser Gly
145                 150                 155                 160

Gly Thr Val Thr Val Leu Glu Lys Val Pro Val Ser Lys Gly Gln Leu
                165                 170                 175

Lys Gln Tyr Phe Tyr Glu Thr Lys Cys Asn Pro Met Gly Tyr Thr Lys
            180                 185                 190

Glu Gly Cys Arg Gly Ile Asp Lys Arg His Trp Asn Ser Gln Cys Arg
        195                 200                 205

Thr Thr Gln Ser Tyr Val Arg Ala Leu Thr Met Asp Ser Lys Lys Arg
    210                 215                 220

Ile Gly Trp Arg Phe Ile Arg Ile Asp Thr Ser Cys Val Cys Thr Leu
225                 230                 235                 240

Thr Ile Lys Arg Gly Arg

<210> SEQ ID NO 27
<211> LENGTH: 194
<212> TYPE: PRT
<213> ORGANISM: Homo sapiens

<400> SEQUENCE: 27

Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
    50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
        115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr

<210> SEQ ID NO 28
<211> LENGTH: 1218
<212> TYPE: PRT
<213> ORGANISM: Homo sapiens

<400> SEQUENCE: 28

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
                20                  25                  30

Gly Gln Phe Glu Leu Glu Ile Leu Ser Met Gln Asn Val Asn Gly Glu
            35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

```
Pro Arg Ser Tyr Thr Leu Leu Val Glu Ala Trp Asp Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540
```

-continued

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
            565                 570                 575

Ser Cys Thr Val Ala Met Ala Ser Asn Asp Thr Pro Glu Gly Val Arg
        580                 585                 590

Tyr Ile Ser Ser Asn Val Cys Gly Pro His Gly Lys Cys Lys Ser Gln
    595                 600                 605

Ser Gly Gly Lys Phe Thr Cys Asp Cys Asn Lys Gly Phe Thr Gly Thr
610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
            645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
            675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
            725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
            755                 760                 765

Val Cys Lys Glu Gly Trp Glu Gly Pro Ile Cys Ala Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
            805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
            885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
            915                 920                 925

Pro Cys Thr Gly Val Gly Glu Cys Arg Ser Ser Leu Gln Pro Val
            930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr

```
                       965                 970                 975
Glu His Ile Cys Ser Glu Leu Arg Asn Leu Asn Ile Leu Lys Asn Val
                   980                 985                 990
Ser Ala Glu Tyr Ser Ile Tyr Ile Ala Cys Glu Pro Ser Pro Ser Ala
               995                1000                1005
Asn Asn Glu Ile His Val Ala Ile Ser Ala Glu Asp Ile Arg Asp
           1010                1015                1020
Asp Gly Asn Pro Ile Lys Glu Ile Thr Asp Lys Ile Ile Asp Leu
           1025                1030                1035
Val Ser Lys Arg Asp Gly Asn Ser Ser Leu Ile Ala Ala Val Ala
           1040                1045                1050
Glu Val Arg Val Gln Arg Arg Pro Leu Lys Asn Arg Thr Asp Phe
           1055                1060                1065
Leu Val Pro Leu Leu Ser Ser Val Leu Thr Val Ala Trp Ile Cys
           1070                1075                1080
Cys Leu Val Thr Ala Phe Tyr Trp Cys Leu Arg Lys Arg Arg Lys
           1085                1090                1095
Pro Gly Ser His Thr His Ser Ala Ser Glu Asp Asn Thr Thr Asn
           1100                1105                1110
Asn Val Arg Glu Gln Leu Asn Gln Ile Lys Asn Pro Ile Glu Lys
           1115                1120                1125
His Gly Ala Asn Thr Val Pro Ile Lys Asp Tyr Glu Asn Lys Asn
           1130                1135                1140
Ser Lys Met Ser Lys Ile Arg Thr His Asn Ser Glu Val Glu Glu
           1145                1150                1155
Asp Asp Met Asp Lys His Gln Gln Lys Ala Arg Phe Ala Lys Gln
           1160                1165                1170
Pro Ala Tyr Thr Leu Val Asp Arg Glu Glu Lys Pro Pro Asn Gly
           1175                1180                1185
Thr Pro Thr Lys His Pro Asn Trp Thr Asn Lys Gln Asp Asn Arg
           1190                1195                1200
Asp Leu Glu Ser Ala Gln Ser Leu Asn Arg Met Glu Tyr Ile Val
           1205                1210                1215

<210> SEQ ID NO 29
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Arg Gly Ser His His His His His His Gly Ser Ile Glu Gly Arg
1               5                   10                  15

Ser Ala Val Thr Cys Asp Asp Tyr Tyr Tyr Gly Phe Gly Cys Asn Lys
            20                  25                  30

Phe Cys Arg Pro Arg Asp Asp Phe Phe Gly His Tyr Ala Cys Asp Gln
        35                  40                  45

Asn Gly Asn Lys Thr Cys Met Glu Gly Trp Met Gly Pro Glu Cys Asn
    50                  55                  60

Arg Ala Ile Cys Arg Gln Gly Cys Ser Pro Lys His Gly Ser Cys Lys
65                  70                  75                  80

Leu Pro Gly Asp Cys Arg Cys Gln Tyr Gly Trp Gln Gly Leu Tyr Cys
                85                  90                  95
```

```
Asp Lys Cys Ile Pro His Pro Gly Cys Val His Gly Ile Cys Asn Glu
            100                 105                 110

Pro Trp Gln Cys Leu Cys Glu Thr Asn Trp Gly Gly Gln Leu Cys Asp
            115                 120                 125

Lys Asp Leu Asn Tyr Cys Gly Thr His Gln Pro Cys Leu Asn Gly Gly
130                 135                 140

Thr Cys Ser Asn Thr Gly Pro Asp Lys Tyr Gln Cys Ser Cys Pro Glu
145                 150                 155                 160

Gly Tyr Ser Gly Pro Asn Cys Glu Ile
                165

<210> SEQ ID NO 30
<211> LENGTH: 17
<212> TYPE: PRT
<213> ORGANISM: Homo sapiens

<400> SEQUENCE: 30

Cys Asp Asp Tyr Tyr Tyr Gly Phe Gly Cys Asn Lys Phe Cys Arg Pro
1               5                   10                  15

Arg

<210> SEQ ID NO 31
<211> LENGTH: 1238
<212> TYPE: PRT
<213> ORGANISM: Homo sapiens

<400> SEQUENCE: 31

Met Arg Ala Gln Gly Arg Gly Arg Leu Pro Arg Leu Leu Leu Leu
1               5                   10                  15

Leu Ala Leu Trp Val Gln Ala Ala Arg Pro Met Gly Tyr Phe Glu Leu
            20                  25                  30

Gln Leu Ser Ala Leu Arg Asn Val Asn Gly Glu Leu Leu Ser Gly Ala
            35                  40                  45

Cys Cys Asp Gly Asp Gly Arg Thr Thr Arg Ala Gly Gly Cys Gly His
            50                  55                  60

Asp Glu Cys Asp Thr Tyr Val Arg Val Cys Leu Lys Glu Tyr Gln Ala
65                  70                  75                  80

Lys Val Thr Pro Thr Gly Pro Cys Ser Tyr Gly His Gly Ala Thr Pro
                85                  90                  95

Val Leu Gly Gly Asn Ser Phe Tyr Leu Pro Pro Ala Gly Ala Ala Gly
            100                 105                 110

Asp Arg Ala Arg Ala Arg Ala Arg Ala Gly Gly Asp Gln Asp Pro Gly
            115                 120                 125

Leu Val Val Ile Pro Phe Gln Phe Ala Trp Pro Arg Ser Phe Thr Leu
130                 135                 140

Ile Val Glu Ala Trp Asp Trp Asp Asn Asp Thr Thr Pro Asn Glu Glu
145                 150                 155                 160

Leu Leu Ile Glu Arg Val Ser His Ala Gly Met Ile Asn Pro Glu Asp
                165                 170                 175

Arg Trp Lys Ser Leu His Phe Ser Gly His Val Ala His Leu Glu Leu
            180                 185                 190

Gln Ile Arg Val Arg Cys Asp Glu Asn Tyr Tyr Ser Ala Thr Cys Asn
            195                 200                 205

Lys Phe Cys Arg Pro Arg Asn Asp Phe Phe Gly His Tyr Thr Cys Asp
210                 215                 220

Gln Tyr Gly Asn Lys Ala Cys Met Asp Gly Trp Met Gly Lys Glu Cys
```

```
                225                 230                 235                 240
        Lys Glu Ala Val Cys Lys Gln Gly Cys Asn Leu Leu His Gly Gly Cys
                        245                 250                 255
        Thr Val Pro Gly Glu Cys Arg Cys Ser Tyr Gly Trp Gln Gly Arg Phe
                        260                 265                 270
        Cys Asp Glu Cys Val Pro Tyr Pro Gly Cys Val His Gly Ser Cys Val
                        275                 280                 285
        Glu Pro Trp Gln Cys Asn Cys Glu Thr Asn Trp Gly Gly Leu Leu Cys
                        290                 295                 300
        Asp Lys Asp Leu Asn Tyr Cys Gly Ser His His Pro Cys Thr Asn Gly
        305                 310                 315                 320
        Gly Thr Cys Ile Asn Ala Glu Pro Asp Gln Tyr Arg Cys Thr Cys Pro
                        325                 330                 335
        Asp Gly Tyr Ser Gly Arg Asn Cys Glu Lys Ala Glu His Ala Cys Thr
                        340                 345                 350
        Ser Asn Pro Cys Ala Asn Gly Gly Ser Cys His Glu Val Pro Ser Gly
                        355                 360                 365
        Phe Glu Cys His Cys Pro Ser Gly Trp Ser Gly Pro Thr Cys Ala Leu
                        370                 375                 380
        Asp Ile Asp Glu Cys Ala Ser Asn Pro Cys Ala Ala Gly Gly Thr Cys
        385                 390                 395                 400
        Val Asp Gln Val Asp Gly Phe Glu Cys Ile Cys Pro Glu Gln Trp Val
                        405                 410                 415
        Gly Ala Thr Cys Gln Leu Asp Ala Asn Glu Cys Glu Gly Lys Pro Cys
                        420                 425                 430
        Leu Asn Ala Phe Ser Cys Lys Asn Leu Ile Gly Gly Tyr Tyr Cys Asp
                        435                 440                 445
        Cys Ile Pro Gly Trp Lys Gly Ile Asn Cys His Ile Asn Val Asn Asp
                        450                 455                 460
        Cys Arg Gly Gln Cys Gln His Gly Gly Thr Cys Lys Asp Leu Val Asn
        465                 470                 475                 480
        Gly Tyr Gln Cys Val Cys Pro Arg Gly Phe Gly Gly Arg His Cys Glu
                        485                 490                 495
        Leu Glu Arg Asp Glu Cys Ala Ser Ser Pro Cys His Ser Gly Gly Leu
                        500                 505                 510
        Cys Glu Asp Leu Ala Asp Gly Phe His Cys His Cys Pro Gln Gly Phe
                        515                 520                 525
        Ser Gly Pro Leu Cys Glu Val Asp Val Asp Leu Cys Glu Pro Ser Pro
                        530                 535                 540
        Cys Arg Asn Gly Ala Arg Cys Tyr Asn Leu Glu Gly Asp Tyr Tyr Cys
        545                 550                 555                 560
        Ala Cys Pro Asp Asp Phe Gly Gly Lys Asn Cys Ser Val Pro Arg Glu
                        565                 570                 575
        Pro Cys Pro Gly Gly Ala Cys Arg Val Ile Asp Gly Cys Gly Ser Asp
                        580                 585                 590
        Ala Gly Pro Gly Met Pro Gly Thr Ala Ala Ser Gly Val Cys Gly Pro
                        595                 600                 605
        His Gly Arg Cys Val Ser Gln Pro Gly Gly Asn Phe Ser Cys Ile Cys
                        610                 615                 620
        Asp Ser Gly Phe Thr Gly Thr Tyr Cys His Glu Asn Ile Asp Asp Cys
        625                 630                 635                 640
        Leu Gly Gln Pro Cys Arg Asn Gly Gly Thr Cys Ile Asp Glu Val Asp
                        645                 650                 655
```

```
Ala Phe Arg Cys Phe Cys Pro Ser Gly Trp Glu Gly Glu Leu Cys Asp
            660                 665                 670

Thr Asn Pro Asn Asp Cys Leu Pro Asp Pro Cys His Ser Arg Gly Arg
            675                 680                 685

Cys Tyr Asp Leu Val Asn Asp Phe Tyr Ala Cys Asp Asp Gly Trp
        690                 695                 700

Lys Gly Lys Thr Cys His Ser Arg Glu Phe Gln Cys Asp Ala Tyr Thr
705                 710                 715                 720

Cys Ser Asn Gly Gly Thr Cys Tyr Asp Ser Gly Asp Thr Phe Arg Cys
                725                 730                 735

Ala Cys Pro Pro Gly Trp Lys Gly Ser Thr Cys Ala Val Ala Lys Asn
            740                 745                 750

Ser Ser Cys Leu Pro Asn Pro Cys Val Asn Gly Gly Thr Cys Val Gly
        755                 760                 765

Ser Gly Ala Ser Phe Ser Cys Ile Cys Arg Asp Gly Trp Glu Gly Arg
        770                 775                 780

Thr Cys Thr His Asn Thr Asn Asp Cys Asn Pro Leu Pro Cys Tyr Asn
785                 790                 795                 800

Gly Gly Ile Cys Val Asp Gly Val Asn Trp Phe Arg Cys Glu Cys Ala
            805                 810                 815

Pro Gly Phe Ala Gly Pro Asp Cys Arg Ile Asn Ile Asp Glu Cys Gln
            820                 825                 830

Ser Ser Pro Cys Ala Tyr Gly Ala Thr Cys Val Asp Glu Ile Asn Gly
            835                 840                 845

Tyr Arg Cys Ser Cys Pro Pro Gly Arg Ala Gly Pro Arg Cys Gln Glu
        850                 855                 860

Val Ile Gly Phe Gly Arg Ser Cys Trp Ser Arg Gly Thr Pro Phe Pro
865                 870                 875                 880

His Gly Ser Ser Trp Val Glu Asp Cys Asn Ser Cys Arg Cys Leu Asp
            885                 890                 895

Gly Arg Arg Asp Cys Ser Lys Val Trp Cys Gly Trp Lys Pro Cys Leu
            900                 905                 910

Leu Ala Gly Gln Pro Glu Ala Leu Ser Ala Gln Cys Pro Leu Gly Gln
            915                 920                 925

Arg Cys Leu Glu Lys Ala Pro Gly Gln Cys Leu Arg Pro Pro Cys Glu
        930                 935                 940

Ala Trp Gly Glu Cys Gly Ala Glu Glu Pro Ser Thr Pro Cys Leu
945                 950                 955                 960

Pro Arg Ser Gly His Leu Asp Asn Asn Cys Ala Arg Leu Thr Leu His
            965                 970                 975

Phe Asn Arg Asp His Val Pro Gln Gly Thr Thr Val Gly Ala Ile Cys
        980                 985                 990

Ser Gly Ile Arg Ser Leu Pro Ala  Thr Arg Ala Val Ala  Arg Asp Arg
        995                 1000                1005

Leu Leu  Val Leu Leu Cys Asp  Arg Ala Ser Ser Gly  Ala Ser Ala
    1010                1015                1020

Val Glu  Val Ala Val Ser Phe  Ser Pro Ala Arg Asp  Leu Pro Asp
    1025                1030                1035

Ser Ser  Leu Ile Gln Gly Ala  Ala His Ala Ile Val  Ala Ala Ile
    1040                1045                1050

Thr Gln  Arg Gly Asn Ser Ser  Leu Leu Leu Ala Val  Thr Glu Val
    1055                1060                1065
```

-continued

```
Lys Val Glu Thr Val Val Thr Gly Gly Ser Ser Thr Gly Leu Leu
1070            1075                1080

Val Pro Val Leu Cys Gly Ala Phe Ser Val Leu Trp Leu Ala Cys
1085            1090                1095

Val Val Leu Cys Val Trp Trp Thr Arg Lys Arg Arg Lys Glu Arg
1100            1105                1110

Glu Arg Ser Arg Leu Pro Arg Glu Ser Ala Asn Asn Gln Trp
1115            1120                1125

Ala Pro Leu Asn Pro Ile Arg Asn Pro Ile Glu Arg Pro Gly Gly
1130            1135                1140

His Lys Asp Val Leu Tyr Gln Cys Lys Asn Phe Thr Pro Pro Pro
1145            1150                1155

Arg Arg Ala Asp Glu Ala Leu Pro Gly Pro Ala Gly His Ala Ala
1160            1165                1170

Val Arg Glu Asp Glu Glu Asp Glu Asp Leu Gly Arg Gly Glu Glu
1175            1180                1185

Asp Ser Leu Glu Ala Glu Lys Phe Leu Ser His Lys Phe Thr Lys
1190            1195                1200

Asp Pro Gly Arg Ser Pro Gly Arg Pro Ala His Trp Ala Ser Gly
1205            1210                1215

Pro Lys Val Asp Asn Arg Ala Val Arg Ser Ile Asn Glu Ala Arg
1220            1225                1230

Tyr Ala Gly Lys Glu
1235
```

```
<210> SEQ ID NO 32
<211> LENGTH: 722
<212> TYPE: PRT
<213> ORGANISM: Homo sapiens

<400> SEQUENCE: 32

Gly Ser Arg Cys Ala Leu Ala Leu Ala Val Leu Ser Ala Leu Cys
1               5                   10                  15

Gln Val Trp Ser Ser Gly Val Phe Glu Leu Lys Leu Gln Glu Phe Val
                20                  25                  30

Asn Lys Lys Gly Leu Leu Gly Asn Arg Asn Cys Cys Arg Gly Gly Ala
        35                  40                  45

Gly Pro Pro Pro Cys Ala Cys Arg Thr Phe Phe Arg Val Cys Leu Lys
    50                  55                  60

His Tyr Gln Ala Ser Val Ser Pro Glu Pro Cys Thr Tyr Gly Ser
65                  70                  75                  80

Ala Val Thr Pro Val Leu Gly Val Asp Ser Phe Ser Leu Pro Asp Gly
                85                  90                  95

Gly Gly Ala Asp Ser Ala Phe Ser Asn Pro Ile Arg Phe Pro Phe Gly
                100                 105                 110

Phe Thr Trp Pro Gly Thr Phe Ser Leu Ile Ile Glu Ala Leu His Thr
            115                 120                 125

Asp Ser Pro Asp Asp Leu Ala Thr Glu Asn Pro Glu Arg Leu Ile Ser
    130                 135                 140

Arg Leu Ala Thr Gln Arg His Leu Thr Val Gly Glu Glu Trp Ser Gln
145                 150                 155                 160

Asp Leu His Ser Ser Gly Arg Thr Asp Leu Lys Tyr Ser Tyr Arg Phe
                165                 170                 175

Val Cys Asp Glu His Tyr Tyr Gly Glu Gly Cys Ser Val Phe Cys Arg
            180                 185                 190
```

```
Pro Arg Asp Asp Ala Phe Gly His Phe Thr Cys Gly Glu Arg Gly Glu
        195                 200                 205

Lys Val Cys Asn Pro Gly Trp Lys Gly Pro Tyr Cys Thr Glu Pro Ile
210                 215                 220

Cys Leu Pro Gly Cys Asp Glu Gln His Gly Phe Cys Asp Lys Pro Gly
225                 230                 235                 240

Glu Cys Lys Cys Arg Val Gly Trp Gln Gly Arg Tyr Cys Asp Glu Cys
                245                 250                 255

Ile Arg Tyr Pro Gly Cys Leu His Gly Thr Cys Gln Gln Pro Trp Gln
                260                 265                 270

Cys Asn Cys Gln Glu Gly Trp Gly Gly Leu Phe Cys Asn Gln Asp Leu
        275                 280                 285

Asn Tyr Cys Thr His His Lys Pro Cys Lys Asn Gly Ala Thr Cys Thr
        290                 295                 300

Asn Thr Gly Gln Gly Ser Tyr Thr Cys Ser Cys Arg Pro Gly Tyr Thr
305                 310                 315                 320

Gly Ala Thr Cys Glu Leu Gly Ile Asp Glu Cys Asp Pro Ser Pro Cys
                325                 330                 335

Lys Asn Gly Gly Ser Cys Thr Asp Leu Glu Asn Ser Tyr Ser Cys Thr
                340                 345                 350

Cys Pro Pro Gly Phe Tyr Gly Lys Ile Cys Glu Leu Ser Ala Met Thr
        355                 360                 365

Cys Ala Asp Gly Pro Cys Phe Asn Gly Gly Arg Cys Ser Asp Ser Pro
        370                 375                 380

Asp Gly Gly Tyr Ser Cys Arg Cys Pro Val Gly Tyr Ser Gly Phe Asn
385                 390                 395                 400

Cys Glu Lys Lys Ile Asp Tyr Cys Ser Ser Ser Pro Cys Ser Asn Gly
                405                 410                 415

Ala Lys Cys Val Asp Leu Gly Asp Ala Tyr Leu Cys Arg Cys Gln Ala
                420                 425                 430

Gly Phe Ser Gly Arg His Cys Asp Asp Asn Val Asp Asp Cys Ala Ser
        435                 440                 445

Ser Pro Cys Ala Asn Gly Gly Thr Cys Arg Asp Gly Val Asn Asp Phe
        450                 455                 460

Ser Cys Thr Cys Pro Pro Gly Tyr Thr Gly Arg Asn Cys Ser Ala Pro
465                 470                 475                 480

Val Ser Arg Cys Glu His Ala Pro Cys His Asn Gly Ala Thr Cys His
                485                 490                 495

Glu Arg Gly His Arg Tyr Val Cys Glu Cys Ala Arg Gly Tyr Gly Gly
                500                 505                 510

Pro Asn Cys Gln Phe Leu Leu Pro Glu Leu Pro Pro Gly Pro Ala Val
        515                 520                 525

Val Asp Leu Thr Glu Lys Leu Glu Gly Gln Gly Gly Pro Phe Pro Trp
530                 535                 540

Val Ala Val Cys Ala Gly Val Ile Leu Val Leu Met Leu Leu Leu Gly
545                 550                 555                 560

Cys Ala Ala Val Val Val Cys Val Arg Leu Arg Leu Gln Lys His Arg
                565                 570                 575

Pro Pro Ala Asp Pro Cys Arg Gly Glu Thr Glu Thr Met Asn Asn Leu
        580                 585                 590

Ala Asn Cys Gln Arg Glu Lys Asp Ile Ser Val Ser Ile Ile Gly Ala
        595                 600                 605
```

```
Thr Gln Ile Lys Asn Thr Asn Lys Lys Ala Asp Phe His Gly Asp His
    610                 615                 620

Ser Ala Asp Lys Asn Gly Phe Lys Ala Arg Tyr Pro Ala Val Asp Tyr
625                 630                 635                 640

Asn Leu Val Gln Asp Leu Lys Gly Asp Thr Ala Val Arg Asp Ala
                645                 650                 655

His Ser Lys Arg Asp Thr Lys Cys Gln Pro Gln Gly Ser Ser Gly Glu
            660                 665                 670

Glu Lys Gly Thr Pro Thr Thr Leu Arg Gly Gly Glu Ala Ser Glu Arg
        675                 680                 685

Lys Arg Pro Asp Ser Gly Cys Ser Thr Ser Lys Asp Thr Lys Tyr Gln
    690                 695                 700

Ser Val Tyr Val Ile Ser Glu Glu Lys Asp Glu Cys Val Ile Ala Thr
705                 710                 715                 720

Glu Val

<210> SEQ ID NO 33
<211> LENGTH: 685
<212> TYPE: PRT
<213> ORGANISM: Homo sapiens

<400> SEQUENCE: 33

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
    195                 200                 205

Leu Pro Gly Trp Thr Gly Glu Tyr Cys Gln Gln Pro Ile Cys Leu Ser
210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255
```

```
Asn Gly Cys Arg His Gly Thr Cys Ser Thr Pro Trp Gln Cys Thr Cys
            260                 265                 270

Asp Glu Gly Trp Gly Leu Phe Cys Asp Gln Asp Leu Asn Tyr Cys
            275                 280                 285

Thr His His Ser Pro Cys Lys Asn Gly Ala Thr Cys Ser Asn Ser Gly
            290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
            325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
            355                 360                 365

Ser Pro Cys Phe Asn Gly Gly Ser Cys Arg Glu Arg Asn Gln Gly Ala
            370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
            405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
            435                 440                 445

Cys Ala His Gly Gly Thr Cys His Asp Leu Glu Asn Gly Leu Met Cys
            450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
            485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
            515                 520                 525

Trp Val Ala Val Ser Leu Gly Val Gly Leu Ala Val Leu Leu Val Leu
530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
            565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
            595                 600                 605

Gln Asn His Thr Leu Asp Tyr Asn Leu Ala Pro Gly Pro Leu Gly Arg
            610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
            645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
```

<210> SEQ ID NO 34
<211> LENGTH: 618
<212> TYPE: PRT
<213> ORGANISM: Homo sapiens

<400> SEQUENCE: 34

```
Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Ala Pro Arg Ser
        35                  40                  45

Pro Cys Ser Ala Arg Leu Pro Cys Arg Leu Phe Phe Arg Val Cys Leu
    50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
    130                 135                 140

Arg Val Ala Gly Arg Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
        355                 360                 365
```

Leu Asp Leu Gly His Ala Leu Arg Cys Arg Cys Arg Ala Gly Phe Ala
370                 375                 380

Gly Pro Arg Cys Glu His Asp Leu Asp Cys Ala Gly Arg Ala Cys
385                 390                 395                 400

Ala Asn Gly Gly Thr Cys Val Glu Gly Gly Ala His Arg Cys Ser
            405                 410                 415

Cys Ala Leu Gly Phe Gly Gly Arg Asp Cys Arg Glu Arg Ala Asp Pro
            420                 425                 430

Cys Ala Ala Arg Pro Cys Ala His Gly Gly Arg Cys Tyr Ala His Phe
                435                 440                 445

Ser Gly Leu Val Cys Ala Cys Ala Pro Gly Tyr Met Gly Ala Arg Cys
450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Pro Pro Ala
            485                 490                 495

Leu Gly Leu Leu Val Ala Ala Gly Val Ala Gly Ala Ala Leu Leu Leu
            500                 505                 510

Val His Val Arg Arg Arg Gly His Ser Gln Asp Ala Gly Ser Arg Leu
515                 520                 525

Leu Ala Gly Thr Pro Glu Pro Ser Val His Ala Leu Pro Asp Ala Leu
530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
            565                 570                 575

Ile Ser Ala Pro Ser Ile Tyr Ala Arg Glu Val Ala Thr Pro Leu Phe
            580                 585                 590

Pro Pro Leu His Thr Gly Arg Ala Gly Gln Arg Gln His Leu Leu Phe
            595                 600                 605

Pro Tyr Pro Ser Ser Ile Leu Ser Val Lys
610                 615

<210> SEQ ID NO 35
<211> LENGTH: 587
<212> TYPE: PRT
<213> ORGANISM: Homo sapiens

<400> SEQUENCE: 35

Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
                20                  25                  30

Gln Ile His Ser Phe Gly Pro Gly Pro Gly Pro Gly Ala Pro Arg Ser
            35                  40                  45

Pro Cys Ser Ala Arg Leu Pro Cys Arg Leu Phe Phe Arg Val Cys Leu
        50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

```
Glu Glu Leu Gly Asp Gln Ile Gly Gly Pro Ala Trp Ser Leu Leu Ala
    130                 135                 140

Arg Val Ala Gly Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                    165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
                195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
                260                 265                 270

Pro Gly Pro Gly Pro Cys Asp Gly Asn Pro Cys Ala Asn Gly Gly Ser
            275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
    355                 360                 365

Leu Asp Leu Gly His Ala Leu Arg Cys Arg Cys Arg Ala Gly Phe Ala
    370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Gly Ala His Arg Cys Ser
                405                 410                 415

Cys Ala Leu Gly Phe Gly Gly Arg Asp Cys Arg Glu Arg Ala Asp Pro
            420                 425                 430

Cys Ala Ala Arg Pro Cys Ala His Gly Gly Arg Cys Tyr Ala His Phe
                435                 440                 445

Ser Gly Leu Val Cys Ala Cys Ala Pro Gly Tyr Met Gly Ala Arg Cys
    450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Pro Pro Ala
                485                 490                 495

Leu Gly Leu Leu Val Ala Ala Gly Val Ala Gly Ala Ala Leu Leu Leu
                500                 505                 510

Val His Val Arg Arg Arg Gly His Ser Gln Asp Ala Gly Ser Arg Leu
    515                 520                 525

Leu Ala Gly Thr Pro Glu Pro Ser Val His Ala Leu Pro Asp Ala Leu
    530                 535                 540
```

```
Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
                565                 570                 575

Ile Ser Ala Pro Ser Ile Tyr Ala Arg Glu Ala
            580                 585
```

```
<210> SEQ ID NO 36
<211> LENGTH: 17
<212> TYPE: PRT
<213> ORGANISM: Homo sapiens

<400> SEQUENCE: 36

Cys Asp Asp Tyr Tyr Tyr Gly Phe Gly Cys Asn Lys Phe Cys Arg Pro
1               5                   10                  15

Arg
```

```
<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Met Ser Arg Leu Leu His Ala Glu Val Val Gly
1               5                   10
```

```
<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
atgtcccgcc tgctgcatgc agaagtagtg ggctgaagtg                         40
```

```
<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
atgtcccgcc tgctgcatgc agaagtagtg ggctgaagt                          39
```

```
<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Met Ser Arg Leu Leu His Ala Glu Glu Trp Ala Glu Val
1               5                   10
```

```
<210> SEQ ID NO 41
<211> LENGTH: 38
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
atgtcccgcc tgctgcatgc agaagagtgg gctgaagt                              38
```

INFLAMMATORY BOWEL DISEASE STEM CELLS, AGENTS WHICH TARGET IBD STEM CELLS, AND USES RELATED THERETO

CROSS-REFERENCE TO RELATED APPLICATIONS

This application is a 35 U.S.C. § 371 filing of International Application No. PCT/US2018/031370, filed on May 7, 2018, which application claims the benefit of U.S. Provisional Application No. 62/501,878, filed May 5, 2017. The entire contents of this application are incorporated herein in their entirety.

SEQUENCE LISTING

The instant application contains a Sequence Listing which has been submitted electronically in ASCII format and is hereby incorporated by reference in its entirety. Said ASCII copy, created on Nov. 5, 2019, is named 617990-TCT-004US-SEQ.TXT and is 126,976 bytes in size.

BACKGROUND

Inflammatory bowel disease (IBD) is a common disease of the Western World. Symptoms include chronic intestinal inflammation, diarrhea, bloody stool, weight loss and bowel obstruction. With no obvious cure, surgery is a frequent outcome. Major IBD-subtypes, Ulcerative colitis and Crohn's disease, share similar demographic and epidemiological features with as much as 10% of the cases being clinically indistinguishable. However, key differences in tissue damage and prognosis suggests distinct underlying pathogenic processes. In UC, inflammatory infiltrates and tissue damage is limited to the mucosal layer with extensive disruption of the mucosa, crypt abscesses, neutrophilic infiltrations. While transmural damage, thickening of intestinal wall and increased trichrome staining for connective tissue are typical of Crohn's disease.

IBD is classically viewed as a multi-step disease with two major players. First, initiating events of environmental origin, such as exotoxins, and other microbial factors. Secondly, the responding host immune system that leads to normal healing in unaffected, but inflammation and tissue response in IBD patients. Thus, past IBD studies have focused on selected environmental factors and cytokines, immune cells and inflammatory proteins.

Crohn's disease is an inflammatory bowel disorder marked by transmural lesions that frequently progress to strictures, fistulas, or perforations requiring repeated surgical intervention. While its onset is typically in the third and fourth decade, about 15 percent of cases arise in children who tend to have a severe phenotype characterized by extensive small and large bowel disease, frequent need for corticosteroids and immunosuppression, growth delay, and enhanced risk for colorectal cancer. Though immunosuppressants and anti-inflammatory biologics can slow the progression of Crohn's disease, it is not clear that they have lessened the need of surgical intervention, an impasse that has fueled the search for therapeutic targets more proximal to the disease. This search is complicated by the large environmental contribution to this disease reflected by the low concordance among monozygotic twins, and by the polygenic nature of the remaining, inherited risk. Nevertheless, genome-wide association (GWAS) and biological studies are beginning to define the underlying genetic structure and pathophysiology of Crohn's disease. In particular, there is a stunning overlap of risk loci associated with Crohn's and the susceptibility to mycobacterial infections, and many of the 170 risk loci discovered to date implicate genes of adaptive and innate immune processes that are likely involved in the containment of gut microbes. Consistent with this emerging "barrier defect" hypothesis are observations of profound deficiencies in the production of anti-microbial peptides by Paneth cells in Crohn's disease patients, defective autophagy processing of microbial antigens by mucosal epithelial cells and altered responsiveness of mucosal immune cells.

Despite its utility in characterizing the disease, the barrier defect hypothesis is mute on key features of the natural history of Crohn's disease including its alternate presentations as ileal, ileo-colonic, and colonic disease, the intermittent or "skip-lesion" patterning of inflammatory foci within these affected regions, and its cycle of flares and remission. Nor does this hypothesis address why the terminal ileum sustains the most severe manifestations of the disease necessitating surgery, or the nature and origin of recurrent disease that so frequently ensues the removal of the terminal ileum.

In the United States alone, more than 600,000 are affected every year. There is currently no satisfactory treatment, as the cause for IBD remains unclear although infectious and immunologic mechanisms have been proposed. IBD treatments aim at controlling inflammatory symptoms, conventionally using corticosteroids, aminosalicylates and standard immunosuppressive agents such as azathioprine (6-mercaptopurine), methotrexate and ciclosporine. Of these, the only disease-modifying therapies are the immunosuppressive agents azathioprine and methotrexate, both of which have a slow onset of action and only a moderate efficacy. Long-term therapy may cause liver damage (fibrosis or cirrhosis) and bone marrow suppression. Also patients often become refractory to such treatment. Other therapeutic regimes merely address symptoms.

SUMMARY

One aspect of the present invention provides isolated epithelial stem cells derived from gastrointestinal biopsies from IBD patients, referred to herein as "IBD Stem Cells". Prior to the invention, intestinal stem cells from disease samples were generally considered unviable in culture and isolation of stem cells from IBD patient biopsies and stable culture and passaging of those stem cells under conditions that maintain the genotype and epigenetics of the stem cell as it existed in the biopsy had not been described.

In certain embodiments, the subject IBD stem cells are derived from disease tissue samples such as biopsies from Crohn's Disease patients, including adult or pediatric patients. In other embodiments, the subject IBD stem cells are derived from disease tissue samples such as biopsies from Ulcerative Colitis patients, including adult or pediatric patients.

The isolation, passaging and maintenance of the subject IBD stem cells can be carried out using, for example, a culture media system comprising (a) a ROCK (Rho Kinase) inhibitor; (b) a Wnt agonist; (c); a Bone Morphogenetic Protein (BMP) antagonist; (d) a Notched Inhibitor; (e) a TGFβ signaling pathway inhibitor (e.g., a TGFβ inhibitor or a TGFβ receptor inhibitor), and (f) nicotinamide or an analog thereof. In another embodiment, the culture media system comprises (a) a ROCK (Rho Kinase) inhibitor; (b) a Wnt agonist; (c); a Bone Morphogenetic Protein (BMP)

antagonist; (d) a Notched Inhibitor; (e) a TGFβ signaling pathway inhibitor (a TGFβ inhibitor or a TGFβ receptor inhibitor), and (f) nicotinamide or an analog thereof. In certain embodiments, the the culture medium optionally further comprising a mitogenic growth factor and/or insulin or IGF. In certain embodiments, the cells from the IBD tissue sample, or the repassaged IBD stem cells, are optionally in fluid or direct contact with mitotically inactive feeder cells and/or in contact with extracellular matrix (such as a basement membrane matrix) or other bio- or synthetic matrix. In the case of the isolation of IBD stem cells from tissue samples, such as biopsies, the method can be performed by culturing dissociated epithelial cells from an IBD tissue sample in the medium, isolating single cells from the epithelial cell clones that arise, and culturing the isolated single cells from to form individual cultures of single cell clones, i.e., in contact with feeder cells and/or a basement membrane matrix in the medium, where each of the single cell clones represents a clonal expansion of the IBD epithelial stem cell.

Another aspect of the invention relates to the genes ("IBD gene sequences") which are over- or under-expressed in IBD Stem cells, such as those genes which are differentiatally expressed relative to GI stem stem cells from patient matched normal tissue. These include gene sequences, such as the coding sequence, mRNA sequence, RNA transcript or genonmic sequence for Atonal BHLH transcription factor 1 (ATOH1), MUC2, glycoprotein A33 (GPA33), claudin 18 (CLDN18), V-set and immunoglobulin domain containing 1 (VSIG1) or to the genes/proteins identified in Table 3, FIG. 1D, FIG. 19 are collectively herein the "pCD Gene Sequences". Genes which are upregulated or downregulated in IBD cells may be targets for diagnostic or therapeutic techniques.

The present invention makes available isolated polypeptides which are isolated from, or otherwise substantially free of other cellular proteins, especially other signal transduction factors and/or transcription factors which may normally be associated with the polypeptide. Subject polypeptides of the present invention include polypeptides encoded by pCD Gene Sequences. Polypeptides of the present invention include those proteins which are differentially regulated in IBD tissue, especially colon UC- and CD-derived cell lines (relative to normal cells, e.g., normal colon tissue).

In certain embodiments, the subject invention also provides antibodies which selectively bind to a polypeptide gene expression product of an IBD gene sequences, such as the pCD Gene Sequences, or other proteins upregulated in a population of IBD stem cells or its progeny, preferably a protein expressed on the cell surface of the IBD stem cell or its progeny. The antibodies of the present invention can be used, to illustrate, for both diagnostic or therapeutic benefits.

In certain embodiments, the antibody is an antibody-drug conjugate, such as an antibody which selectively bind to a polypeptide gene expression product of a pCD Gene Sequence or other protein that is upregulated in a population of IBD stem cells or its progeny, which antibody is conjugated to a drug that has a cytotoxic effect, cytostatic effect or epigenetic effect on the IBD stem cell and/or its progeny.

The subject invention further provides a method of determining whether a cell sample obtained from a subject possesses an abnormal amount of marker polypeptide which comprises (a) obtaining a cell sample from the subject, (b) quantitatively determining the amount of the marker polypeptide in the sample so obtained, and (c) comparing the amount of the marker polypeptide so determined with a known standard, so as to thereby determine whether the cell sample obtained from the subject possesses an abnormal amount of the marker polypeptide. Such marker polypeptides may be detected by immunohistochemical assays, dot-blot assays, ELISA and the like.

Another aspect invention relates in part to novel methods for identifying and/or classifying patients with inflammatory bowel diseases (IBD), particularly patients with Crohn's disease or ulcerative colitis. Gene expression profiling, for the first time, shows broad and fundamental differences in the pathogenic mechanism of UC and CD. The subject method is based on the findings that certain genes are differentially expressed in intestinal tissue of IBD patients compared with related normal cells, such as normal colon cells. That change can be used to thereby identify or classify IBD cells by the upregulation and/or downregulation of expression of particular genes, alterations in protein levels or modification, or changes at the genomic level (such as mutation, methylation, etc), e.g., an event which is implicated in the pathology of inflammatory bowel diseases. Unlike prior methods, the invention provides a means for identifying IBD patients, and IBD cells at an early stage of development, so that treatment can be determined for early intervention. As described below, certain IBDs are associated with higher risks of cancer, e.g., colon cancer. This allows early detection of potentially cancerous conditions, and treatment of those cancerous conditions prior to spread of the cancerous cells throughout the body, or prior to development of an irreversible cancerous condition.

Still another aspect of the present invention provides drug screening assays for identifying agents which can be used to treat or manage the effects of an inflammatory bowel disease or disorder, e.g., by counteracting the effects of the up- or down-regulation of one or more of the subject IBD genes, such as the pCD Gene Sequences. Such assays include formats which detect agents that inhibit or potentiate expression (transcription or translation) of an IBD gene, formats which detect agents that inhibit or potentiate an activity of an IBD gene product (enzymatic activity, protein-protein interaction, protein-DNA interaction, etc), formats which detect agents that which alter the splicing of IBD gene transcripts, and formats which detect agents that which shorten or extend the half-life of an IBD gene product. For each of the assay embodiments set out above, the assay is preferably repeated for a variegated library of at least 100 different test compounds, though preferably libraries of at least $10^3$, $10^5$, $10^7$, and $10^9$ compunds are tested. The test compound can be, for example, peptides, carbohydrates, nucleic acids and other small organic molecules, and/or natural product extracts.

In yet another aspect, the invention provides pharmaceutical compositions including agents, e.g., which have been identified by the assays described herein, which alter the level of expression or splicing of one or more IBD genes, alter the activity or half-life of an IBD gene product, or which alter the post-translational modification of an IBD gene product.

Another aspect of the present invention relates to transgenic non-human animals having germline and/or somatic cells in which the biological activity of one or more of the IBD Genes Set, such as one or more of the pCD Gene Sequences, are altered by a chromosomally incorporated transgene. Such animals can be used as models for inflammatory bowel diseases or disorders, e.g., for understanding the pathology of disease and/or drug screening.

BRIEF DESCRIPTION OF THE DRAWINGS

FIG. 1C. Heat map of differential gene expression (>1.5-fold, $p<0.05$) between stem cells of Normal category (FC1, fetal TI, subset of CD3) and Crohn's category (CD1, CD2, subset of CD3). The Crohn's cluster differentially expressed approximately 800 genes (>1.5-fold, $p<0.05$) compared to the Control cluster. Filtering these genes against known inflammatory gene sets yielded nearly 200 that populate innate immune and antigen presentation pathways previously linked to Crohn's.

FIG. 1D. IPA analysis of genes both differentially expressed in Crohn's terminal ileum stem cells and overlapping with Organ Inflammation genes segregated bottom to top into nuclear, cytoplasmic, membrane, and secreted sets.

FIG. 1E. Venn diagram of IPA Inflammation, genes differentially expressed in stem cells of Crohn's terminal ileum (TI) and of right colon (RC).

FIG. 1F. Histogram of extent and polarity of expression of three-way overlapping genes of Venn diagram in e. For stem cells of the Crohn's cluster, gene expression profiling of ALI-differentiated terminal ileum stem cells reveals an enrichment of genes associated with inflammatory pathways involving antigen presentation, innate immune responses, cytokine signaling FIG. 2A, FIG. 2B, FIG. 2C, FIG. 2D, and FIG. 2E. In vitro differentiated epithelia from Crohn's stem cells FIG. 2A. 2-D colonies of single cell-derived stem cell pedigree (left) and phase contrast image differentiated epithelia produced from pedigree (right).

FIG. 3A-3F. Secretory cell defect in in vitro-differentiated Crohn's stem cells. Homeotic transformation of Crohn's stem cells.

FIG. 3A and FIG. 3B. Crohn's stem cells fail to generate goblet, Paneth, and endocrine cells, and yet express other antigens (CLDN18 and VSIG1) normally expressed in proximal gastrointestinal tract. In addition to an extensive inflammatory gene signature and defective maturation of secretory cells, Crohn's cluster epithelia are distinguished by the ectopic expression of a host of metabolic enzymes that had no obvious links to either inflammation or secretory cell differentiation. BUT these enzymes, which function in the hydrolysis and transport of lipids, carbohydrates, and proteins, are normally expressed in proximal portions of gastrointestinal tract 12-14 feet anterior to the terminal ileum. Histological comparison between normal and Crohn's in vitro-differentiated terminal ileum via hematoxylin-eosin staining, and immunofluorescence of antibodies to Muc2/Ecad, CHGA/Ki67, DefA6, and GPA33.

FIG. 3C. Comparative expression heatmap of genes associated with gastrointestinal goblet cells (ZG16, CLCA1), Paneth cells (DEFA5, DEFA6), and endocrine cells (SST, GCG) in in vitro-differentiated terminal ileum stem cells. Mapped the gene expression profiles of the Crohn's cluster terminal ileum stem cells against those of each region of the gastrointestinal tract and their corresponding differentiated epithelia derived from a 22-week fetal demise case. Analysis yielded a set of 271 genes that were both differentially expressed between Crohn's and Normal epithelia and showed regional expression along the normal fetal gastrointestinal tract. Pathway analysis of these genes showed the most significant categories to be related to the metabolism and transport of nutrients.

FIG. 3D and FIG. 3E. Histological comparison of in vitro-differentiated normal (left) and Crohn's right colon stem cells via (from top) hematoxylin-eosin staining, and Muc2/Ecad, CHGA/Ki67, DefA6, and GPA33 immunofluorescence.

FIG. 3F. Comparative expression intensity heatmap of genes associated with gastrointestinal goblet, Paneth, and enteroendocrine cells and Crohn's in general in in vitro-differentiated normal and Crohn's right colon stem cells.

FIG. 4B. Left, Venn diagram of CD1 and CD2 terminal ileum gene sets selected for both differential expression in Crohn's and along fetal gastrointestinal tract. Right, Pathway analysis of overlapping genes in Venn diagram. p*z, combined p-value, z-score via Enrichr analysis (Mount Sinai Sch. Med.). Pathway analysis of these genes showed the most significant categories to be related to the metabolism and transport of nutrients. Mapped the gene expression profiles of the Crohn's cluster terminal ileum stem cells against those of each region of the gastrointestinal tract and their corresponding differentiated epithelia derived from a 22-week fetal demise case. Analysis yielded a set of 271 genes that were both differentially expressed between Crohn's and Normal epithelia and showed regional expression along the normal fetal gastrointestinal tract FIG. 4C. Mapping of genes differentially expressed (>1.5-fold, p<0.05) in in vitro-generated Crohn's terminal ileum to those differentially expressed (>1.8-fold, p<0.05) along the fetal gastrointestinal tract including over-represented in Crohn's (left) and over-represented in normal terminal epithelia (right). A, gastric fundus, B, gastric body, C, antrum, D, duodenum, E, jejunum, F, ileum, G, right colon, H, transverse colon, I, left colon. Mapping the genes over-represented in the Crohn's cluster terminal ileum epithelia to discrete regions of the fetal gastrointestinal tract revealed a shift in their distribution to one centered around gastric, duodenum and jejunum epithelia, whereas those over-represented in control terminal ileum generally mapped throughout the colon. Suggest that the terminal ileum stem cells of the Crohn's cluster displayed a switch in gene expression reminiscent of those driven by "homeotic" mutations.

FIG. 4D. Mapping of genes differentially expressed (>1.5-fold, p<0.05) in Crohn's terminal ileum stem cells to those differentially expressed (>1.8-fold, p<0.05) along the fetal gastrointestinal tract including over-represented in Crohn's (left) and over-represented in normal terminal ileum stem cells (right).

Mapping the genes over-represented in the Crohn's cluster terminal ileum epithelia to discrete regions of the fetal gastrointestinal tract revealed a shift in their distribution to one centered around gastric, duodenum and jejunum epithelia, whereas those over-represented in control terminal ileum generally mapped throughout the colon. Suggest that the terminal ileum stem cells of the Crohn's cluster displayed a switch in gene expression reminiscent of those driven by "homeotic" mutations.

Figure 4A:
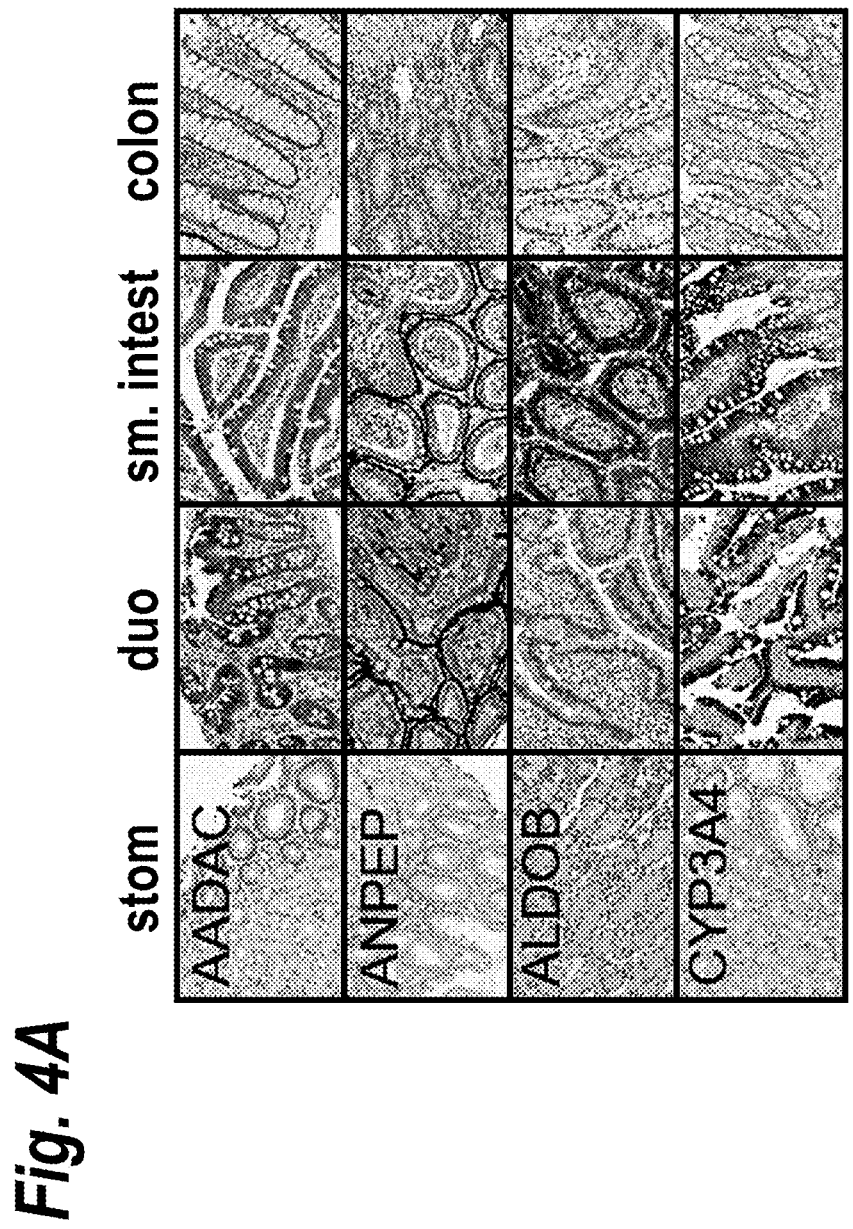
FIG. 4A, FIG. 4B, FIG. 4C, FIG. 4D, FIG. E, and FIG. 4F. Homeotic transformation of Crohn's terminal ileum FIG. 4A. Immunohistochemical staining patterns across the gastrointestinal tract of metabolic enzymes differentially expressed in Crohn's terminal (via Human Protein Atlas).
Figure 4B:
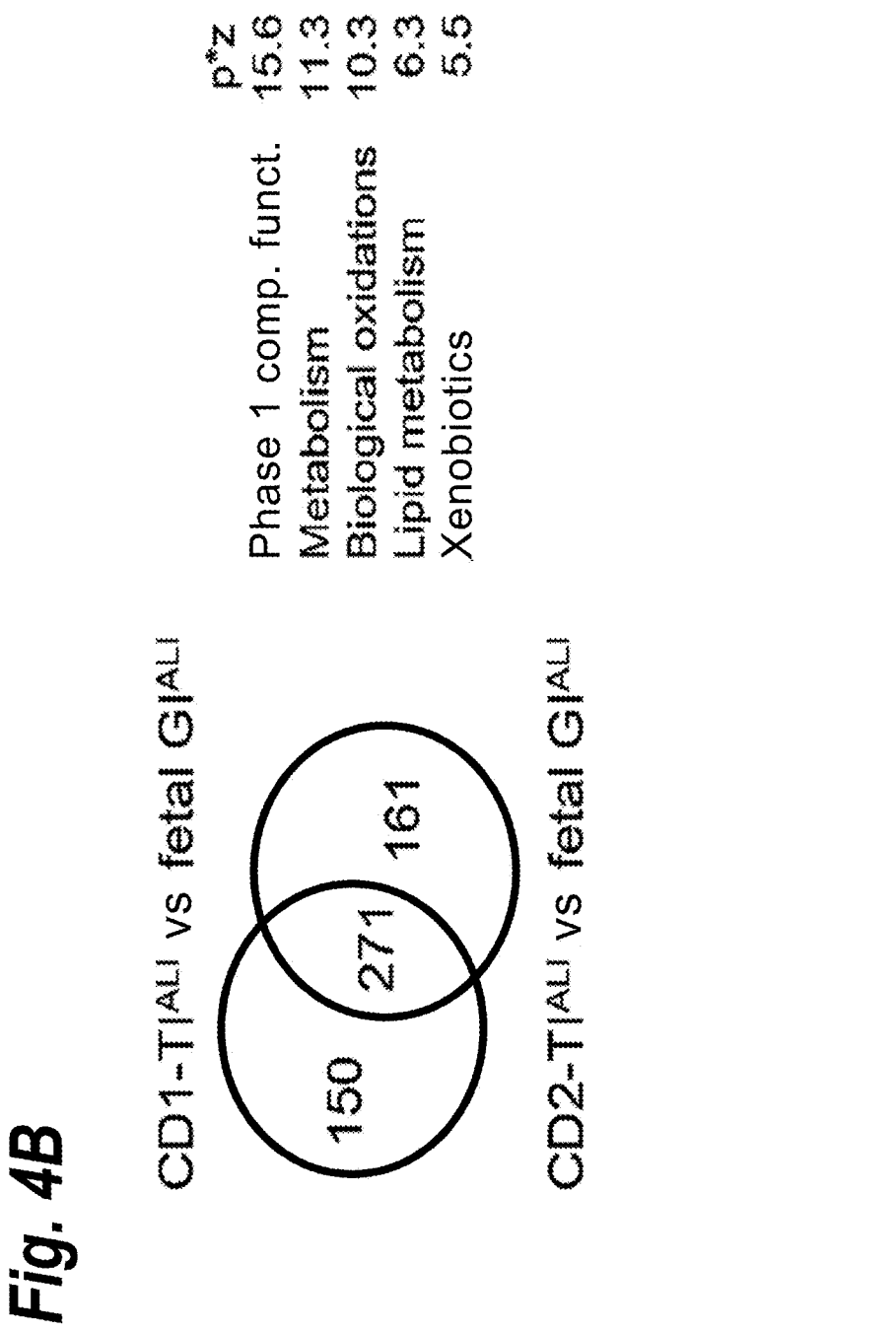
Figure 4C:
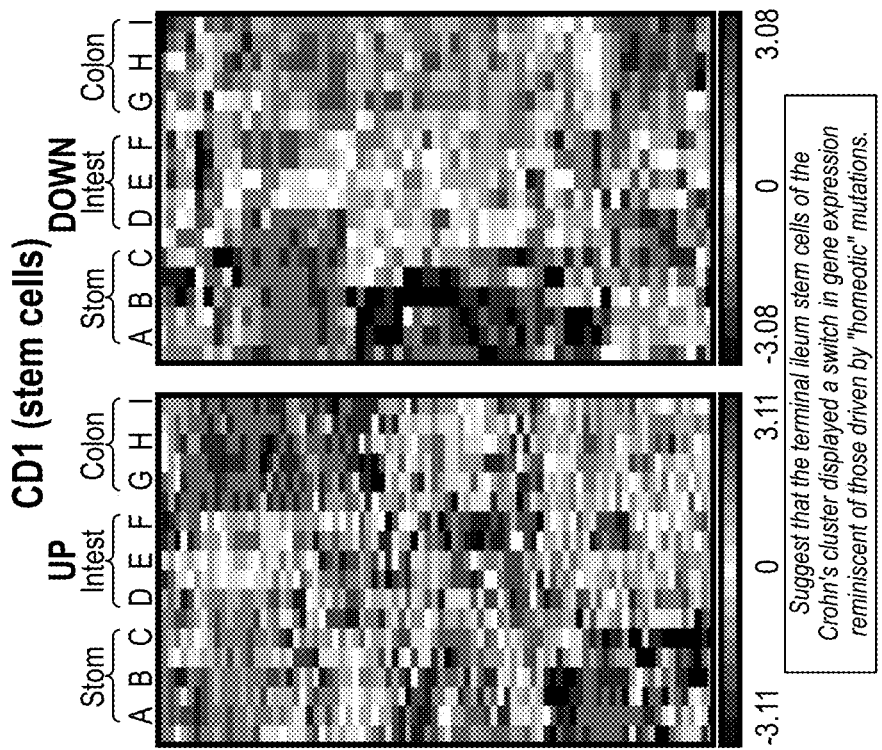
Figure 4D:
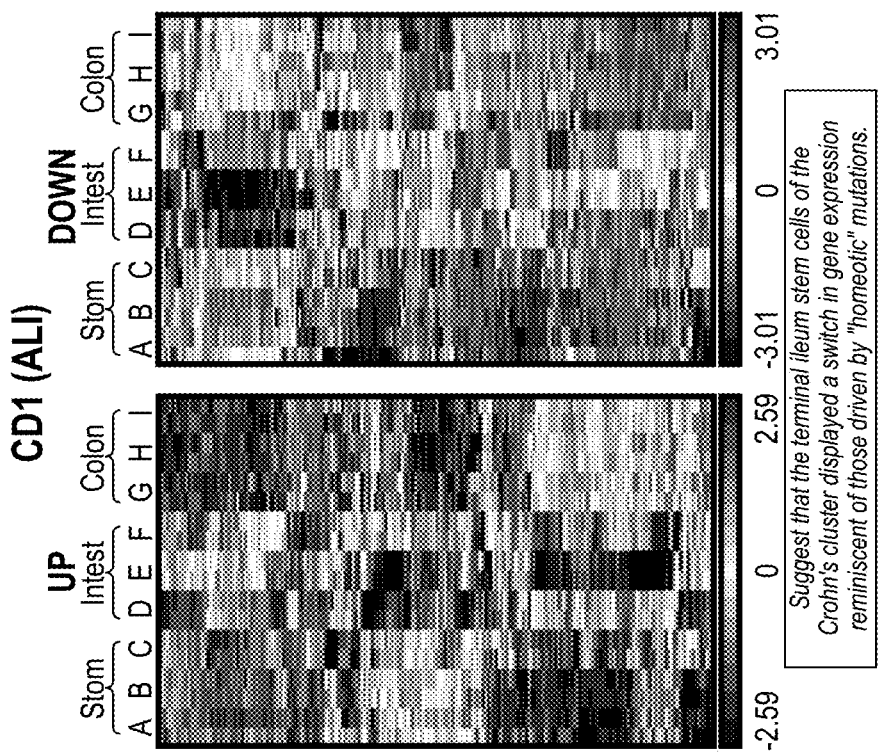
Figure 4E:
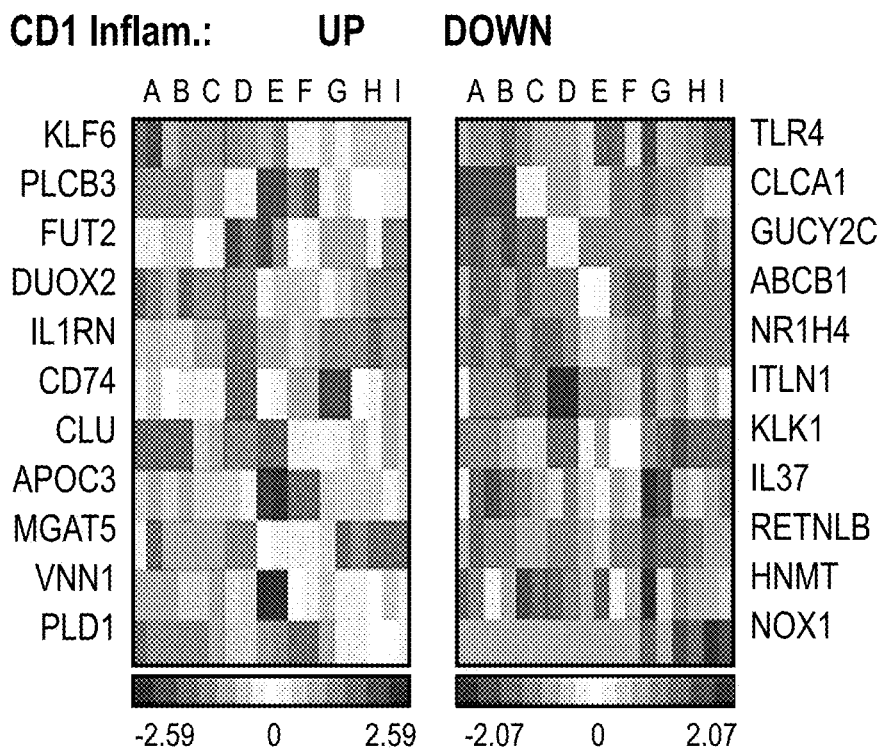

FIG. 4E. Heatmap of differential gene expression (>1.8-fold, p<0.05) along the fetal gastrointestinal tract of inflammatory genes overexpressed (left) and underexpressed (right) (1.5-fold, p<0.05) in Crohn's terminal ileum stem cells post-differentiation.

Figure 4F:
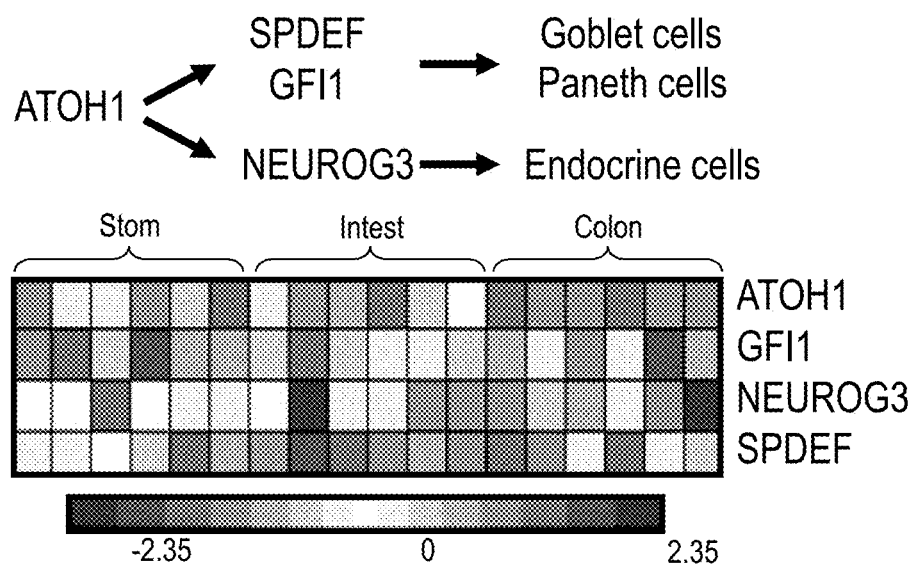

FIG. 4F. Top, Transcription factors implicated in the generation of indicated secretory cells in the gastrointestinal tract. Bottom, Differential expression of indicated transcription factors along the fetal gastrointestinal tract.

FIG. 5A, FIG. 5B, FIG. 5C, FIG. 5D, FIG. 5E, FIG. 5F, FIG. 5G, FIG. 5H, FIG. 5I, FIG. 5J, FIG. 5K, and FIG. 5L. ATOH1 in secretory cell differentiation of intestinal mucosa FIG. 5A. Box plot of ATOH1 gene expression intensity for multiple terminal ileum stem cell pedigrees of Crohn's cases (CD1, CD2, CD3) and controls (FC1 and fetal terminal ileum). The top whisker shows maximum, the boxed zone shows 1st quartile, median and 3rd quartile, while the lower whisker shows minimum with outliers indicated (see Methods section).

Figure 5A:
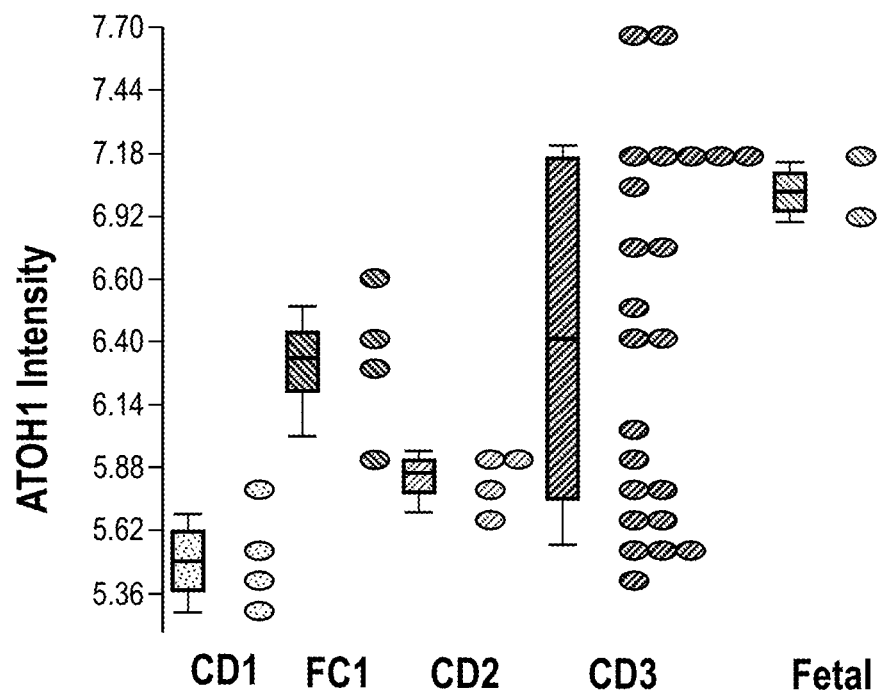
Figure 5B:
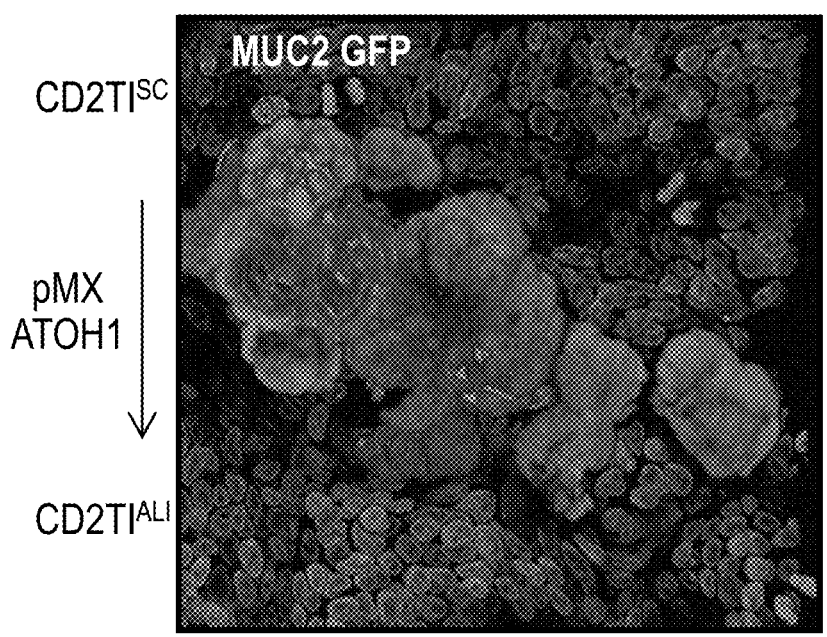

FIG. 5B. Clusters of Muc2/GFP-positive goblet cells in retrovirally transduced CD2 terminal ileum stem cells following differentiation in ALI culture.

Figure 5C:
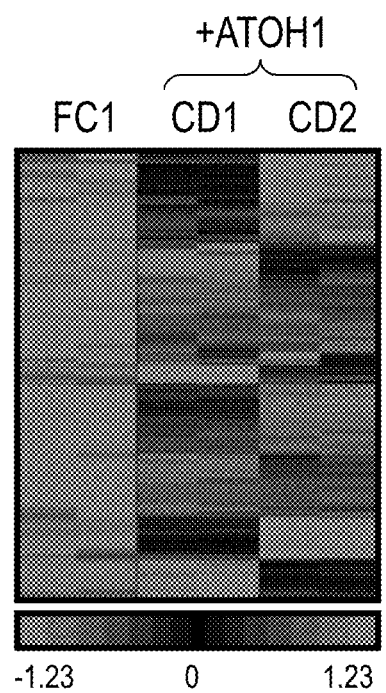

FIG. 5C. Differential gene expression heatmap comparing epithelia derived from normal (FC1) and ATOH1-transduced Crohn's (CD1, CD2) stem cells.

Figure 5D:
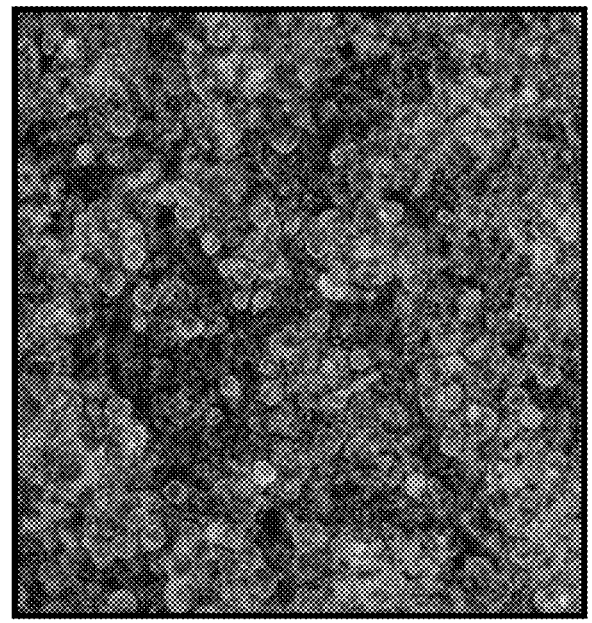

FIG. 5D. Immunofluorescence micrographs of Muc2 and GFP expressing terminal ileum epithelia derived from ATOH1/GFP transduced and sorted CD2 stem cells.

Figure 5E:
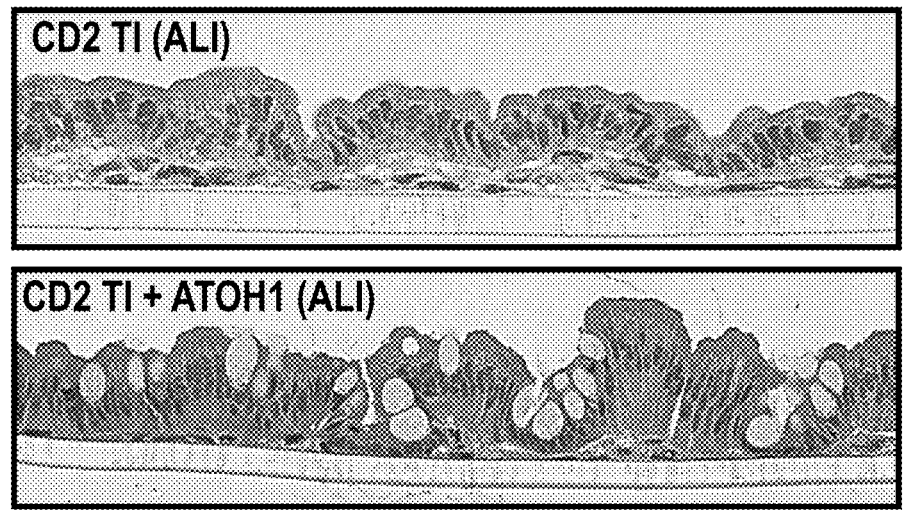

FIG. 5E. Histological sections of differentiated CD2 terminal ileum stem cells (top) and differentiated ATOH1-transduced and sorted CD2 stem cells (bottom).

Figure 5F:
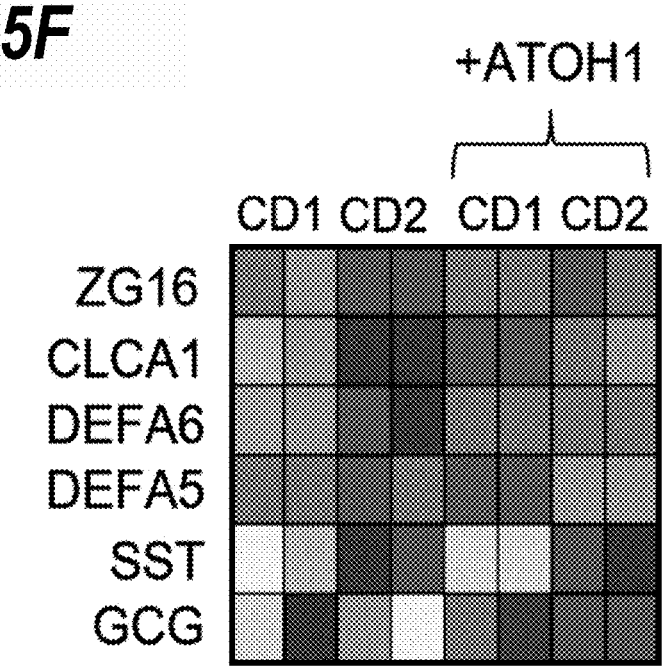

FIG. 5F. Expression heatmap of indicated secretory cell genes in differentiated terminal ileum CD1, CD2, as well as CD1 and CD2 following ATOH1 transduction.

Figure 5G:
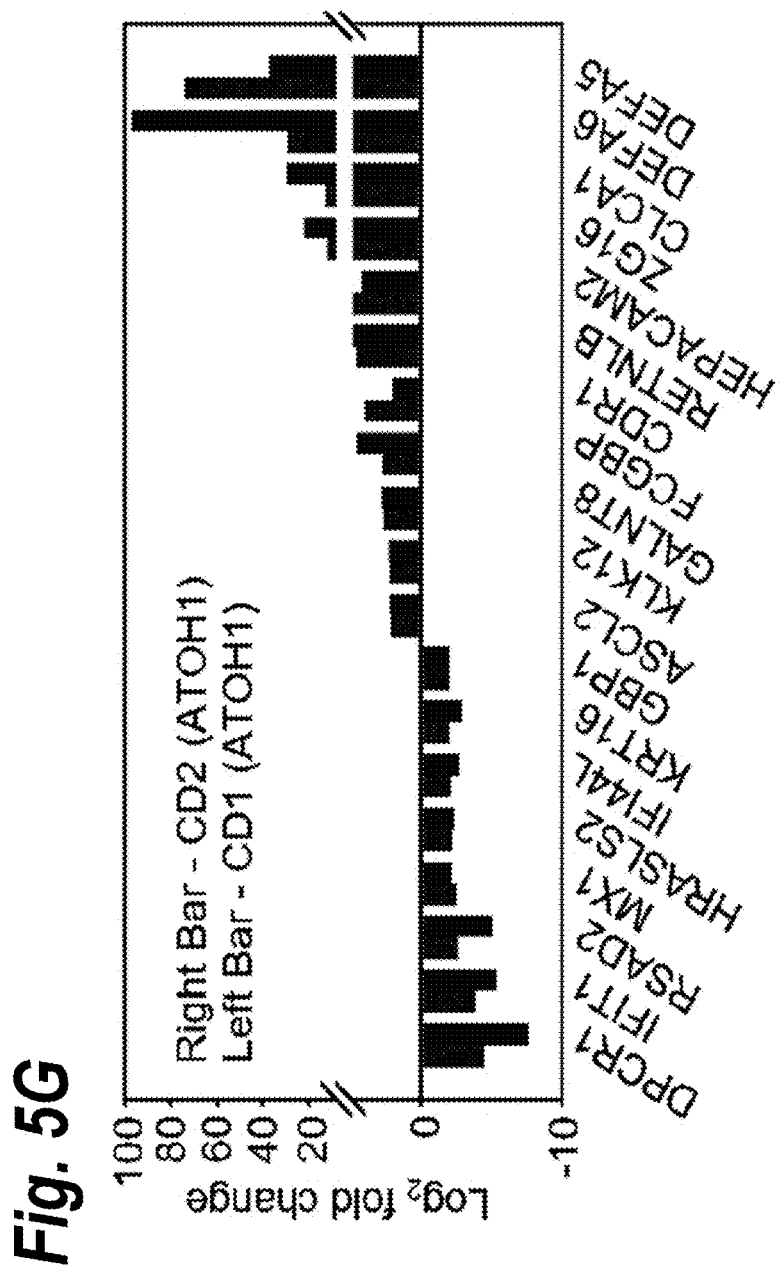

FIG. 5G. Histogram of differentially expressed genes in ATOH1-transduced CD1 and CD2 compared to corresponding CD1 and CD2 following ALI differentiation.

Figure 5H:
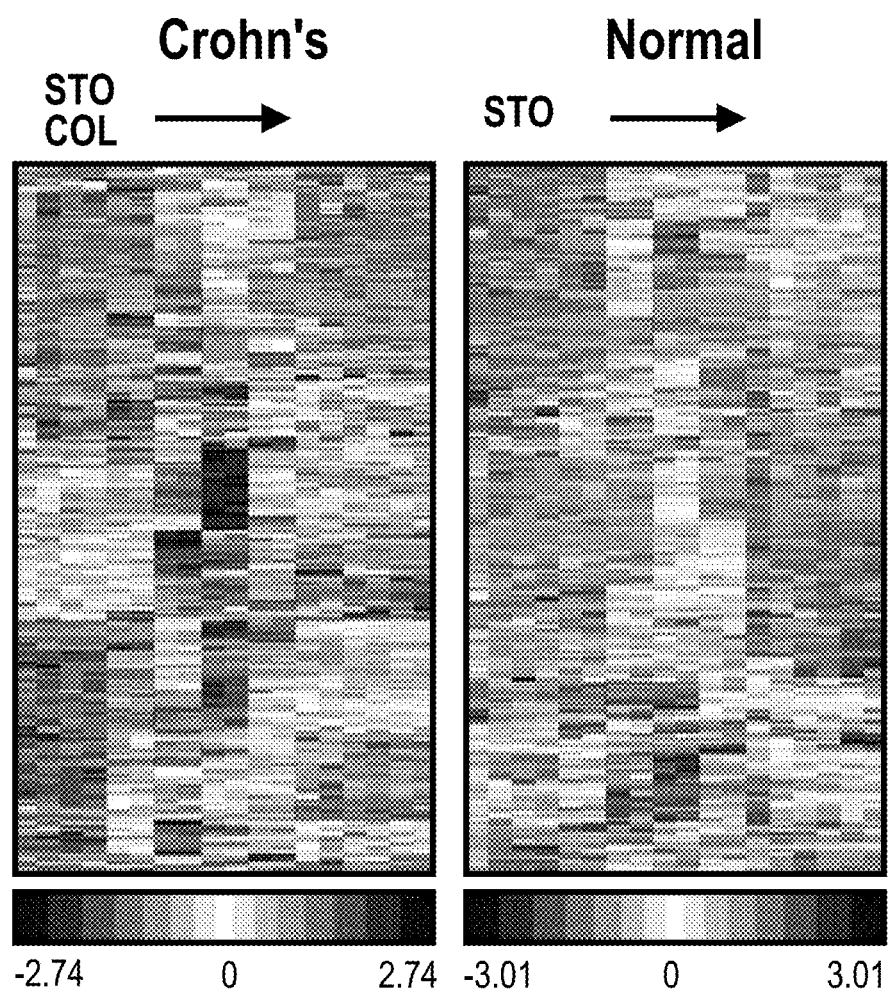

FIG. 5H. Mapping of genes differentially expressed (>1.5-fold, p<0.05) in in vitro-generated CD2 terminal ileum to those differentially expressed (>1.8-fold, p<0.05) along the fetal gastrointestinal tract including over-represented in Crohn's (left) and over-represented in normal terminal epithelia (right).

Figure 5I:
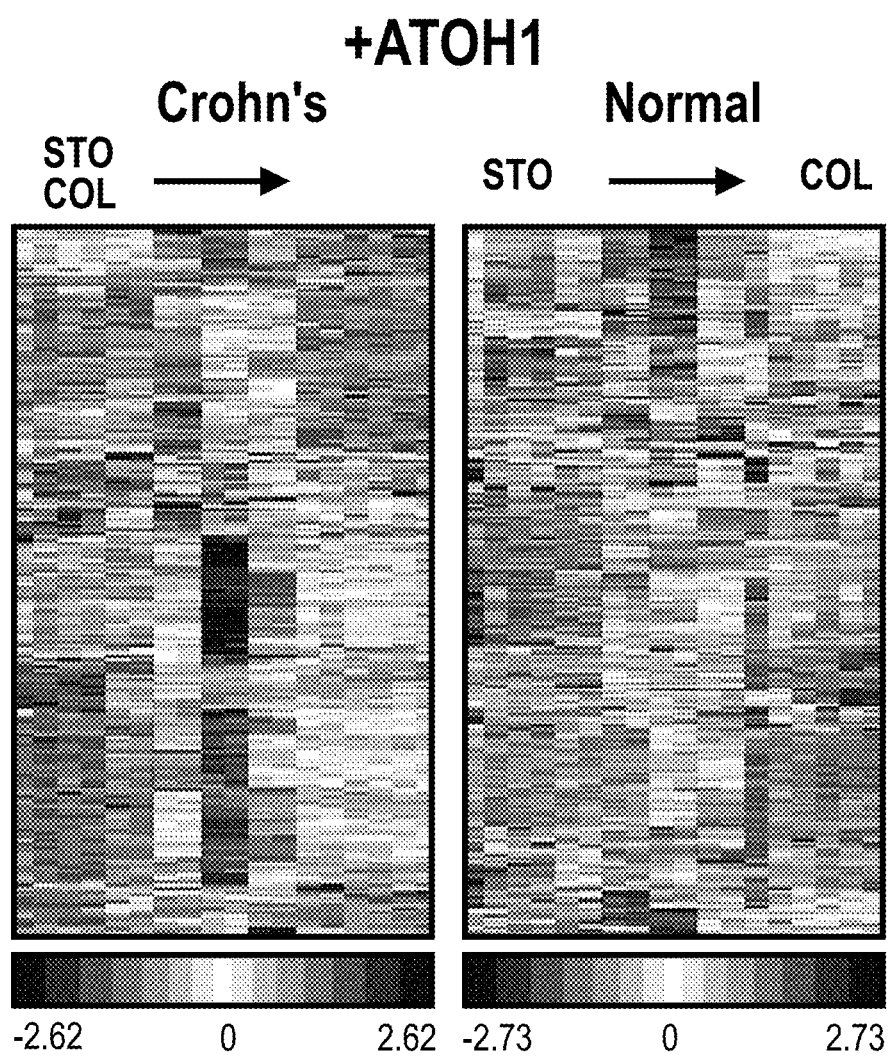

FIG. 5I. Mapping of genes differentially expressed (>1.5-fold, p<0.05) in in vitro-generated terminal ileum from ATOH1-transduced CD2 stem cells to those differentially expressed (>1.8-fold, p<0.05) along the fetal gastrointestinal tract including over-represented in CD2-ATOH1 (left) and over-represented in normal terminal epithelia (right).

Figure 5J:
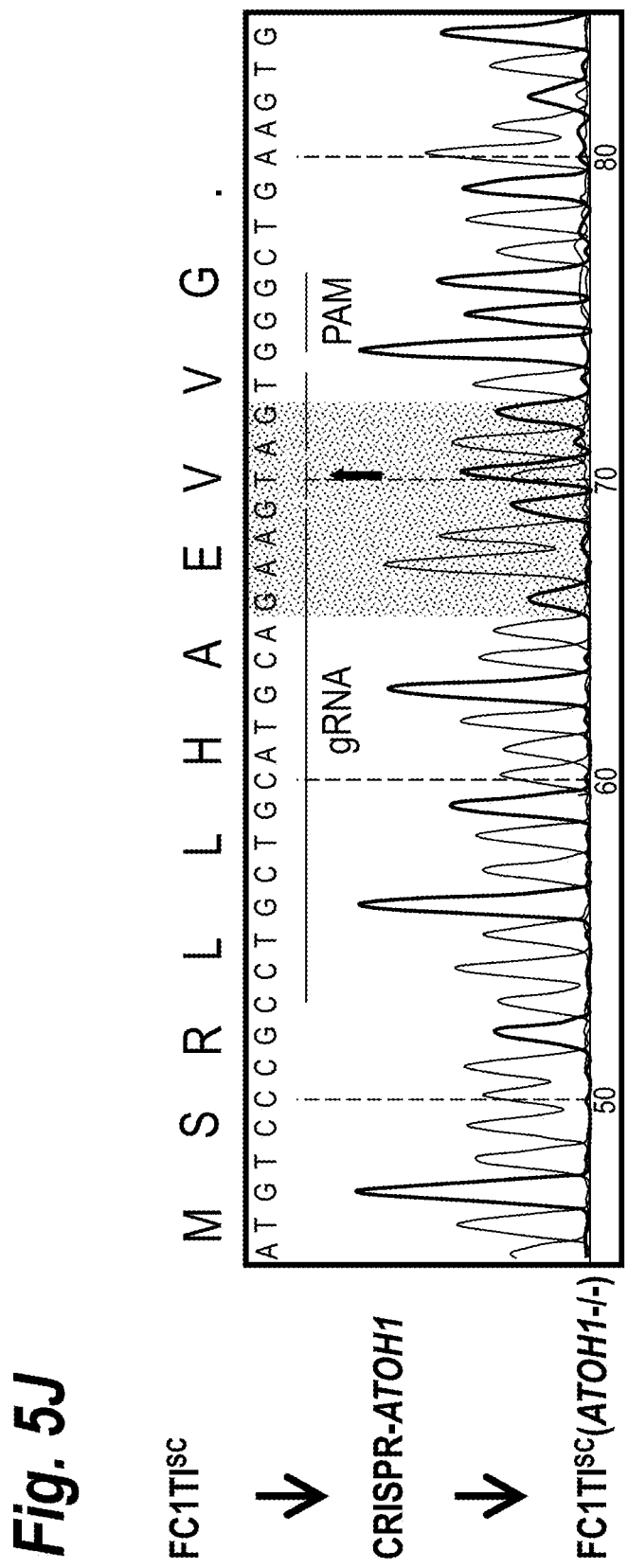

FIG. 5J. Generation and of biallelic frameshift and early stop codon in ATOH1 coding sequence in FC1 terminal ileum stem cells using CRISPR-Cas9-mediated editing. Guide RNA, PAM sequence, and site of cleavage and final insertion of single nucleotide are indicated.

Figure 5K:

FIG. 5K. Expression heatmap of genes associated with secretory cell types comparing differentiated FC1 stem cells and FC1 cells lacking ATOH1 expression FIG. 5L. Histological sections of differentiated FC1 terminal ileum stem cells and differentiated $FC1^{ATOH1-/-}$ stem cells.

FIG. 6A, FIG. 6B, FIG. 6C, FIG. 6D, FIG. 6E. Epigenetically maintained heterogeneity in Crohn's stem cells FIG. 6A. Left, Rhodamine red stained stem cell clones from CD3 terminal ileum biopsy on a lawn of irradiated feeder cells. Right, Differential anti-CLDN18 antibody staining of colonies within the CD3 pool of colonies.

FIG. 6B. Characterization of two CD3 terminal ileum stem cell pedigrees having "Crohn's" and "Normal" expression profiles using phase contrast microscopy and immunofluorescence with antibodies to E-cadherin (ECAD), SOX9, and CLDN18.

Figure 6C:
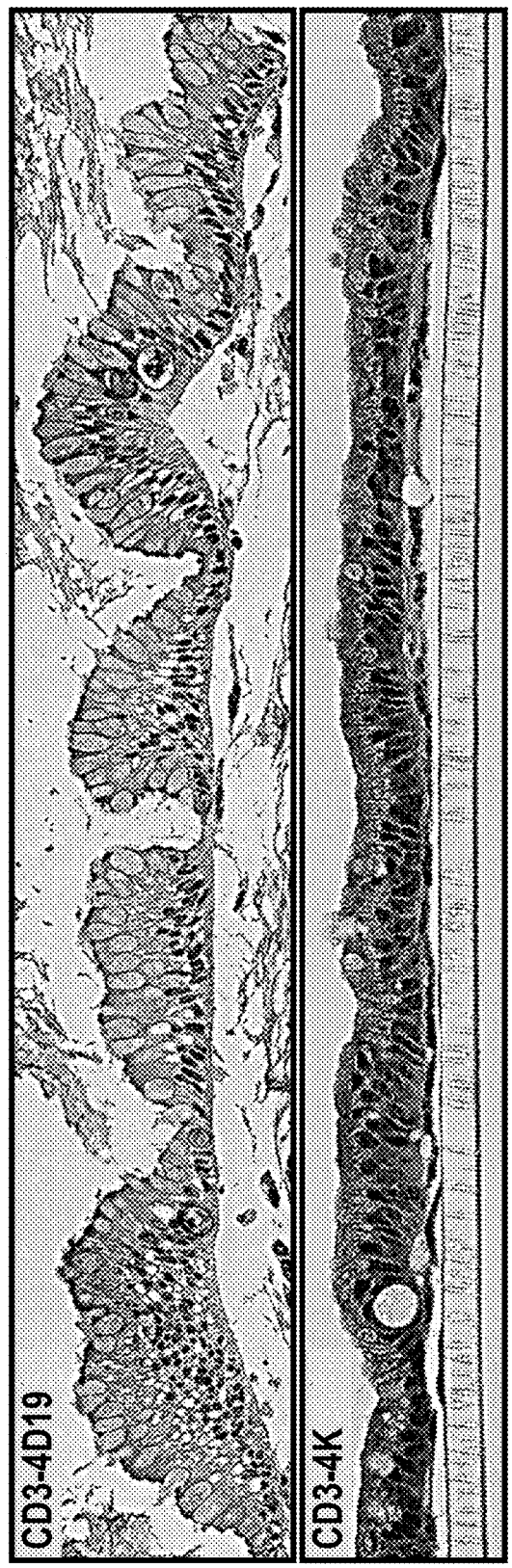

FIG. 6C. In vitro differentiation patterns in two distinct CD3 stem cell pedigrees having Crohn's (CD3-4K) and Normal (CD3-4D19) gene expression profiles.

Figure 6D:
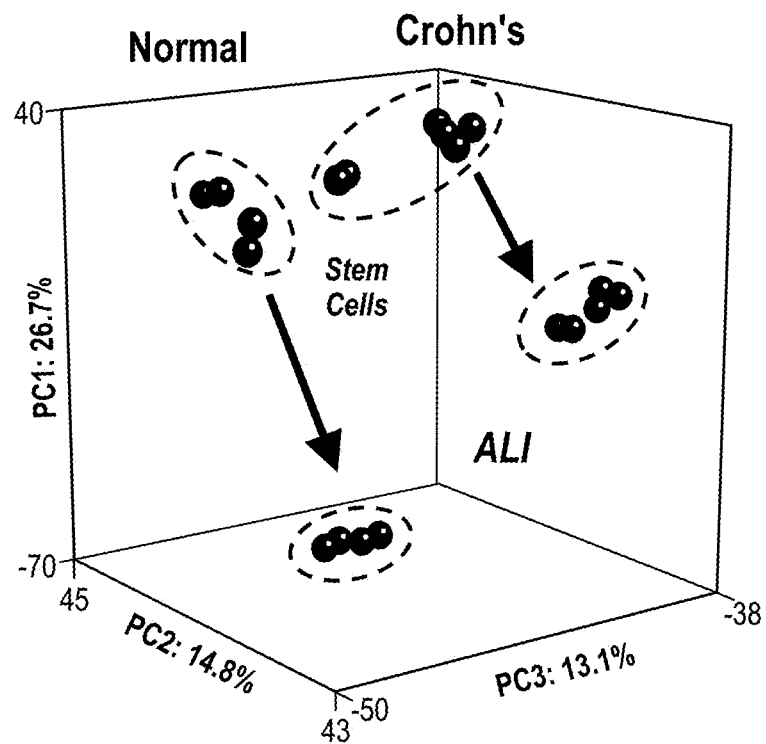

FIG. 6D. Principal component analysis of whole genome expression profiles of multiple CD3 terminal ileum stem cells and differentiated counterparts.

Figure 6E:
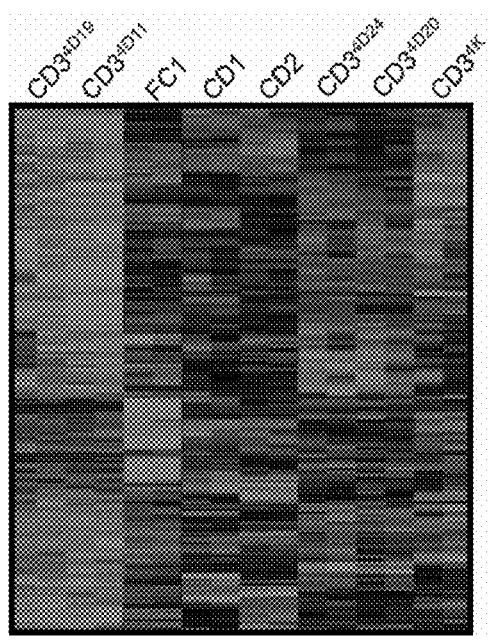

FIG. 6E. Gene expression heatmap of differentiated CD3 terminal ileum stem cells along with normal controls (FC1) and Crohn's cases (CD1 and CD2).

Figure 7:
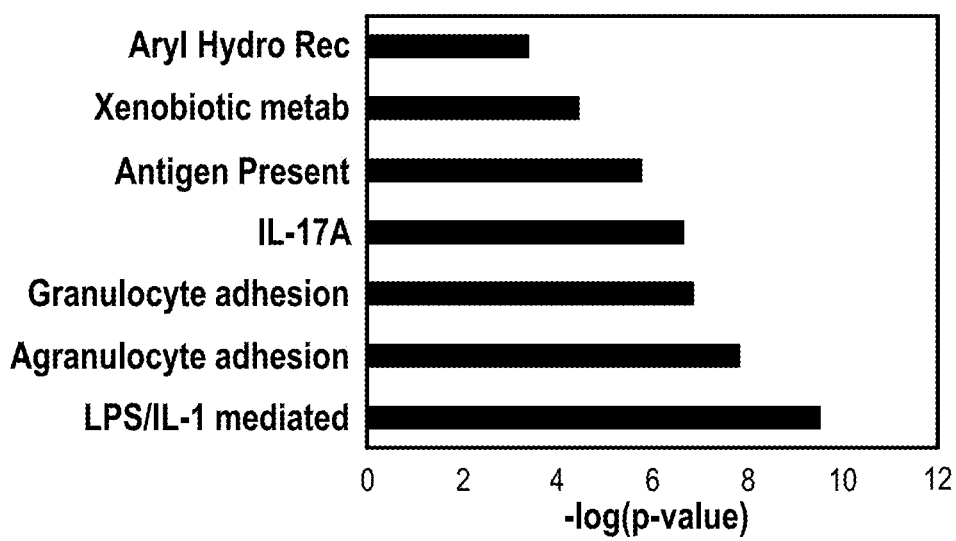

FIG. 7. GSEA of Crohn's terminal ileum stem cells. Most significantly enriched inflammatory pathways from differentially expressed genes in Crohn's terminal ileum stem cells.

Figure 8:
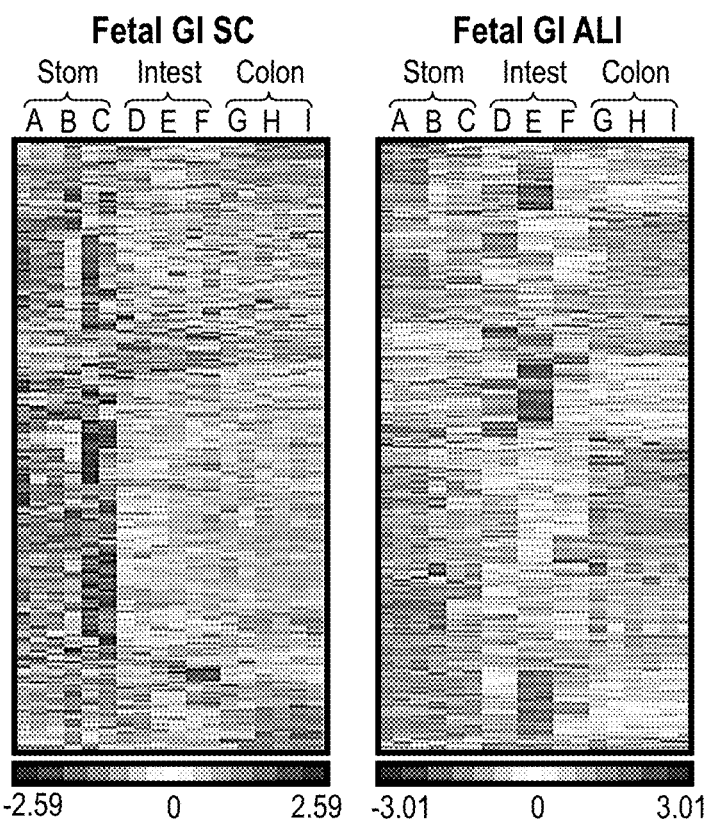

FIG. 8. Differential gene expression along fetal gastrointestinal tract. Heatmap of differentially expressed genes along the human fetal gastrointestinal tract stem cells and ALI differentiated epithelia.

Figure 9:
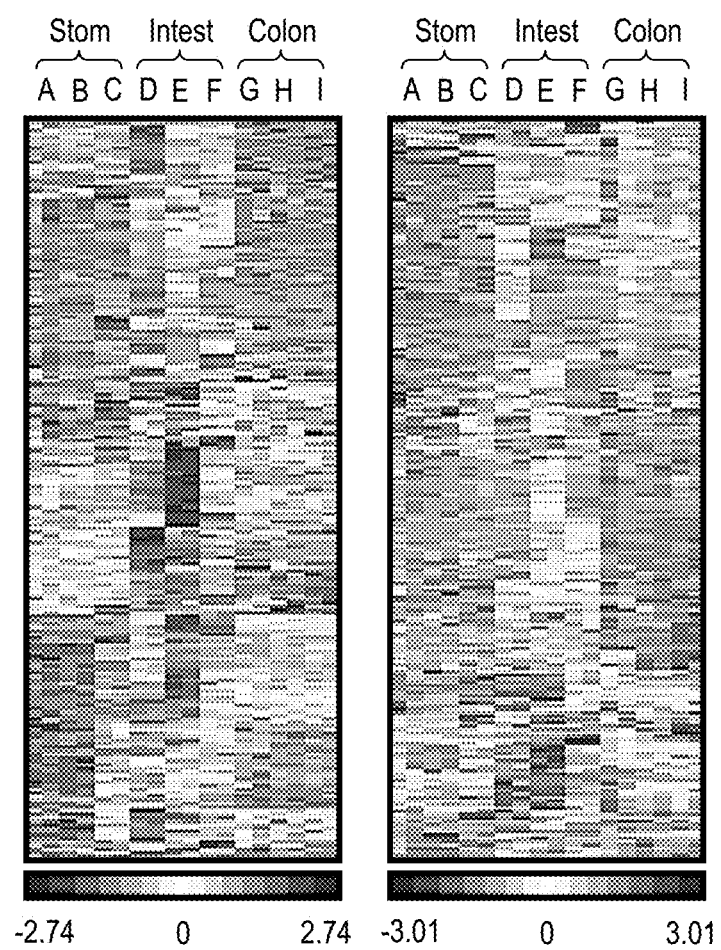

FIG. 9. Mapping differential gene expression in CD2 to fetal GI tract. Heatmap of differentially expressed genes along the human fetal gastrointestinal tract stem cells and ALI differentiated epithelia selected from gene set differentially expressed in the respective stem cells and ALI differentiated epithelia of CD2 terminal ileum.

Figure 10:
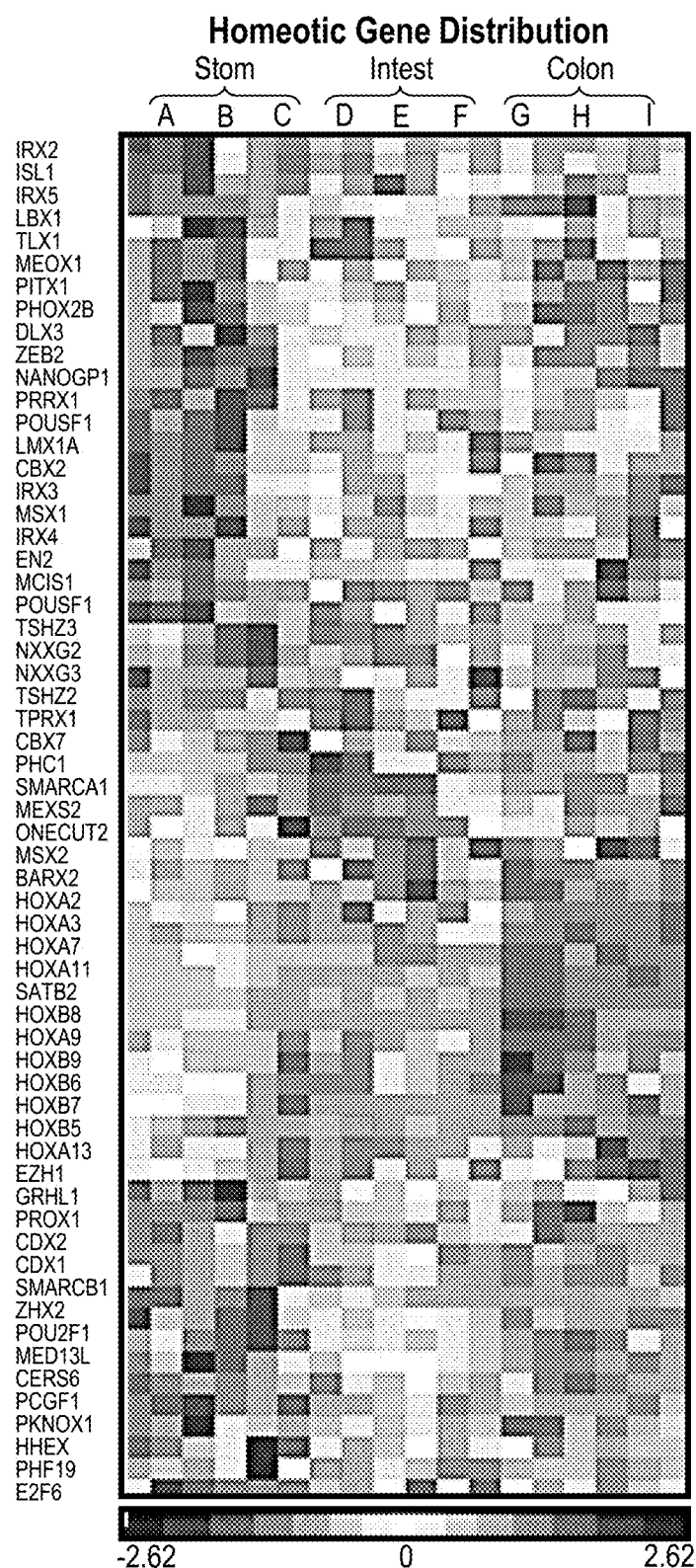

FIG. 10. Differential expression of homeotic genes along fetal GI tract. Heatmap of differentially expressed homeotic genes in stem cells and ALI differentiated epithelia derived from multiple regions of the human fetal gastrointestinal tract.

Figure 11:
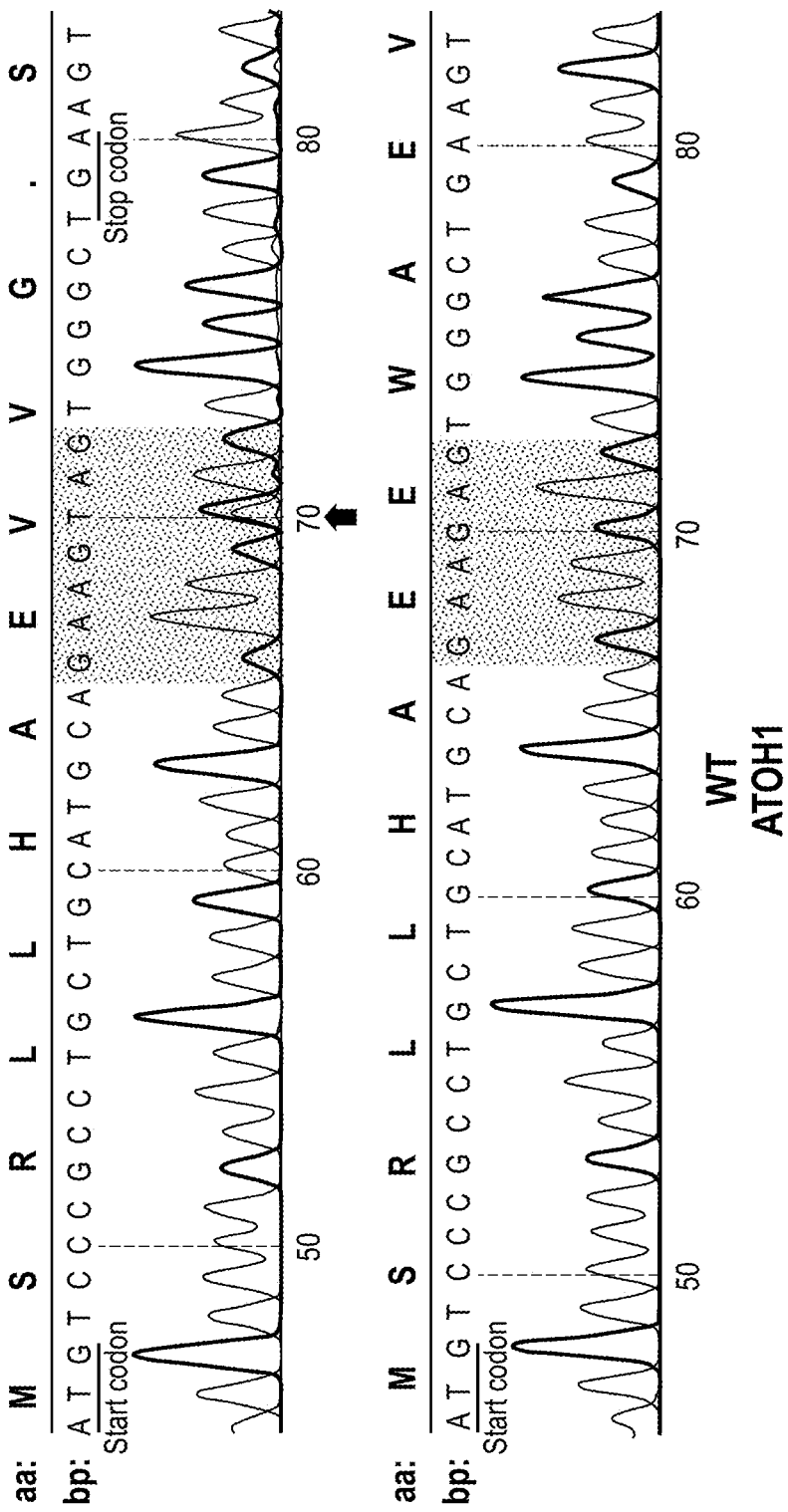

FIG. 11. Targeted ATOH1 disruption in normal terminal ileum stem cells. Schematic of CRISPR-Cas9-mediated targeting and disruptive repair of the ATOH1 locus in normal terminal ileum stem cells and sequencing profiles of the ATOH1 loci in normal and targeted cells. The disrupted alleles in the targeted cells show the insertion of single nucleotides (G/T).

Figure 12:
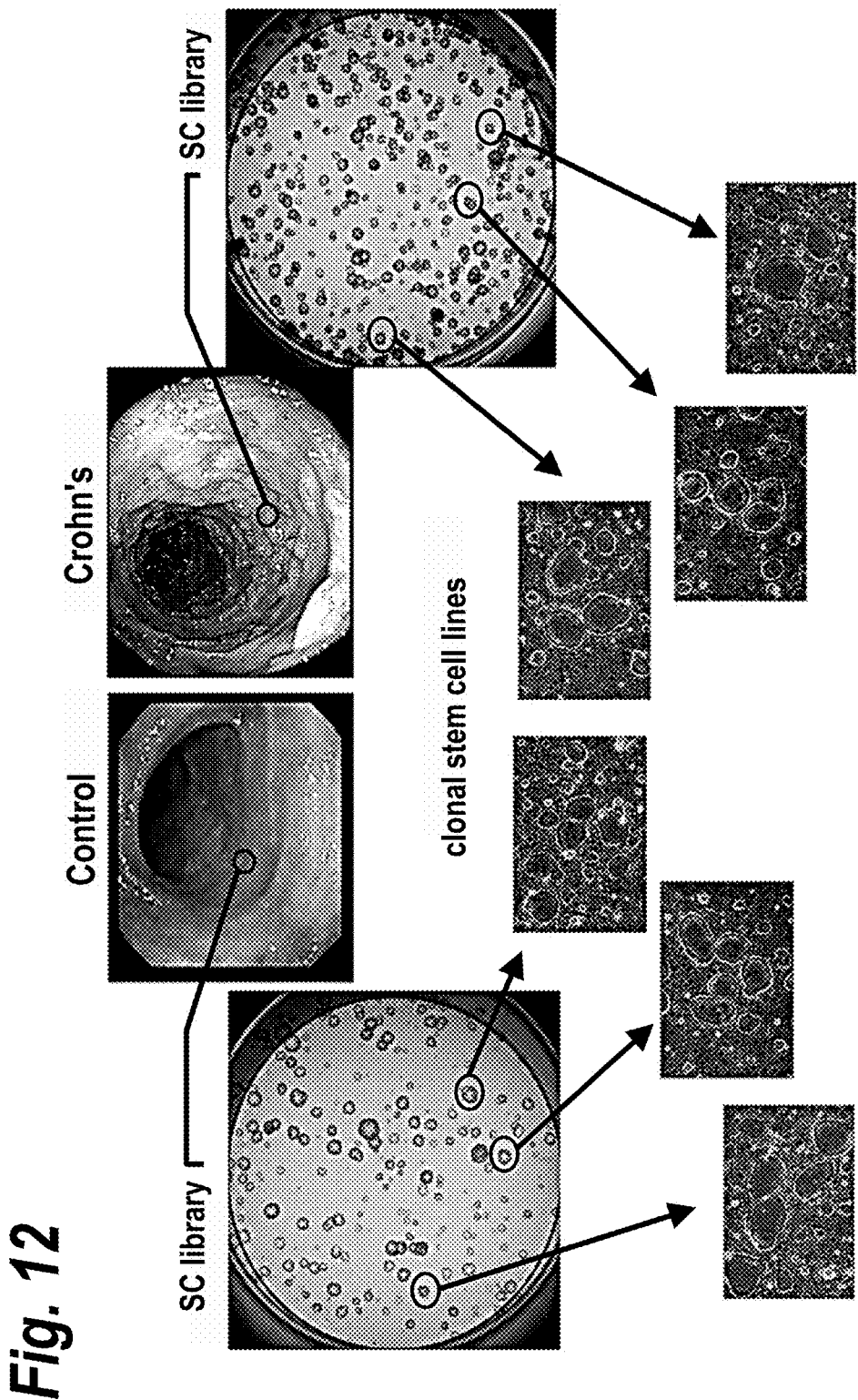

FIG. 12. Further exemplars of endoscopic sampling of biopsies from the Terminal Ileum (TI) and Right Colon (RC).

Figure 13:
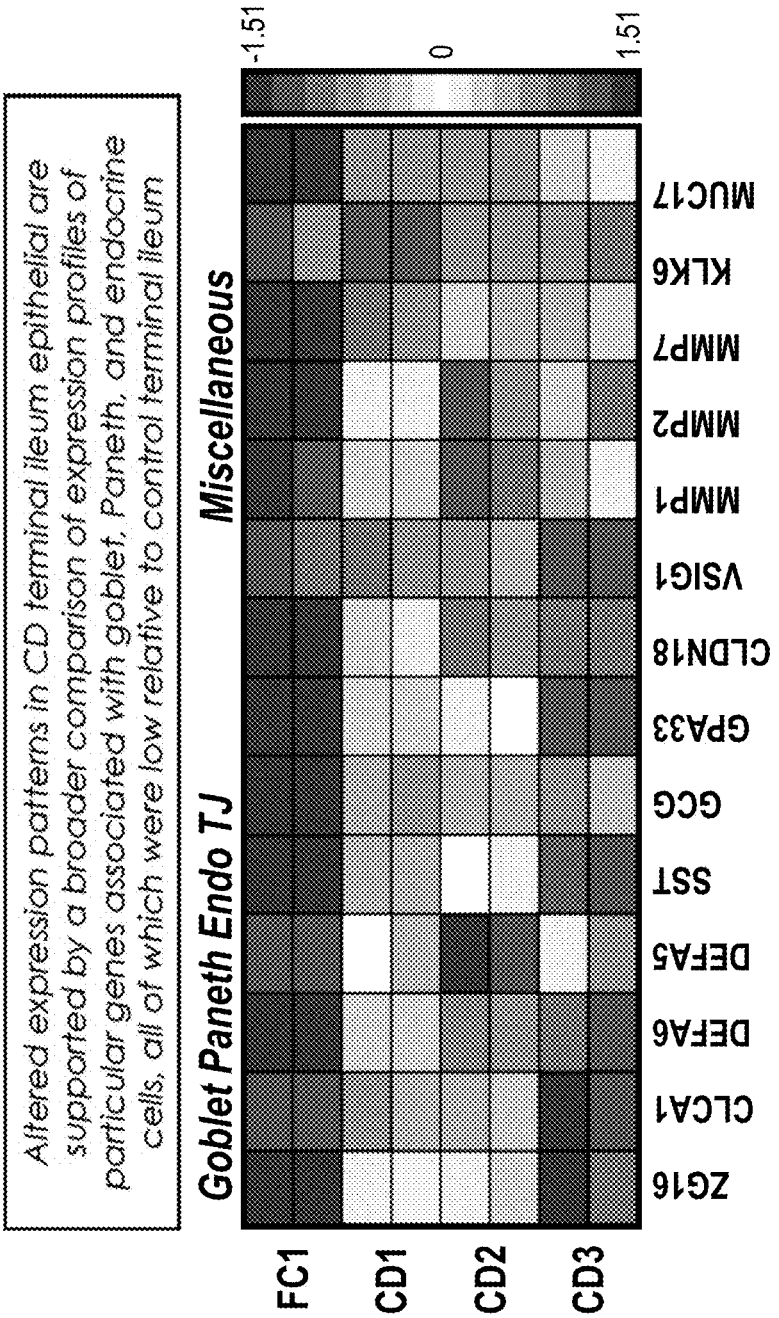

FIG. 13. Crohn's Cluster Stem Cells of the Terminal Ileum show consistent abnormalities in both secretory cell differentiation and intercellular junctional assembly. Altered expression patterns in CD terminal ileum epithelial are supported by a broader comparison of expression profiles of particular genes associated with goblet, Paneth, and endocrine cells, all of which were low relative to control terminal ileum. Among pathways apparently under-represented in the Crohn's epithelia were inflammasome signaling, LPS and IL-1 mediated inhibition of retinoid signaling, certain steroid receptor (LXR/RXR and FXR/RXR) signaling, and serotonin degradation. The simultaneous loss and gain of particular inflammatory pathways is consistent with emerging concepts of Crohn's as both a pro-inflammatory condition and one remarkable defective in managing the containment of intestinal microbes FIG. 14. Traits of inflammation, secretory cell defects, and homeotic transformations of terminal ileum stem cells are interdependent. Approximately 80% of the genes over-represented in the inflammatory signature are normally expressed in proximal (gastric, duodenum, jejunum) portions of the gastrointestinal tract but not in the colon. This represents a shift to producing epithelial linings of absorptive function and is an explanation for ongoing inflammatory signals initiating from the terminal ileum lining.

FIG. 15A and FIG. 15B. Homeotic transformation of Crohn's stem cells. In addition to an extensive inflammatory gene signature and defective maturation of secretory cells, Crohn's cluster epithelia are distinguished by the ectopic expression of a host of metabolic enzymes that had no obvious links to either inflammation or secretory cell differentiation. Howefver these enzymes, which function in the hydrolysis and transport of lipids, carbohydrates, and proteins, are normally expressed in proximal portions of gastrointestinal tract 12-14 feet anterior to the terminal ileum.

Figure 16A:
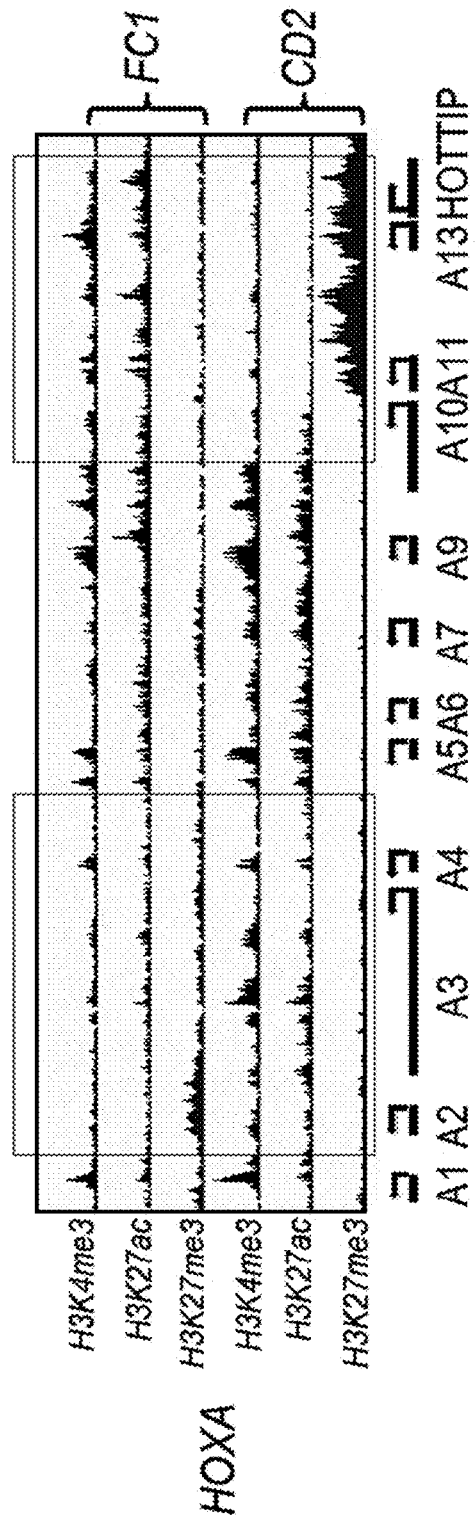
Figure 16B:
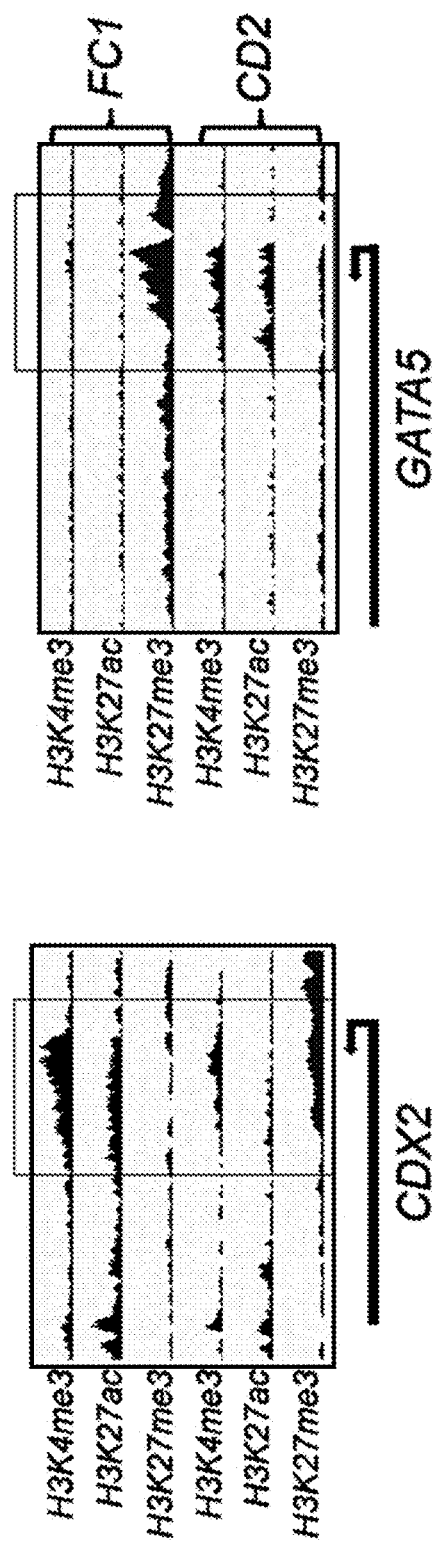
Figure 16C:
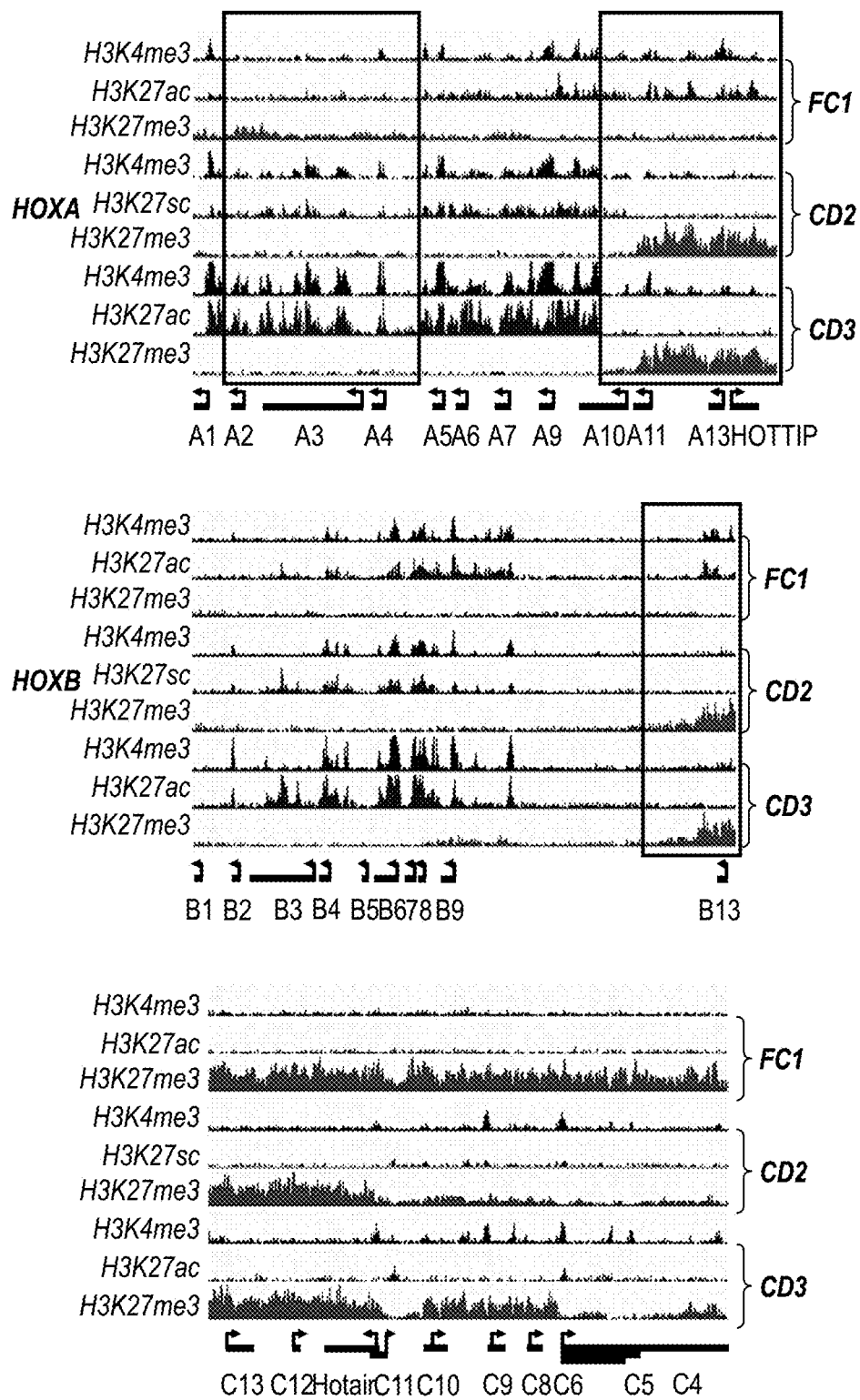

FIG. 16A, FIG. 16B and FIG. 16C. Homeotic transformation of Crohn's stem cells. To further illustrate, using whole-genome analyses of epigenetic histone marks, we identified multiple alterations in the epigenetic profiles of the HOX loci of stem cells of the Crohn's cluster compared to those of the Normal cluster. Among these genes are a host of transcription factors including CDX2 and GATA5, whose respective roles distal and proximal gastrointestinal tract differentiation are well established.

Figure 17A:
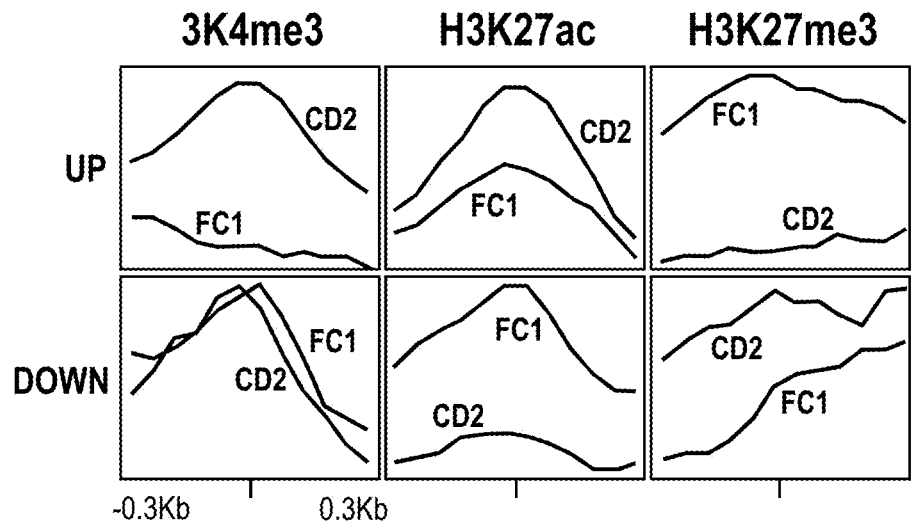
Figure 17B:
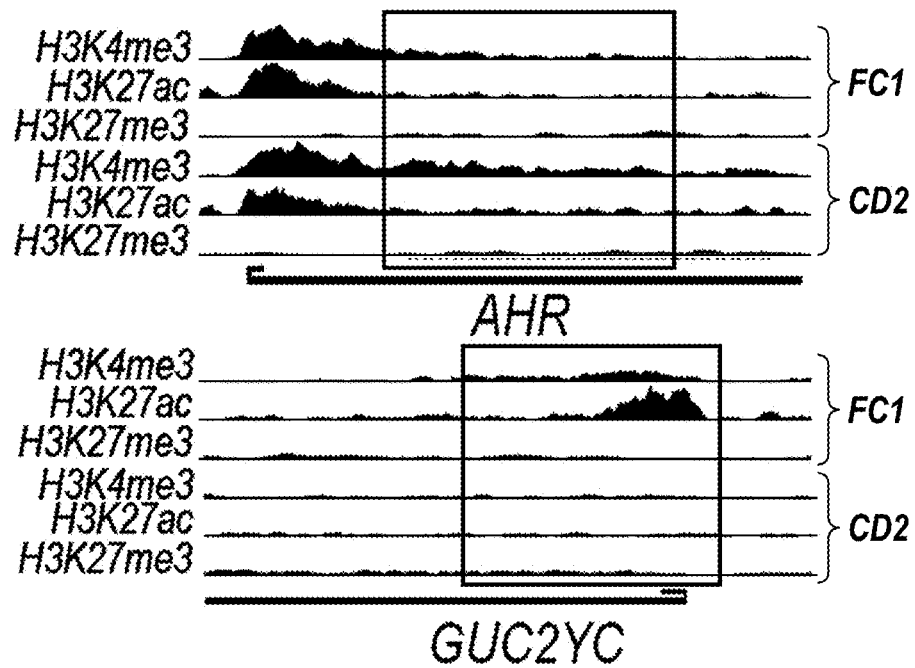

FIG. 17A and FIG. 17B. Inflammatory signature driven by homeotic shift in Crohn's stem cells. Consistent with the stability of the inflammatory signature in the Crohn's stem cells, 71% of the 180 genes showing enhanced expression in the inflammatory signature also had differential histone modifications marked by increased H3K4-trimethylation and a loss of H3K27-trimethylation typical of active or potentially active genes. Of down-regulated genes in the inflammatory gene signature, 48% had differential histone modifications and these were dominated by a loss of H3K27-acetylation and a gain of H3K27-trimethylation associated with gene repression. Examples of such over- and under-represented genes with histone modifications include the transcription factor aryl hydrocarbon receptor (AHR) and the enterotoxin receptor GUCY2C.

Figure 18:
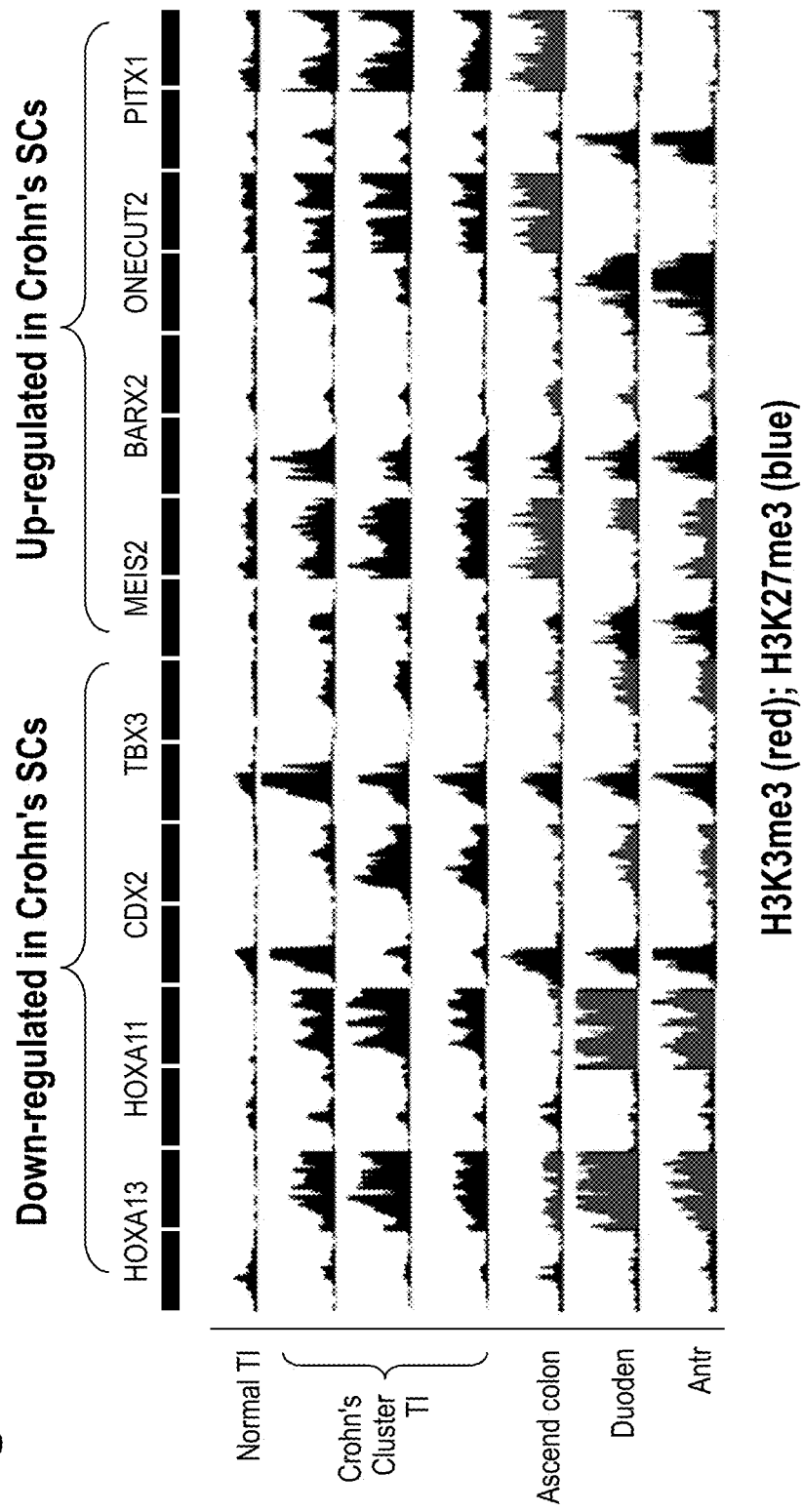

FIG. 18. The molecular genetics of the nodal genes responsible for this identity shift can be identified using the system of the present application. Epigenetic repression of homeoboxtranscription factors typically expressed in distal gastrointestinal tract in Crohn's Cluster stem cells paralleling similar differences between normal colon and proximal intestine. Conversely, homeobox transcription factors upregulated in Crohn's Cluster stem cells show enhanced activating marks (H3K4me3) paralleling similar differences between normal colon and proximal gastrointestinal tract.

Figure 19A:
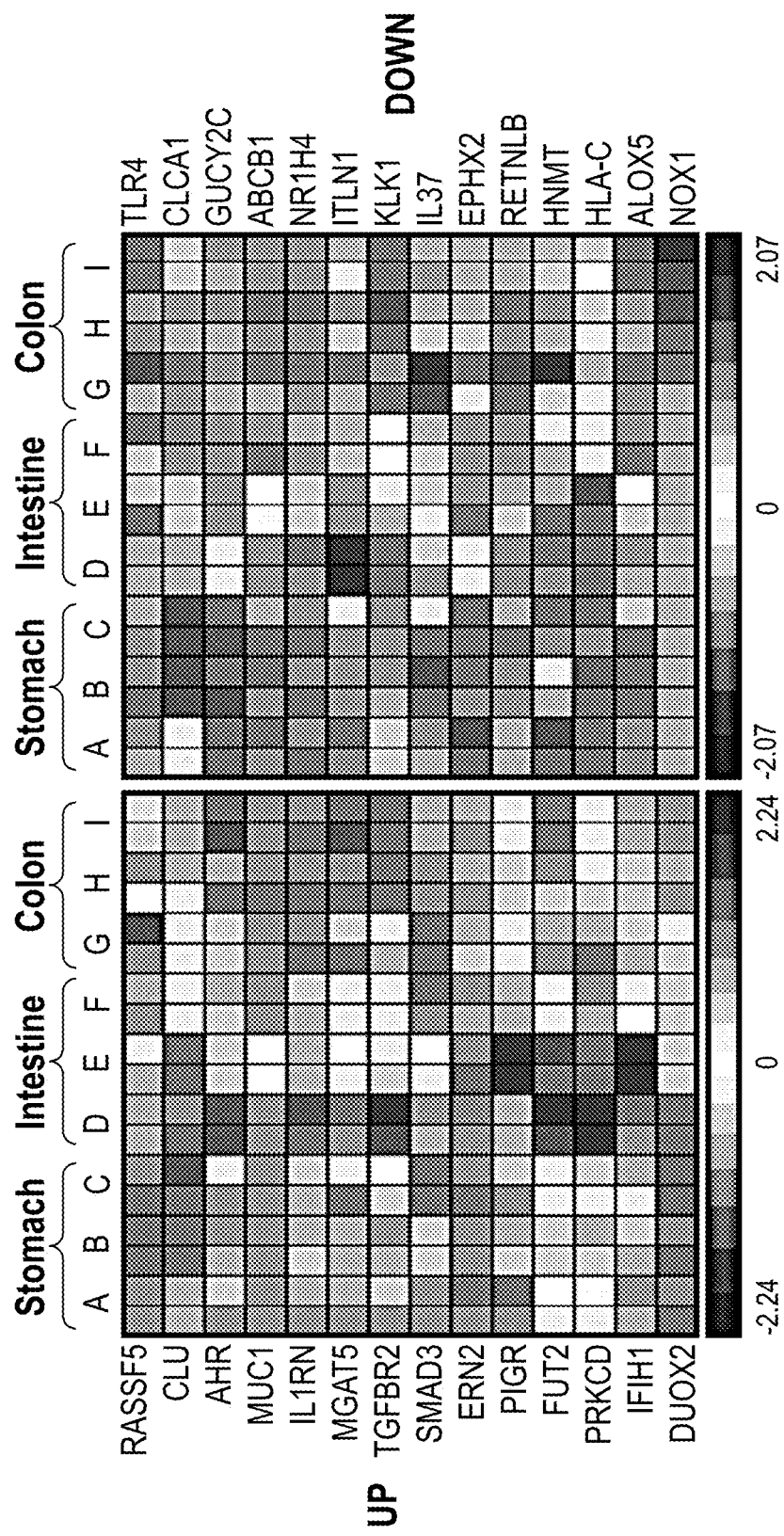
Figure 19B:
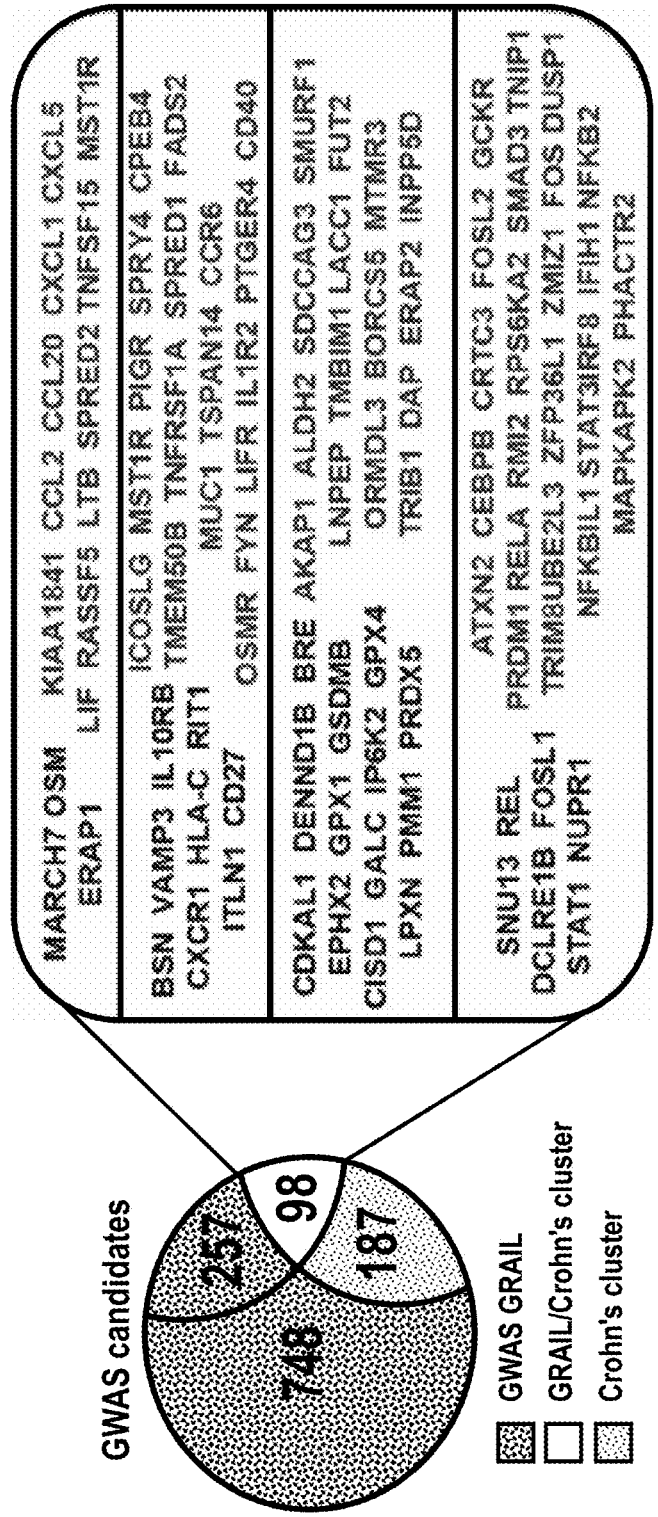

FIG. 19A and FIG. 19B. Inflammatory signature driven by homeotic shift.

FIG. 19A. A sampling of genes whose over- (e.g. AHR, URN, MGAT5, SMAD3, FUT2, and DUOX2) and under- (e.g. CLCA1, GUCY2C, IL37, and NOX1) representation might be a consequence of the homeotic transformation underscores the potential immunoregulatory impact of such a conversion.

FIG. 19B. Comparing the relationship between Crohn's cluster stem cells and the genetic architecture of Crohn's Disease. Comparison of the set of genes linked by GWAS to Crohn's from multiple studies with those differentially expressed genes by Crohn's cluster stem cells and the epithelia generated from them and those predicted by disease association algorithms (e.g. GRAIL). Overlap of 28% of genes implicated by GRAIL and those differentially expressed by the Crohn's cluster cells, as well as another set of genes that were not captured by GRAIL and whose significance Tract is exploring. The overlap between genes implicated by GWAS and those differentially expressed in Crohn's disease epithelia suggests broad links between these mucosal stem cells and the disease process.

Figure 20:
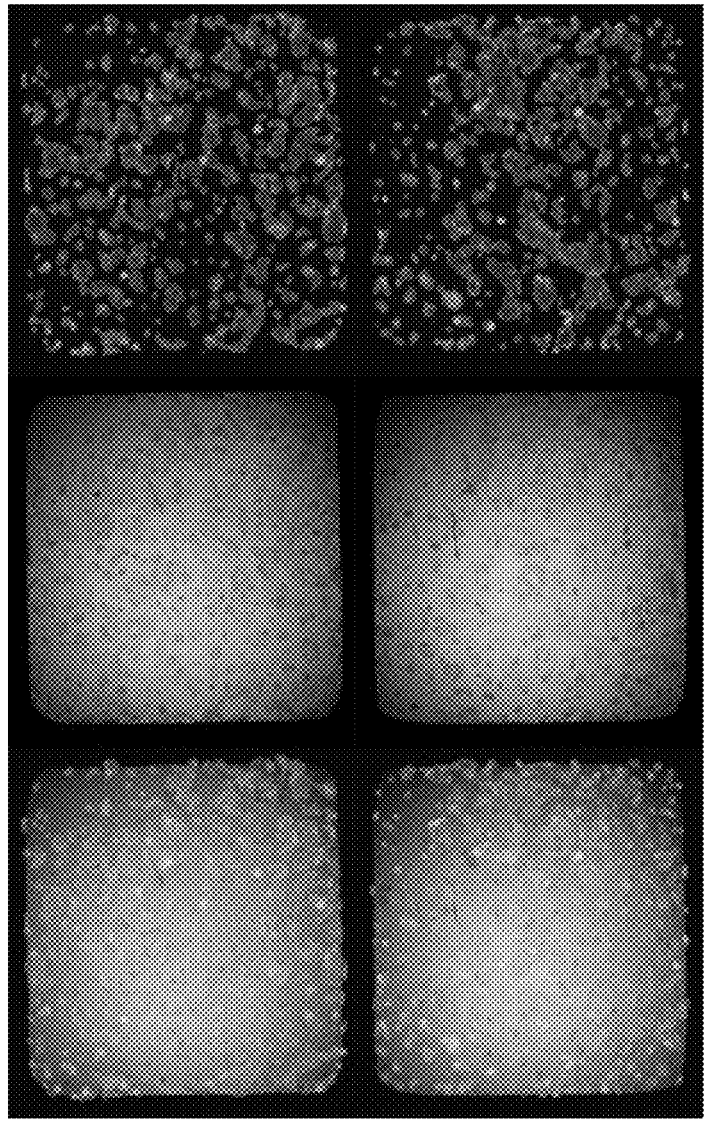
Figure 21:
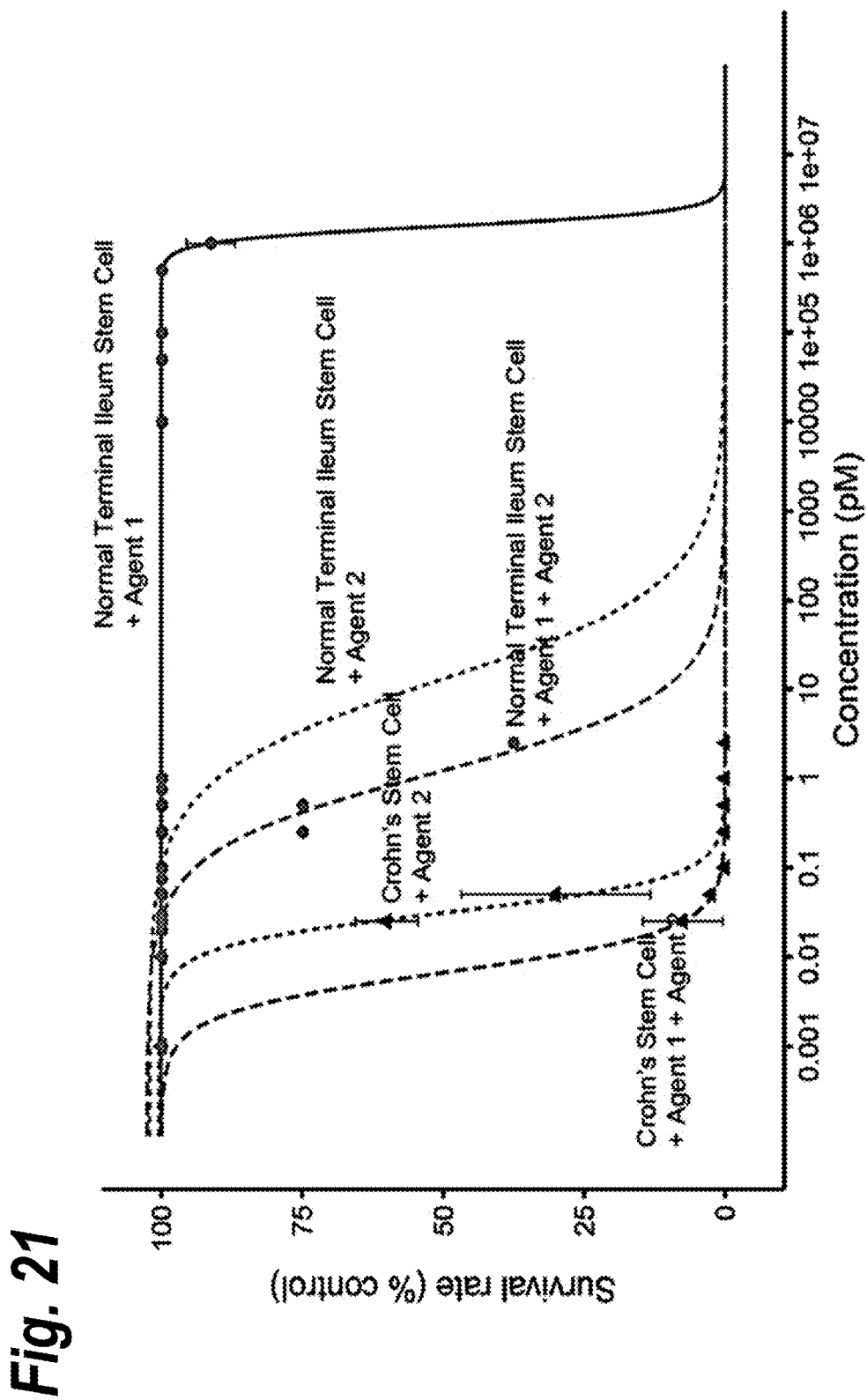

FIG. 20 and FIG. 21. Crohn's stem cells and normal terminal ileum stem cells can be readily adapted to multiwell culture formats for high throughput drug screening. Screening with libraries of compounds of reveal the opportunity to develop selective cytotoxic agents and synergistic drug combinations.

FIG. 22. Animal model generating ileum xenografts, with polarization and myofibroblasts. This xenograft model of the present invention entails a simple subcutaneous injection of stem cell pools or clones in Matrigel into immunodeficient mice. By two weeks, these cells form a polarized normal or Crohn's stem cells around an acellular lumen. Remarkably, the vesicles generated by Crohn's epithelia become surrounded by a dense mat of α-smooth muscle actin (SMA)-positive myofibroblasts whereas the normal control ileum stem cells do not. In the immunodeficient mice at least, this fibrosis is not accompanied by macrophages or other obvious leukocytes, suggesting the trigger is not going through such cells but rather directly via the Crohn's stem cells.

Figure 23:
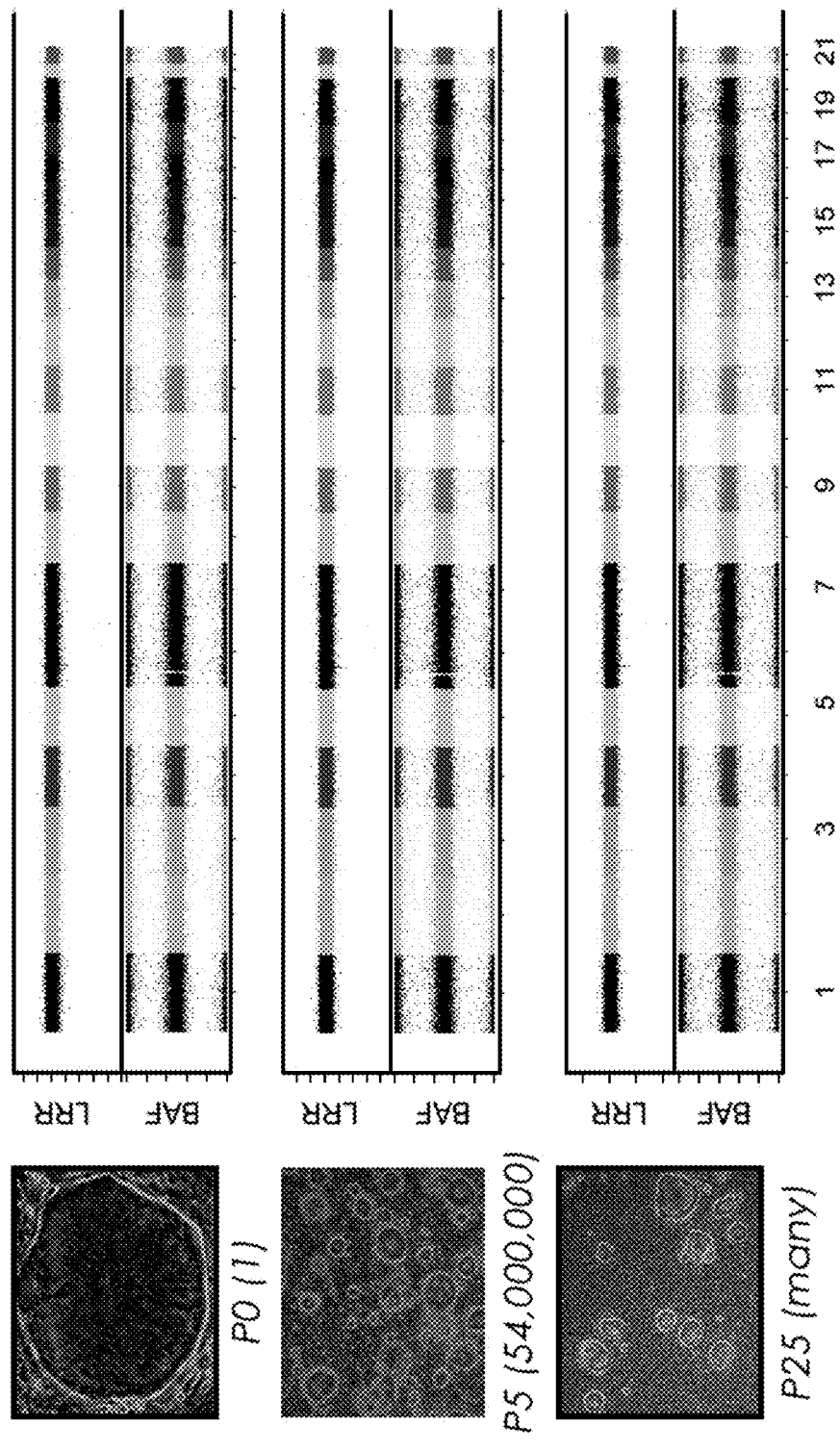

FIG. 23. B allele frequency (BAF) and log R ratio (LRR) plots show the genetic stability of a colon ground state stem cells clone from passage 0 to passage 25. This stability has been observed beyond passage 75.

DETAILED DESCRIPTION

I. Overview

Crohn's disease is an inflammatory bowel disorder marked by transmural lesions that frequently progress to strictures, fistulas, or perforations requiring repeated surgical intervention[1]. While its onset is typically in young adults, 15 percent of cases arise in children who tend to have severe and extensive disease, frequent need for corticosteroids and immunosuppression, and enhanced risk for colorectal cancer[2]. Though immunosuppressants and anti-inflammatory biologics can slow the progression of Crohn's disease, it is not clear that they have lessened the need of surgical intervention, an impasse that has fueled the search for therapeutic targets more proximal to the disease[3]. This search is complicated by the large environmental contribution to this disease reflected by the low concordance among monozygotic twins", and by the polygenic nature of the remaining, inherited risk. Nevertheless, genome-wide association studies (GWAS) and pathophysiology are beginning to define the underlying genetic structure and biology of Crohn's disease[3,6]. In particular, there is a stunning overlap of risk loci for Crohn's and mycobacterial infections[7], and many of the 170 loci discovered to date implicate genes of adaptive and innate immune processes that are likely involved in the containment of gut microbes[7-10]. Consistent with this emerging "barrier defect" hypothesis are deficiencies in antimicrobial functions of Paneth cells in Crohn's disease patients[11], defective autophagy processing of microbial antigens by mucosal epithelial cells[11-17] and altered responsiveness of mucosal immune cells[18]. Despite these emerging data on mucosal barrier abnormalities in Crohn's, it remains unclear whether they are primary events or secondary consequences of the inflammatory state of this disease. It is also unclear how defective barrier function might explain the alternate regional presentations of Crohn's[19], its skip-lesion patterning, or the high rates of recurrence following ileo-colonic resection[1,3].

Most approaches to the treatment of Crohn's disease, Ulcerative Colitis and other forms of Inflammatory Bowel Diseases (IBD) focus on reducing or inhibiting the inflammatory components of these diseases. However, as described here, the inflammatory symptoms of Crohn's and other forms of IBD are a consequence of an altered epithelial lining generated by an epigenetically shifted stem cell in the tissue—with inflammation being caused by the altered epithelia. As described in greater detail below and the attached figures, in the case of inflammatory bowel diseases such as Crohn's, we have found an epigenetic shift in the stem cells of the terminal ileum—where the inflammatory storm that characterizes this disease occurs. In this case, the stem cells that give rise to the lining of the terminal ileum are altered in a way that cause them to give rise to an epithelial lining that is similar to what occurs further up the digestive tract where absorption of nutrients occur and is not serving as a barrier to bacteria the way the terminal ileum should. In addition, this epigenetic change to the stem cells is also turning on genes which attract immune cells, such as a signals and activators of the innate and/or adaptive immune systems. Whatever the initial insult is that causes this shift, the immune response in the gut is perpetuated by this altered epithelial lining produced by these stem cells.

The present invention addresses IBD from the standpoint of mucosal stem cells cloned from defined regions of the gastrointestinal tract. In the case of pediatric Crohn's disease, for example, isolation of those stem cells according to the methods of the present invention reveals a pattern of inflammatory gene expression in stem cells from the terminal ileum and colon that is epigenetically maintained despite months of continuous cultivation in the absence of immune or stromal cells, or of intestinal microbes. Superimposed on this distributed inflammatory phenotype is a differentiation defect that profoundly and specifically alters the mucosal barrier properties of the terminal ileum. And while the immediate basis of this barrier defect can be traced to a loss of ATOH1, a transcription factor required for secretory cell differentiation in the colon, this repression of ATOH1 is only emblematic of a more profound alteration of the terminal ileum in Crohn's disease involving a homeotic transformation of stem cells to a developmental ground state represented by the duodenum and jejunum. Lastly, the co-existence of diseased and normal stem cells within the same endoscopic biopsies of Crohn's disease patients implicates an epigenetically enforced heterogeneity among mucosal stem cells in the dynamics of this condition.

II. Definitions

"Inflammatory bowel disease", or "IBD", is a term that encompasses both ulcerative colitis (inflammation of the lining of the large intestine) and Crohn's disease (inflammation of the lining and wall of the large and/or small intestine). When inflamed, the lining of the intestinal wall is red and swollen, becomes ulcerated, and bleeds. Although lesions associated with IBD can heal by themselves, most are recurrent. Chronic lesions occur in individuals with underlying diseases of various types whose medical conditions compromise the body's ability to repair injured tissue on its own (e.g., diabetes).

One type of lesion associated with IBD is an ulcer. A lesion is an open sore, an abrasion, a blister, or a shallow crater resulting from the sloughing or erosion of the top layer of epithelial cells and, sometimes, subcutaneous tissues. Although an ulcer can technically occur anywhere on the skin (e.g., a wound), the term "ulcer", which is used loosely and interchangeably with "gastric ulcer" and "peptic ulcer", usually refers to disorders in the upper digestive tract.

The term "an aberrant expression", as applied to a nucleic acid of the present invention, refers to level of expression of that nucleic acid which differs from the level of expression of that nucleic acid in healthy gastrointestinal tissue, or which differs from the activity of the polypeptide present in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in the activity; for example, an aberrant polypeptide can interact with a different target peptide. A cell can have an aberrant expression level of a gene due to overexpression or underexpression of that gene.

"Amino acid sequence" as used herein refers to an oligopeptide, peptide, polypeptide, or protein sequence, and fragment thereof, and to naturally occurring or synthetic molecules. Fragments of an expression product of an IBD gene sequence (an "IBD gene product") are preferably about 5 to about 15 amino acids in length and retain the biological activity or the immunological activity of an IBD gene product. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

The term "antibody" broadly refers to any immunoglobulin (Ig) molecule and immunologically active portions of immunoglobulin molecules (i.e., molecules that contain an antigen binding site that immunospecifically bind an antigen) comprised of four polypeptide chains, two heavy (H)

chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below, and include but are not limited to a variety of forms, including full length antibodies and antigen-binding portions thereof; including, for example, an immunoglobulin molecule, a monoclonal antibody, a chimeric antibody, a CDR-grafted antibody, a human antibody, a humanized antibody, a single chain antibody, a Fab, a F(ab'), a F(ab')2, a Fv antibody, fragments produced by a Fab expression library, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference) and/or antigen-binding fragments of any of the above (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). Antibodies also refer to immunoglobulin molecules and immunologically active portions of immunoglobulin molecules, i.e., molecules that contain antigen or target binding sites or "antigen-binding fragments." The antibody or immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art. Furthermore, in humans, the light chain can be a kappa chain or a lambda chain.

The term "specific affinity binder" refers to an antibody as well as to a non-antibody protein scaffold i.e., smaller proteins that are capable of achieving comparable affinity and specificity using molecular structures that can be for example one-fifth to one-tenth the size of full antibodies, and also to nucleic acid aptamers. In some embodiments, the specific affinity binder of the present invention is a non-antibody polypeptide. In some embodiments, the non-antibody polypeptide can include but is not limited to peptibodies, DARPins, avimers, adnectins, anticalins, affibodies, affilins, atrimers, bicyclic peptides, centryins, Cys-knots, Fynomers, Kunitz domains, Obodies, pronectins, Tn3, maxibodies, or other protein structural scaffold, or a combination thereof.

A disease, disorder, or condition "associated with" or "characterized by" an aberrant expression of an IBD gene sequence refers to a disease, disorder, or condition in a subject which is caused by, contributed to by, or causative of an aberrant level of expression of a nucleic acid.

"Biological activity" or "bioactivity" or "activity" or "biological function", which are used interchangeably, herein mean an effector or antigenic function that is directly or indirectly performed by a polypeptide (whether in its native or denatured conformation), or by any subsequence thereof. Biological activities include binding to polypeptides, binding to other proteins or molecules, activity as a DNA binding protein, as a transcription regulator, ability to bind damaged DNA, etc. A bioactivity can be modulated by directly affecting the subject polypeptide. Alternatively, a bioactivity can be altered by modulating the level of the polypeptide, such as by modulating expression of the corresponding gene.

The terms "complementary" or "complementarity," as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding an IBD gene product or fragments thereof may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

The term "correlates with expression of a polynucleotide", as used herein, indicates that the detection of the presence of ribonucleic acid that is similar to one of IBD genes by northern analysis is indicative of the presence of mRNA encoding an IBD gene product in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

As is well known, genes or a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding an IBD polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a polypeptide with the same biological activity.

As used herein, the terms "gene", "recombinant gene", and "gene construct" refer to a nucleic acid of the present invention associated with an open reading frame, including both exon and (optionally) intron sequences.

A "recombinant gene" refers to nucleic acid encoding a polypeptide and comprising exon sequences, though it may optionally include intron sequences which are derived from, for example, a related or unrelated chromosomal gene. The term "intron" refers to a DNA sequence present in a given gene which is not translated into protein and is generally found between exons.

The term "growth" or "growth state" of a cell refers to the proliferative state of a cell as well as to its differentiative state. Accordingly, the term refers to the phase of the cell cycle in which the cell is, e.g., G0, G1, G2, prophase, metaphase, or telophase, as well as to its state of differentiation, e.g., undifferentiated, partially differentiated, or fully differentiated. Without wanting to be limited, differentiation of a cell is usually accompanied by a decrease in the proliferative rate of a cell.

"Homology" or "identity" or "similarity" refers to sequence similarity between two peptides or between two nucleic acid molecules, with identity being a more strict comparison. Homology and identity can each be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. An "unrelated" or "non-homologous" sequence shares less than 40% identity, though preferably less than 25% identity, with one of the sequences of the present invention. The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors.

Nucleic acid-encoded amino acid sequences can be used to search both protein and DNA databases.

Databases with individual sequences are described in Methods in Enzymology, ed. Doolittle, supra. Databases include Genbank, EMBL, and DNA Database of Japan (DDBJ).

The term "hybridization", as used herein, refers to any process by which a strand of nucleic acid binds with a complementary strand through base pairing.

An "insertion" or "addition", as used herein, refers to a change in an amino acid or nucleotide sequence resulting in the addition of one or more amino acid residues or nucleotides, respectively, as compared to the naturally occurring molecule.

The term "isolated" as used herein with respect to nucleic acids, such as DNA or RNA, refers to molecules separated from other DNAs, or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

"Microarray" refers to an array of distinct polynucleotides or oligonucleotides synthesized on a substrate, such as paper, nylon or other type of membrane, filter, chip, glass slide, or any other suitable solid support.

The terms "modulated" and "differentially regulated" as used herein refer to both upregulation (i.e., activation or stimulation (e.g., by agonizing or potentiating)) and downregulation (i.e., inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between that of a homozygous and that of a heterozygous subject (for that gene), the mutation is said to be co-dominant.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

As used herein, "gene silencing" or "gene silenced" in reference to an activity of an RNAi molecule, for example a siRNA or miRNA refers to a decrease in the mRNA level in a cell for a target gene (i.e., an IBD gene sequence) by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of downstream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene. By way of an example only, in some embodiments RNAi agents which serve to inhibit or gene silence are useful in the methods, kits and compositions disclosed herein to alter the expression of, such as in particular inhibit the expression of an IBD gene sequence.

As used herein, a "siRNA" refers to a nucleic acid that forms a double stranded RNA, which double stranded RNA has the ability to reduce or inhibit expression of a target IBD gene sequence when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

As used herein, the term "promoter" means a DNA sequence that regulates expression of a selected DNA sequence operably linked to the promoter, and which effects expression of the selected DNA sequence in cells. The term encompasses "tissue specific" promoters, i.e., promoters which effect expression of the selected DNA sequence only in specific cells (e.g., cells of a specific tissue). The term also covers so-called "leaky" promoters, which regulate expression of a selected DNA primarily in one tissue, but cause expression in other tissues as well. The term also encompasses non-tissue specific promoters and promoters that constitutively expressed or that are inducible (i.e., expression levels can be controlled).

The terms "protein", "polypeptide", and "peptide" are used interchangeably herein when referring to a gene product.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays of the invention to identify compounds that modulate a bioactivity.

A "substitution", as used herein, refers to the replacement of one or more amino acids or nucleotides by different amino acids or nucleotides, respectively.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of the polypeptide.

As used herein, the term "transgene" means a nucleic acid sequence (or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extra-chromosomally replicating DNA. In the typical transgenic animals described herein, the transgene causes cells to express a recombinant form of one of the subject polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

As used herein, the terms "treatment" and "treating" refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as used herein encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" as used herein refers to any animal, such as a mammal, for example a human. The methods and compositions described herein can be useful in both human therapeutics and veterinary applications. In some embodiments, the patient is a mammal, and in some embodiments, the patient is human. For veterinary purposes, the terms "subject" and "patient" include, but are not limited to, farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

III. Exemplary Embodiments a. IBD Stem Cells Generally

One aspect of the present invention provides isolated epithelial stem cells derived from gastrointestinal biopsies from IBD patients, referred to herein as "IBD Stem Cells". Prior to the invention, intestinal stem cells from disease samples were generally considered unviable in culture and isolation of stem cells from IBD patient biopsies and stable culture and passaging of those stem cells under conditions that maintain the genotype and epigenetics of the stem cell as it existed in the biopsy had not been described.

In certain embodiments, the IBD Stem Cells are clonal, i.e., the stem cell preparation is derived from passaging a single IBD Stem Cell clone.

In certain embodiments, the progeny of an IBD Stem Cell clone remain genetically and epigenetically stable over many passages, i.e., compared to early passage (P1, P2 or P3), the stem cells are substantially genetically and epigenetically indentical, and preferably are genetically and epigenetically identical, to the early passage stem cells even after passage 10, 20, 30, 40, 50, 75 or even 100. For instance, the late passage IBD Stem Cells are substantially epigenetically identical to early passage stem cells as measured by chromatin immunoprecipitation (ChIP), which serves to monitor changes in chromatin structure, and bisulfite modification and/or CpG island microarray, which tracks changes in DNA methylation.

In certain embodiments, the late passage progeny (even after passage 10, 20, 30, 40, 50, 75 or even 100) of an IBD Stem Cell clone remain predisposed to differentiating to substantial the same epithelial cells or tissue under the same air-liquid interface conditions as the early passage (e.g., P1, P2 or P3), e.g., substantially identical as measured by principle component analysis (PCA) of gene expression, i.e., less than a 1.5 fold, even more preferably less than a 1.0 fold or even 0.5 fold in the level of expression of the 1200 most highly expressed genes by the differentiated tissues/cells with a p<0.05.

In certain embodiments, the late passage progeny (even after passage 10, 20, 30, 40, 50, 75 or even 100) of Crohn's Disease stem cell clone remain predisposed to differentiating to substantial the same epithelial cells or tissue under the same air-liquid interface conditions as the early passage (e.g., P1, P2 or P3), e.g., substantially identical as measured by principle component analysis (PCA) of pCD gene expression, i.e., less than a 1.5 fold, even more preferably less than a 1.0 fold or even 0.5 fold in the level of expression of the 1200 most highly expressed genes by the differentiated tissues/cells with a p<0.05.

In certain embodiments, the subject IBD stem cells are derived from disease tissue samples such as biopsies from Crohn's Disease patients, including adult or pediatric patients. In other embodiments, the subject IBD stem cells are derived from disease tissue samples such as biopsies from Ulcerative Colitis patients, including adult or pediatric patients.

In certain embodiments, the subject IBD stem cells, such as the pediatric Crohn's Disease stem cells, are characterized by a gene expression profile the same or similar to the differential gene expression profiles illustrated in FIG. 1B, FIG. 1F, FIG. 2C, FIG. 2D and/or Table 3 and/or upregulated expression in a cellular pathway shown in FIG. 4B, relative to epithelial stem cells derived from normal gastrointestinal tract from same area, particularly normal gastrointestinal epithelial stem cells derived from patient matched biopsies. In certain embodiments, the IBD stem cells will have a gene expression profile that is similar to expression profiles illustrated in FIG. 1B, FIG. 1F, FIG. 2C, FIG. 2D and/or Table 3 so as to provide at least a 75% confidence interval that the IBD stem cells are the same or similar to the IBD stem cells characterized in FIG. 1B, FIG. 1F, FIG. 2C, FIG. 2D and/or Table 3, and more preferably a confidence interval of at least 80%, 85%, 90% or even 95%.

In certain embodiments, the subject IBD stem cells, such as the pediatric Crohn's Disease stem cells, can be differentiated, such as in an air-liquid interface format, to produce differentiated epithelial tissue in culture that is consistent in gene expression and pathology with inflammatory bowel disease. In certain embodiments, the IBD stem cell is characterized by the ability to produce ALI-differentiated epithelial progeny having a gene expression profile the same or similar to the differential gene expression profiles illustrated in FIG. 2C, FIG. 2D, FIG. 2E, FIG. 3C, FIG. 3F, FIG. 4C, FIG. 4E, FIG. 7 and/or FIG. 19 or downregulated expression of Atonal BHLH transcription factor 1 (ATOH1), relative to ALI-differentiated epithelial cells derived from epithelial stem cells derived from normal gastrointestinal tract from same area, particularly from normal gastrointestinal epithelial stem cells derived from patient matched biopsies. In certain embodiments, the IBD stem cells is characterized by the ability to produce ALI-differentiated epithelial progeny having a gene expression profile that is similar to expression profiles illustrated in FIG. 2C, FIG. 2D and/or FIG. 19B so as to provide at least a 75% confidence interval that the differentiated epithelail cells from the subject IBD stem cells are the same or similar to the the differentiated epithelail cells from the IBD stem cells characterized in FIG. 2C, FIG. 2D and/or FIG. 19B, and more preferably a confidence interval of at least 80%, 85%, 90% or even 95%.

In certain embodiments, the IBD stem cell is characterized by the ability to produce ALI-differentiated 3-D mucosa that substantially lack goblet cells and have little or no expression of MUC2 (i.e., less than 10% of cells expressing detectable MUC2, and more preferably less than 5% or even 2%), and/or little or no staining by antibodies to the enteroendocrine marker CHGA or the Paneth cell marker DEFA6 (i.e., less than 10% of cells staining for DEFA6, and more preferably less than 5% or even 2%).

In addition to the defects in secretory cell differentiation, in certain embodiments the subject IBD stem cells can be characterized based on in vitro-generated epithelia having aberrant distribution pattern of glycoprotein A33 (GPA33, see FIGS. 3A and 3B), a protein that forms an integral part of the tight junction in the colon and whose engineered deletion in mice yields a chronic inflammatory phenotype of the gastrointestinal tract. In certain embodiments, the subject IBD stem cells can be characterized based on in vitro-generated epithelia having a high, ectopic expression of claudin 18 (CLDN18), a tight junction protein, and of V-set and immunoglobulin domain containing 1 (VSIG1), a junctional adhesion protein (see FIG. 3A and FIG. 3B) relative to epithelial stem cells derived from normal gastrointestinal tract from same area, particularly normal gastrointestinal epithelial stem cells derived from patient matched biopsies.

In certain embodiments, the subject IBD stem cells can be altered epigenetic patterns relative to epithelial stem cells derived from normal gastrointestinal tract from same area, particularly normal gastrointestinal epithelial stem cells derived from patient matched biopsies. For instance, certain of the subject IBD stem cells may show extensive regions of repressive histone 3 lysine 27 trimethylation (H3K27me3) at the 5' ends of each of the HOXA and HOXB loci (such as shown in FIG. 16A and FIG. 16C) and/or be characterized by the 3' portions of the HOXA, B, and C loci of those IBD stem cells showing a pattern of histone marks consistent with an overall potentiation or activation of 3' HOX genes relative to the normal gastrointestinal tract from same area, particularly normal gastrointestinal epithelial stem cells derived from patient matched biopsies.

In certain embodiments, the subject IBD stem cells are provided as pure or substantially pure cultures of IBD stem cells, the cells in the culture being at least 85% pure IBD stem cells, and even more preferably 90%, 95% or even 98% pure IBD stem cells.

In other embodiments, the invention provides pure or substantially pure cultures of epithelial cells, including in the form of 3-D mucosa, which are differentiated from the subject IBD stem cells, the cells in the differentiated culture being at least 85% pure differentiated IBD epithelial tissue, and even more preferably 90%, 95% or even 98% pure differentiated IBD epithelial tissue.

In certain embodiments, the subject Crohn's Disease (CD) stem cells are provided as pure or substantially pure cultures of IBD stem cells, the cells in the culture being at least 85% pure CD stem cells, and even more preferably 90%, 95% or even 98% pure CD stem cells.

In other embodiments, the invention provides pure or substantially pure cultures of epithelial cells, including in the form of 3-D mucosa, which are differentiated from the subject CD stem cells, the cells in the differentiated culture being at least 85% pure differentiated Crohn's Disease epithelial tissue, and even more preferably 90%, 95% or even 98% pure differentiated Crohn's Disease epithelial tissue.

The IBD stem cells and differentiated cell cultures derived therefrom can be provided in a multitude of different culture formats as will be apparent to those skilled in the art. These may include adherent and non-adherent cultures, and may be in such forms as clusters or sheets of cells and disassociated cell suspensions. In certain embodiments, such as for drug screening or other analysis, the cells or differentiated tissues are arrayed in multiwell format plates or culture dishes.

In certain embodiments, the IBD stem cells or differentiated cell cultures are cryopreserved preparations.

b. IBD Stem Cells Engineered for Animal Model and Drug Screening Assays

In certain embodiments, the IBD stem cell can be engineered in order to alter the disease phenotype, i.e., for therapeutic, drug screening or animal model uses. The cells can be engineered by addition of recombinant sequences (i.e., integrated genomically or episomally) to cause expression of recombinant gene products (proteins or RNA) or engineered to decrease or remove the expression of gene product otherwise expressed by diseases stem cell. In certain embodiments, the IBD stem cells are engineered to alter the phenotype of differentiated tissue resulting arising from the IBD stem cells to a phenotype resembling normal epithelial for the region of the gastrointestinal tract from which the IBD stem cell was isolated. In certain embodiments, the IBD stem cells are engineered to express detectable markers that are useful in drug discovery or following cell fate in animal models. For instance, the coding sequence for one or more detectable markers can be engineered in the IBD stem cell so as correlate with the proliferative capacity of the stem cell, the death (or conversely viability) of the IBD stem cell, the differentiation fate of the IBD stem cell, the proliferative capacity and/or viability of a differentiated cell derived from an IBD stem cell, the epigenetic state of the IBD stem cell or of a differentiated cell derived from the IBD stem cells.

In certain embodiments, the IBD stem cell can be engineered with coding sequences for one or more selectable traits when expressed in the IBD stem cell or differentiated cells derived therefrom. For instance, the IBD stem cell can be engineered with coding sequences for one or more drug selection traits.

In certain embodiments, the IBD stem cell can be engineered with coding sequences for one or more "suicide" genes which provide for sensitivity to culture conditions, such as the presence or absence of a small molecule agent (drug) that causes inducible killing of the engineered cell but not the unengineered version of the cell.

For further illustration, any portion of the genome of an engineered IBD stem cells can be deleted to disrupt the expression of an endogenous IBD stem cells gene. Non-limiting examples of genomic regions that can be deleted or disrupted in the genome of IBD stem cells include a promoter, an activator, an enhancer, an exon, an intron, a non-coding RNA, a micro-RNA, a small-nuclear RNA, variable number tandem repeats (VNTRs), short tandem repeat (STRs), SNP patterns, hypervariable regions, mini-satellites, dinucleotide repeats, trinucleotide repeats, tetra-nucleotide repeats, or simple sequence repeats. In some cases, the deleted a portion of the genome ranges between 1 nucleic acid to about 10 nucleic acids, 1 nucleic acid to about 100 nucleic acids, 1 nucleic acid to about 1,000 nucleic acids, 1 nucleic acid to about 10,000 nucleic acids, 1 nucleic acid to about 100,000 nucleic acids, 1 nucleic acid to about 1,000,000 nucleic acids, or other suitable range.

Various techniques known in the art can be used to introduce a cloned, or synthetically engineered, nucleic acid comprising the genetic code for a gene product of interest, sucha s protein, into a specific location within the genome of an engineered IBD stem cells. The RNA-guided Cas9 nuclease from the microbial clustered regularly interspaced short palindromic repeats (CRISPR) system, zinc finger nucleases (ZFNs), transcription activator-like effector nucleases (TALENs), and meganuclease technologies, as described, respectively by WO201409370, WO2003087341, WO2014134412, and WO2011090804, each of which is incorporated by reference herein in its entireties, can be used to provide efficient genome engineering in IBD stem cells(s). The technologies described herein can also be used to insert the expression cassette into a genomic location that simultaneously provides a knock-out of one gene and a knock-in of another gene.

U.S. Pat. Nos. 5,416,260; 5,413,923; 5,574,205; 6,139,835; 6,514,752 describe an approach using homologous recombination to either inactivate a target gene, or to inactivate genes that regulate the expression of the gene of interest. Because the approach results in only the required sequence changes, the likelihood of secondary mutations is reduced. The technology provides additional methods and targeting constructs that increase the detection of low frequency homologous recombination events.

To illustrate another approach, gene editing techniques such as Cre-LoxP, TALEN and CRISPR systems can be deployed to disrupt expression of a gene of interest, or to insert the coding sequence for an exogenous gene encoding a desired gene product. In other representative embodiments, expression of a target gene can be downregulated by introducing an RNA interference construct, such as a small interfering RNA or hairpin RNA, targeting the gene of interest.

Torikai et al. Blood. 2013 Aug. 22; 122(8): 1341-1349 describes a zinc finger nucleases system employing a "hit-and-run" approach to genetic editing for selective elimination of expression of a target, particular at the point of engineering the pluripotent stem cells from which they are derived. Hacke et al. Immunol Res. 2009; 44(1-3):112-26 describe the suppression of gene expression by lentivirus-mediated gene transfer of siRNA cassettes which can be readily applied in the generation of the engineered IBD stem cells of the present invention. For efficient and stable delivery of short hairpin-type RNAi constructs (shRNA), those authors employed lentivirus-based gene transfer vectors that integrate into genomic DNA, thereby permanently modifying transduced donor cells. PCT Application WO2016183041 and Mesissner et al. J Immunol May 1, 2015, 194 (1 Supplement) 140.28 describe a using modern genome editing tools such as Talen and CRISPR/Cas9 system that can be used in the generation of engineered IBD stem cells pursuant to the current invention.

Such CRISPR/Cas systems can employ a variety of Cas proteins (Haft et al. PLoS Comput Biol. 2005; 1(6)e60). In some embodiments, the CRISPR/Cas system is a CRISPR type I system. In some embodiments, the CRISPR/Cas system is a CRISPR type II system. In some embodiments, the CRISPR/Cas system is a CRISPR type V system. For example, CRISPR/Cas systems may be used to target transcriptional regulators of a target gene to either produce an engineered IBD cell in which expression of the target gene is downregulated or otherwise disrupted in the IBD stem cell or differentiated progeny, as well as embodiments in which the expression of the target gene is upregulated in the IBD stem cell or differentiated progeny or in which the transcriptional regulation of the target gene can be regulated by the addition of exogenous factors such as a small molecules.

In some embodiments, the alteration is an indel. As used herein, "indel" refers to a mutation resulting from an insertion, deletion, or a combination thereof. As will be appreciated by those skilled in the art, an indel in a coding region of a genomic sequence will result in a frameshift mutation, unless the length of the indel is a multiple of three. In some embodiments, the alteration is a point mutation. As used herein, "point mutation" refers to a substitution that replaces one of the nucleotides. A CRISPR/Cas system can be used to induce an indel of any length or a point mutation in a target polynucleotide sequence.

In some embodiments, the alteration results in a knock out of the target polynucleotide sequence or a portion thereof. For example, knocking out a target polynucleotide sequence in a cell can be performed in vitro, in vivo or ex vivo for both therapeutic and research purposes. Knocking out a target polynucleotide sequence in an IBD stem cell can be useful in understanding the role of that gene in an inflammatory bowel disease or if the resulting engineered cells is intended to be used therapeutically in treating or preventing a disorder associated with expression of the target polynucleotide sequence (e.g., by knocking out a mutant allele in a cell ex vivo and introducing those cells comprising the knocked out mutant allele into a subject). As used herein, "knock out" includes deleting all or a portion of the target polynucleotide sequence in a way that interferes with the function of the target polynucleotide sequence or its expression product.

In some embodiments, the alteration results in reduced expression of the target polynucleotide sequence. The terms "decrease," "reduced," "reduction," and "decrease" are all used herein generally to mean a decrease by a statistically significant amount. However, for avoidance of doubt, "decreased," "reduced," "reduction," "decrease" includes a decrease by at least 10% as compared to a reference level, for example a decrease by at least about 20%, or at least about 30%, or at least about 40%, or at least about 50%, or at least about 60%, or at least about 70%), or at least about 80%, or at least about 90% or up to and including a 100% decrease (i.e. absent level as compared to a reference sample), or any decrease between 10-100% as compared to a reference level.

In some embodiments, such as upregulation of tolerogenic gene products, the genome editing resulted in increased expression of a gene product. The terms "increased," "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%), or at least about 60%, or at least about 70%, or at least about 80%, or at least about 90% or up to and including a 100% increase or any increase between 10-100%) as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

In some embodiments, the alteration is a homozygous alteration. In some embodiments, the alteration is a heterozygous alteration.

In those embodiments intended for drug discovery, the engineered IBD stem cells (or resulting differentiated cells and tissue) can include a reporter gene which ultimately measures the end stage of a cascade of events, such as transcriptional modulation, cell death or resistance to bacterial toxins (such as *Clostridium difficile* toxins, i.e., TcdA and/or TcdB). A "reporter gene" includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Accordingly, in practicing one embodiment of the assay, a reporter gene construct is inserted into the IBD stem cell in order to generate a detection signal dependent on a desired change in the characteristics of the IBD stem cell (or progeny) or the proliferation, senescence/quiescence or death of the IBD stem cell (or progeny). Typically, the reporter gene construct will include a reporter gene in operative linkage with one or more transcriptional regulatory elements with the level of expression of the reporter gene providing a detection signal dependent on the associated transcriptional regulatory sequence(s). Many reporter genes and transcriptional regulatory elements useful in the subject engeineered cells and drug screening assays are known to those of skill in the art and others may be readily identified or synthesized.

Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), Mol. Cell. Biol. 7:725-737); bacterial luciferase (Engebrecht and Silverman (1984), PNAS 1: 4154-4158; Baldwin et al. (1984), Biochemistry 23: 3663-3667); phycobiliproteins (especially phycoerythrin); green fluorescent protein (GFP: see Valdivia et al. (1996) Mol Microbiol 22: 367-78; Cornack et al. (1996) Gene 173 (1 Spec No): 33-8; and Fey et al. (1995) Gene 165:127-130; alkaline phosphatase (Toh et al. (1989) Eur. J Biochem. 182: 231-238, Hall et al. (1983) J Mol. Appl. Gen. 2: 101), secreted alkaline phosphatase (Cullen and Malim (1992) Methods in Enzymol 216:362-368). Other examples of suitable reporter genes include those which encode proteins conferring drug/antibiotic resistance to the host bacterial cell, or which encode proteins required to complement an auxotrophic phenotype. A preferred reporter gene is the spc gene, which confers resistance to spectinomycin.

The amount of transcription from the reporter gene may be measured using any method known to those of skill in the art to be suitable. For example, specific mRNA expression may be detected using Northern blots or specific protein product may be identified by a characteristic stain or an intrinsic activity.

In preferred embodiments, the gene product of the reporter is detected by an intrinsic activity associated with that product. For instance, the reporter gene may encode a gene product that, by enzymatic activity, gives rise to a detection signal based on color, fluorescence, or luminescence. Merely to illustrate, the amount of expression from the reporter gene is then compared to the amount of expression in either the same cell in the absence of a test compound or it may be compared with the amount of transcription in a substantially identical cell treated with a known control agent.

In other preferred embodiments, the reporter gene provides a selection method such that cells in which the reporter gene is activated have a growth advantage. For example the reporter could enhance cell viability, e.g., by relieving a cell nutritional requirement, and/or provide resistance to a drug. For example the reporter gene could encode a gene product which confers the ability to grow in the presence of a selective agent, e.g., chorlamphenicol or kanamycin.

Another class of useful reporter genes encode cell surface proteins for which antibodies or ligands are available. Expression of the reporter gene allows cells to be detected or affinity purified by the presence of the surface protein.

In appropriate assays, so-called counterselectable or negatively selectable genes may be used.

The marker gene may also be a screenable gene. The screened characteristic may be a change in cell morphology, metabolism or other screenable features. Suitable markers include .beta.-galactosidase, alkaline phosphatase, horseradish peroxidase, luciferase, bacterial green fluorescent protein; secreted alkaline phosphatase (SEAP); and chloramphenicol transferase (CAT).

c. Cell Cultures and Media Systems for IBD Stem Cells

The isolation, passaging and maintenance of the subject IBD stem cells can be carried out using, for example, a culture media system comprising (a) a ROCK (Rho Kinase) inhibitor; (b) a Wnt agonist; (c); a Bone Morphogenetic Protein (BMP) antagonist; (d) a Notched Inhibitor; and (e) a TGFβ signaling pathway inhibitor (e.g., a TGFβ inhibitor or a TGFβ receptor inhibitor). In certain embodiments, the the culture medium optionally further comprising: a mitogenic growth factor; and/or insulin or IGF; and/or nicotinamide or an analog thereof. In certain embodiments, the cells from the IBD tissue sample, or the repassaged IBD stem cells, are optionally in fluid or direct contact with mitotically inactive feeder cells and/or in contact with extracellular matrix (such as a basement membrane matrix) or other bio- or synthetic matrix. In the case of the isolation of IBD stem cells from tissue samples, such as biopsies, the method can be performed by culturing dissociated epithelial cells from an IBD tissue sample in the medium, isolating single cells from the epithelial cell clones that arise, and culturing the isolated single cells from to form individual cultures of single cell clones, i.e., in contact with feeder cells and/or a basement membrane matrix in the medium, where each of the single cell clones represents a clonal expansion of the IBD epithelial stem cell.

In certain embodiments, the (epithelial) cells are dissociated from the tissue sample through enzymatic digestion with an enzyme. For example, the enzyme may comprise collagenase, protease, dispase, pronase, elastase, hyaluronidase, Accutase or trypsin.

In certain embodiments, the (epithelial) cells are dissociated from the tissue sample through dissolving extracellular matrix surrounding the (epithelial) cells.

In certain embodiments, the mitotically inactivated cells are mitotically-inactivated fibroblasts, preferably human or murine fibroblasts, such as 3T3-J2 cells. Mitotic inactivation can be accomplished by the administration of mitomycin C or other chemically-based mitotic inhibitors, irradiation with γ-rays, irradiation with X-rays, and/or irradiation with UV light.

In certain embodiments, the extracellular matrix is a basement membrane matrix, such as a laminin-containing basement membrane matrix (e.g., MATRIGEL™ basement membrane matrix (BD Biosciences)), and is preferably growth factor-reduced. In other embodiments, the biopolymer is selected from the group consisting of collagen, chitosan; fibronectin, fibrin, and mixtures thereof.

In certain embodiments, the basement membrane matrix does not support 3-dimensional growth, or does not form a 3-dimensional matrix necessary to support 3-dimensional growth.

In certain embodiments, the medium further comprises serum, preferably FBS (and even more preferably FBS that is not heat inactivated), such as in a concentration of 5%-15%, such as 10% FBS.

In certain embodiments, the medium further comprises 10% FBS that is not heat inactivated.

In certain embodiments, the medium includes a mitogenic growth factor such as EGF, Keratinocyte Growth Factor (KGF), TGFa, BDNF, HGF, and/or bFGF (e.g., FGF7 or FGF10).

(i) Rock (Rho-kinase) Inhibitor

While not wishing to be bound by any particular theory, the addition of a Rock inhibitor may prevent anoikis, especially when culturing single stem cells. The Rock inhibitor may be (1R,4R)-4-((R)-1-aminoethyl)-N-(pyridin-4-yl)cyclohexanecarboxamide dihydrochloride monohydrate (Y-27632, Sigma-Aldrich), 5-(1,4-diazepan-1-ylsulfonyl)isoquinoline (fasudil or HA1077, Cayman Chemical), (1S)-(+)-2-methyl-1-[(4-methyl-5-isoquinolinyl)sulfonyl]-hexahydro-1H-1,4-diazepine dihydrochloride (H-1152, Tocris Bioscience), and N-(6-fluoro-1H-indazol-5-yl)-2-methyl-6-oxo-4-(4-(trifluoromethyl)phenyl)-1,4,5,6-tetrahydropyridine-3-carboxamide (GSK429286A, Stemgent).

In certain embodiments, the final concentration for Y27632 is about 1-5 µM, or 2.5 µM.

The Rho-kinase inhibitor, e.g. Y-21632, may be added to the culture medium every 1, 2, 3, 4, 5, 6, or 7 days during the first seven days of culturing the stem cells.

(ii) Wnt Agonist

The Wnt signaling pathway is defined by a series of events that occur when a Wnt protein ligand binds to a cell-surface receptor of a Frizzled receptor family member. This results in the activation of Dishevelled (Dsh) family proteins which inhibit a complex of proteins that includes axin, GSK-3, and the protein APC to degrade intracellular β-catenin. The resulting enriched nuclear β-catenin enhances transcription by TCF/LEF family of transcription factors. A "Wnt agonist" as used herein includes an agent that directly or indirectly activates TCF/LEF-mediated transcription in a cell, such as through modulating the activity of any one of the proteins/genes in the Wnt signaling cascade (e.g., enhancing the activity of a positive regulator of the Wnt signaling pathway, or inhibiting the activity of a negative regulator of the Wnt signaling pathway).

Wnt agonists are selected from true Wnt agonists that bind and activate a Frizzled receptor family member including any and all of the Wnt family proteins, an inhibitor of intracellular β-catenin degradation, and activators of TCF/LEF. The Wnt agonist may stimulate a Wnt activity in a cell by at least about 10%, at least about 20%, at least about 30%, at least about 50%, at least about 70%, at least about 90%, at least about 100%, at least about 2-fold, 3-fold, 5-fold, 10-fold, 20-fold, 50-fold, 100-fold, 200-fold, 500-fold, or 1000-fold or more relative to a level of the Wnt activity in the absence of the Wnt agonist. As is known to a person of skill in the art, a Wnt activity can be determined by measuring the transcriptional activity of Wnt, for example by pTOPFLASH and pFOPFLASH Tcf luciferase reporter constructs (see Korinek et al, Science 275: 1784-1787, 1997, incorporated herein by reference).

Representative Wnt agonist may comprise a secreted glycoprotein including Wnt-1/Int-I, Wnt-2/Irp (Int-1-related Protein), Wnt-2b/13, Wnt-3/Int-4, Wnt-3a (R&D systems), Wnt-4, Wnt-5a, Wnt-5b, Wnt-6 (Kirikoshi et al, Biochem. Biophys. Res. Com., 283:798-805, 2001), Wnt-7a (R&D systems), Wnt-7b, Wnt-8a/8d, Wnt-8b, Wnt-9a/14, Wnt-9b/14b/15, Wnt-10a, Wnt-10b/12, Wnt-11, and Wnt-16. An overview of human Wnt proteins is provided in "The Wnt Family of Secreted Proteins," R&D Systems Catalog, 2004 (incorporated herein by reference).

Further Wnt agonists include the R-spondin family of secreted proteins, which is implicated in the activation and regulation of Wnt signaling pathway, and which comprises at least 4 members, namely R-spondin 1 (NU206, Nuvelo, San Carlos, Calif.), R-spondin 2 (R&D systems), R-spondin 3, and R-spondin 4. Wnt agonists also include Norrin (also known as Norrie Disease Protein or NDP) (R&D systems), which is a secreted regulatory protein that functions like a Wnt protein in that it binds with high affinity to the Frizzled-4 receptor and induces activation of the Wnt signaling pathway (Kestutis Planutis et al, BMC Cell Biol. 8: 12, 2007).

Wnt agonists further include a small-molecule agonist of the Wnt signaling pathway, an aminopyrimidine derivative ($N^4$-(benzo[d][1,3]dioxol-5-ylmethyl)-6-(3-methoxyphenyl)pyrimidine-2,4-diamine) of the following structure, as described in Liu et al. (Angew Chem. Int. Ed. Engl. 44 13): 1987-1990, 2005, incorporated herein by reference).

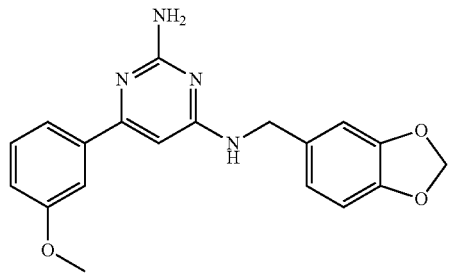 [SMILES: COc1cccc(-c2cc(NCc3ccc4c(c3)OCO4)nc(N)n2)c1]

GSK-inhibitors comprise small-interfering RNAs (siRNA, Cell Signaling), lithium (Sigma), kenpaullone (Biomol International, Leost et al., Eur. J. Biochem. 267:5983-5994, 2000), 6-Bromoindirubin-30-acetoxime (Meyer et al., Chem. Biol. 10:1255-1266, 2003), SB 216763, and SB 415286 (Sigma-Aldrich), and FRAT-family members and FRAT-derived peptides that prevent interaction of GSK-3 with axin. An overview is provided by Meijer et al. (Trends in Pharmacological Sciences 25:471-480, 2004, incorporated herein by reference). Methods and assays for determining a level of GSK-3 inhibition are known in the art, and may comprise, for example, the methods and assay as described in Liao et al. (Endocrinology 145(6):2941-2949, 2004, incorporated herein by reference).

In certain embodiments, Wnt agonist is selected from: one or more of a Wnt family member, R-spondin 1-4 (such as R-spondin 1), Norrin, Wnt3a, Wnt-6, and a GSK-inhibitor. In certain embodiments, the Wnt agonist comprises or consists of R-spondin 1. R-spondin 1 may be added to the subject culture medium at a concentration of at least about 50 ng/mL, at least about 75 ng/mL, at least about 100 ng/mL, at least about 125 ng/mL, at least about 150 ng/mL, at least about 175 ng/mL, at least about 200 ng/mL, at least about 300 ng/mL, at least about 500 ng/mL. In certain embodiments, R-spondin 1 is about 125 ng/mL.

In certain embodiments, any of the specific protein-based Wnt agonist referenced herein, such as R-spondin 1 to R-spondin 4, any Wnt family member, etc. may be replaced by a natural, synthetic, or recombinantly produced homologs or fragments thereof that retain at least about 80%, 85%, 90%, 95%, 99% of the respective Wnt agonist activity, and/or homologs or fragments thereof that share at least about 60%, 70%, 80%, 90%, 95%, 97%, 99% amino acid sequence identity as measured by any art recognized sequence alignment software based on either a global alignment technique (e.g., the Needleman-Wunsch algorithm) or a local alignment technique (e.g., the Smith-Waterman algorithm). The sequences of the representative Wnt agonist referenced herein are represented in SEQ ID NOs. 10-17.

During culturing of the subject stem cells, the Wnt family member may be added to the medium every day, every second day, every third day, while the medium is refreshed, e.g., every 1, 2, 3, 4, 5, or more days.

In certain embodiments, a Wnt agonist is selected from the group consisting of: an R-spondin, Wnt-3a and Wnt-6, or combinations thereof. In certain embodiments, an R-spondin and Wnt-3a are used together as Wnt agonist. In certain embodiments, R-spondin concentration is about 125 ng/mL, and Wnt3a concentration is about 100 ng/mL.

(iii) BMP Inhibitor

Bone Morphogenetic Proteins (BMPs) bind as a dimeric ligand to a receptor complex consisting of two different receptor serine/threonine kinases, type I and type II receptors. The type II receptor phosphorylates the type I receptor, resulting in the activation of this receptor kinase. The type I receptor subsequently phosphorylates specific receptor substrates (such as SMAD), resulting in a signal transduction pathway leading to transcriptional activity.

A BMP inhibitor as used herein includes an agent that inhibits BMP signaling through its receptors. In one embodiment, a BMP inhibitor binds to a BMP molecule to form a complex such that BMP activity is neutralized, for example, by preventing or inhibiting the binding of the BMP molecule to a BMP receptor. Examples of such BMP inhibitors may include an antibody specific for the BMP ligand, or an antigen-binding portion thereof. Other examples of such BMP inhibitors include a dominant negative mutant of a BMP receptor, such as a soluble BMP receptor that binds the BMP ligand and prevents the ligand from binding to the natural BMP receptor on the cell surface.

Alternatively, the BMP inhibitor may include an agent that acts as an antagonist or reverse agonist. This type of inhibitor binds with a BMP receptor and prevents binding of a BMP to the receptor. An example of such an agent is an antibody that specifically binds a BMP receptor and prevents binding of BMP to the antibody-bound BMP receptor.

In certain embodiments, the BMP inhibitor inhibits a BMP-dependent activity in a cell to at most 90%, at most 80%, at most 70%, at most 50%, at most 30%, at most 10%, or about 0% (near complete inhibition), relative to a level of a BMP activity in the absence of the inhibitor. As is known to one of skill in the art, a BMP activity can be determined by, for example, measuring the transcriptional activity of BMP as exemplified in Zilberberg et al. ("A rapid and sensitive bioassay to measure bone morphogenetic protein activity," BMC Cell Biology 8:41, 2007, incorporated herein by reference).

Several classes of natural BMP-binding proteins are known, including Noggin (Peprotech), Chordin, and chordin-like proteins comprising a chordin domain (R&D systems) comprising chordin domains, Follistatin and follistatin-related proteins comprising a follistatin domain (R&D systems) comprising a follistatin domain, DAN and DAN-like proteins comprising a DAN Cystine-knot domain {e.g., Cerberus and Gremlin) (R&D systems), sclerostin/SOST (R&D systems), decorin (R&D systems), and alpha-2 macroglobulin (R&D systems) or as described in U.S. Pat. No. 8,383,349. An exemplary BMP inhibitor for use in a method of the invention is selected from Noggin, DAN, and DAN-like proteins including Cerberus and Gremlin (R&D systems). These diffusible proteins are able to bind a BMP ligand with varying degrees of affinity, and inhibit BMPs' access to their signaling receptors.

Any of the above-described BMP inhibitors may be added either alone or in combination to the subject culture medium when desirable.

In certain embodiments, the BMP inhibitor is Noggin. Noggin may be added to the respective culture medium at a concentration of at least about 10 ng/mL, or at least about 20 ng/mL, or at least about 50 ng/mL, or at least about 100 ng/mL (e.g., 100 ng/mL).

In certain embodiments, any of the specific BMP inhibitors referenced herein, such as Noggin, Chordin, Follistatin, DAN, Cerberus, Gremlin, sclerostin/SOST, decorin, and alpha-2 macroglobulin may be replaced by a natural, synthetic, or recombinantly produced homologs or fragments thereof that retain at least about 80%, 85%, 90%, 95%, 99% of the respective BMP inhibiting activity, and/or homologs or fragments thereof that share at least about 60%, 70%, 80%, 90%, 95%, 97%, 99% amino acid sequence identity as measured by any art recognized sequence alignment software based on either a global alignment technique (e.g., the Needleman-Wunsch algorithm) or a local alignment technique (e.g., the Smith-Waterman algorithm).

The sequences of the representative BMP inhibitors referenced herein are represented in SEQ ID NOs. 1-9.

During culturing of the subject stem cells, the BMP inhibitor may be added to the culture medium every day, every 2nd day, every 3rd day, or every 4th day, while the culture medium is refreshed every day, every second day, every third day, or every fourth day as appropriate.

(iv) TGF-Beta or TGF-Beta Receptor Inhibitor

TGF-β signaling is involved in many cellular functions, including cell growth, cell fate and apoptosis. Signaling typically begins with binding of a TGF-β superfamily ligand to a Type II receptor, which recruits and phosphorylates a Type I receptor. The Type 1 receptor then phosphorylates SMADs, which act as transcription factors in the nucleus and regulate target gene expression. Alternatively, TGF-β signaling can activate MAP kinase signaling pathways, for example, via p38 MAP kinase.

The TGF-β superfamily ligands comprise bone morphogenetic proteins (BMPs), growth and differentiation factors (GDFs), anti-Mullerian hormone (AMH), activin, nodal and TGF-βs.

A TGF-β inhibitor as used herein includes an agent that reduces the activity of the TGF-β signaling pathway. There are many different ways of disrupting the TGF-β signaling pathway known in the art, any of which may be used in conjunction with the subject invention. For example, TGF-β signaling may be disrupted by: inhibition of TGF-β expression by a small-interfering RNA strategy; inhibition of furin (a TGF-β activating protease); inhibition of the pathway by physiological inhibitors, such as inhibition of BMP by Noggin, DAN or DAN-like proteins; neutralization of TGF-β with a monoclonal antibody; inhibition with small-molecule inhibitors of TGF-β receptor kinase 1 (also known as activin receptor-like kinase, ALK5), ALK4, ALK6, ALK7 or other TGFβ-related receptor kinases; inhibition of Smad 2 and Smad 3 signaling by overexpression of their physiological inhibitor, Smad 7, or by using thioredoxin as an Smad anchor disabling Smad from activation (Fuchs, Inhibition of TGF-β Signaling for the Treatment of Tumor Metastasis and Fibrotic Diseases. Current Signal Transduction Therapy 6(1):29-43(15), 2011).

For example, a TGF-β inhibitor may target a serine/threonine protein kinase selected from: TGF-β receptor kinase 1, ALK4, ALK5, ALK7, or p38. ALK4, ALK5 and ALK7 are all closely related receptors of the TGF-β superfamily. ALK4 has GI number 91; ALK5 (also known as TGF-β receptor kinase 1) has GI number 7046; and ALK7 has GI number 658. An inhibitor of any one of these kinases is one that effects a reduction in the enzymatic activity of any one (or more) of these kinases. Inhibition of ALK and p38 kinase has previously been shown to be linked in B-cell lymphoma (Bakkebo et al, "TGFβ-induced growth inhibition in B-cell lymphoma correlates with Smad 1/5 signaling and constitutively active p38MAPK," BMC Immunol. 11:57, 2010).

In certain embodiments, a TGF-β inhibitor may bind to and inhibit the activity of a Smad protein, such as R-SMAD or SMAD1-5 {i.e., SMAD1, SMAD2, SMAD3, SMAD4 or SMAD5}.

In certain embodiments, a TGF-β inhibitor may bind to and reduces the activity of Ser/Thr protein kinase selected from: TGF-β receptor kinase 1, ALK4, ALK5, ALK7, or p38.

In certain embodiments, the medium of the invention comprises an inhibitor of ALK5. In certain embodiments, the TGF-β inhibitor or TGF-β receptor inhibitor does not include a BMP antagonist {i.e., is an agent other than BMP antagonist).

Various methods for determining if a substance is a TGF-β inhibitor are known. For example, a cellular assay may be used in which cells are stably transfected with a reporter construct comprising the human PAI-1 promoter or Smad binding sites, driving a luciferase reporter gene. Inhibition of luciferase activity relative to control groups can be used as a measure of compound activity (De Gouville et al, Br. J. Pharmacol. 145(2): 166-177, 2005, incorporated herein by reference). Another example is the ALPHASCREEN® phosphosensor assay for measurement of kinase activity (Drew et al, J. Biomol. Screen. 16(2): 164-173, 2011, incorporated herein by reference).

A TGF-β inhibitor useful for the present invention may be a protein, a peptide, a small-molecule, a small-interfering RNA, an antisense oligonucleotide, an aptamer, an antibody or an antigen-binding portion thereof. The inhibitor may be naturally occurring or synthetic. Examples of small-molecule TGF-β inhibitors that can be used in the context of this invention include, but are not limited to, the small molecule inhibitors listed in Table 1A below:

TABLE 1A

Small-molecule TGF-inhibitors targeting receptor kinases

| Inhibitor | Targets | IC50 (nM) | Mol Wt | Name | Formula |
|---|---|---|---|---|---|
| A83-01 | ALK5 (TGF-β B1) | 12 | 421.52 | 3-(6-Methyl-2-pyridinyl)-N-phenyl-4-(4-quinolinyl)-1H-pyrazole-1-carbothioamide | C25H19N5S |
|  | ALK4 | 45 |  |  |  |
|  | ALK7 | 7.5 |  |  |  |
| SB-431542 | ALK5 | 94 | 384.39 | 4-[4-(1,3-benzodioxol-5-yl)-5-(2-pyridinyl)-1H-imidazol-2-yl]benzamide | C22H16N4O3 |
|  | ALK4 |  |  |  |  |
|  | ALK7 |  |  |  |  |
| SB-505124 | ALK5 | 47 | 335.4 | 2-(5-benzo[1,3]dioxol-5-yl-2-tert-butyl-3Himidazol-4-yl)-6-methylpyridine hydrochloride hydrate | C20H21N3O2 |
|  | ALK4 | 129 |  |  |  |
| SB-525334 | ALK5 | 14.3 | 343.42 | 6-[2-(1,1-Dimethylethyl)-5-(6-methyl-2-pyridinyl)-1H-imidazol-4-yl]quinoxaline | C21H21N5 |
| SD-208 | ALK5 | 49 | 352.75 | 2-(5-Chloro-2-fluorophenyl)-4-[(4-pyridyl)amino]pteridine | C17H10ClFN6 |
| LY-36494 | TGR-β RI | 59 | 272.31 | 4-[3-(2-Pridinyl)-1H-pyrazol-4-yl]-quinoline | C17H12N4 |
|  | TGF-β RII | 400 |  |  |  |
|  | MLK-7K | 1400 |  |  |  |
| SJN-2511 | ALK5 | 23 | 287.32 | 2-(3-(6-Methylpyridine-2-yl)-1H-pyrazol-4-yl)-1,5-naphthyridine | C17H13N5 |

One or more of any of the inhibitors listed in Table 1 above, or a combination thereof, may be used as a TGF-β inhibitor in the subject invention. In certain embodiments, the combination may include: SB-525334 and SD-208 and A83-01; SD-208 and A83-01; or SD-208 and A83-01.

One of skill in the art will appreciate that a number of other small-molecule inhibitors exist that are primarily designed to target other kinases, but at high concentrations may also inhibit TGF-β receptor kinases. For example, SB-203580 is a p38 MAP kinase inhibitor that, at high concentrations (for example, approximate 10 μM or more) may inhibit ALK5. Any such inhibitor that inhibits the TGF-β signaling pathway may also be used in this invention. In certain embodiments, A83-01 may be added to the culture medium at a concentration of between 10 nM and 10 μM, or between 20 nM and 5 μM, or between 50 nM and 1 μM. In certain embodiments, A83-01 may be added to the medium at about 500 nM. In certain embodiments, A83-01 may be added to the culture medium at a concentration of between 350-650 nM, 450-550 nM, or about 500 nM. In certain embodiments, A83-01 may be added to the culture medium at a concentration of between 25-75 nM, 40-60 nM, or about 50 nM.

SB-431542 may be added to the culture medium at a concentration of between 80 nM and 80 μM, or between 100 nM and 40 μM, or between 500 nM and 10 μM, or between 1-5 μM. For example, SB-431542 may be added to the culture medium at about 2 μM.

SB-505124 may be added to the culture medium at a concentration of between 40 nM and 40 μM, or between 80 nM and 20 μM, or between 200 nM and 1 μM. For example, SB-505124 may be added to the culture medium at about 500 nM.

SB-525334 may be added to the culture medium at a concentration of between 10 nM and 10 μM, or between 20 nM and 5 μM, or between 50 nM and 1 μM. For example, SB-525334 may be added to the culture medium at about 100 nM.

LY 364947 may be added to the culture medium at a concentration of between 40 nM and 40 μM, or between 80 nM and 20 μM, or between 200 nM and 1 μM. For example, LY 364947 may be added to the culture medium at about 500 nM.

SD-208 may be added to the culture medium at a concentration of between 40 nM and 40 μM, or between 80 nM and 20 μM, or between 200 nM and 1 μM. For example, SD-208 may be added to the culture medium at abut 500 nM.

S JN 2511 may be added to the culture medium at a concentration of between 20 nM and 20 μM, or between 40 nM and 10 μM, or between 100 nM and 1 μM. For example, A83-01 may be added to the culture medium at approximately 200 nM.

(v) Notch Agonist

Notch signaling has been shown to play an important role in cell-fate determination, as well as in cell survival and proliferation. Notch receptor proteins can interact with a number of surface-bound or secreted ligands, including but not limited to Jagged-1, Jagged-2, Delta-1 or Delta-like 1, Delta-like 3, Delta-like 4, etc. Upon ligand binding, Notch receptors are activated by serial cleavage events involving members of the ADAM protease family, as well as an intramembranous cleavage regulated by the gamma secretase presenilin. The result is a translocation of the intracellular domain of Notch to the nucleus, where it transcriptionally activates downstream genes.

A "Notch agonist" as used herein includes a molecule that stimulates a Notch activity in a cell by at least about 10%, at least about 20%, at least about 30%, at least about 50%, at least about 70%, at least about 90%, at least about 100%, at least about 3-fold, 5-fold, 10-fold, 20-fold, 50-fold, 100-fold, 200-fold, 500-fold, 1000-fold or more, relative to a level of a Notch activity in the absence of the Notch agonist. As is known in the art, Notch activity can be determined by, for example, measuring the transcriptional activity of Notch, by a 4×wtCBF1-luciferase reporter construct described by Hsieh et al. (Mol. Cell. Biol. 16:952-959, 1996, incorporated herein by reference).

In certain embodiments, the Notch agonist is selected from: Jagged-1, Delta-1 and Delta-like 4, or an active fragment or derivative thereof. In certain embodiments, the Notch agonist is DSL peptide (Dontu et al., Breast Cancer Res., 6:R605-R615, 2004), having the amino acid sequence CDDYYYGFGCNKFCRPR (SEQ ID NOs: 36). The DSL peptide (ANA spec) may be used at a concentration between 10 μM and 100 nM, or at least 10 μM and not higher than 100 nM. In certain embodiments, the final concentration of Jagged-1 is about 0.1-10 μM; or about 0.2-5 μM; or about 0.5-2 μM; or about 1 μM.

In certain embodiments, any of the specific Notch agonist referenced herein, such as Jagged-1, Jagged-2, Delta-1 and Delta-like 4 may be replaced by a natural, synthetic, or recombinantly produced homologs or fragments thereof that retain at least about 80%, 85%, 90%, 95%, 99% of the respective Notch agonist activity, and/or homologs or fragments thereof that share at least about 60%, 70%, 80%, 90%, 95%, 97%, 99% amino acid sequence identity as measured by any art recognized sequence alignment software based on either a global alignment technique (e.g., the Needleman-Wunsch algorithm) or a local alignment technique (e.g., the Smith-Waterman algorithm).

The sequences of the representative Notch agonists referenced herein are represented in SEQ ID NOs. 28-35.

The Notch agonist may be added to the culture medium every 1, 2, 3, or 4 days during the first 1-2 weeks of culturing the stem cells.

(vi) Nicotinamide

The culture medium of the invention may additionally be supplemented with nicotinamide or its analogs, precursors, or mimics, such as methyl-nicotinamid, benazamid, pyrazinamide, thymine, or niacin. Nicotinamide may be added to the culture medium to a final concentration of between 1 and 100 mM, between 5 and 50 mM, or preferably between 5 and 20 mM. For example, nicotinamide may be added to the culture medium to a final concentration of approximately 10 mM. The similar concentrations of nicotinamide analogs, precursors, or mimics can also be used alone or in combination.

(vii) p38 inhibitor

A "p38 inhibitor" may be included in the media, in addition to or as part of a TGF-β inhibitory function, and include an inhibitor that, directly or indirectly, negatively regulates p38 signaling, such as an agent that binds to and reduces the activity of at least one p38 isoform. p38 protein kinases (see, GI number 1432) are part of the family of mitogen-activated protein kinases (MAPKs). MAPKs are serine/threonine-specific protein kinases that respond to extracellular stimuli, such as environmental stress and inflammatory cytokines, and regulate various cellular activities, such as gene expression, differentiation, mitosis, proliferation, and cell survival/apoptosis. The p38 MAPKs exist as α, β, β2, γ and δ isoforms.

Various methods for determining if a substance is a p38 inhibitor are known, such as: phospho-specific antibody detection of phosphorylation at Thr180/Tyr182, which provides a well-established measure of cellular p38 activation or inhibition; biochemical recombinant kinase assays; tumor necrosis factor alpha (TNFa) secretion assays; and DiscoverRx high throughput screening platform for p38 inhibitors. Several p38 activity assay kits also exist (e.g. Millipore, Sigma-Aldrich).

In certain embodiments, high concentrations (e.g., more than 100 nM, or more than 1 µM, more than 10 µM, or more than 100 µM) of a p38 inhibitor may have the effect of inhibiting TGF-β. In other embodiments, the p38 inhibitor does not inhibit TGF-β signaling.

Various p38 inhibitors are known in the art (for example, see Table 2). In some embodiments, the inhibitor that directly or indirectly negatively regulates p38 signaling is selected from the group consisting of SB-202190, SB-203580, VX-702, VX-745, PD-169316, RO-4402257 and BIRB-796.

In certain embodiments, the medium comprises both: a) an inhibitor that binds to and reduces the activity of any one or more of the kinases from the group consisting of: ALK4, ALK5 and ALK7; and b) an inhibitor that binds to and reduces the activity of p38.

In certain embodiments, the medium comprises an inhibitor that binds to and reduces the activity of ALK5 and an inhibitor that binds to and reduces the activity of p38.

In one embodiment, the inhibitor binds to and reduces the activity of its target (for example, TGF-β and/or p38) by more than 10%; more than 30%; more than 60%; more than 80%; more than 90%; more than 95%; or more than 99% compared to a control, as assessed by a cellular assay. Examples of cellular assays for measuring target inhibition are well known in the art as described above.

An inhibitor of TGF-β and/or p38 may have an IC50 value equal to or less than 2000 nM; less than 1000 nM; less than 100 nM; less than 50 nM; less than 30 nM; less than 20 nM or less than 10 nM. The IC50 value refers to the effectiveness of an inhibitor in inhibiting its target's biological or biochemical function. The IC50 indicates how much of a particular inhibitor is required to inhibit a kinase by 50%. IC50 values can be calculated in accordance with the assay methods set out above. An inhibitor of TGF-β and/or p38 may exist in various forms, including natural or modified substrates, enzymes, receptors, small organic molecules, such as small natural or synthetic organic molecules of up to 2000 Da, preferably 800 Da or less, peptidomimetics, inorganic molecules, peptides, polypeptides, antisense oligonucleotides aptamers, and structural or functional mimetics of these including small molecules.

In certain embodiments, the inhibitor of TGF-β and/or p38 may also be an aptamer. As used herein, the term "aptamer" refers to strands of oligonucleotides (DNA or RNA) that can adopt highly specific three-dimensional conformations. Aptamers are designed to have high binding affinities and specificities towards certain target molecules, including extracellular and intracellular proteins. Aptamers may be produced using, for example, Systematic Evolution of Ligands by Exponential Enrichment (SELEX) process (see, for example, Tuerk and Gold, Systematic evolution of ligands by exponential enrichment: RNA ligands to bacteriophage T4 DNA Polymerase. Science 249:505-510, 1990, incorporated herein by reference).

In certain embodiments, the TGF-β and/or p38 inhibitor may be a small synthetic molecule with a molecular weight of between 50 and 800 Da, between 80 and 700 Da, between 100 and 600 Da, or between 150 and 500 Da.

In certain embodiments, the TGF-β and/or p38 inhibitor comprises a pyridinylimidazole or a 2,4-disubstituted teridine or a quinazoline, for example comprises:

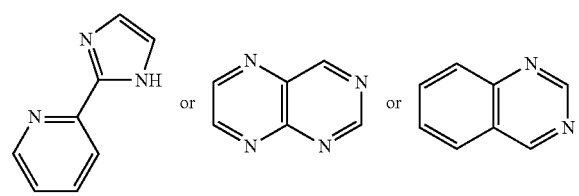

Particular examples of TGF-β and/or p38 inhibitors that may be used in accordance with the invention include, but are not limited to: SB-202190, SB-203580, SB-206718, SB-227931, VX-702, VX-745, PD-169316, RO-4402257, BIRB-796, A83-01 SB-431542, SB-505124, SB-525334, LY 364947, SD-208, SJ 2511 (see Table 2).

For example, SB-202190 may be added to the culture medium at a concentration of between 50 nM and 100 µM, or between 100 nM and 50 µM, or between 1 µM and 50 µM. For example, SB-202190 may be added to the culture medium at approximately 10 µM.

SB-203580 may be added to the culture medium at a concentration of between 50 nM and 100 µM, or between 100 nM and 50 µM, or between 1 µM and 50 µM. For example, SB-203580 may be added to the culture medium at approximately 10 µM.

VX-702 may be added to the culture medium at a concentration of between 50 nM and 100 µM, or between 100 nM and 50 µM, or between 1 µM and 25 µM. For example, VX-702 may be added to the culture medium at approximately 5 µM.

VX-745 may be added to the culture medium at a concentration of between 10 nM and 50 µM, or between 50 nM and 50 µM, or between 250 nM and 10 µM. For example, VX-745 may be added to the culture medium at approximately 1 µM.

PD-169316 may be added to the culture medium at a concentration of between 100 nM and 200 µM, or between 200 nM and 100 µM, or between 1 µM and 50 µM. For example, PD-169316 may be added to the culture medium at approximately 20 µM.

RO-4402257 may be added to the culture medium at a concentration of between 10 nM and 50 µM, or between 50 nM and 50 µM, or between 500 nM and 10 µM. For example, RO-4402257 may be added to the culture medium at approximately 1 µM.

BIRB-796 may be added to the culture medium at a concentration of between 10 nM and 50 µM, or between 50 nM and 50 µM, or between 500 nM and 10 µM. For example, BIRB-796 may be added to the culture medium at approximately 1 µM.

TABLE 2

Exemplary TGF-β and/or p38 Inhibitors

| Inhibitor | Targets | IC50 (nM) | Mol Wt | Name | Formula |
|---|---|---|---|---|---|
| A83-01 | ALK5 (TGF-βRI) ALK4 ALK7 | 12 45 7.5 | 421.52 | 3-(6-Methyl-2-pyridinyl)-N-phenyl-4-(4-quinolinyl)-1H-pyrazole-1-carbothioamide | C25H19N5S |
| SB-431542 | ALK5 ALK4 ALK7 | 94 | 384.39 | 4-[4-(1,3-benzodioxol-5-yl)-5-(2-pyridinyl)-1H-imidazol-2-yl]benzamide | C22H16N4O3 |
| SB-505124 | ALK5 ALK4 | 47 129 | 335.4 | 2-(5-benzo[1,3]dioxol-5-yl-2-tert-butyl-3Himidazol-4-yl)-6-methylpyridine hydrochloride hydrate | C20H21N3O2 |
| SB-525334 | ALK5 | 14.3 | 343.42 | 6-[2-(1,1-Dimethylethyl)-5-(6-methyl-2-pyridinyl)-1H-imidazol-4-yl]quinoxaline | C21H21N5 |
| SD-208 | ALK5 | 49 | 352.75 | 2-(5-Chloro-2-fluorophenyl)-4-[(4-pyridyl)amino]pteridine | C17H10ClFN6 |
| LY-36494 | TGR-βRI TGF-βRII MLK-7K | 59 400 1400 | 272.31 | 4-[3-(2-Pridinyl)-1H-pyrazol-4-yl]-quinoline | C17H12N4 |
| LY364947 | ALK5 | 59 | 272.30 | 4-[3-(2-pyridinyl)-1H-pyrazol-4-yl]-quinoline | $C_{17}H_{12}N_4$ |
| SJN-2511 | ALK5 | 23 | 287.32 | 2-(3-(6-Methylpyridine-2-yl)-1H-pyrazol-4-yl)-1,5-naphthyridine | C17H13N5 |
| SB-202190 | p38 MAP kinase p38α p38β | 38 50 100 | 331.35 | 4-[4-(4-Fluorophenyl)-5-(4-pyridinyl)-1H-imidazol-2-yl]phenol | C20H14N3OF |
| SB-203580 | p38 p38β2 | 50 500 | 377.44 | 4-[5-(4-Fluorophenyl)-2-[4-(methylsulfonyl)phenyl]-1H-imidazol-4-yl]pyridine | C21H16FN3OS |
| VX-702 | p38α p38β | 4-20; (Kd = 3.7) Kd = 17 | 404.32 | 6-[(Aminocarbonyl)(2,6-difluorophenyl)amino]-2-(2,4-difluorophenyl)-3-pyridinecarboxamide | C19H12F4N4O2 |
| VX-745 | p38α | 10 | 436.26 | 5-(2,6-Dichlorophenyl)-2-[2,4-difluorophenyl)thio]-6H-pyrimido[1,6-b]pyridazin-6-one | C19H9Cl2F2N3OS |
| PD-169316 | p38 | 89 | 360.3 | 4-[5-(4-fluorophenyl)-2-(4-nitrophenyl)-1H-imidazol-4-yl]-pyridine | C20H13FN4O |
| RO-4402257 | p38α p38β | 14 480 | | Pyrido[2,3-d]pyrimidin-7(8H)-one,6-(2,4-difluorophenoxy)-2-[[3-hydroxy-1-(2-hydroxyethyl)propyl]amino]-8-methyl- | |
| BIRB-796 | p38 | 4 | 527.67 | 1-[2-(4-methylphenyl)-5-tert-butyl-pyrazol-3-yl]-3-[4-(2-morpholin-4-ylethoxy)naphthalen-1-yl]urea::3-[2-(4-methylphenyl)-5-tert-butyl-pyrazol-3-yl]-1-[4-(2-morpholin-4-ylethoxy)naphthalen-1-yl]urea::3-[3-tert-butyl-1-(4-methylphenyl)-1H-pyrazol-5-yl]-1-{4-[2-(morpholin-4-yl)ethoxy]naphthalen-1-yl}urea | C31H37N5O3 |

Thus, in some embodiments, the inhibitor that directly or indirectly, negatively regulates TGF-β and/or p38 signaling is added to the culture medium at a concentration of between 1 nM and 100 µM, between 10 nM and 100 µM, between 100 nM and 10 µM, or about 1 µM. For example, wherein the total concentration of the one or more inhibitor is between 10 nM and 100 µM, between 100 nM and 10 µM, or about 1 µM.

(viii) Mitogenic Growth Factors

Mitogenic growth factors suitable for the invention may include a family of growth factors comprising epidermal growth factor (EGF) (Peprotech), Transforming Growth Factor-α (TGFa, Peprotech), basic Fibroblast Growth Factor (bFGF, Peprotech), brain-derived neurotrophic factor (BDNF, R&D Systems), and Keratinocyte Growth Factor (KGF, Peprotech).

EGF is a potent mitogenic factor for a variety of cultured ectodermal and mesodermal cells, and has a profound effect on the differentiation of specific cells in vivo and in vitro, and of some fibroblasts in cell culture. The EGF precursor exists as a membrane-bound molecule, which is proteolytically cleaved to generate the 53-amino acid peptide hormone that stimulates cells. EGF may be added to the subject culture medium at a concentration of between 1-500 ng/mL. In certain embodiments, final EGF concentration in the medium is at least about 1, 2, 5, 10, 20, 25, 30, 40, 45, or 50 ng/mL, and is not higher than about 500, 450, 400, 350, 300, 250, 200, 150, 100, 50, 30, 20 ng/mL. In certain embodiments, final EGF concentration is about 1-50 ng/mL, or about 2-50 ng/mL, or about 5-30 ng/mL, or about 5-20 ng/mL, or about 10 ng/mL.

The same concentrations may be used for an FGF, such as FGF10 or FGF7. If more than one FGF is used, for example FGF7 and FGF 10, the concentration of FGF above may refer to the total concentration of all FGF used in the medium.

In certain embodiments, any of the specific mitogenic growth factors referenced herein, such as EGF, TGFa, bFGF, BDNF, KGF, etc. may be replaced by a natural, synthetic, or recombinantly produced homologs or fragments thereof that retain at least about 80%, 85%, 90%, 95%, 99% of the respective mitogenic growth factor activity, and/or homologs or fragments thereof that share at least about 60%, 70%, 80%, 90%, 95%, 97%, 99% amino acid sequence identity as measured by any art recognized sequence alignment software based on either a global alignment technique (e.g., the Needleman-Wunsch algorithm) or a local alignment technique (e.g., the Smith-Waterman algorithm).

The sequences of the representative mitogenic growth factors referenced herein are represented in SEQ ID NOs. 18-27.

During culturing of the subject stem cells, the mitogenic growth factor may be added to the culture medium every day, every 2nd day, while the culture medium is refreshed, e.g.; every day.

Any member of the bFGF family may be used. In certain embodiments, FGF7 and/or FGF10 is used. FGF7 is also known as KGF (Keratinocyte Growth Factor). In certain embodiments, a combination of mitogenic growth factors, such as EGF and KGF, or EGF and BDNF, is added to the subject culture medium. In certain embodiments, a combination of mitogenic growth factors, such as EGF and KGF, or EGF and FGF10, is added to the subject culture medium.

(ix) Extracellular Matrix (ECM)

Extracellular matrix (ECM), used interchangeably herein with "basement membrane matrix," is secreted by connective tissue cells, and comprises a variety of polysaccharides, water, elastin, and proteins that may comprise proteoglycans, collagen, entactin (nidogen), fibronectin, fibrinogen, fibrillin, laminin, and hyaluronic acid. ECM may provide the suitable substrate and microenvironment conductive for selecting and culturing the subject stem cells.

In certain embodiments, the subject stem cells are attached to or in contact with an ECM. Different types of ECM are known in the art, and may comprise different compositions including different types of proteoglycans and/or different combination of proteoglycans. The ECM may be provided by culturing ECM-producing cells, such as certain fibroblast cells. Examples of extracellular matrix-producing cells include chondrocytes that mainly produce collagen and proteoglycans; fibroblast cells that mainly produce type IV collagen, laminin, interstitial procollagens, and fibronectin; and colonic myofibroblasts that mainly produce collagens (type I, III, and V), chondroitin sulfate proteoglycan, hyaluronic acid, fibronectin, and tenascin-C.

In certain embodiments, at least some ECM is produced by the murine 3T3-J2 clone, which may be grown on top of the MATRIGEL™ basement membrane matrix (BD Biosciences) as feeder cell layer.

Alternatively, the ECM may be commercially provided. Examples of commercially available extracellular matrices are extracellular matrix proteins (Invitrogen) and MATRIGEL™ basement membrane matrix (BD Biosciences). The use of an ECM for culturing stem cells may enhance long-term survival of the stem cells and/or the continued presence of undifferentiated stem cells. An alternative may be a fibrin substrate or fibrin gel—or a scaffold, such as glycerolized allografts that are depleted from the original cells.

In certain embodiments, the ECM for use in a method of the invention comprises at least two distinct glycoproteins, such as two different types of collagen or a collagen and laminin. The ECM may be a synthetic hydrogel extracellular matrix, or a naturally occurring ECM. In certain embodiments, the ECM is provided by MATRIGEL™ basement membrane matrix (BD Biosciences), which comprises laminin, entactin, and collagen IV.

(x) Basal Medium

A cell culture medium that is used in a method of the invention may comprise any basal cell culture medium, such as culture medium buffered at about pH 7.4 (e.g., between about pH 7.2-7.6) with a carbonate-based buffer. Many commercially available tissue culture media are potentially suitable for the methods of the invention, including, but are not limited to, Dulbecco's Modified Eagle Media (DMEM, e.g., DMEM without L-glutamine but with high glucose), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media and Minimal Essential Media (MEM), Ham's F-10, Ham's F-12, Medium 199, cFAD and RPMI 1640 Media.

In certain embodiments, the epithelial stem cell culture system is cFAD, which consists of DMEM and Ham's F12 (Life Technologies, CH) medium (e.g., v/v 3:1), supplemented with, e.g., 20% of fetal bovine serum (FBS) (Life Technologies, Australia), adenine (e.g., 24.3 µg/mL, Merck, CH), insulin (e.g., 5 µg/mL, Sigma, CH), 3,3,5-triiodo-L-thyronine (T3) (e.g., 2 nM, Sigma, CH), hydrocortisone (e.g., 0.4 µg/mL, Sigma, CH), cholera toxin (e.g., 0.1 nM, Sigma, CH), and, e.g., 1% penicillin/streptomycin (Life Technologies, CH).

The cells may be cultured in an atmosphere comprising between 5-10% C02 (e.g; at least about 5% but no more than 10% C02, or about 5% C02). In certain embodiments, the cell culture medium is DMEM/F12 (e.g., 3:1 mixture) or RPMI 1640, supplemented with L-glutamine, insulin, Penicillin/streptomycin, and/or transferrin. In certain embodiments, Advanced DMEM/F12 or Advanced RPMI is used, which is optimized for serum free culture and already includes insulin. The Advanced DMEM/F12 or Advanced RPMI medium may be further supplemented with L-glutamine and Penicillin/streptomycin. In certain embodiments, the cell culture medium is supplemented with one or more a purified, natural, semi-synthetic and/or synthetic factors described herein. In certain embodiments, the cell culture medium is supplemented by about 10% fetal bovine serum (FBS) that is not heat inactivated prior to use. Additional supplements, such as, for example, B-270 Serum Free Supplement (Invitrogen), N-Acetylcysteine (Sigma) and/or N2 serum free supplement (Invitrogen), or Neurobasal (Gibco), TeSR (StemGent) may also be added to the medium.

In certain embodiments, the medium may contain one or more antibiotics to prevent contamination (such as Penicillin/streptomycin). In certain embodiments, the medium may have an endotoxin content of less that 0.1 endotoxin units per mL, or may have an endotoxin content less than 0.05 endotoxin units per mL. Methods for determining the endotoxin content of culture media are known in the art.

A cell culture medium according to the invention allows the survival and/or proliferation and/or differentiation of epithelial stem cells on an extracellular matrix. The term "cell culture medium" as used herein is synonymous with "medium," "culture medium," or "cell medium."

The modified (growth) medium of the invention comprises, in a base medium, (a) a ROCK (Rho Kinase) inhibitor; (b) a Wnt agonist; (c) a mitogenic growth factor; (d) a TGF-beta signaling pathway inhibitor, such as TGF-beta inhibitor, or a TGF-beta receptor inhibitor); and (e) insulin or IGF; and the medium optionally further comprising a Bone Morphogenetic Protein (BMP) antagonist.

Thus in one aspect, the invention provides a base medium (Base Medium) comprising: insulin or an insulin-like growth factor; T3 (3,3',5-Triiodo-L-Thyronine); hydrocortisone; adenine; EGF; and 10% fetal bovine serum (without heat inactivation), in DMEM:F12 3:1 medium supplemented with L-glutamine.

In certain embodiments, the Base Medium comprises about: 5 µg/mL insulin; 2×10"9 M T3 (3,3',5-Triiodo-L-Thyronine); 400 ng/mL hydrocortisone; 24.3 µg/mL adenine; 10 ng/mL EGF; and 10% fetal bovine serum (without heat inactivation), in DMEM:F12 3:1 medium supplemented with 1.35 mM L-glutamine.

In certain embodiments, the concentration for each of the medium components referenced in the immediate preceding paragraph is independently 2%, 5%, 10%, 15%, 20%, 25%, 30%, 35%, 40%, 45%, 50%, 60%, 70%, 80%, 90%, 95% higher or lower than the respective recited value, or 2-fold, 3-fold, 5-fold, 10-fold, 20-fold higher than the respective recited value. For example, in an illustrative medium, insulin concentration may be 6 µg/mL (20% higher than the recited 5 µg/mL), EGF concentration may be 5 ng/mL (50% lower than the recited 10 ng/mL), while the remaining components each has the same concentration recited above.

In a related aspect, the invention provides a base medium containing cholera enterotoxin. In other embodiments, the base medium does not contain cholera enterotoxin.

The Base Medium may further comprise one or more antibiotics, such as Pen/Strep, and/or gentamicin.

The base media may be used to produce Modified Growth Medium (or simply Modified Medium) by adding one or more of the factors above.

(xi) Protein Sequences of the Representative Medium Factors

Several representative (non-limiting) protein factors used in the media and methods of the invention are provided below. For each listed factor, numerous homologs or functional equivalents are known in the art, and can be readily retrieved from public databases such as GenBank, EMBL, and/or NCBI RefSeq, just to name a few. Additional proteins or peptide fragments thereof, or polynucleotides encoding the same, including functional homologs from human or non-human mammals, can be readily retrieved from public sources through, for example, sequence-based searches such as NCBI BLASTp or BLASTn or both.

```
BMP inhibitors
Noggin: (GenBank: AAA83259.1), Homo sapiens:
                                                                    (SEQ ID NO: 1)
MERCPSLGVT LYALVVVLGL RATPAGGQHY LHIRPAPSDN LPLVDLIEHP DPIFDPKEKD

LNETLLRSLL GGHYDPGFMA TSPPEDRPGG GGGAAGGAED LAELDQLLRQ

RPSGAMPSEI KGLEFSEGLA QGKKQRLSKK LRRKLQMWLW SQTFCPVLYA

WNDLGSRFWP RYVKVGSCFS KRSCSVPEGM VCKPSKSVHL TVLRWRCQRR

GGQRCGWIPI QYPIISECKC SC

Chordin (GenBank: AAG35767.1), Homo sapiens:
                                                                    (SEQ ID NO 2)
MPSLPAPPAP LLLLGLLLLG SRPARGAGPE PPVLPIRSEK EPLPVRGAAG CTFGGKVYAL

DETWHPDLGE PFGVMRCVLC ACEAPQWGRR TRGPGRVSCK NIKPECPTPA

CGQPRQLPGH CCQTCPQERS SSERQPSGLS FEYPRDPEHR SYSDRGEPGA

EERARGDGHT DFVALLTGPR SQAVARARVS LLRSSLRFSI SYRRLDRPTR

IRFSDSNGSV LFEHPAAPTQ DGLVCGVWRA VPRLSLRLLR AEQLHVALVT

LTHPSGEVWG PLIRHRALAA ETFSAILTLE GPPQQGVGGI TLLTLSDTED SLHFLLLFRG

LLEPRSGGLT QVPLRLQILH QGQLLRELQA NVSAQEPGFA EVLPNLTVQE
```

-continued

```
MDWLVLGELQ MALEWAGRPG LRI SGHIAAR KSCDVLQSVL CGADALIPVQ

TGAAGSASLT LLGNGSLIYQ VQVVGTSSEV VAMTLETKPQ RRDQRTVLCH

MAGLQPGGHT AVGICPGLGA RGAHMLLQNE LFLNVGTKDF PDGELRGHVA

ALPYCGHSAR HDTLPVPLAG ALVLPPVKSQ AAGHAWLSLD THCHLHYEVL

LAGLGGSEQG TVTAHLLGPP GTPGPRRLLK GFYGSEAQGV VKDLEPELLR

HLAKGMASLL ITTKGSPRGE LRGQVHIANQ CEVGGLRLEA AGAEGVRALG

APDTASAAPP VVPGLPALAP AKPGGPGRPR DPNTCFFEGQ QRPHGARWAP

NYDPLCSLCT CQRRTVICDP VVCPPPSCPH PVQAPDQCCP VCPEKQDVRD

LPGLPRSRDP GEGCYFDGDR SWRAAGTRWH PVVPPFGLIK CAVCTCKGGT

GEVHCEKVQC PRLACAQPVR VNPTDCCKQC PVGSGAHPQL GDPMQADGPR

GCRFAGQWFP ESQSWHPSVP PFGEMSCITC RCGAGVPHCE RDDCSLPLSC

GSGKESRCCS RCTAHRRPAP ETRTDPELEK EAEGS
```

Follistatin (GenBank: AAH04107.1) *Homo sapiens*:
(SEQ ID NO: 3)
```
MVRARHQPGG LCLLLLLLCQ FMEDRSAQAG NCWLRQAKNG RCQVLYKTEL

SKEECCSTGR LSTSWTEEDV NDNTLFKWMI FNGGAPNCIP CK-ETCENVDC
GPGKKCRMNK KNKPRCVCAP

DCSNITWKGP VCGLDGKTYR NECALLKARC KEQPELEVQY QGRCKKTCRD

VFCPGSSTCV VDQTNNAYCV TCNRICPEPA SSEQYLCGND GVTYSSACHL

RKATCLLGRS IGLAYEGKCI KAKSCEDIQC TGGKKCLWDF KVGRGRCSLC

DELCPDSKSD EPVCASDNAT YASECAMKEA ACSSGVLLEV KHSGSCNSIS

EDTEEEEEDE DQDYSFPISS ILEW
```

DAN (GenBank: BAA92265.1) *Homo sapiens*:
(SEQ ID NO: 4)
```
MLRVLVGAVL PAMLLAAPPP INKLALFPDK SAWCEAKNIT QIVGHSGCEA KSIQNRACLG

QCFSYSVPNT FPQSTESLVH CDSCMPAQSM WEIVTLECPG HEEVPRVDKL

VEKILHCSCQ ACGKEPSHEG LSVYVQGEDG PGSQPGTHPH PHPHPHPGGQ

TPEPEDPPGA PHTEEEGAED
```

Cerberus (NCBI Reference Sequence: NP_005445.1) *Homo sapiens*:
(SEQ ID NO: 5)
```
MHLLLFQLLV LLPLGKTTRH QDGRQNQSSL SPVLLPRNQR ELPTGNHEEA

EEKPDLFVAV PHLVATSPAG EGQRQREKML SRFGRFWKKP EREMHPSRDS

DSEPFPPGTQ SLIQPIDGMK MEKSPLREEA KKFWHHFMFR KTPASQGVIL

PIKSHEVHWE TCRTVPFSQT ITHEGCEKVV VQNNLCFGKC GSVHFPGAAQ

HSHTSCSHCL PAKFTTMHLP LNCTELSSVI KVVMLVEECQ CKVKTEHEDG

HILHAGSQDS FIPGVSA
```

Gremlin (GenBank: AAF06677.1) *Homo sapiens*:
(SEQ ID NO: 6)
```
MSRTAYTVGA LLLLLGTLLP AAEGKKKGSQ GAIPPPDKAQ HNDSEQTQSP

QQPGSRNRGR GQGRGTAMPG EEVLESSQEA LHVTERKYLK RDWCKTQPLK

QTIHEEGCNS RTI INRFCYG QCNSFYIPRH IRKEEGSFQS CSFCKPKKFT TMMVTLNCPE

LQPPTKKKRV TRVKQCRCIS IDLD
```

-continued

Sclerostin/SOST (GenBank: AAK13451.1) Homo sapiens:
(SEQ ID NO: 7)
MQLPLALCLV CLLVHTAFRV VEGQGWQAFK NDATEI IPEL GEYPEPPPEL

ENNKTMNRAE NGGRPPHHPF ETKDVSEYSC RELHFTRYVT DGPCRSAKPV

TELVCSGQCG PARLLPNAIG RGKWWRPSGP DFRCIPDRYR AQRVQLLCPG

GEAPRARKVR LVASCKCKRL TRFHNQSELK DFGTEAARPQ KGRKPRPRAR

SAKANQAELE NAY

Decorin (GenBank: AAB60901.1) Homo sapiens:
(SEQ ID NO: 8)
MKATI ILLLL AQVSWAGPFQ QRGLFDFMLE DEASGIGPEV PDDRDFEPSL

GPVCPFRCQC HLRVVQCSDL alpha-2 macroglobulin (GenBank: EAW88590.1) Homo sapiens:
(SEQ ID NO 9)
MGKNKLLHPS LVLLLLVLLP TDASVSGKPQ YMVLVPSLLH TETTEKGCVL LSYLNETVTV

SASLESVRGN RSLFTDLEAE NDVLHCVAFA VPKSSSNEEV MFLTVQVKGP

TQEFKKRTTV MVKNEDSLVF VQTDKSIYKP GQTVKFRVVS MDENFHPLNE LIPLVYIQDP

KGNRIAQWQS FQLEGGLKQF SFPLSSEPFQ GSYKVVVQKK SGGRTEHPFT

VEEFVLPKFE VQVTVPKIIT ILEEEMNVSV CGLYTYGKPV PGHVTVSICR KYSDASDCHG

EDSQAFCEKF SGQLNSHGCF YQQVKTKVFQ LKRKEYEMKL HTEAQIQEEG

TVVELTGRQS SEITRTITKL SFVKVDSHFR QGIPFFGQVR LVDGKGVPIP NKVIFIRGNE

ANYYSNATTD EHGLVQFSIN TTNVMGTSLT VRVNYKDRSP CYGYQWVSEE

HEEAHHTAYL VFSPSKSFVH LEPMSHELPC GHTQTVQAHY ILNGGTLLGL KKLSFYYLIM

AKGGIVRTGT HGLLVKQEDM KGHFSISIPV KSDIAPVARL LIYAVLPTGD VIGDSAKYDV

ENCLANKVDL SFSPSQSLPA SHAHLRVTAA PQSVCALRAV DQSVLLMKPD

AELSASSVYN LLPEKDLTGF PGPLNDQDDE DCINRHNVYI NGITYTPVSS TNEKDMYSFL

EDMGLKAFTN SKIRKPKMCP QLQQYEMHGP EGLRVGFYES DVMGRGHARL

VHVEEPHTET VRKYFPETWI WDLVVVNSAG VAEVGVTVPD TITEWKAGAF

CLSEDAGLGI SSTASLRAFQ PFFVELTMPY SVIRGEAFTL KATVLNYLPK CIRVSVQLEA

SPAFLAVPVE KEQAPHCICA NGRQTVSWAV TPKSLGNVNF TVSAEALESQ

ELCGTEVPSV PEHGRKDTVI KPLLVEPEGL EKETTFNSLL CPSGGEVSEE LSLKLPPNVV

EESARASVSV LGDILGSAMQ NTQNLLQMPY GCGEQNMVLF APNIYVLDYL

NETQQLTPEI KSKAIGYLNT GYQRQLNYKH YDGSYSTFGE RYGRNQGNTW

LTAFVLKTFA QARAYIFIDE AHITQALIWL SQRQKDNGCF RSSGSLLNNA IKGGVEDEVT

LSAYITIALL EIPLTVTHPV VRNALFCLES AWKTAQEGDH GSHVYTKALL AYAFALAGNQ

DKRKEVLKSL NEEAVKKDNS VHWERPQKPK APVGHFYEPQ APSAEVEMTS

YVLLAYLTAQ PAPTSEDLTS ATNIVKWITK QQNAQGGFSS TQDTVVALHA LSKYGAATFT

RTGKAAQVTI QSSGTFSSKF QVDNNNRLLL QQVSLPELPG EYSMKVTGEG

CVYLQTSLKY NILPEKEEFP FALGVQTLPQ TCDEPKAHTS FQISLSVSYT GSRSASNMAI

VDVKMVSGFI PLKPTVKMLE RSNHVSRTEV SSNHVLIYLD KVSNQTLSLF FTVLQDVPVR

DLKPAIVKVY DYYETDEFAI AEYNAPCSKD LGNA

Wnt Agonists
R-spondin 1 (GenBank: ABC54570.1) Homo sapiens:
(SEQ ID NO: 10)
MRLGLCVVAL VLSWTHLTIS SRGIKGKRQR RISAEGSQAC AKGCELCSEV

NGCLKCSPKL FILLERNDIR QVGVCLPSCP PGYFDARNPD MNKCIKCKIE HCEACFSHNF

```
CTKCKEGLYL HKGRCYPACP EGSSAANGTM ECSSPAQCEM SEWSPWGPCS

KKQQLCGFRR GSEERTRRVL HAPVGDHAAC SDTKETRRCT VRRVPCPEGQ

KRRKGGQGRR ENANRNLARK ESKEAGAGSR RRKGQQQQQQ QGTVGPLTSA GPA
```

R-spondin 2 (NCBI Reference Sequence: NP_848660.3) *Homo sapiens*:
(SEQ ID NO: 11)
```
MQFRLFSFAL I ILNCMDYSH CQGNRWRRSK RASYVSNPIC KGCLSCSKDN

GCSRCQQKLF FFLRREGMRQ YGECLHSCPS GYYGHRAPDM NRCARCRIEN

CDSCFSKDFC TKCKVGFYLH RGRCFDECPD GFAPLEETME CVEGCEVGHW

SEWGTCSRNN RTCGFKWGLE TRTRQIVKKP VKDTILCPTI AESRRCKMTM

RHCPGGKRTP KAKEKRNKKK KRKLIERAQE QHSVFLATDR ANQ
```

R-spondin 3 (NCBI Reference Sequence: NP_116173.2) *Homo sapiens*:
(SEQ ID NO: 12)
```
MHLRLISWLF I ILNFMEYIG SQNASRGRRQ RRMHPNVSQG CQGGCATCSD YNGCLSCKPR

LFFALERIGM KQIGVCLSSC PSGYYGTRYP DINKCTKCKA DCDTCFNKNF CTKCKSGFYL

HLGKCLDNCP EGLEANNHTM ECVSIVHCEV SEWNPWSPCT KKGKTCGFKR GTETRVREI I

QHPSAKGNLC PPTNETRKCT VQRKKCQKGE RGKKGRERKR KKPNKGESKE AIPDSKSLES

SKEIPEQREN KQQQKKRKVQ DKQKSVSVST VH
```

R-spondin 4 (NCBI Reference Sequence: NP_001025042.2) *Homo sapiens*: isoform 1
(SEQ ID NO: 13)
```
MRAPLCLLLL VAHAVDMLAL NRRKKQVGTG LGGNCTGCI I CSEENGCSTC QQRLFLFIRR

EGIRQYGKCL HDCPPGYFGI RGQEVNRCKK CGATCESCFS QDFCIRCKRQ FYLYKGKCLP

TCPPGTLAHQ NTRECQGECE LGPWGGWSPC THNGKTCGSA WGLESRVREA GRAGHEEAAT

CQVLSESRKC PIQRPCPGER SPGQKKGRKD RRPRKDRKLD RRLDVRPRQP GLQP
```

R-spondin 4 (NCBI Reference Sequence: NP_001035096.1) *Homo sapiens*: isoform 2
(SEQ ID NO: 14)
```
MRAPLCLLLL VAHAVDMLAL NRRKKQVGTG LGGNCTGCI I CSEENGCSTC QQRLFLFIRR

EGIRQYGKCL HDCPPGYFGI RGQEVNRCKK CGATCESCFS QDFCIRCKRQ FYLYKGKCLP

TCPPGTLAHQ NTRECQERSP GQKKGRKDRR PRKDRKLDRR LDVRPRQPGL QP
```

Norrin
norrin precursor [*Homo sapiens*]
NCBI Reference Sequence: NP_000257.1
(SEQ ID NO: 15)
```
MRKHVLAASF SMLSLLVIMG DTDSKTDSSF IMDSDPRRCM RHHYVDS I SH

PLYKCSSKMV LLARCEGHCS QASRSEPLVS FSTVLKQPFR SSCHCCRPQT

SKLKALRLRC SGGMRLTATY RYILSCHCEE CNS
```

WNT3A [*Homo sapiens*]
GenBank: BAB61052.1
(SEQ ID NO: 16)
```
MAPLGYFLLL CSLKQALGSY PIWWSLAVGP QYSSLGSQPI LCASIPGLVP KQLRFCRNYV

EIMPSVAEGI KIGIQECQHQ FRGRRWNCTT VHDSLAIFGP VLDKATRESA FVHAIASAGV

AFAVTRSCAE GTAAICGCSS RHQGSPGKGW KWGGCSEDIE FGGMVSREFA

DARENRPDAR SAMNRHNNEA GRQAIASHMH LKCKCHGLSG SCEVKTCWWS

QPDFRAIGDF LKDKYDSASE MVVEKHRESR GWVETLRPRY TYFKVPTERD

LVYYEASPNF CEPNPETGSF GTRDRTCNVS SHGIDGCDLL CCGRGHNARA

ERRREKCRCV FHWCCYVSCQ ECTRVYDVHT CK
```

WNT6 [*Homo sapiens*]
GenBank: AAG45154.1
(SEQ ID NO: 17)
```
AVGSPLVMDP TSICRKARRL AGRQAELCQA EPEVVAELAR GARLGVRECQ

FQFRFRRWNC SSHSKAFGRI LQQDIRETAF VFAITAAGAS HAVTQACSMG
```

-continued

ELLQCGCQAP RGRAPPRPSG LPGTPGPPGP AGSPEGSAAW EWGGCGDDVD

FGDEKSRLFM DARHKRGRGD IRALVQLHNN EAGRLAVRSH TRTECKCHGL

SGSCALRTCW QKLPPFREVG ARLLERFHGA SRVMGTNDGK ALLPAVRTLK

PPGRADLLYA ADSPDFCAPN RRTGSPGTRG RACNSSAPDL SGCDLLCCGR

GHRQESVQLE ENCLCRFHWC CVVQCHRCRV RKELSLCL

Mitogenic Factors
FGF-2 = bFGF (niProtKB/Swiss-Prot: P09038.3) *Homo sapiens*:
(SEQ ID NO: 18)
MVGVGGGDVE DVTPRPGGCQ I SGRGARGCN GIPGAAAWEA ALPRRRPRRH PSVNPRSRAA

GSPRTRGRRT EERPSGSRLG DRGRGRALPG GRLGGRGRGR APERVGGRGR GRGTAAPRAA

PAARGSRPGP AGTMAAGSIT TLPALPEDGG SGAFPPGHFK DPKRLYCKNG GFFLRIHPDG

RVDGVREKSD PHIKLQLQAE ERGVVSIKGV CANRYLAMKE DGRLLASKCV TDECFFFERL

ESNNYNTYRS RKYTSWYVAL KRTGQYKLGS KTGPGQKAIL FLPMSAKS

FGF7 (GenBank: CAG46799.1) *Homo sapiens*:
(SEQ ID NO: 19)
MHKWILTWIL PTLLYRSCFH IICLVGTISL ACNDMTPEQM ATNVNCSSPE RHTRSYDYME

GGDIRVRRLF CRTQWYLRID KRGKVKGTQE MKNNYNIMEI RTVAVGIVAI KGVESEFYLA

MNKEGKLYAK KECNEDCNFK ELILENHYNT YASAKWTHNG GEMFVALNQK

GIPVRGKKTK KEQKTAHFLP MAIT

FGF10 (GenBank: CAG46489.1) *Homo sapiens*:
(SEQ ID NO: 20)
MWKWILTHCA SAFPHLPGCC CCFLLLFLV SSVPVTCQAL GQVMVSPEAT

NSSSSSFSSP SSAGRHVRSY NHLQGDVRWR KLFSFTKYFL KIEKNGKVSG

TKKENCPYS I LEITSVEIGV VAVKAINSNY YLAMNKKGKL YGSKEFNNDC KLKERIEENG

YNTYASFNWQ HNGRQMYVAL NGKGAPRRGQ KTRRKNTSAH FLPMVVHS

EGF (GenBank: EAX06257.1) *Homo sapiens*:
(SEQ ID NO 21)
MLLLTLI ILLP VVSKFSFVSL SAPQHWSCPE GTLAGNGNST CVGPAPFLIF SHGNSIFRID

TEGTNYEQLV VDAGVSVIMD FHYNEKRIYW VDLERQLLQR VFLNGSRQER

VCNIEKNVSG MAINWINEEV IWSNQQEGII TVTDMKGNNS HILLSALKYP ANVAVDPVER

FIFWSSEVAG SLYRADLDGV GVKALLETSE KITAVSLDVL DKRLFWIQYN REGSNSLICS

CDYDGGSVHI SKHPTQHNLF AMSLFGDRIF YSTWKMKTIW IANKHTGKDM

VRINLHSSFV PLGELKVVHP LAQPKAEDDT WEPEQKLCKL RKGNCSSTVC

GQDLQSHLCM CAEGYALSRD RKYCEDVNEC AFWNHGCTLG CKNTPGSYYC

TCPVGFVLLP DGKRCHQLVS CPRNVSECSH DCVLTSEGPL CFCPEGSVLE

RDGKTCSGCS SPDNGGCSQL CVPLSPVSWE CDCFPGYDLQ LDEKSCAASG

PQPFLLFANS QDIRHMHFDG TDYGTLLSQQ MGMVYALDHD PVENKIYFAH

TALKWIERAN MDGSQRERLI EEGVDVPEGL AVDWIGRRFY WTDRGKSLIG

RSDLNGKRSK IITKENISQP RGIAVHPMAK RLFWTDTGIN PRIESSSLQG LGRLVIASSD

LIWPSGITID FLTDKLYWCD AKQSVIEMAN LDGSKRRRLT QNDVGHPFAV

AVFEDYVWFS DWAMPSVMRV NKRTGKDRVR LQGSMLKPSS LVVVHPLAKP

GADPCLYQNG GCEHICKKRL GTAWCSCREG FMKASDGKTC LALDGHQLLA

GGEVDLKNQV TPLDILSKTR VSEDNITESQ HMLVAEIMVS DQDDCAPVGC

SMYARCISEG EDATCQCLKG FAGDGKLCSD IDECEMGVPV CPPASSKCIN

TEGGYVCRCS EGYQGDGIHC LDIDECQLGE HSCGENASCT NTEGGYTCMC

-continued

AGRLSEPGLI CPDSTPPPHL REDDHHYSVR NSDSECPLSH DGYCLHDGVC

MYIEALDKYA CNCVVGYIGE RCQYRDLKWW ELRHAGHGQQ QKVIVVAVCV

VVLVMLLLLS LWGAHYYRTQ KLLSKNPKNP YEESSRDVRS RRPADTEDGM

SSCPQPWFVV IKEHQDLKNG GQPVAGEDGQ AADGSMQPTS WRQEPQLCGM

GTEQGCWIPV SSDKGSCPQV MERSFHMPSY GTQTLEGGVE KPHSLLSANP

LWQQRALDPP HQMELTQ

TGFa Homo sapiens: protransforming growth factor alpha isoform 1
preproprotein [Homo sapiens] NCBI Reference Sequence: NP_003227.1
(SEQ ID NO: 22)
MVPSAGQLAL FALGIVLAAC QALENSTSPL SADPPVAAAV VSHFNDCPDS

HTQFCFHGTC RFLVQEDKPA CVCHSGYVGA RCEHADLLAV VAASQKKQAI

TALVVVSIVA LAVLIITCVL IHCCQVRKHC EWCRALICRH EKPSALLKGR TACCHSETVV protransforming growth factor alpha isoform 2 preproprotein
[Homo sapiens] NCBI Reference Sequence: NP_001093161.1
(SEQ ID NO: 23)
MVPSAGQLAL FALGIVLAAC QALENSTSPL SDPPVAAAVV SHFNDCPDSH

TQFCFHGTCR FLVQEDKPAC VCHSGYVGAR CEHADLLAVV AASQKKQAIT

ALVVVSIVAL AVLIITCVLI HCCQVRKHCE WCRALICRHE KPSALLKGRT ACCHSETVV

Transforming growth factor alpha [synthetic construct]
GenBank: AAX43291.1
(SEQ ID NO: 24)
MVPLAGQLAL FALGIVLAAC QALENSTSPL SDPPVAAAVV SHFNDCPDSH

TQFCFHGTCR FLVQEDKPAC VCHSGYVGAR CEHADLLAVV AASQKKQAIT

ALVVVSIVAL AVLIITCVLI HCCQVRKHCE WCRALICRHE KPSALLKGRT ACCHSETVVL

TGF alpha containing:
(SEQ ID NO: 25)
VVSHFNDCPD SHTQFCFHGT CRFLVQEDKP ACVCHSGYVG ARCEHA DLLA BDNF (UniProtKB/Swiss-Prot: P23560.1) Homo sapiens:
(SEQ ID NO 26)
MTILFLTMVI SYFGCMKAAP MKEA IRGQG GLAYPGVRTH GTLESVNGPK AGSRGLTSLA

DTFEHVIEEL LDEDQKVRPN EENNKDADLY TSRVMLSSQV PLEPPLLFLL EEYKNYLDAA

NMSMRVRRHS DPARRGELSV CDSISEWVTA ADKKTAVDMS GGTVTVLEKV PVSKGQLKQY

FYETKCNPMG YTKEGCRGID KRHWNSQCRT TQSYVRALTM DSKKRIGWRF IRIDTSCVCT

LTIKRGR

KGF (GenBank: AAB21431.1) Homo sapiens:
(SEQ ID NO: 27)
MHKWILTWIL PTLLYRSCFH IICLVGTISL ACNDMTPEQM ATNVNCSSPE RHTRSYDYME

GGDIRVRRLF CRTQWYLRID KRGKVKGTQE MKNNYNIMEI RTVAVGIVAI KGVESEFYLA

MNKEGKLYAK KECNEDCNFK ELILENHYNT YASAKWTHNG GEMFVALNQK

GIPVRGKKTK KEQKTAHFLP MAIT

Notch Agonist
Jagged-1 (GenBank: ACJ68517.1) Homo sapiens:
(SEQ ID NO: 28)
MRSPRTRGRS GRPLSLLLAL LCALRAKVCG ASGQFELEIL SMQNVNGELQ NGNCCGGARN

PGDRKCTRDE CDTYFKVCLK EYQSRVTAGG PCSFGSGSTP VIGGNTFNLK ASRGNDRNRI

VLPFSFAWPR SYTLLVEAWD SSNDTVQPDS IIEKASHSGM INPSRQWQTL KQNTGVAHFE

YQIRVTCDDY YYGFGCNKFC RPRDDFFGHY ACDQNGNKTC MEGWMGPECN RAICRQGCSP

KHGSCKLPGD CRCQYGWQGL YCDKCIPHPG CVHGICNEPW QCLCETNWGG QLCDKDLNYC

GTHQPCLNGG TCSNTGPDKY QCSCPEGYSG PNCEIAEHAC LSDPCHNRGS CKETSLGFEC

-continued

ECSPGWTGPT CSTNIDDCSP NNCSHGGTCQ DLVNGFKCVC PPQWTGKTCQ LDANECEAKP

CVNAKSCKNL IASYYCDCLP GWMGQNCDIN INDCLGQCQN DASCRDLVNG YRCICPPGYA

GDHCERDIDE CASNPCLNGG HCQNEINRFQ CLCPTGFSGN LCQLDIDYCE PNPCQNGAQC

YNRASDYFCK CPEDYEGKNC SHLKDHCRTT PCEVIDSCTV AMASNDTPEG VRYISSNVCG

PHGKCKSQSG GKFTCDCNKG FTGTYCHENI NDCESNPCRN GGTCIDGVNS YKCICSDGWE

GAYCETNIND CSQNPCHNGG TCRDLVNDFY CDCKNGWKGK TCHSRDSQCD EATCNNGGTC

YDEGDAFKCM CPGGWEGTTC NIARNSSCLP NPCHNGGTCV VNGESFTCVC KEGWEGPICA

QNTNDCSPHP CYNSGTCVDG DNWYRCECAP GFAGPDCRIN INECQSSPCA FGATCVDEIN

GYRCVCPPGH SGAKCQEVSG RPCITMGSVI PDGAKWDDDC NTCQCLNGRI ACSKVWCGPR

PCLLHKGHSE CPSGQSCIPI LDDQCFVHPC TGVGECRSSS LQPVKTKCTS DSYYQDNCAN

ITFTFNKEMM SPGLTTEHIC SELRNLNILK NVSAEYSIYI ACEPSPSANN EIHVAISAED

IRDDGNPIKE ITDKIIDLVS KRDGNSSLIA AVAEVRVQRR PLKNRTDFLV PLLSSVLTVA

WICCLVTAFY WCLRKRRKPG SHTHSASEDN TTNNVREQLN QIKNPIEKHG ANTVPIKDYE

NKNSKMSKIR THNSEVEEDD MDKHQQKARF AKQPAYTLVD REEKPPNGTP TKHPNWTNKQ

DNRDLESAQS LNRMEYIV

Jagged-1 peptide (SEQ ID NO: 29)
MRGSHHHHHH GSIEGRSAVT CDDYYYGFGC NKFCRPRDDF FGHYACDQNG NKTCMEGWMG

PECNRAICRQ GCSPKHGSCK LPGDCRCQYG WQGLYCDKCI PHPGCVHGIC NEPWQCLCET

NWGGQLCDKD LNYCGTHQPC LNGGTCSNTG PDKYQCSCPE GYSGPNCEI

Jagged-1 peptide (SEQ ID NO: 30)
CDDYYYGFGCNKFCRPR

Jagged2 [Homo sapiens]
GenBank: AAD15562.1

(SEQ ID NO: 31)
MRAQGRGRLP RRLLLLLALW VQAARPMGYF ELQLSALRNV NGELLSGACC DGDGRTTRAG

GCGHDECDTY VRVCLKEYQA KVTPTGPCSY GHGATPVLGG NSFYLPPAGA AGDRARARAR

AGGDQDPGLV VIPFQFAWPR SFTLIVEAWD WDNDTTPNEE LLIERVSHAG MINPEDRWKS

LHFSGHVAHL ELQIRVRCDE NYYSATCNKF CRPRNDFFGH YTCDQYGNKA CMDGWMGKEC

KEAVCKQGCN LLHGGCTVPG ECRCSYGWQG RFCDECVPYP GCVHGSCVEP WQCNCETNWG

GLLCDKDLNY CGSHHPCTNG GTCINAEPDQ YRCTCPDGYS GRNCEKAEHA CTSNPCANGG

SCHEVPSGFE CHCPSGWSGP TCALDIDECA SNPCAAGGTC VDQVDGFECI CPEQWVGATC

QLDANECEGK PCLNAFSCKN LIGGYYCDCI PGWKGINCHI NVNDCRGQCQ HGGTCKDLVN

GYQCVCPRGF GGRHCELERD ECASSPCHSG GLCEDLADGF HCHCPQGFSG PLCEVDVDLC

EPSPCRNGAR CYNLEGDYYC ACPDDFGGKN CSVPREPCPG GACRVIDGCG SDAGPGMPGT

AASGVCGPHG RCVSQPGGNF SCICDSGFTG TYCHENIDDC LGQPCRNGGT CIDEVDAFRC

FCPSGWEGEL CDTNPNDCLP DPCHSRGRCY DLVNDFYCAC DDGWKGKTCH SREFQCDAYT

CSNGGTCYDS GDTFRCACPP GWKGSTCAVA KNSSCLPNPC VNGGTCVGSG ASFSCICRDG

WEGRTCTHNT NDCNPLPCYN GGICVDGVNW FRCECAPGFA GPDCRINIDE CQSSPCAYGA

TCVDEINGYR CSCPPGRAGP RCQEVIGFGR SCWSRGTPFP HGSSWVEDCN SCRCLDGRRD

CSKVWCGWKP CLLAGQPEAL SAQCPLGQRC LEKAPGQCLR PPCEAWGECG AEEPPSTPCL

PRSGHLDNNC ARLTLHFNRD HVPQGTTVGA ICSGIRSLPA TRAVARDRLL VLLCDRASSG

ASAVEVAVSF SPARDLPDSS LIQGAAHAIV AAITQRGNSS LLLAVTEVKV ETVVTGGSST

-continued

```
GLLVPVLCGA FSVLWLACVV LCVWWTRKRR KERERSRLPR EESANNQWAP LNPIRNPIER

PGGHKDVLYQ CKNFTPPPRR ADEALPGPAG HAAVREDEED EDLGRGEEDS LEAEKFLSHK

FTKDPGRSPG RPAHWASGPK VDNRAVRSIN EARYAGKE
```

Delta 1 = delta-like protein 1 (NCBI Reference Sequence:
P_005609.3; GenBank: AF196571.1) *Homo sapiens*:
(SEQ ID NO: 32)

```
GSRCALALA VLSALLCQVW SSGVFELKLQ EFVNKKGLLG NRNCCRGGAG PPPCACRTFF

RVCLKHYQAS VSPEPPCTYG SAVTPVLGVD SFSLPDGGGA DSAFSNPIRF PFGFTWPGTF

SLIIEALHTD SPDDLATENP ERLISRLATQ RHLTVGEEWS QDLHSSGRTD LKYSYRFVCD

EHYYGEGCSV FCRPRDDAFG HFTCGERGEK VCNPGWKGPY CTEPICLPGC DEQHGFCDKP

GECKCRVGWQ GRYCDECIRY PGCLHGTCQQ PWQCNCQEGW GGLFCNQDLN YCTHHKPCKN

GATCTNTGQG SYTCSCRPGY TGATCELGID ECDPSPCKNG GSCTDLENSY SCTCPPGFYG

KICELSAMTC ADGPCFNGGR CSDSPDGGYS CRCPVGYSGF NCEKKIDYCS SSPCSNGAKC

VDLGDAYLCR CQAGFSGRHC DDNVDDCASS PCANGGTCRD GVNDFSCTCP PGYTGRNCSA

PVSRCEHAPC HNGATCHERG HRYVCECARG YGGPNCQFLL PELPPGPAVV DLTEKLEGQG

GPFPWVAVCA GVILVLMLLL GCAAVVVCVR LRLQKHRPPA DPCRGETETM NNLANCQREK

DISVSIIGAT QIKNTNKKAD FHGDHSADKN GFKARYPAVD YNLVQDLKGD DTAVRDAHSK

RDTKCQPQGS SGEEKGTPTT LRGGEASERK RPDSGCSTSK DTKYQSVYVI SEEKDECVIA

TEV
```

Delta-4 = delta-like protein 4 precursor [*Homo sapiens*]
NCBI Reference Sequence: NP_061947.1
(SEQ ID NO: 33)

```
MAAASRSASG WALLLLVALW QQRAAGSGVF QLQLQEFINE RGVLASGRPC EPGCRTFFRV

CLKHFQAVVS PGPCTFGTVS TPVLGTNSFA VRDDSSGGGR NPLQLPFNFT WPGTFSLIIE

AWHAPGDDLR PEALPPDALI SKIAIQGSLA VGQNWLLDEQ TSTLTRLRYS YRVICSDNYY

GDNCSRLCKK RNDHFGHYVC QPDGNLSCLP GWTGEYCQQP ICLSGCHEQN GYCSKPAECL

CRPGWQGRLC NECIPHNGCR HGTCSTPWQC TCDEGWGGLF CDQDLNYCTH HSPCKNGATC

SNSGQRSYTC TCRPGYTGVD CELELSECDS NPCRNGGSCK DQEDGYHCLC PPGYYGLHCE

HSTLSCADSP CFNGGSCRER NQGANYACEC PPNFTGSNCE KKVDRCTSNP CANGGQCLNR

GPSRMCRCRP GFTGTYCELH VSDCARNPCA HGGTCHDLEN GLMCTCPAGF SGRRCEVRTS

IDACASSPCF NRATCYTDLS TDTFVCNCPY GFVGSRCEFP VGLPPSFPWV AVSLGVGLAV

LLVLLGMVAV AVRQLRLRRP DDGSREAMNN LSDFQKDNLI PAAQLKNTNQ KKELEVDCGL

DKSNCGKQQN HTLDYNLAPG PLGRGTMPGK FPHSDKSLGE KAPLRLHSEK PECRISAICS

PRDSMYQSVC LISEERNECV IATEV
```

Delta-like protein 3 isoform 1 precursor [*Homo sapiens*]
NCBI Reference Sequence: NP_058637.1
(SEQ ID NO: 34)

```
MVSPRMSGLL SQTVILALIF LPQTRPAGVF ELQIHSFGPG PGPGAPRSPC SARLPCRLFF

RVCLKPGLSE EAAESPCALG AALSARGPVY TEQPGAPAPD LPLPDGLLQV PFRDAWPGTF

SFIIETWREE LGDQIGGPAW SLLARVAGRR RLAAGGPWAR DIQRAGAWEL RFSYRARCEP

PAVGTACTRL CRPRSAPSRC GPGLRPCAPL EDECEAPLVC RAGCSPEHGF CEQPGECRCL

EGWTGPLCTV PVSTSSCLSP RGPSSATTGC LVPGPGPCDG NPCANGGSCS ETPRSFECTC

PRGFYGLRCE VSGVTCADGP CFNGGLCVGG ADPDSAYICH CPPGFQGSNC EKRVDRCSLQ

PCRNGGLCLD LGHALRCRCR AGFAGPRCEH DLDDCAGRAC ANGGTCVEGG GAHRCSCALG

FGGRDCRERA DPCAARPCAH GGRCYAHFSG LVCACAPGYM GARCEFPVHP DGASALPAAP
```

```
PGLRPGDPQR YLLPPALGLL VAAGVAGAAL LLVHVRRRGH SQDAGSRLLA GTPEPSVHAL

PDALNNLRTQ EGSGDGPSSS VDWNRPEDVD PQGIYVISAP SIYAREVATP LFPPLHTGRA

GQRQHLLFPY PSSILSVK

Delta-like protein 3 isoform 2 precursor [Homo sapiens]
NCBI Reference Sequence: NP_982353.1
                                                                 (SEQ ID NO: 35)
MVSPRMSGLL SQTVILALIF LPQTRPAGVF ELQIHSFGPG PGPGAPRSPC SARLPCRLFF

RVCLKPGLSE EAAESPCALG AALSARGPVY TEQPGAPAPD LPLPDGLLQV PFRDAWPGTF

SFIIETWREE LGDQIGGPAW SLLARVAGRR RLAAGGPWAR DIQRAGAWEL RFSYRARCEP

PAVGTACTRL CRPRSAPSRC GPGLRPCAPL EDECEAPLVC RAGCSPEHGF CEQPGECRCL

EGWTGPLCTV PVSTSSCLSP RGPSSATTGC LVPGPGPCDG NPCANGGSCS ETPRSFECTC

PRGFYGLRCE VSGVTCADGP CFNGGLCVGG ADPDSAYICH CPPGFQGSNC EKRVDRCSLQ

PCRNGGLCLD LGHALRCRCR AGFAGPRCEH DLDDCAGRAC ANGGTCVEGG GAHRCSCALG

FGGRDCRERA DPCAARPCAH GGRCYAHFSG LVCACAPGYM GARCEFPVHP DGASALPAAP

PGLRPGDPQR YLLPPALGLL VAAGVAGAAL LLVHVRRRGH SQDAGSRLLA GTPEPSVHAL

PDALNNLRTQ EGSGDGPSSS VDWNRPEDVD PQGIYVISAP SIYAREA
``` d. IBD Gene Sequence/pCD Gene Sequences

Figure 1A:
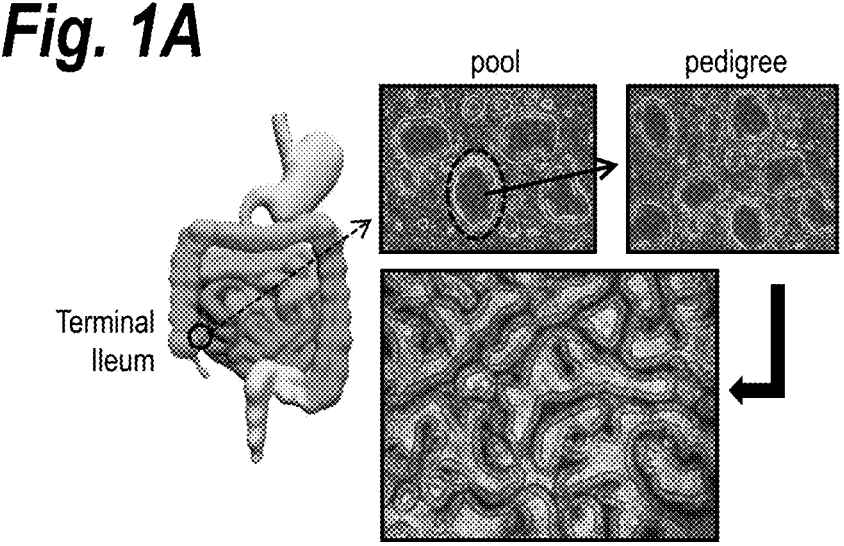
FIG. 1A, FIG. 1B, FIG. 1C, FIG. 1D, FIG. 1E, and FIG. 1F. Mucosal stem cells from pediatric Crohn's FIG. 1A. Schematic of endoscopic sampling of biopsies from the terminal ileum (TI) and right colon (RC) and images of the pools of single cell-derived epithelial colonies from the TI in 2-D culture subsequent generation of discrete pedigrees for analysis. We cloned and propagated mucosal stem cells from endoscopic biopsies of children newly diagnosed with Crohn's disease and age-matched controls were cloned and propagated according to the methods of the present application. 150-200 independent stem cell colonies derived per 1 cubic millimeter biopsies of the terminal ileum. Stem cells were maintained in culture for >8 weeks as either "pools" of clones or as subcloned "pedigrees" derived from single cells. Pedigrees consist of highly immature stem cells that can be differentiated to a 3-D intestinal mucosa by exposure to an air-liquid interface FIG. 1B. Principal component analysis of whole genome expression profiles from discrete pedigrees of terminal ileum of Crohn's (CD1, CD2, and CD3), normal functional control (FC1), and 22-week fetus (fetal TI) as indicated. Cluster Analysis revealed a bimodal distribution of gene expression profiles with a Normal cluster dominated by control and fetal terminal ileum pedigrees, and a Crohn's cluster occupied by most of the stem cell pedigrees from Crohn's patients.
Figure 1B:
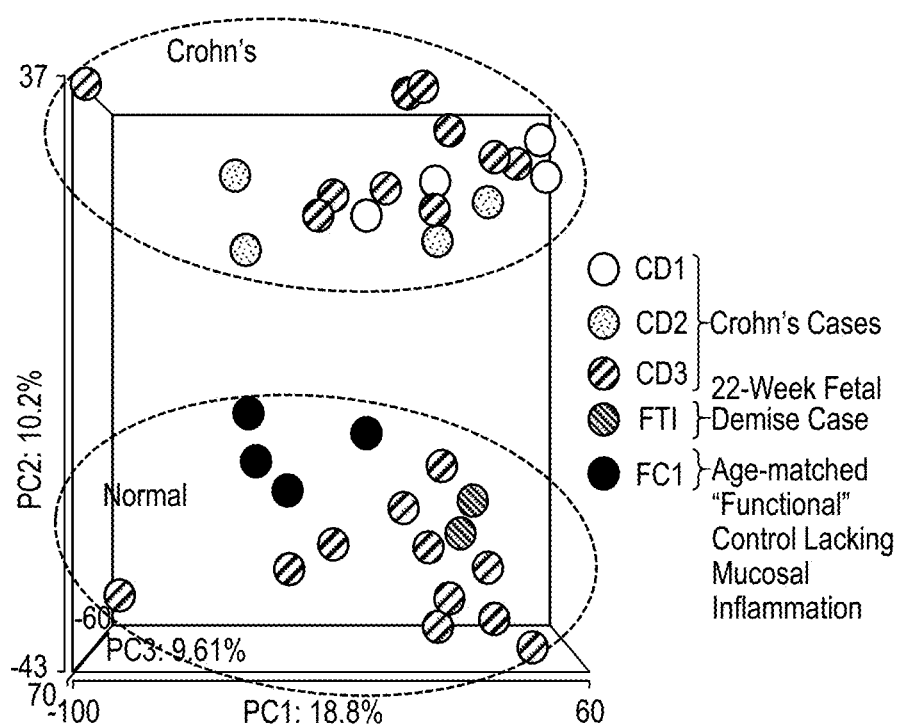
Figure 1C:
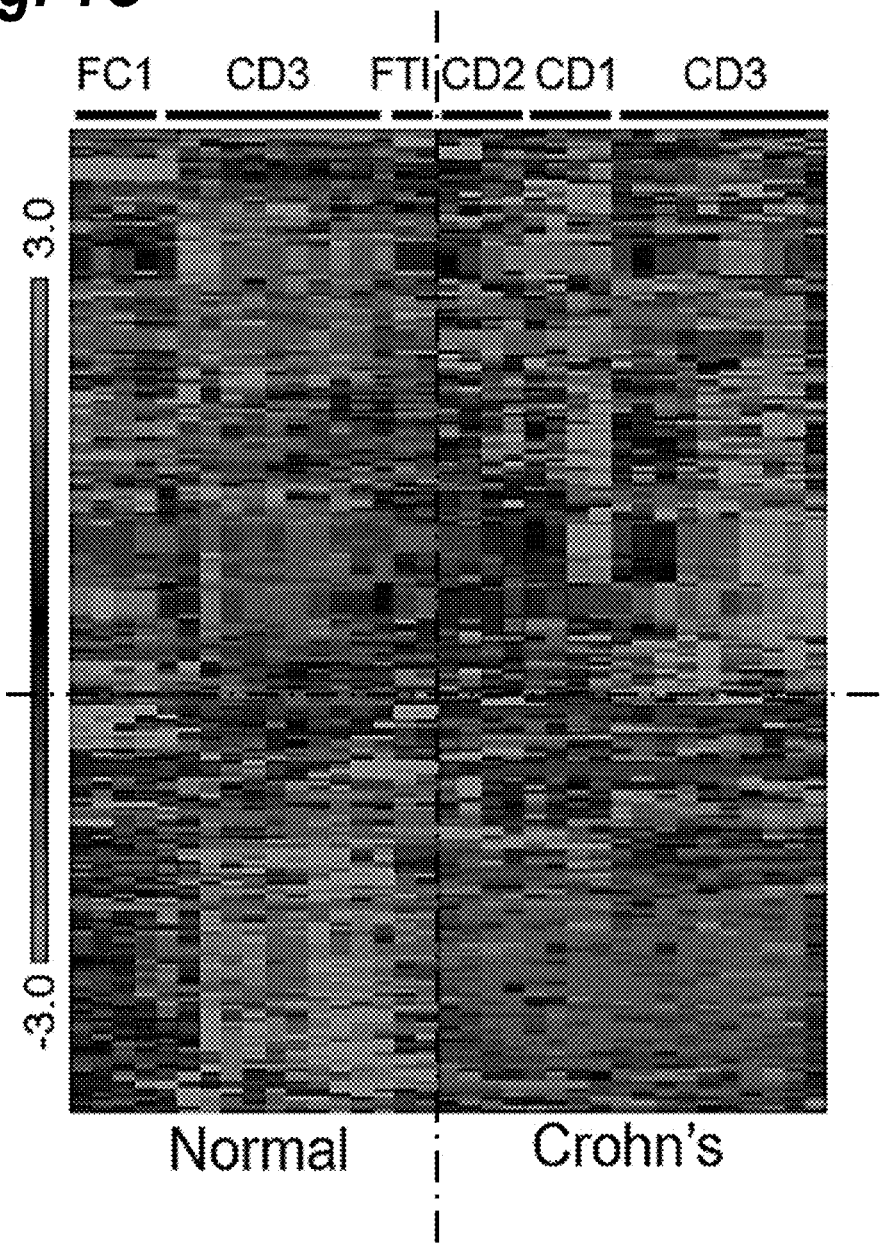
Figure 1D:
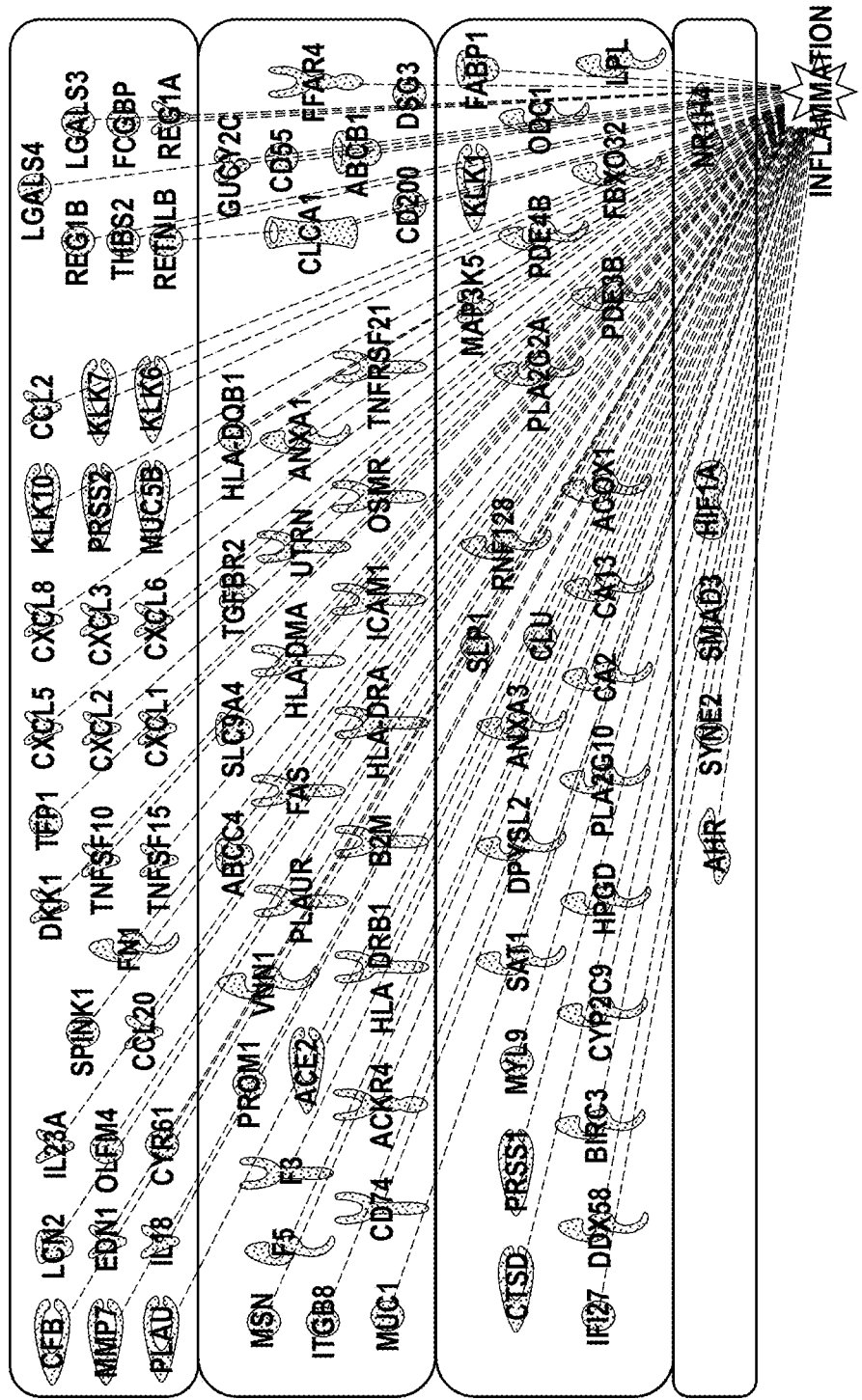
Figure 1E:
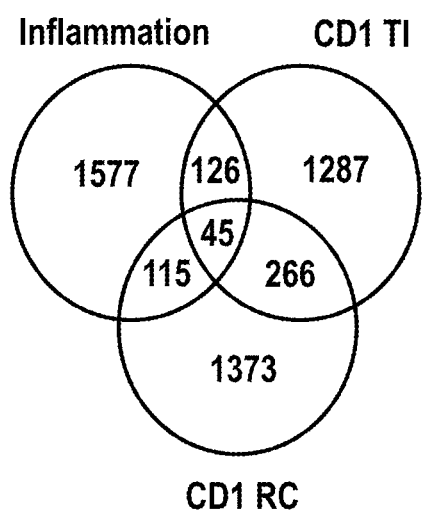
Figure 1F:
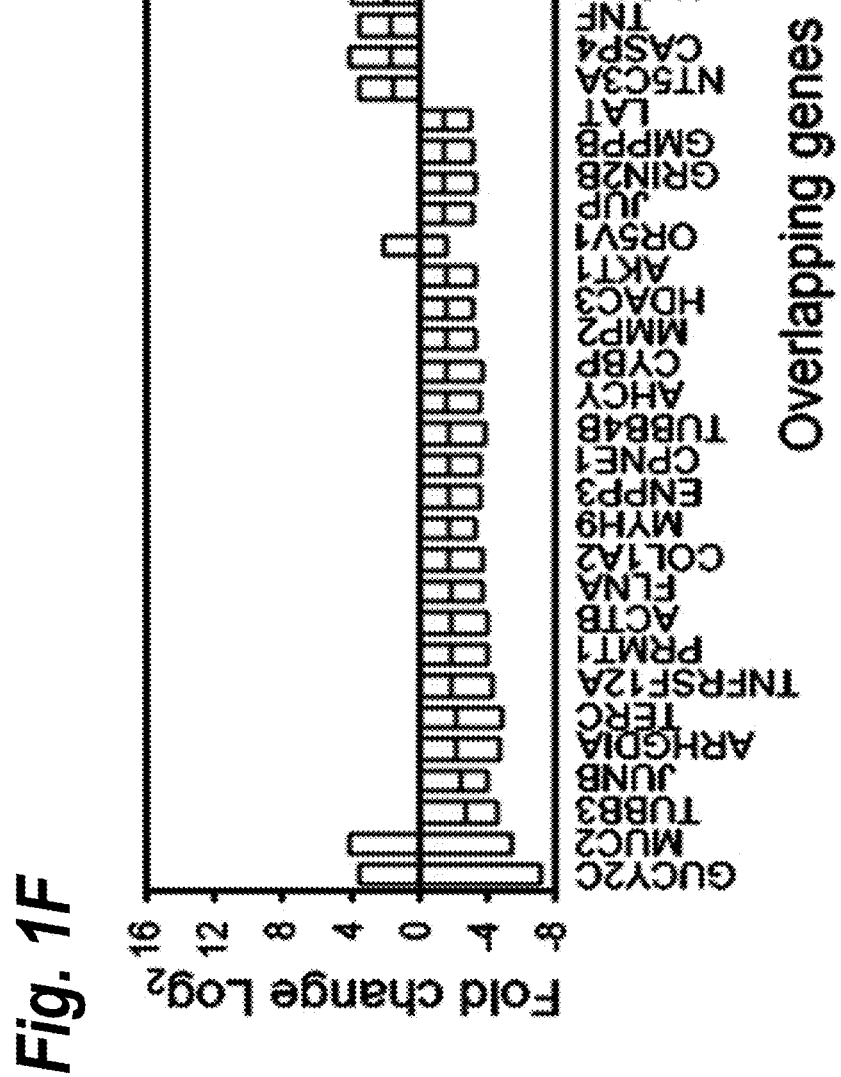

Table 3 provides examples of IBD Gene Sequences from certain classes of proteins which are over- or underexpressed in a pediatric Crohn's-derived cells relative to GI stem stem cells from patient matched normal tissue. The gene sequences, such as the coding sequence, mRNA sequence, RNA transcipt or genonmic sequence for Atonal BHLH transcription factor 1 (ATOH1), MUC2, glycoprotein A33 (GPA33), claudin 18 (CLDN18), V-set and immunoglobulin domain containing 1 (VSIG1) or to the genes/proteins identified in Table 3, FIG. 1D, FIG. 19 are collectively herein the "pCD Gene Sequences".

TABLE 3

| Gene Symbol | CD3(crohn) vs CD3(normal) Fold change |
|---|---|
| Secretory Proteins | |
| MMP7 | 18.6425 |
| SPINK1 | 16.2246 |
| MSMB | 12.4069 |
| ODAM | 10.9916 |
| LCN2 | 10.1571 |
| TCN1 | 7.91054 |
| CXCL5 | 7.19345 |
| SAA1 | 6.97362 |
| SAA1 | 6.96736 |
| SERPINB2 | 6.52824 |
| CXCL2 | 6.25885 |
| BPIFB1 | 5.9948 |
| C3 | 5.69447 |
| KLK7 | 5.578 |
| CCL20 | 5.44504 |
| CXCL8 | 4.37114 |
| F5 | 4.30107 |
| CCL2 | 4.2844 |
| KLK6 | 4.20245 |
| CFB | 4.04815 |
| TNFSF15 | 3.77782 |
| FN1 | 3.70026 |
| PLA2G10 | 3.19833 |
| CXCL1 | 3.10111 |
| SERPINA3 | 3.0374 |
| COLGALT2 | 2.96838 |
| VCAN | 2.71083 |

TABLE 3-continued

| Gene Symbol | CD3(crohn) vs CD3(normal) Fold change |
|---|---|
| CTGF | 2.66206 |
| PRSS1 | 2.63647 |
| LYPD6B | 2.58959 |
| ZG16B | 2.56711 |
| DKK1 | 2.53906 |
| CXCL6 | 2.47013 |
| PLA2G7 | 2.46657 |
| RNASE1 | 2.42255 |
| QPCT | 2.35499 |
| EDN1 | 2.33992 |
| C1GALT1 | 2.30045 |
| SERPINA4 | 2.29423 |
| CLU | 2.2164 |
| ADAMTS9 | 2.16422 |
| PRSS23 | 2.16278 |
| CYP2C18 | 2.11768 |
| KLK13 | 2.08632 |
| LEAP2 | 2.07364 |
| VNN1 | 2.05267 |
| CCL28 | 2.00196 |
| COL4A5 | 1.97145 |
| CTSH | 1.96368 |
| LAMA3 | 1.95609 |
| DVNLT3 | 1.95361 |
| CHST4 | 1.9077 |
| PON3 | 1.89537 |
| SEMA3E | 1.88366 |
| FAM107B | 1.84363 |
| LIPA | 1.81876 |
| HABP2 | 1.8133 |
| FUCA1 | 1.80839 |
| SERPINA1 | 1.80052 |
| SCPEP1 | 1.79306 |
| GNS | 1.78012 |
| TRIM24 | 1.7754 |
| CYP2C9 | 1.77381 |
| EPHX3 | 1.7508 |
| BTD | 1.74476 |
| NTF3 | 1.74126 |
| TTR | 1.73938 |
| CYR61 | 1.73531 |
| DST | 1.70862 |
| TIMP3 | 1.687 |
| KLK11 | 1.68034 |

TABLE 3-continued

| Gene Symbol | CD3(crohn) vs CD3(normal) Fold change |
|---|---|
| FMOD | 1.67048 |
| LIPH | 1.66971 |
| PON2 | 1.66062 |
| EHBP1 | 1.64904 |
| CTSO | 1.64866 |
| CTSL | 1.63894 |
| CD24 | 1.62882 |
| SMOC1 | 1.62494 |
| NPFF | 1.61212 |
| REPS2 | 1.58951 |
| PDGFC | 1.58758 |
| EHF | 1.58743 |
| RMDN1 | 1.56526 |
| IGFBP3 | 1.56392 |
| B2M | 1.56092 |
| HS3ST1 | 1.53637 |
| EDEM2 | 1.52645 |
| FSTL4 | 1.52022 |
| SPINK5 | 1.50946 |
| B3GALNT2 | −1.50138 |
| DDT | −1.51147 |
| TFF3 | −1.51359 |
| MRPL24 | −1.52982 |
| KDM1A | −1.5446 |
| RNPEP | −1.56895 |
| CES3 | −1.57035 |
| CCL24 | −1.62428 |
| ITLN2 | −1.62539 |
| CLEC3B | −1.62923 |
| BMP6 | −1.63385 |
| MGAT4A | −1.66197 |
| CHGB | −1.67242 |
| SERPINE2 | −1.67562 |
| GUCA2A | −1.69943 |
| C4BPB | −1.7051 |
| MDK | −1.77843 |
| CCDC108 | −1.82922 |
| TPD52 | −1.83204 |
| PLA2G12B | −1.86556 |
| ERP27 | −1.87949 |
| TDP2 | −1.88318 |
| IDNK | −1.89564 |
| INSL4 | −2.0073 |
| PI3 | −2.14133 |
| KLK1 | −2.36205 |
| CNTN1 | −2.39373 |
| LPL | −2.41327 |
| CHGA | −2.4657 |
| DPEP1 | −2.49415 |
| GAL | −2.51528 |
| KLK12 | −2.77691 |
| THBS2 | −2.8468 |
| MT1G | −2.89101 |
| FGFBP1 | −3.04474 |
| SPON1 | −3.44665 |
| CPE | −3.51691 |
| FRZB | −4.18361 |
| TGFBI | −6.42048 |
| SST | −8.87655 |
| FCGBP | −8.90851 |
| PCSK1 | −9.40761 |
| PLA2G2A | −9.90775 |
| GCG | −11.6852 |
| RETNLB | −11.8939 |
| REG1A | −14.0148 |
| ITLN1 | −18.3747 |
| CLCA1 | −22.4519 |
| CEACAM5 | −25.0919 |
| ZG16 | −35.2239 |
| Cell surface Proteins | |
| VSIG1 | 10.9645 |
| HLA-DRA | 9.92033 |
| CD74 | 7.27127 |
| LAMP5 | 6.45444 |
| CLDN18 | 6.40613 |
| SLC6A14 | 5.53851 |
| UGT2B15 | 5.10951 |
| DUOX2 | 4.55094 |
| DPCR1 | 4.5179 |
| LRRN1 | 4.47016 |
| TNFSF10 | 4.21837 |
| FUT9 | 4.13202 |
| HLA-DMB | 3.82396 |
| TM4SF1 | 3.54072 |
| GPR87 | 3.47508 |
| SLC16A4 | 3.3677 |
| RARRES3 | 3.19634 |
| FLRT3 | 3.00196 |
| FREM2 | 2.98464 |
| GJC1 | 2.85637 |
| TMC5 | 2.79718 |
| PVRL3 | 2.74792 |
| SLC26A9 | 2.73852 |
| PCDH7 | 2.72838 |
| STEAP1 | 2.66904 |
| ITM2A | 2.65516 |
| GPRC5B | 2.61305 |
| INPP4B | 2.44147 |
| SYNE2 | 2.3778 |
| BAMBI | 2.348 |
| KITLG | 2.33155 |
| SLC38A11 | 2.30978 |
| ITGB8 | 2.30459 |
| ACSL5 | 2.17559 |
| LPHN3 | 2.16047 |
| SLC9A2 | 2.12626 |
| PDZK1IP1 | 2.08572 |
| TUSC3 | 2.07371 |
| SLC40A1 | 2.05513 |
| CFTR | 2.03502 |
| HLA-DMA | 2.02634 |
| C18orf32 | 1.98721 |
| TMPRSS2 | 1.96923 |
| RNF19A | 1.95918 |
| GINM1 | 1.93847 |
| FUT8 | 1.91954 |
| SLC28A3 | 1.90876 |
| CYP4F3 | 1.90556 |
| PHLDB2 | 1.8956 |
| UST | 1.88504 |
| AQP5 | 1.88295 |
| LAMP2 | 1.87832 |
| ITGA3 | 1.85308 |
| YIPF1 | 1.82643 |
| PRAF2 | 1.8102 |
| NDRG2 | 1.79109 |
| SLC7A7 | 1.7893 |
| ARL6IP5 | 1.78108 |
| RTP4 | 1.77623 |
| PTRH2 | 1.77244 |
| TMEM47 | 1.75282 |
| TMEM27 | 1.73888 |
| PEX11B | 1.73138 |
| CYP3A5 | 1.71648 |
| TSPAN1 | 1.71491 |
| OR4B1 | 1.71443 |
| CLDN2 | 1.70997 |
| WRB | 1.70886 |
| BCL2L1 | 1.69254 |
| MYLK | 1.68351 |
| GPR22 | 1.67825 |
| TATDN1 | 1.67432 |
| SMG8 | 1.67254 |
| ITGA2 | 1.67151 |
| CAV2 | 1.67071 |
| ATP10D | 1.6631 |
| DUOXA2 | 1.65735 |
| RNF128 | 1.65313 |
| MAOB | 1.6479 |
| GJA10 | 1.64737 |
| PTPRK | 1.6442 |

TABLE 3-continued

| Gene Symbol | CD3(crohn) vs CD3(normal) Fold change |
|---|---|
| ITM2B | 1.64335 |
| OR7A17 | 1.64124 |
| TNFRSF10C | 1.63969 |
| TNFRSF21 | 1.63762 |
| SPTLC3 | 1.63283 |
| ENPP5 | 1.62833 |
| TGFBR2 | 1.62244 |
| KCNS3 | 1.62217 |
| SLCO3A1 | 1.62112 |
| CASK | 1.62014 |
| CD58 | 1.61747 |
| MYRF | 1.61415 |
| MPZL2 | 1.60863 |
| KCNJ2 | 1.60648 |
| PLA2G16 | 1.59827 |
| RNF144B | 1.58819 |
| LPAR4 | 1.58255 |
| SLC1A3 | 1.58241 |
| CD47 | 1.58209 |
| ABCC4 | 1.58178 |
| GJB4 | 1.58011 |
| SLC1A1 | 1.57987 |
| STEAP4 | 1.57841 |
| NBEA | 1.57445 |
| DNAJC10 | 1.5692 |
| FAM174A | 1.56841 |
| PCDH11X | 1.56408 |
| PROM2 | 1.56129 |
| GPR75 | 1.55423 |
| SSBP2 | 1.55329 |
| SLC4A11 | 1.55277 |
| LPCAT1 | 1.55157 |
| SLC9B2 | 1.5513 |
| ABCC3 | 1.5384 |
| MAPKAPK3 | 1.53352 |
| VMP1 | 1.53084 |
| CD70 | 1.5287 |
| C5orf15 | 1.52455 |
| CYP4X1 | 1.51405 |
| ALCAM | 1.50869 |
| PTPLB | 1.50557 |
| STEAP2 | 1.50264 |
| SI | −1.51668 |
| COQ7 | −1.5284 |
| DENND1B | −1.53351 |
| MGST3 | −1.53673 |
| HILPDA | −1.5446 |
| SLC50A1 | −1.5532 |
| SLC17A4 | −1.56964 |
| TMEM81 | −1.57936 |
| STX2 | −1.58659 |
| MAN1A1 | −1.59255 |
| IFITM1 | −1.59353 |
| EBP | −1.59749 |
| H56ST2 | −1.601 |
| CYC1 | −1.6059 |
| SNRPF | −1.6079 |
| SLC7A2 | −1.61533 |
| ADORA2B | −1.61844 |
| KCNG3 | −1.63455 |
| TMEM200A | −1.64079 |
| CREB3L1 | −1.64363 |
| SLC43A1 | −1.64561 |
| PARM1 | −1.64616 |
| ITM2C | −1.65145 |
| LPCAT2 | −1.65299 |
| LPGAT1 | −1.6539 |
| MALL | −1.65539 |
| CES2 | −1.66016 |
| NEO1 | −1.66058 |
| MYEOV | −1.66126 |
| BRI3BP | −1.67212 |
| AGPAT9 | −1.6791 |
| ACSS2 | −1.67991 |
| TMEM211 | −1.69115 |
| ABCB1 | −1.6979 |
| TSPAN7 | −1.69978 |
| CLDN3 | −1.70949 |
| SLC25A44 | −1.71404 |
| SLC16A9 | −1.72989 |
| RPS15A | −1.73547 |
| DSC2 | −1.7499 |
| MBOAT1 | −1.75177 |
| INSIG1 | −1.75482 |
| MEP1B | −1.7555 |
| HRASLS | −1.7617 |
| FAM3D | −1.78224 |
| CYBRD1 | −1.78332 |
| FAR2 | −1.78763 |
| P2RX4 | −1.82197 |
| TMEM141 | −1.83296 |
| SLC7A8 | −1.83533 |
| HSD11B2 | −1.84618 |
| PLN | −1.84645 |
| TLR4 | −1.86452 |
| TMEM171 | −1.87842 |
| ST6GALNAC1 | −1.88797 |
| PLXDC2 | −1.90262 |
| SLC7A5 | −1.90363 |
| RNF217 | −1.9064 |
| MBOAT2 | −1.96393 |
| FOLH1 | −1.97633 |
| TRPA1 | −1.98184 |
| LBR | −2.01092 |
| PRUNE2 | −2.04644 |
| TMED6 | −2.07513 |
| GOLT1A | −2.11216 |
| SIDT1 | −2.21768 |
| FAM105A | −2.22724 |
| CLRN3 | −2.35285 |
| NXPE1 | −2.36114 |
| CYP3A4 | −2.47472 |
| NOX1 | −2.62837 |
| KCNJ3 | −2.7739 |
| BTNL3 | −2.80196 |
| SLC18A1 | −2.83488 |
| DSC3 | −3.11227 |
| PRUNE2 | −3.12621 |
| NMUR2 | −3.21375 |
| FFAR4 | −3.72254 |
| TM4SF20 | −3.75394 |
| GPA33 | −3.79356 |
| CD52 | −3.79522 |
| PMP22 | −3.86656 |
| ANPEP | −3.89573 |
| CEACAM6 | −3.96798 |
| GUCY2C | −7.22138 |
| HEPACAM2 | −10.8708 |
| Peptidases | |
| MMP7 | 18.642 |
| C3 | 5.694 |
| KLK7 | 5.578 |
| KLK6 | 4.202 |
| CFB | 4.048 |
| CAPN6 | 3.802 |
| PRSS1 | 2.636 |
| ADAMTS9 | 2.164 |
| PRSS23 | 2.163 |
| KLK13 | 2.086 |
| ADAM28 | 2.025 |
| TMPRSS2 | 1.969 |
| CTSH | 1.964 |
| HABP2 | 1.813 |
| SCPEP1 | 1.793 |
| BACE2 | 1.742 |
| PIGK | 1.693 |
| KLK11 | 1.68 |
| CTSO | 1.649 |
| CTSL | 1.639 |
| CPM | 1.58 |
| PSMB3 | −1.536 |

TABLE 3-continued

| Gene Symbol | CD3(crohn) vs CD3(normal) Fold change |
|---|---|
| MYO7B | -1.551 |
| RNPEP | -1.569 |
| MYO1A | -1.582 |
| SPAG5 | -1.637 |
| MEP1B | -1.756 |
| CAPN9 | -1.847 |
| CASP6 | -1.861 |
| FOLH1 | -1.976 |
| KLK1 | -2.362 |
| DPEP1 | -2.494 |
| KLK12 | -2.777 |
| PRSS2 | -2.974 |
| CPE | -3.517 |
| ANPEP | -3.896 |
| PCSK1 | -9.408 |
| Kinases | |
| PLK2 | 2.887 |
| SGK1 | 2.113 |
| PRKCA | 1.806 |
| NME5 | 1.719 |
| RIPK2 | 1.708 |
| ROR1 | 1.691 |
| MYLK | 1.684 |
| TGFBR2 | 1.622 |
| CASK | 1.62 |
| NCK1 | 1.569 |
| MAPKAPK3 | 1.534 |
| CDKL5 | 1.517 |
| NEK2 | -1.506 |
| THNSL1 | -1.52 |
| PIK3C2B | -1.526 |
| RPS6KA1 | -1.583 |
| EPHB2 | -1.61 |
| CIT | -1.657 |
| GUK1 | -1.675 |
| PRKCZ | -1.698 |
| TRIB3 | -1.707 |
| PDK1 | -1.803 |
| CKB | -2.097 |
| NDRG1 | -4.009 |
| GUCY2C | -7.221 |

Nucleic acids of the present invention have been identified as differentially expressed in IBD cells, e.g., UC- or CD-derived stem cell lines (relative to the expression levels in normal tissue, e.g., normal colon tissue and/or normal non-colon tissue), such as pCD Gene Sequences. In certain embodiments, the subject nucleic acids are differentially expressed by at least a factor of two, preferably at least a factor of five, even more preferably at least a factor of twenty, still more preferably at least a factor of fifty. In particular, wherein the assay detects a difference in the level of expression of at least a factor of about two, about four, about six, about eight, about ten, about twelve, about fourteen, about sixteen, about eighteen, or about twenty; and more preferably a factor of about twenty-five, about thirty, about thirty-five, about forty, about forty-five, or about fifty.

Genes which are upregulated or downregulated in IBD cells may be targets for diagnostic or therapeutic techniques.

Preferred nucleic acids of the present invention encode a polypeptide comprising at least a portion of a polypeptide encoded by one of the pCD Gene Sequences, or can hybridize to the coding sequences thereof. For example, preferred nucleic acid molecules for use as probes/primers or antisense molecules (i.e., noncoding nucleic acid molecules) can comprise at least about 12, 20, 30, 50, 60, 70, 80, 90, or 100 base pairs in length up to the length of the complete gene. Coding nucleic acid molecules can comprise, for example, from about 50, 60, 70, 80, 90, or 100 base pairs up to the length of the complete gene.

Another aspect of the invention provides a nucleic acid which hybridizes under low, medium, or high stringency conditions to a nucleic acid sequence represented by one of the pCD Gene Sequences, or a sequence complementary thereto. Appropriate stringency conditions which promote DNA hybridization, for example, 6.0×sodium chloride/sodium citrate (SSC) at about 45 C, followed by a wash of 2.0×SSC at 50 C, are known to those skilled in the art or can be found in Current Protocols in Molecular Biology, John Wiley & Sons, N.Y. 6.3.1-12.3.6 (1989). For example, the salt concentration in the wash step can be selected from a low stringency of about 2.0×SSC at 50 C to a high stringency of about 0.2×SSC at 50 C. In addition, the temperature in the wash step can be increased from low stringency conditions at room temperature, about 22 C, to high stringency conditions at about 65 C. Both temperature and salt may be varied, or temperature or salt concentration may be held constant while the other variable is changed. In a preferred embodiment, a nucleic acid of the present invention will hybridize to one of the pCD Gene Sequences, or a sequence complementary thereto, under moderately stringent conditions, for example at about 2.0×SSC and about 40 C. In a particularly preferred embodiment, a nucleic acid of the present invention will hybridize to one of the pCD Gene Sequences, or a sequence complementary thereto, under high stringency conditions.

In one embodiment, the invention provides nucleic acids which hybridize under low stringency conditions of 6×SSC at room temperature followed by a wash at 2×SSC at room temperature.

In another embodiment, the invention provides nucleic acids which hybridize under high stringency conditions of 2×SSC at 65° C. followed by a wash at 0.2×SSC at 65° C.

Nucleic acids having a sequence that differs from the nucleotide sequences of a pCD Gene Sequence, or a sequence complementary thereto, due to degeneracy in the genetic code, are also within the scope of the invention. Such nucleic acids encode functionally equivalent peptides (i.e., a peptide having equivalent or similar biological activity) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a polypeptide. However, it is expected that DNA sequence polymorphisms that do lead to changes in the amino acid sequences of the subject polypeptides will exist among mammals. One skilled in the art will appreciate that these variations in one or more nucleotides (e.g., up to about 3-5% of the nucleotides) of the nucleic acids encoding polypeptides having an activity of a polypeptide may exist among individuals of a given species due to natural allelic variation.

Also within the scope of the invention are nucleic acids encoding splicing variants of proteins encoded by a nucleic acid of a pCD Gene Sequence, or a sequence complementary thereto, or natural homologs of such proteins. Such homologs can be cloned by hybridization or PCR, as further described herein.

The IBD probes of the present invention can be useful because they provide a method for detecting mutations in wild-type IBD genes of the present invention. Nucleic acid probes which are complementary to a wild-type gene of the present invention and can form mismatches with mutant genes are provided, allowing for detection by enzymatic or chemical cleavage or by shifts in electrophoretic mobility.

Likewise, probes based on the subject sequences can be used to detect the level of transcripts of IBD genes, for use, for example, in prognostic or diagnostic assays. In preferred embodiments, the probe further comprises a label group attached thereto and able to be detected, e.g., the label group is selected from radioisotopes, fluorescent compounds, chemiluminescent compounds, enzymes, and enzyme cofactors.

e. Targeting Expression of IBD Gene Sequence/pCD Gene Sequences

One aspect of the invention relates to the use of the isolated nucleic acid, e.g., from a pCD Gene Sequence that is upregulated in an IBD stem cell population, or a sequence complementary thereto, in antisense therapy or RNA intereference therapy (such as small interfering RNA (siRNA), micro RNA (miRNA) or short-hairpin RNA (shRNA)), a sequence-directed ribozyme or gene inactivating CRISPR RNA (crRNA)

As used herein, antisense therapy refers to administration or in situ generation of oligonucleotide molecules or their derivatives which specifically hybridize (e.g., bind) under cellular conditions with the cellular mRNA and/or genomic DNA, thereby inhibiting transcription and/or translation of that gene. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA. Alternatively, the antisense construct is an oligonucleotide probe which is generated ex vivo and which, when introduced into the cell, causes inhibition of expression by hybridizing with the mRNA and/or genomic sequences of a subject nucleic acid. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al., Bio-Techniques 6:958-976 (1988); and Stein et al., Cancer Res. 48:2659-2668 (1988). With respect to antisense DNA, oligodeoxyribonucleotides derived from the translation initiation site, e.g., between the −10 and +10 regions of the nucleotide sequence of interest, are preferred.

Antisense approaches involve the design of oligonucleotides (either DNA or RNA) that are complementary to mRNA. The antisense oligonucleotides will bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner, Nature 372:333 (1994)). Therefore, oligonucleotides complementary to either the 5' or 3' untranslated, non-coding regions of a gene could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are typically less efficient inhibitors of translation but could also be used in accordance with the invention. Whether designed to hybridize to the 5, 3, or coding region of subject mRNA, antisense nucleic acids should be at least six nucleotides in length, and are preferably less that about 100 and more preferably less than about 50, 25, 17 or 10 nucleotides in length.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytriethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al., Proc. Natl. Acad. Sci. U.S.A. 93:14670 (1996) and in Eglom et al., Nature 365:566 (1993). One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an—anomeric oligonucleotide. An—anomeric oligonucleotide forms specific double-stranded hybrids with complementary RNA in which, contrary to the usual—units, the strands run parallel to each other (Gautier et al., Nucl.

Acids Res. 15:6625-6641 (1987)). The oligonucleotide is a 2-O-methylribonucleotide (Inoue et al., Nucl. Acids Res. 15:6131-12148 (1987)), or a chimeric RNA-DNA analogue (Inoue et al., FEBS Lett. 215:327-330 (1987)).

The antisense molecules can be delivered to cells which express the target nucleic acid in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

In another aspect of the invention, ribozyme molecules designed to catalytically cleave target mRNA transcripts corresponding to one or more pCD Gene Sequence can be used to prevent translation of target mRNA and expression of a target protein by the IBD stem cell or its progeny (See, e.g., PCT International Publication WO90/11364; Sarver et al., Science 247:1222-1225 (1990) and U.S. Pat. No. 5,093, 246). While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5-UG-3. The construction and production of hammerhead ribozymes is well known in the art and is described more fully in Haseloff and Gerlach, 1988, Nature, 334:585-591. Preferably the ribozyme is engineered so that the cleavage recognition site is located near the 5' end of the target mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., Science, 224:574-578 (1984); Zaug and Cech, Science, 231:470-475 (1986); Zaug, et al., Nature, 324:429-433 (1986); published International patent application No. WO88/04300; Been and Cech, Cell, 47:207-216 (1986)). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target pCD Gene Sequence.

As in the antisense approach, the ribozymes can be composed of modified oligonucleotides (e.g., for improved stability, targeting, etc.) and should be delivered to cells which express the target pCD Gene Sequence in vivo. A preferred method of delivery involves using a DNA construct "encoding" the ribozyme under the control of a strong constitutive pol III or pol II promoter, so that transfected cells will produce sufficient quantities of the ribozyme to destroy endogenous messages and inhibit translation. Because ribozymes, unlike antisense molecules, are catalytic, a lower intracellular concentration is required for efficiency.

Antisense RNA, DNA, RNA Interference constructs and ribozyme molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

In other embodiments, the nucleic acid is a a "decoy" nucleic acid which corresponds to a transcriptional regulatory sequence and binds to a transcription factor that is involved in upregulated expression of one or more genes in an IBD Stem Cell population. The decoy nucleic acid therefore competes with natural binding target for the binding of the transcription factor and acts an antagonist to reduce the expression of those genes under the transcriptional control of the targeted transcription factor.

f. Therapeutic Nucleic Acids

In some embodiments, a genomic modification (e.g., a deletion of edit of the genome) of an IBD coding sequence is carried out in vivo in a patient using one or more DNA-binding nucleic acids, such as disruption via an RNA-guided endonuclease (RGEN). For example, the disruption can be carried out using clustered regularly interspaced short palindromic repeats (CRISPR) and CRISPR-associated (Cas) proteins. In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derived from a type I, type II, or type III CRISPR system, e.g., derived from a particular organism comprising an endogenous CRISPR system, such as *Streptococcus pyogenes*.

In some aspects, a Cas nuclease and gRNA (including a fusion of crRNA specific for the target sequence and fixed tracrRNA) are introduced into the patient's cells, i.e., IBD stem cells or cells derived therefrom. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20 nucleotides of the guide RNA to correspond to the target DNA sequence. In general, a CRISPR system is characterized by elements that promote the formation of a CRISPR complex at the site of a target sequence. Typically, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The CRISPR system can induce double stranded breaks (DSBs) at the target site, followed by disruptions as discussed herein. In other embodiments, Cas9 variants, deemed "nickases," are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a "cloning site"). In some embodiments, one or more insertion sites are located upstream and/or downstream of one or more sequence elements of one or more vectors. When multiple different guide sequences are used, a single expression construct may be used to target CRISPR activity to multiple different, corresponding target sequences within a cell, such as IBD gene sequences such as pCD gene sequences.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known, for example, the amino acid sequence of S. pyogenes Cas9 protein may be found in the SwissProt database under accession number Q99ZW2, incorporated herein by reference.

The CRISPR enzyme can be Cas9 (e.g., from S. pyogenes or S. pneumonia). The CRISPR enzyme can direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ.

In general, a guide sequence is any polynucleotide sequence having sufficient complementarity with a target polynucleotide sequence of an IBD gene sequence to hybridize with the target sequence and direct sequence-specific binding of the CRISPR complex to the target IBD gene sequence. In some embodiments, the degree of complementarity between a guide sequence and its corresponding target IBD gene sequence, when optimally aligned using a suitable alignment algorithm, is about or more than about 50%, 60%, 75%, 80%, 85%, 90%, 95%, 97.5%, 99%, or more.

In another embodiment, the gene of interest is useful for inhibiting the expression and/or activity of a nucleic acid or protein of interest. For example, target biomolecule expression and/or activity, such as an RNA coding region, may be reduced or inhibited using inhibitory RNAs. An "RNA coding region" is a nucleic acid that may serve as a template for the synthesis of an RNA molecule, such as an siRNA. "RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see, for example, Coburn and Cullen (2002) J. Virol. 76:9225), thereby inhibiting expression of the target biomarker nucleic acid. In one embodiment, the RNA coding region is a DNA sequence. The ability to down-regulate a target IBD gene sequence has many therapeutic and research applications, including identifying the biological functions of particular genes. Moreover, such inhibition may be achieved in screening assays that take advantage of pooling techniques, whereby groups of 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more, or any number or range in between, of RNA inhibitory agents, either co-expressed from the same vector or more than one vector, are transduced into cells of interest. Suitable inhibitory RNAs include, but are not limited to siRNAs, shRNAs, miRNAs, Piwis, dicer-substrate 27-mer duplexes, single-stranded interfering RNA, and the like. In particular, the combination of RNA inhibitory technology and lentiviruses as a tool for a gene specific knock-down in animal models is well known in the art (see, for example, U.S. Pat. Publ. 2005/0251872; EP Pat. Publ. 2166107; PCT Publs. WO 2004/022722 and 2007/109131; Tiscornia et al. (2003) Proc. Natl. Acad. Sci. U.S.A. 100:1844-1848; Rubinson et al. (2003) Nat. Genet. 33:401-406; and Dann et al. (2006) Proc. Natl. Acad. Sci. U.S.A. 103:11246-11251). As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 10%, 20%, 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

siRNAs typically refer to a double-stranded interfering RNA unless otherwise noted. In various embodiments, suitable siRNA molecules include double-stranded ribonucleic acid molecules comprising two nucleotide strands, each strand having about 19 to about 28 nucleotides (i.e. about 19, 20, 21, 22, 23, 24, 25, 26, 27, or 28 nucleotides). Thus, the phrase "interfering RNA having a length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules may be used. Examples of other interfering RNA molecules that may to inhibit target biomolecules include, but are not limited to, short hairpin RNAs (shRNAs), single-stranded siRNAs, microRNAs (miRNAs), piwiRNA, dicer-substrate 27-mer duplexes, and variants thereof containing one or more chemically modified nucleotides, one or more non-nucleotides, one or more deoxyribonucleotides, and/or one or more non-phosphodiester linkages. Typically, all RNA or RNA-like molecules that may interact with transcripts RISC complexes and participate in RISC-related changes in gene expression may be referred to as "interfering RNAs" or "interfering RNA molecules." Suitable interfering RNAs may readily be produced based on the well-known nucleotide sequences of target biomolecules. In various embodiments interfering RNAs that inhibit target biomolecules may comprise partially purified RNA, substantially pure RNA, synthetic RNA, recombinantly produced RNA, as well as altered RNA that differs from naturally-occurring RNA by the addition, deletion, substitution, and/or alteration of one or more nucleotides. Such alterations may include, for example, addition of non-nucleotide material, such as to the end(s) of the interfering RNAs or to one or more internal nucleotides of the interfering RNAs, including modifications that make the interfering RNAs resistant to nuclease digestion. Such alterations result in sequences that are generally at least about 80%, 81%, 82%, 83%, 84%, 85%, 86%, 87%, 88%, 89%, 90%, 91%, 92%, 93%, 94%, 95%, 96%, 97%, 98%, 99%, 99.5%, or more, or 100% identical to the sequence of the target biomolecule. When the gene to be down regulated is in a family of highly conserved genes, the sequence of the duplex region may be chosen with the aid of sequence comparison to target only the desired gene. On the other hand, if there is sufficient identity among a family of homologous genes within an organism, a duplex region may be designed that would down regulate a plurality of genes simultaneously.

In various embodiments one or both strands of the interfering RNAs may comprise a 3' overhang. As used herein, a "3' overhang" refers to at least one unpaired nucleotide extending from the 3'-end of an RNA strand. Thus in one embodiment, the interfering RNAs comprises at least one 3' overhang of from 1 to about 6 nucleotides (which includes ribonucleotides or deoxynucleotides) in length, from 1 to about 5 nucleotides in length, from 1 to about 4 nucleotides in length, or about 2 to about 4 nucleotides in length. In an illustrative embodiment in which both strands of the interfering RNAs molecule comprise a 3' overhang, wherein the length of the overhangs may be the same or different for each strand. In certain embodiments the 3' overhang is present on both strands of the interfering RNAs and is one, two, or three nucleotides in length. For example, each strand of the interfering RNAs may comprise 3' overhangs of dithymidylic acid ("TT") or diuridylic acid ("uu").

In order to enhance the stability of the interfering RNAs, the 3' overhangs may be also stabilized against degradation. In one embodiment, the overhangs are stabilized by including purine nucleotides, such as adenosine or guanosine nucleotides. In certain embodiments, substitution of pyrimidine nucleotides by modified analogues, e.g., substitution of uridine nucleotides in the 3' overhangs with 2'-deoxythymidine, is tolerated and does not affect the efficiency of RNA interference degradation. In particular, it is believed the absence of a 2' hydroxyl in the 2'-deoxythymidine may significantly enhance the nuclease resistance of the 3' overhang.

Interfering RNAs may be expressed from a vector described herein either as two separate, complementary RNA molecules, or as a single RNA molecule with two complementary regions. Selection of vectors suitable for expressing interfering RNAs, methods for inserting nucleic acid sequences for expressing the interfering RNAs into the vector, and methods of delivering the recombinant plasmid to the cells of interest are well known in the art (Tuschl (2002) Nat. Biotechnol. 20: 446-448; Brummelkamp et al. (2002) Science 296:550 553; Miyagishi et al. (2002) Nat. Biotechnol. 20:497-500; Paddison et al. (2002) Genes Dev. 16:948-958; Lee et al. (2002) Nat. Biotechnol. 20:500-505; and Paul et al. (2002) Nat. Biotechnol. 20:505-508).

In certain embodiments, the interfering RNAs may be delivered as a small hairpin RNA or short hairpin RNA (shRNA) (see, for example, U.S. Pat. Nos. 8,697,359 and 8,642,569). shRNA is a sequence of RNA that makes a tight hairpin turn that may be used to silence gene expression via RNA interference. In typical embodiments, shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA that is bound to it.

In certain embodiments, the sense sequence of the shRNA will be from about 19 to about 30, more nucleotides (e.g. about 19, 20, 21, 22, 23, 24, 25, 26, 27, 28, 29, or 30 nucleotides) in length, more typically from about 19 to about 22 nucleotides in length, the antisense sequence will be from about 19 to about 30, more typically from 19 to about 22 nucleotides (e.g. about 19, 20, 21 or 22 nucleotides), in length, and the loop region will be from about 3 to about 19 nucleotides (e.g., about 3, 4, 5, 6, 7, 8, 9, 10, 11, 12, 13, 14, 15, 16, 17, 18, and 19 nucleotides) in length. In some embodiments, the sense and antisense sequences are the same length, i.e. the shRNA will form a symmetrical hairpin, but this is not necessarily the case. In some cases, the sense or antisense strand may be shorter than its complementary strand, and an asymmetric hairpin is formed. Further, while in some instances the base pairing between the sense and antisense sequences is exact, this also need not be the case. Thus, some mismatch between the sequences may be tolerated, or even desired, e.g. to decrease the strength of the hydrogen bonding between the two strands. However, in one illustrative embodiment, the sense and antisense sequences are the same length, and the base pairing between the two is exact and does not contain any mismatches. The shRNA molecule may also comprise a 5'-terminal phosphate group that may be chemically modified. In addition, the loop portion of the shRNA molecule may comprise, for example, nucleotides, non-nucleotides, linker molecules, conjugate molecules, etc.

In certain embodiments, the PIWI RNA pathway is used to provide inhibition of target biomolecules. Piwi-interacting RNAs (piRNAs) were identified through association with Piwi proteins in mammalian testes (Aravin et al. (2006); Girard et al. (2006); Grivna et al. (2006); Lau et al. (2006). piRNAs and methods of making and using same to target and degrade nucleic acids are well known in the art (see, for example, U.S. Pat. Publ. 2011-0207625). These RNAs range from 26-30 nucleotides in length and are produced from discrete loci. Generally, genomic regions spanning 50-100 kB in length give rise to abundant piRNAs with profound strand asymmetry. Although the piRNAs themselves are not conserved, even between closely related species, the positions of piRNA loci in related genomes are conserved, with virtually all major piRNA-producing loci having syntenic counterparts in mice, rats and humans (Girard et al. (2006)). The loci and consequently the piRNAs themselves are relatively depleted of repeat and transposon sequences, with only 17% of human piRNAs corresponding to known repetitive elements as compared to a nearly 50% repeat content for the genome as a whole. In certain embodiments, methods are provided for inhibiting such targets in a cell, comprising administering an effective amount of a siRNA/shRNA/piwiRNA to the cell, such that target mRNA is degraded.

In those embodiments for which altered gene expression of an IBD gene sequence, such as a pCD gene sequence, is desired and the therapeutic agent is a nucleic acid, the nucleic acid can be targeted to the IBD stem cells or IBD stem cell derived tissue. "Therapeutic nucleic acids" such as coding sequences for inhibitory domains (dominant negative) versions of the IBD gene sequence, or a CRISPR or other gene editing construct, or antisense or RNA interference construct to inhibit expression of the IBD gene sequence can be delivered by vector or as DNA or mRNA directly to the targeted IBD stem cells or tissue in vivo.

A multitude of clinical studies have illustrated the utility of in vivo gene and nucleic acid transfer into cells using a variety of different delivery systems. Where the therapeutic agent is a polypeptide, or an expressed CRISPR component or an in vivo produced RNA interference or antisense molecule, a number of expression platforms can be pursued in vivo to which delivery of a therapeutic nucleic acid can be adapted: these include viral vectors, naked DNA and RNA.

An array of physical and chemical nonviral methods have been used to transfer DNA and mRNA to mammalian cells and a substantial number of these have been developed as clinical stage technologies for gene therapy, both ex vivo and in vivo, and are readily adapted for delivery of the therapeutic nucleic acids of the present invention. To illustrate, cationic liposome technology can be employed, which is based on the ability of amphipathic lipids, possessing a positively charged head group and a hydrophobic lipid tail, to bind to negatively charged DNA or RNA and form particles that generally enter cells by endocytosis. Some cationic liposomes also contain a neutral co-lipid, thought to enhance liposome uptake by mammalian cells. See, for example, Feigner et al. (1987) Lipofection: a highly efficient, lipid-mediated DNA-transfection procedure. MNAS 84:7413-7417; San et al. (1983) "Safety and short term toxicity of a novel cationic lipid formulation for human gene therapy" Hum. Gene Ther. 4:781-788; Xu et al. (1996) "Mechanism of DNA release from cationic liposome/DNA complexes used in cell transfection" Biochemistry 35:5616-5623; and Legendre et al. (1992) "Delivery of plasmid DNA into mammalian cell lines using pH-sensitive liposomes: comparison with cationic liposomes" Pharm. Res. 9, 1235-1242.

Similarly, other polycations, such as poly-1-lysine and polyethylene-imine, can be used to deliver therapeutic nucleic acid. These polycations complex with nucleic acids via charge interaction and aid in the condensation of DNA or RNA into nanoparticles, which are then substrates for endosome-mediated uptake. Several of these cationic nucleic acid complex technologies have been developed as potential clinical products, including complexes with plasmid DNA, oligodeoxynucleotides, and various forms of synthetic RNA. Modified (and unmodified or "naked") DNA and RNA have also been shown to mediate successful gene transfer in a number of circumstances and can also be used as systems for delivery of therapeutic nucleic acid. These include the use of plasmid DNA by direct intramuscular injection, the use of intratumoral injection of plasmid DNA. See, for example, Rodrigo et al. (2012) "De novo automated design of small RNA circuits for engineering synthetic riboregulation in living cells" PNAS 109:15271-15276; Oishi et al. (2005) "Smart polyion complex micelles for targeted intracellular delivery of PEGylated antisense oligonucleotides containing acid-labile linkages" Chembiochem. 6:718-725; Bhatt et al. (2015) "Microbeads mediated oral plasmid DNA delivery using polymethacrylate vectors: an effectual groundwork for colorectal cancer" Drug Deliv. 22:849-861; Ulmer et al. (1994) Protective immunity by intramuscular injection of low doses of influenza virus DNA vaccines" Vaccine 12: 1541-1544; and Heinzerling et al. (2005) "Intratumoral injection of DNA encoding human interleukin 12 into patients with metastatic melanoma: clinical efficacy" Hum. Gene Ther. 16:35-48.

Increased efficiency can also be gained through other techniques, such as in which delivery of the therapeutic nucleic acid is improved by use of chemical carriers—cationic polymers or lipids—or via a physical approach—gene gun delivery or electroporation. See Tranchant et al. (2004) "Physicochemical optimisation of plasmid delivery by cationic lipids" J. Gene Med., 6 (Suppl. 1):524-535; and Niidome et al. (2002) "Gene therapy progress and prospects: nonviral vectors" Gene Ther., 9:1647-1652. Electroporation is especially regarded as an interesting technique for non-viral gene delivery. Somiari, et al. (2000) "Theory and in vivo application of electroporative gene delivery" Mol. Ther. 2:178-187; and Jaroszeski et al. (1999) "In vivo gene delivery by electroporation" Adv. Drug Delivery Rev., 35:131-137. With electroporation, pulsed electrical currents are applied to a local tissue area to enhance cell permeability, resulting in gene transfer across the membrane. Research has shown that in vivo gene delivery can be at least 10-100 times more efficient with electroporation than without. See, for example, Aihara et al. (1998) "Gene transfer into muscle by electroporation in vivo" Nat. Biotechnol. 16:867-870; Mir, et al. (1999) "High-efficiency gene transfer into skeletal muscle mediated by electric pulses" PNAS 96:4262-4267; Rizzuto, et al. (1999) "Efficient and regulated erythropoietin production by naked DNA injection and muscle electroporation" PNAS 96: 6417-6422; and Mathiesen (1999) "Electropermeabilization of skeletal muscle enhances gene transfer in vivo" Gene Ther., 6:508-514.

The therapeutic nucleic acids of the present invention can be delivered by a wide range of gene delivery system commonly used for gene therapy including viral, non-viral, or physical. See, for example, Rosenberg et al., Science, 242:1575-1578, 1988, and Wolff et al., Proc. Natl. Acad. Sci. USA 86:9011-9014 (1989). Discussion of methods and compositions for use in gene therapy include Eck et al., in Goodman & Gilman's The Pharmacological Basis of Therapeutics, Ninth Edition, Hardman et al., eds., McGraw-Hill, New York, (1996), Chapter 5, pp. 77-101; Wilson, Clin. Exp. Immunol. 107 (Suppl. 1):31-32, 1997; Wivel et al., Hematology/Oncology Clinics of North America, Gene Therapy, S. L. Eck, ed., 12(3):483-501, 1998; Romano et al., Stem Cells, 18:19-39, 2000, and the references cited therein. U.S. Pat. No. 6,080,728 also provides a discussion of a wide variety of gene delivery methods and compositions. The routes of delivery include, for example, systemic administration and administration in situ.

g. Polypeptides

The present invention makes available isolated polypeptides which are isolated from, or otherwise substantially free of other cellular proteins, especially other signal transduction factors and/or transcription factors which may normally be associated with the polypeptide. Subject polypeptides of the present invention include polypeptides encoded by pCD Gene Sequences. Polypeptides of the present invention include those proteins which are differentially regulated in IBD tissue, especially colon UC- and CD-derived cell lines (relative to normal cells, e.g., normal colon tissue).

The term "substantially free of other cellular proteins" (also referred to herein as "contaminating proteins") or "substantially pure or purified preparations" are defined as encompassing preparations of polypeptides having less than about 20% (by dry weight) contaminating protein, and preferably having less than about 5% contaminating protein. Functional forms of the subject polypeptides can be prepared, for the first time, as purified preparations by using a cloned nucleic acid as described herein. Full length proteins or fragments corresponding to one or more particular motifs and/or domains or to arbitrary sizes, for example, at least about 5, 10, 25, 50, 75, or 100 amino acids in length are within the scope of the present invention.

h. Antibodies and other Specific Affinity Binders

The term "specific affinity binder" refers to an antibody as well as to a non-antibody protein scaffold i.e., smaller proteins that are capable of achieving comparable affinity and specificity using molecular structures that can be for example one-fifth to one-tenth the size of full antibodies, and also to nucleic acid aptamers. In some embodiments, the specific affinity binder of the present invention is a non-antibody polypeptide. In some embodiments, the non-antibody polypeptide can include but is not limited to peptibodies, DARPins, avimers, adnectins, anticalins, affibodies, affilins, atrimers, bicyclic peptides, centryins, Cys-knots, Fynomers, Kunitz domains, Obodies, pronectins, Tn3, maxibodies, or other protein structural scaffold, or a combination thereof.

In certain embodiments, the subject invention also provides specific affinity binders, such as antibodies, which selectively bind to a polypeptide gene expression product of a pCD Gene Sequence or other protein that is upregulated in a population of IBD stem cells or its progeny, preferably a protein expressed on the cell surface of the IBD stem cell or its progeny. The binding of the antibody can result in inhibition of the function of the cell, such as proliferation or differentation of IBD stem cells or progeny, cell death, or alteration of the function of the cell in the tissue. As used herein, "selectively binds" or "specifically binds" or "specific binding" in reference to the interaction of an antibody, or antibody fragment thereof, means that the interaction is dependent upon the presence of a particular structure (e.g., an antigenic determinant or epitope or target) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In certain embodiments, a binding protein or antibody or antigen-binding fragment thereof that specifically binds to an antigen binds to that antigen with a $K_D$ greater than $10^{-6}$M, $10^{-7}$M, $10^{-8}$M, $10^{-9}$M, $10^{-10}$ M, $10^{-11}$ M, $10^{-12}$ M, $10^{-13}$ M, $10^{-14}$ M. In other embodiments, a binding protein or antibody or antigen binding fragment thereof that specifically binds to an antigen binds to that antigen with a $K_D$ between $10^{-6}$ and $10^{-7}$M, $10^{-6}$ and $10^{-8}$M, $10^{-6}$ and $10^{-9}$M, $10^{-6}$ and $10^{-10}$ M, $10^{-6}$ and $10^{-11}$ M, $10^{-6}$ and $10^{-12}$ M, $10^{-6}$ and $10^{-13}$ M, $10^{-6}$ and $10^{-14}$ M, $10^{-9}$ and $10^{-10}$ M, $10^{-9}$ and $10^{-11}$ M, $10^{-9}$ and $10^{-12}$ M, $10^{-9}$ and $10^{-13}$ M, $10^{-9}$ and $10^{-14}$ M. In some embodiments, a binding protein or antibody or antigen-binding fragment thereof binds to an epitope, with a $K_D$ $10^{-5}$M or less, e.g., $10^{-6}$ M, $10^{-7}$M, $10^{-8}$M, $10^{-9}$M, $10^{10}$ M, $10^{-11}$ M, $10^{-12}$M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. In certain embodiments, a binding protein or antibody or antigen-binding fragment thereof is said to "specifically bind" an antigen when it preferentially recognizes its target antigen in a complex mixture of proteins and/or macromolecules. Binding proteins, antibodies or antigen-binding fragments that bind to the same or similar epitopes will likely cross-compete (one prevents the binding or modulating effect of the other). Cross-competition, however, can occur even without epitope overlap, e.g., if epitopes are adjacent in three-dimensional space and/or due to steric hindrance.

In certain embodiments, the antibody is an antibody-drug conjugate, such as an antibody which selectively bind to a polypeptide gene expression product of a pCD Gene Sequence or other protein that is upregulated in a population of IBD stem cells or its progeny, which antibody is conjugated to a drug that has a cytotoxic effect, cytostatic effect or epigenetic effect on the IBD stem cell and/or its progeny. "Cytotoxic effect," in reference to the effect of an agent on a cell, means killing of the cell. "Cytostatic effect" means an inhibition of cell proliferation. A "cytotoxic agent" means an agent that has a cytotoxic or cytostatic effect on a cell, thereby depleting or inhibiting the growth of, respectively, cells within a cell population.

When used for diagnostic or in vivo imaging purposes, the antibody can be conjugated to a detectable label, such as such as enzymes, DNA segments, fluorescent compounds, imaging agents, dyes and the like.

Antibodies suitable for use in accordance with the present compositions and methods are typically monoclonal and can include, for example, chimeric (e.g., having a human constant region and mouse variable region), humanized, or human antibodies; single chain antibodies; or the like. The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments, the antibody is an antigen-binding antibody fragment such as, for example, a Fab, a F(ab'), a F(ab')2, a Fd chain, a single-chain Fv (scFv), a single-chain antibody, a disulfide-linked Fv (sdFv), a fragment comprising either a VL or VH domain, or fragments produced by a Fab expression library, or an antigen-binding fragments of any of the above antibodies described supra. Antigen-binding antibody fragments, including single-chain antibodies, can comprise the variable region(s) alone or in combination with the entirety or a portion of the following: hinge region, CH1, CH2, CH3 and CL domains. Also, antigen-binding fragments can comprise any combination of variable region (s) with a hinge region, CH1, CH2, CH3 and CL domains. Typically, the antibodies are human, rodent (e.g., mouse and rat), donkey, sheep, rabbit, goat, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulin, as described infra and, for example in U.S. Pat. Nos. 5,939,598 and 6,111,166.

The antibodies maybe monospecific, bispecific, trispecific, or of greater multispecificity. Multispecific antibodies maybe specific for different epitopes of the same protein or may be specific for two different proteins. (See, e.g., PCT publications WO 93/17715; WO 92/08802; WO 91/00360; and WO 92/05793; Tutt et al., 1991, J Immunol 147:60-69; U.S. Pat. Nos. 4,474,893; 4,714,681; 4,925,648; 5,573,920; and 5,601,819; Kostelny et al., 1992, J Immunol 148:1547-1553.) Multispecific antibodies, including bispecific and trispecific antibodies, useful for practicing the methods described include herein are antibodies that immunospecifically bind to both an antigen on a protein selectively expressed by the IBD stem cell or its progeny, such as may be encoded by a pCD Gene Sequence and a second cell surface receptor or receptor complex, such as an immunoglobulin gene superfamily member, a TNF receptor superfamily member, an integrin, a cytoliine receptor, a chemokine receptor, a major histocompatibility protein, a lectin (C-type, S-type, or I-type), or a complement control protein. In a typical embodiment, the binding of the portion of the multispecific antibody to the second cell surface molecule or receptor complex enhances the cytotoxic or cytostatic effect of an antibody-drug conjugate.

In certain specific embodiments, the antibody is agonistic, non-agonistic or antagonistic with respective to the function of the protein to which is binds.

(i) Selective Delivery of Drug Conjugates

In certain embodiments, the IBD targeting antibody or other IBD selective affinity binder has a drug, toxin or other pharmacologically active moiety (collectively a "therapeutic agent" attached thereto, either covalently or non-covalently, such that the drug conjugate is preferentially released when the specific affinity binder is associated with tissue expressing the antigen to which the specific affinity binder binds, such as an antigen on the surface of an IBD stem cells or tissue derived therefrom.

As used herein, the term "therapeutic agent" refers to a substance that may be used in the cure, mitigation, treatment, or prevention of an inflammatory bowel disease in a human or another animal. Such therapeutic agents include substances recognized in the official United States Pharmacopeia, official Homeopathic Pharmacopeia of the United States, official National Formulary, or any supplement thereof, and include but are not limited to small molecules, nucleotides, oligopeptides, polypeptides, etc.

Therapeutic agents that may be attached to specific affinity binder polypeptides for selective killing of IBD stem cells or IBD stem cell derived tissues include, but are not limited to, cytotoxic agents, anti-metabolites, alkylating agents, antibiotics, growth factor, cytokines, anti-angiogenic agents, anti-mitotic agents, toxins, apoptotic agents or the like, such as DNA alkylating agents, topoisomerase inhibitors, endoplasmic reticulum stress inducing agents, platinum compounds, antimetabolites, vincalkaloids, taxanes, epothilones, enzyme inhibitors, receptor antagonists, therapeutic antibodies, tyrosine kinase inhibitors, radiosensitizers, and chemotherapeutic combination therapies, such as illustrations.

Non-limiting examples of DNA alkylating agents are nitrogen mustards, such as Mechlorethamine, Cyclophosphamide (Ifosfamide, Trofosfamide), Chlorambucil (Melphalan, Prednimustine), Bendamustine, Uramustine and Estramustine; nitrosoureas, such as Carmustine (BCNU), Lomustine (Semustine), Fotemustine, Nimustine, Ranimustine and Streptozocin; alkyl sulfonates, such as Busulfan (Mannosulfan, Treosulfan); Aziridines, such as Carboquone, ThioTEPA, Triaziquone, Triethylenemelamine; Hydrazines (Procarbazine); Triazenes such as Dacarbazine and Temozolomide; Altretamine and Mitobronitol.

Non-limiting examples of Topoisomerase I inhibitors include Campothecin derivatives including CPT-11 (irinotecan), SN-38, APC, NPC, campothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as described in Pommier Y. (2006) Nat. Rev. Cancer 6(10): 789-802 and U.S. Patent Publication No. 200510250854; Protoberberine alkaloids and derivatives thereof including berberrubine and coralyne as described in Li et al. (2000) Biochemistry 39(24):7107-7116 and Gatto et al. (1996) Cancer Res. 15(12):2795-2800; Phenanthroline derivatives including Benzo[i]phenanthridine, Nitidine, and fagaronine as described in Makhey et al. (2003) Bioorg. Med. Chem. 11 (8): 1809-1820; Terbenzimidazole and derivatives thereof as described in Xu (1998) Biochemistry 37(10):3558-3566; and Anthracycline derivatives including Doxorubicin, Daunorubicin, and Mitoxantrone as described in Foglesong et al. (1992) Cancer Chemother. Pharmacol. 30(2):123-]25, Crow et al. (1994) J. Med. Chem. 37(19):31913194, and Crespi et al. (1986) Biochem. Biophys. Res. Commun. 136(2):521-8. Topoisomerase II inhibitors include, but are not limited to Etoposide and Teniposide. Dual topoisomerase I and II inhibitors include, but are not limited to, Saintopin and other Naphthecenediones, DACA and other Acridine-4-Carboxamindes, Intoplicine and other Benzopyridoindoles, TAS-103 and other 7H-indeno[2,1-c]Quinoline-7-ones, Pyrazoloacridine, XR 11576 and other Benzophenazines, XR 5944 and other Dimeric compounds, 7-oxo-7H-dibenz[f,ij]Isoquinolines and 7-oxo-7H-benzo[e] Perimidines, and Anthracenyl-amino Acid Conjugates as described in Denny and Baguley (2003) Curr. Top. Med. Chem. 3(3):339-353. Some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

Examples of endoplasmic reticulum stress inducing agents include, but are not limited to, dimethyl-celecoxib (DMC), nelfinavir, celecoxib, and boron radiosensitizers (i.e. velcade (Bortezomib)).

Non-limiting examples of platinum-based compound include Carboplatin, Cisplatin, Nedaplatin, Oxaliplatin, Triplatin tetranitrate, Satraplatin, Aroplatin, Lobaplatin, and JM-216. (see McKeage et al. (1997) J. Clin. Oncol. 201: 1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

Non-limiting examples of antimetabolite agents include Folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU). Equivalents to 5-FU include prodrugs, analogs and derivative thereof such as 5'-deoxy-5-fluorouridine (doxifluoroidine), 1-tetrahydrofuranyl-5-fluorouracil (ftorafur), Capecitabine (Xeloda), S-I (MBMS-247616, consisting of tegafur and two modulators, a 5-chloro-2,4-dihydroxypyridine and potassium oxonate), ralititrexed (tomudex), no latrexed (Thymitaq, AG337), LY231514 and ZD9331, as described for example in Papamicheal (1999) The Oncologist 4:478-487.

Examples of vincalkaloids, include, but are not limited to Vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifamib); CDK inhibitor (Alvocidib, Seliciclib); proteasome inhibitor (Bortezomib); phosphodiesterase inhibitor (Anagrelide; rolipram); IMP dehydrogenase inhibitor (Tiazofurine); and lipoxygenase inhibitor (Masoprocol). Examples of receptor antagonists include, but are not limited to ERA (Atrasentan); retinoid X receptor (Bexarotene); and a sex steroid (Testolactone).

Examples of therapeutic antibodies include, but are not limited to anti-HER1/EGFR (Cetuximab, Panitumumab); Anti-HER2/neu (erbB2) receptor (Trastuzumab); Anti-EpCAM (Catumaxomab, Edrecolomab) Anti-VEGF-A (Bevacizumab); Anti-CD20 (Rituximab, Tositumomab, Ibritumomab); Anti-CD52 (Alemtuzumab); and Anti-CD33 (Gemtuzumab). U.S. Pat. Nos. 5,776,427 and 7,601,355.

Examples of tyrosine kinase inhibitors include, but are not limited to inhibitors to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib), FLT3 (Lestaurtinib), PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib).

Chemotherapeutic agents that can be attached to the present specific affinity binder polypeptides may also include amsacrine, Trabectedin, retinoids (Alitretinoin, Tretinoin), Arsenic trioxide, asparagine depleter Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

Examples of specific therapeutic agents that can be linked, ligated, or associated with the specific affinity binder polypeptides of the invention are flomoxef; fortimicin(s); gentamicin(s); glucosulfone solasulfone; gramicidin S; gramicidin(s); grepafloxacin; guamecycline; hetacillin; isepamicin; josamycin; kanamycin(s); flomoxef; fortimicin(s); gentamicin(s); glucosulfone solasulfone; gramicidin S; gramicidin(s); grepafloxacin; guamecycline; hetacillin; isepamicin; josamycin; kanamycin(s); bacitracin; bambermycin(s); biapenem; brodimoprim; butirosin; capreomycin; carbenicillin; carbomycin; carumonam; cefadroxil; cefamandole; cefatrizine; cefbuperazone; cefclidin; cefdinir; cefditoren; cefepime; cefetamet; cefixime; cefmenoxime; cefminox; cladribine; apalcillin; apicycline; apramycin; arbekacin; aspoxicillin; azidamfenicol; aztreonam; cefodizime; cefonicid; cefoperazone; ceforamide; cefotaxime; cefotetan; cefotiam; cefozopran; cefpimizole; cefpiramide; cefpirome; cefprozil; cefroxadine; cefteram; ceftibuten; cefuzonam; cephalexin; cephaloglycin; cephalosporin C; cephradine; chloramphenicol; chlortetracycline; clinafloxacin; clindamycin; clomocycline; colistin; cyclacillin; dapsone; demeclocycline; diathymosulfone; dibekacin; dihydrostreptomycin; 6-mercaptopurine; thioguanine; capecitabine; docetaxel; etoposide; gemcitabine; topotecan; vinorelbine; vincristine; vinblastine; teniposide; melphalan; methotrexate; 2-p-sulfanilyanilinoethanol; 4,4'-sulfinyldianiline; 4-sulfanilamidosalicylic acid; butorphanol; nalbuphine. streptozocin; doxorubicin; daunorubicin; plicamycin; idarubicin; mitomycin C; pentostatin; mitoxantrone; cytarabine; fludarabine phosphate; butorphanol; nalbuphine. streptozocin; doxorubicin; daunorubicin; plicamycin; idarubicin; mitomycin C; pentostatin; mitoxantrone; cytarabine; fludarabine phosphate; acediasulfone; acetosulfone; amikacin; amphotericin B; ampicillin; atorvastatin; enalapril; ranitidine; ciprofloxacin; pravastatin; clarithromycin; cyclosporin; famotidine; leuprolide; acyclovir; paclitaxel; azithromycin; lamivudine; budesonide; albuterol; indinavir; metformin; alendronate; nizatidine; zidovudine; carboplatin; metoprolol; amoxicillin; diclofenac; lisinopril; ceftriaxone; captopril; salmeterol; xinafoate; imipenem; cilastatin; benazepril; cefaclor; ceftazidime; morphine; dopamine; bialamicol; fluvastatin; phenamidine; podophyllinic acid 2-ethylhydrazine; acriflavine; chloroazodin; arsphenamine; amicarbilide; aminoquinuride; quinapril; oxymorphone; buprenorphine; floxuridine; dirithromycin; doxycycline; enoxacin; enviomycin; epicillin; erythromycin; leucomycin(s); lincomycin; lomefloxacin; lucensomycin; lymecycline; meclocycline; meropenem; methacycline; micronomicin; midecamycin(s); minocycline; moxalactam; mupirocin; nadifloxacin; natamycin; neomycin; netilmicin; norfloxacin; oleandomycin; oxytetracycline; p-sulfanilylbenzylamine; panipenem; paromomycin; pazufloxacin; penicillin N; pipacycline; pipemidic acid; polymyxin; primycin; quinacillin; ribostamycin; rifamide; rifampin; rifamycin SV; rifapentine; rifaximin; ristocetin; ritipenem; rokitamycin; rolitetracycline; rosaramycin; roxithromycin; salazosulfadimidine; sancycline; sisomicin; sparfloxacin; spectinomycin; spiramycin; streptomycin; succisulfone; sulfachrysoidine; sulfaloxic acid; sulfamidochrysoidine; sulfanilic acid; sulfoxone; teicoplanin; temafloxacin; temocillin; tetroxoprim; thiamphenicol; thiazolsulfone; thiostrepton;

ticarcillin; tigemonam; tobramycin; tosufloxacin; trimethoprim; trospectomycin; trovafloxacin; tuberactinomycin; vancomycin; azaserine; candicidin(s); chlorphenesin; dermostatin(s); filipin; fungichromin; mepartricin; nystatin; oligomycin(s); perimycin A; tubercidin; 6-azauridine; 6-diazo-5-oxo-L-norleucine; aclacinomycin(s); ancitabine; anthramycin; azacitadine; azaserine; bleomycin(s); ethyl biscoumacetate; ethylidene dicoumarol; iloprost; lamifiban; taprostene; tioclomarol; tirofiban; amiprilose; bucillamine; gusperimus; gentisic acid; glucamethacin; glycol salicylate; meclofenamic acid; mefenamic acid; mesalamine; niflumic acid; olsalazine; oxaceprol; S-enosylmethionine; salicylic acid; salsalate; sulfasalazine; tolfenamic acid; carubicin; carzinophillin A; chlorozotocin; chromomycin(s); denopterin; doxifluridine; edatrexate; eflornithine; elliptinium; enocitabine; epirubicin; mannomustine; menogaril; mitobronitol; mitolactol; mopidamol; mycophenolic acid; nogalamycin; olivomycin(s); peplomycin; pirarubicin; piritrexim; prednimustine; procarbazine; pteropterin; puromycin; ranimustine; streptonigrin; thiamiprine; mycophenolic acid; procodazole; romurtide; sirolimus (rapamycin); tacrolimus; butethamine; fenalcomine; hydroxytetracaine; naepaine; orthocaine; piridocaine; salicyl alcohol; 3-amino-4-hydroxybutyric acid; aceclofenac; alminoprofen; amfenac; bromfenac; bromosaligenin; bumadizon; carprofen; diclofenac; diflunisal; ditazol; enfenamic acid; etodolac; etofenamate; fendosal; fepradinol; flufenamic acid; Tomudex (N-[[5-[[(1,4-Dihydro-2-methyl-4-oxo-6-quinazolinyl) methyl]methylamino]-2-thienyl]carbonyl]-L-glutamic acid), trimetrexate, tubercidin, ubenimex, vindesine, zorubicin; argatroban; coumetarol or dicoumarol.

In certain embodiments, the IBD targeting antibody or other selective affinity binder includes a conjugated cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, Phytoiacca americana proteins PAPI, PAPII, and PAP-S, *Momordica charantia* inhibitor, curcin, crotin, *Saponaria officinalis* inhibitor, mitogellin, restrictocin, phenomycin, and enomycin.

In certain embodiments, the IBD targeting antibody or other selective affinity binder includes a conjugated anti-inflammatory or immunosuppressive agent that is released in the area of the targeted IBD stem cell or IBD stem cell derived tissue.

In certain embodiments, the IBD targeting antibody or other selective affinity binder includes a conjugated epigenetic agent that induces one or more epigenetic changes to the targeted IBD stem cell or IBD stem cell derived tissue, such as resulting in cell death, inhibition of proliferation, inhibition of differentiation, and/or altered tissue fate upon differentiation of the targeted IBD stem cell such that the resulting tissue is either normal or at least results in reduced symptoms or inflammation during the course of the disease.

Any method known in the art for conjugating to antibodies and other proteins may be employed in generating the conjugates of the present invention, including those methods described by Hunter, et al., (1962) Nature 144:945; David, et al., (1974) Biochemistry 13:1014; Pain, et al., (1981) J. Immunol. Meth. 40:219; and Nygren, J., (1982) Histochem. and Cytochem. 30:407. Methods for conjugating peptide, polypeptide and organic and inorganic moieties to antibodies and other proteins are conventional and very well known in the art and readily adapted for generating those versions of the subject IBD targeting antibody or other IBD selective affinity binder.

Where the conjugated moiety is a peptide or polypeptide, that moiety can be chemically cross-linked to the specific affinity binder, or can be included as part of a fusion protein with the specific affinity binder polypeptide. And illustrative example would be a diptheria toxin-antibody fusion protein. In the case of non-peptide entities, the addition to the specific affinity binder polypeptide will generally be by way of chemical conjugation to the specific affinity binder polypeptide—such as through a functional group on an amino acid side chain or the carboxyl group at the C-terminal or amino group at the N-terminal end of the polypeptide. In certain embodiment, whether as a fusion protein or chemically cross-linked moiety, the conjugated moiety will include one or more sites that can be cleaved by an enzyme or are otherwise sensitive to an environmental condition (such as pH) that permits the conjugated moiety to be released from the specific affinity binder polypeptide, such as in the tumour or other diseased tissue (or tissue to be protected if the conjugated moiety functions to protect healthy tissue).

i. Diagnostics

The subject invention further provides a method of determining whether a cell sample obtained from a subject possesses an abnormal amount of marker polypeptide which comprises (a) obtaining a cell sample from the subject, (b) quantitatively determining the amount of the marker polypeptide in the sample so obtained, and (c) comparing the amount of the marker polypeptide so determined with a known standard, so as to thereby determine whether the cell sample obtained from the subject possesses an abnormal amount of the marker polypeptide. Such marker polypeptides may be detected by immunohistochemical assays, dot-blot assays, ELISA and the like.

Immunoassays are commonly used to quantitate the levels of proteins in cell samples, and many other immunoassay techniques are known in the art. The invention is not limited to a particular assay procedure, and therefore is intended to include both homogeneous and heterogeneous procedures. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art.

In another embodiment, the level of the encoded product, i.e., the product encoded by an IBD gene (such as an pCD Gene Sequence) or a sequence complementary thereto, in a biological fluid (e.g., blood or urine) of a patient may be determined as a way of monitoring the level of expression of the marker nucleic acid sequence in cells of that patient. Such a method would include the steps of obtaining a sample of a biological fluid from the patient, contacting the sample (or proteins from the sample) with an antibody specific for a encoded marker polypeptide, and determining the amount of immune complex formation by the antibody, with the amount of immune complex formation being indicative of the level of the marker encoded product in the sample. This determination is particularly instructive when compared to the amount of immune complex formation by the same antibody in a control sample taken from a normal individual or in one or more samples previously or subsequently obtained from the same person.

As set out above, one aspect of the present invention relates to diagnostic assays for determining, in the context of cells isolated from a patient, if the level of a marker polypeptide is significantly reduced in the sample cells. The term "significantly reduced" refers to a cell phenotype wherein the cell possesses a reduced cellular amount of the marker polypeptide relative to a normal cell of similar tissue origin. For example, a cell may have less than about 50%, 25%, 10%, or 5% of the marker polypeptide that a normal control cell. In particular, the assay evaluates the level of marker polypeptide in the test cells, and, preferably, compares the measured level with marker polypeptide detected in at least one control cell, e.g., a normal cell and/or a transformed cell of known phenotype.

Of particular importance to the subject invention is the ability to quantitate the level of marker polypeptide as determined by the number of cells associated with a normal or abnormal marker polypeptide level. The number of cells with a particular marker polypeptide phenotype may then be correlated with patient prognosis. In one embodiment of the invention, the marker polypeptide phenotype of the lesion is determined as a percentage of cells in a biopsy which are found to have abnormally high/low levels of the marker polypeptide. Such expression may be detected by immunohistochemical assays, dot-blot assays, ELISA and the like.

Where tissue samples are employed, immunohistochemical staining may be used to determine the number of cells having the marker polypeptide phenotype. For such staining, a multiblock of tissue is taken from the biopsy or other tissue sample and subjected to proteolytic hydrolysis, employing such agents as protease K or pepsin. In certain embodiments, it may be desirable to isolate a nuclear fraction from the sample cells and detect the level of the marker polypeptide in the nuclear fraction.

The tissue samples are fixed by treatment with a reagent such as formalin, glutaraldehyde, methanol, or the like. The samples are then incubated with an antibody, preferably a monoclonal antibody, with binding specificity for the marker polypeptides. This antibody may be conjugated to a label for subsequent detection of binding. Samples are incubated for a time sufficient for formation of the immuno-complexes. Binding of the antibody is then detected by virtue of a label conjugated to this antibody. Where the antibody is unlabeled, a second labeled antibody may be employed, e.g., which is specific for the isotype of the anti-marker polypeptide antibody. Examples of labels which may be employed include radionuclides, fluorescers, chemiluminescers, enzymes and the like.

Where enzymes are employed, the substrate for the enzyme may be added to the samples to provide a colored or fluorescent product. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

In one embodiment, the assay is performed as a dot blot assay. The dot blot assay finds particular application where tissue samples are employed as it allows determination of the average amount of the marker polypeptide associated with a single cell by correlating the amount of marker polypeptide in a cell-free extract produced from a predetermined number of cells.

In one embodiment, the present invention also provides a method wherein nucleic acid probes are immobilized on a DNA chip in an organized array. Oligonucleotides can be bound to a solid support by a variety of processes, including lithography. For example a chip can hold up to 250,000 oligonucleotides (GeneChip, Affymetrix). These nucleic acid probes comprise a nucleotide sequence at least about 12 nucleotides in length, preferably at least about 15 nucleotides, more preferably at least about 25 nucleotides, and most preferably at least about 40 nucleotides, and up to all or nearly all of a sequence which is complementary to a portion of the coding sequence of one or more marker nucleic acid sequence for pCD Gene Sequences.

The method includes obtaining a biopsy, which is optionally fractionated by cryostat sectioning to enrich tumor cells to about 80% of the total cell population. The DNA or RNA is then extracted, amplified, and analyzed with a DNA chip to determine the presence of absence of the marker nucleic acid sequences.

In one embodiment, the nucleic acid probes are spotted onto a substrate in a two-dimensional matrix or array. Samples of nucleic acids can be labeled and then hybridized to the probes. Double-stranded nucleic acids, comprising the labeled sample nucleic acids bound to probe nucleic acids, can be detected once the unbound portion of the sample is washed away.

The probe nucleic acids can be spotted on substrates including glass, nitrocellulose, etc. The probes can be bound to the substrate by either covalent bonds or by non-specific interactions, such as hydrophobic interactions. The sample nucleic acids can be labeled using radioactive labels, fluorophores, chromophores, etc.

Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. Nos. 5,593,839; 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734.

In yet another embodiment, the invention contemplates using a panel of antibodies which are generated against the marker polypeptides of this invention, such as polypeptides encoded by one or more of the pCD Gene Sequences. Such a panel of antibodies may be used as a reliable diagnostic probe for IBD. The assay of the present invention comprises contacting a biopsy sample containing cells, e.g., colon cells, with a panel of antibodies to one or more of the encoded products to determine the presence or absence of the marker polypeptides.

The diagnostic methods of the subject invention may also be employed as follow-up to treatment, e.g., quantitation of the level of marker polypeptides may be indicative of the effectiveness of current or previously employed IBD therapies as well as the effect of these therapies upon patient prognosis.

Accordingly, the present invention makes available diagnostic assays and reagents for detecting gain and/or loss of marker polypeptides from a cell in order to aid in the diagnosis and phenotyping of proliferative disorders arising from, for example, tumorigenic transformation of cells.

The diagnostic assays described above can be adapted to be used as prognostic assays, as well. Such an application takes advantage of the sensitivity of the assays of the invention to events which take place at characteristic stages in the progression of the disorder.

The methods of the invention can also be used to follow the clinical course of an IBD. For example, the assay of the invention can be applied to a tissue sample from a patient; following treatment of the patient for the IBD, another tissue sample is taken and the test repeated. Successful treatment will result in either removal of all cells which demonstrate differential expression characteristic of the IBD.

In yet another embodiment, the invention provides methods for determining whether a subject is at risk for developing a disease, such as a predisposition to develop IBD, for example UC or CD, associated with an aberrant activity of any one of the polypeptides encoded by nucleic acids of an IBD gene, such as a pCD Gene Sequence, wherein the aberrant activity of the polypeptide is characterized by detecting the presence or absence of a genetic lesion characterized by at least one of (i) an alteration affecting the integrity of a gene encoding a marker polypeptides, or (ii) the mis-expression of the encoding nucleic acid. To illustrate, such genetic lesions can be detected by ascertaining the existence of at least one of (i) a deletion of one or more nucleotides from the nucleic acid sequence, (ii) an addition of one or more nucleotides to the nucleic acid sequence, (iii) a substitution of one or more nucleotides of the nucleic acid sequence, (iv) a gross chromosomal rearrangement of the nucleic acid sequence, (v) a gross alteration in the level of a messenger RNA transcript of the nucleic acid sequence, (vii) aberrant modification of the nucleic acid sequence, such as of the methylation pattern of the genomic DNA, (vii) the presence of a non-wild type splicing pattern of a messenger RNA transcript of the gene, (viii) a non-wild type level of the marker polypeptide, (ix) allelic loss of the gene, and/or (x) inappropriate post-translational modification of the marker polypeptide.

The present invention provides assay techniques for detecting lesions in the encoding nucleic acid sequence. These methods include, but are not limited to, methods involving sequence analysis, Southern blot hybridization, restriction enzyme site mapping, and methods involving detection of absence of nucleotide pairing between the nucleic acid to be analyzed and a probe.

Specific diseases or disorders, e.g., genetic diseases or disorders, are associated with specific allelic variants of polymorphic regions of certain genes, which do not necessarily encode a mutated protein. Thus, the presence of a specific allelic variant of a polymorphic region of a gene in a subject can render the subject susceptible to developing a specific disease or disorder. Polymorphic regions in genes, can be identified, by determining the nucleotide sequence of genes in populations of individuals. If a polymorphic region is identified, then the link with a specific disease can be determined by studying specific populations of individuals, e.g, trig individuals which developed a specific disease, such as an IBD. A polymorphic region can be located in any region of a gene, e.g., exons, in coding or non coding regions of exons, introns, and promoter region.

In an exemplary embodiment, there is provided a nucleic acid composition comprising a nucleic acid probe including a region of nucleotide sequence which is capable of hybridizing to a sense or antisense sequence of a gene or naturally occurring mutants thereof, or 5' or 3' flanking sequences or intronic sequences naturally associated with the subject genes or naturally occurring mutants thereof. The nucleic acid of a cell is rendered accessible for hybridization, the probe is contacted with the nucleic acid of the sample, and the hybridization of the probe to the sample nucleic acid is detected. Such techniques can be used to detect lesions or allelic variants at either the genomic or mRNA level, including deletions, substitutions, etc., as well as to determine mRNA transcript levels.

A preferred detection method is allele specific hybridization using probes overlapping the mutation or polymorphic site and having about 5, 10, 20, 25, or 30 nucleotides around the mutation or polymorphic region. In a preferred embodiment of the invention, several probes capable of hybridizing specifically to allelic variants are attached to a solid phase support, e.g., a "chip". Mutation detection analysis using these chips comprising oligonucleotides, also termed "DNA probe arrays" is described e.g., in Cronin et al. Human Mutation 7:244 (1996). In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

In certain embodiments, detection of the lesion comprises utilizing the probe/primer in a polymerase chain reaction (PCR) (see, e.g. U.S. Pat. Nos. 4,683,195 and 4,683,202), such as anchor PCR, Reverse transcription PCR (RT-PCR) or RACE PCR, or, alternatively, in a ligase chain reaction (LCR) (see, e.g., Landegran et al. Science 241:1077-1080 (1988); and Nakazawa et al. Proc. Natl. Acad. Sci. USA 91:360-364 (1994)), the latter of which can be particularly useful for detecting point mutations in the gene (see Abravaya et al. Nuc. Acid. Res. 23:675-682 (1995)). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a nucleic acid sequence under conditions such that hybridization and amplification of the nucleic acid (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., Proc. Natl. Acad. Sci. USA 87:1874-1878 1990), transcriptional amplification system (Kwoh et al., Proc. Natl. Acad. Sci. USA 86:1173-1177 (1989)), Q-Beta Replicase (Lizardi et al., Bio/Technology 6:1197 (1988)), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in, or allelic variants, of a gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

Another aspect of the present invention relates to methods for identifying genes which are up- or down-regulated in intestinal tissue of patients who have, or are at risk of developing, an inflammatory bowel disease or disorder. In general, the method provides for (i) generating a first library of nucleic acid probes representative of genes expressed by intestinal tissue of an animal without apparent symptoms and/or risk for an inflammatory bowel disease or disorder;

(ii) generating a second library of nucleic acid probes representative of genes expressed by intestinal tissue of an animal which has symptoms of, and/or is at risk for developing, an inflammatory bowel disease or disorder; and (iii) identifying genes that up- or down-regulated, e.g., by at least a predetermined fold difference, in the second library of nucleic acids relative to the first library of nucleic acids.

The subject method can include such further steps as: cloning those genes which are up- or down-regulated; generating nucleic acid probes for detecting the level of expression of those genes which are up- or down-regulated; and providing kits, such as microarrays, including probes for detecting the level of expression of those genes which are up- or down-regulated.

In one preferred embodiment, the present invention relates to methods of determining the phenotype of a cell, particularly a cell of intestinal origin, comprising detecting the differential expression, relative to a normal cell, of at least one gene (and more preferably 10, 25 or even 50 different genes) of the pCD Gene Sequences or other IBD genes identified according to the subject differential display methodology. In particular, the present invention provides methods of determining the phenotype of a cell, particularly a cell of intestinal origin, comprising detecting the differential expression, relative to a normal cell, or at least one gene, or at least about two genes, about four genes, about six genes, about eight genes, about ten genes, about twelve genes, about fourteen genes, about sixteen genes, about eighteen genes, or about twenty genes; and more preferably about twenty-five genes, about thirty genes, about thirty-five genes, about forty genes, about forty-five genes, or about fifty genes. The assay detects a difference in the level of expression of at least a factor of two, preferably by at least a factor of five, and more preferably by at least a factor of twenty, or at least a factor of fifty. In particular, wherein the assay detects a difference in the level of expression of at least a factor of about two, about four, about six, about eight, about ten, about twelve, about fourteen, about sixteen, about eighteen, or about twenty; and more preferably a factor of about twenty-five, about thirty, about thirty-five, about forty, about forty-five, or about fifty. In certain embodiments, a change in the level of expression of at least 10 percent, and more preferably at least 25, 50, 75, or 90 percent, of the IBD gene set indicates an increased risk of the patient having, or developing, an inflammatory bowel disease. In preferred embodiments, the changes (up- or down-regulation) of IBD genes which indicate an increased risk of the patient having, or developing, an inflammatory bowel disease are in the same direction, and more preferably of the same approximate magnitude.

In other embodiments, the assay can be used to detect mutations or epigenetic changes effecting the chromosomal integrity of an IBD gene, e.g., by detecting mutations (insertions, deletions, point mutations, methylation levels) to the coding sequence or transcriptional regulatory sequences and, e.g., effecting one or more alleles of an IBD gene. In still other embodiments, the method can be used to detect alterations in splicing of IBD transcripts, changes in the levels of IBD proteins, changes in post-translational modification of IBD proteins, and/or changes in half-lives for IBD proteins.

In addition to detecting alterations at the nucleic acid level, the subject method can be carried out by detecting the level of protein encoded by an IBD gene, e.g., by immunoassay or other proteometric technique.

The subject method can be used diagnostically, e.g., to identify patients who have developed, or are at risk of developing, an inflammatory bowel disease. In this regard, the subject method can also be used to distinguish the cause of inflammatory bowel symptoms, e.g., to distinguish between UC and CD. The subject method can also be used prognostically for patients already diagnosed with an IBD, e.g., to determine the aggressive or stage of their disease. In either case, the subject method can be used to augment treatment decisions.

The samples used to determine the level of expression of an IBD gene or gene product can include biopsied materials. However, in certain embodiments, genes which are up- or down-regulated in inflammatory bowel diseases encode proteins which can be detected in bodily fluids or in fecal matter. For example, as described in further detail below, certain of the IBD genes encode secreted factors. Accordingly, the present invention specifically contemplates assays which detect a change in the serum level (or other bodily fluid) of one or more secreted IBD gene products. In such embodiments, the method may make use of an immunoassay, e.g., including an antibody panel (or other binding protein) to detect the level of an IBD gene product in the fluid sample.

Another aspect of the present invention provides libraries of nucleic acid probes ("IBD probes") for indexing the level of expression of one or more IBD genes. For instance, such nucleic acid probes can be immobilized on a solid support, e.g., paper, membranes, filters, chips, pins or glass slides, or any other appropriate substrate. In preferred embodiments, the invention provides a microarray of IBD probes for detecting transcripts of at least 5 different IBD genes, more preferably at least 10, and even more preferably at least 25, 50, 75, 100, 125 or all of the genes in the IBD gene set described herein. In particular, the present invention provides a microarray of IBD probes for detecting transcripts of at least about five different IBD genes, about seven different IBD genes, about nine different IBD genes, about thirteen different IBD genes, or about fifteen different IBD genes; preferably at least about twenty different IBD genes, about twenty-five different IBD genes, about thirty different IBD genes, about thirty-five different IBD genes, about forty different IBD genes, about forty-five different IBD genes, or about fifty different IBD genes; and more preferably at least about sixty different IBD genes, about seventy different IBD genes, about eighty different IBD genes, about ninety different IBD genes, about one hundred different IBD genes, or all of the genes of the IBD gene set.

In general, the subject IBD probes will be isolated nucleic acids (oligonucleotides) comprising a nucleotide sequence which hybridizes under stringent conditions to a pCD Gene Sequence or a sequence complementary thereto. In a related embodiment, the nucleic acid is at least about 80% or about 100% identical to a sequence corresponding to at least about 12, at least about 15, at least about 25, or at least about 40 consecutive nucleotides up to the full length of one of the pCD Gene Sequences or a sequence complementary thereto or up to the full length of the gene of which said sequence is a fragment. In certain embodiments, a nucleic acid of the present invention includes at least about five, at least about ten, or at least about twenty nucleic acids from a novel coding sequence region of an IBD gene. The IBD probes may include a label group attached thereto and able to be detected. The label group may be selected from radioisotopes, fluorescent compounds, enzymes, and enzyme cofactors.

In certain embodiments, the kit may further include instructions for using the kit, solutions for suspending or fixing the cells, detectable tags or labels, solutions for rendering a nucleic acid susceptible to hybridization, solutions for lysing cells, or solutions for the purification of nucleic acids.

j. Drug Screening

Still another aspect of the present invention provides drug screening assays for identifying agents which can be used to treat or manage the effects of an inflammatory bowel disease or disorder, e.g., by counteracting the effects of the up- or down-regulation of one or more of the subject IBD genes, such as the pCD Gene Sequences. Such assays include formats which detect agents that inhibit or potentiate expression (transcription or translation) of an IBD gene, formats which detect agents that inhibit or potentiate an activity of an IBD gene product (enzymatic activity, protein-protein interaction, protein-DNA interaction, etc), formats which detect agents that which alter the splicing of IBD gene transcripts, and formats which detect agents that which shorten or extend the half-life of an IBD gene product. For each of the assay embodiments set out above, the assay is preferably repeated for a variegated library of at least 100 different test compounds, though preferably libraries of at least $10^3$, $10^5$, $10^7$, and $10^9$ compunds are tested. The test compound (or test agents) can be, for example, peptides, carbohydrates, nucleic acids and other small organic molecules, and/or natural product extracts, such as, but not limited to small molecules, peptide, peptidomimetic, natural compound, siRNA, anti-sense nucleic acid, aptamer, or antibodies and other specific affinity binders.

In yet another aspect, the invention provides pharmaceutical compositions including agents, e.g., which have been identified by the assays described herein, which alter the level of expression or splicing of one or more IBD genes, alter the activity or half-life of an IBD gene product, or which alter the post-translational modification of an IBD gene product.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning—A Laboratory—Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

Another aspect of the invention is directed to the identification of agents capable of modulating the growth state of an IBD stem cell or its progeny, where the drug screening method involves contact the cell or resulting in vitro tissue (such as 3-D muscosa) with one or more candidate agents, including small organic molecules, nucleic acids, peptides and polypeptides, natural extracts and carbohydrates (as examples). In this regard, the invention provides assays for detecting changes at the cellular level, such as by gross physiological consequences (proliferation, differentiation, cell death) or specified changes, such as modulation of the expression of marker nucleic acids (such as a pCD Gene Sequence) or protein it encodes, changes in expression of a reporter construct, or other detectable discrete changes in the cells morphology, gene expression profile and/or epigenetic profile. The availability according to the present invention of normal tissues and cells, particularly patient matched normal tissue (stem cells and differentiated cells), for counter-screening makes this approach particularly robust.

Exemplary high through out screening using whole cell assays of the IBD stem cells or differentiated tissue include synthetic lethality screens, such as screens using shRNA/siRNA/CRISPR libraries for loss-of-function assays to identify genes for which inhibition is synthetically lethal to IBD stem cell. The nucleic acid library can, in certain embodiments, be biased to identify cell surface proteins and channels (GPCRs, etc) for which antagonist antibodies and small molecule ligands can be generated, or biased to identify enzyme classes for subsequent small molecule inhibitor development.

Another embodiment of the whole cell drug discovery platform involves differential expression profiling to identify genes/gene products up or down regulated in the IBD stem cell or differentiated tissue thereof which may be potential targets for drugs that can reverse or diminish the role of IBD stem cells in inflammatory bowel diseases. Targets upregulated in IBD stem cells or their progeny, particular those have extracellular cell surface domains, are also particularly amenable to targeting in the development of Antibody-Drug Conjugate agents. Intracellular targets, particularly signal transduction pathways and transcriptional factors, that may be upregulated in the IBD stem cells or differentiated tissue derived therefrom are also potential targets for drugs that can reverse or diminish the role of IBD stem cells in inflammatory bowel diseases, especially small molecule and nucleic acid drug agents. Enzymes, such as proteases, kinases, phosphatases and the like, that may be upregulated in the IBD stem cells or differentiated tissue derived therefrom can be targets for drugs that can reverse or diminish the role of IBD stem cells in inflammatory bowel diseases, especially small molecules and antibodies. Cell surface receptors and channels, such as ligand binding receptors and ion channels, that may be upregulated in the IBD stem cells or differentiated tissue derived therefrom can be targets for drugs that can reverse or diminish the role of IBD stem cells in inflammatory bowel diseases, especially small molecules and antibodies and ligand antagonists.

Several in vitro cell based methods can be used to identify compounds that modulate expression of the marker nucleic acids (e.g., an IBD gene) and/or alter for example, inhibit the bioactivity of the encoded polypeptide. Merely to illustrate, in certain embodiments drug screening is performed by adding a test compound to a sample of IDB stem cells, and than monitoring the effect. A parallel sample which does not receive the test compound is also monitored as a control. To find agents that are selective for IBD stem cells, a third set of stem cells—derived from normal GI epithelia—are also monitored with and without adding the test compound. The treated and untreated cells are then compared by any suitable phenotypic criteria, including but not limited to microscopic analysis, viability testing, ability to replicate, histological examination, the level of a particular RNA or polypeptide associated with the cells, the level of enzymatic activity expressed by the cells or cell lysates, and the ability of the cells to interact with other cells or compounds, cell viability, epigenetic changes, etc. Differences between treated and untreated cells indicates effects attributable to the test compound. A greater difference in responsiveness in the case of the IBD stem cells relative to the normal GI epithelial stem cells indicates selectivity.

Desirable effects of a test compound include an effect on any phenotype that was conferred by the IBD-associated marker nucleic acid sequence. Examples include a test compound that limits the overabundance of mRNA, limits production of the encoded protein, or limits the functional effect of the protein. The effect of the test compound would be apparent when comparing results between treated and untreated cells.

High throughput screening (HTS) is used for analyzing many discrete compounds in parallel, so that large numbers of test compounds can be quickly screened. The most widely established techniques utilize 96-well, 384-well or 1536-well microtiter plates. The wells of the microtiter plates typically require assay volumes that range from 5 to 500 microliters. In addition to the plates, many instruments, materials, pipettors, robotics, plate washers, and plate readers are commercially available to fit the micro well formats.

The chemical entity or biological product is preferably, but not necessarily a low molecular weight compound, but may also be a larger compound, or any organic or inorganic molecule effective in the given situation, including modified and unmodified nucleic acids such as antisense nucleic acids, RNAi, such as siRNA or shRNA, CRISPR-Cas systems, peptides, peptidomimetics, receptors, ligands, and antibodies, aptamers, polypeptides, nucleic acid analogues or variants thereof. Examples include an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. Agents can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), modified RNA (mod-RNA), single guide RNA etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mR-NAi), antisense oligonucleotides, CRISPR guide RNA, for example that target a CRISPR enzyme to a specific DNA target sequence etc. A protein and/or peptide or fragment thereof can be any protein of interest, for example, but are not limited to: mutated proteins; therapeutic proteins; and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies and other specific affinity binders (including humanized antibodies, chimeric antibodies and the like), modified proteins and fragments thereof. Alternatively, the agent can be intracellular within the cell as a result of introduction of a nucleic acid sequence into the cell and its transcription resulting in the production of the nucleic acid and/or protein modulator of a gene within the cell. In some embodiments, the agent is any chemical, entity or moiety, including without limitation synthetic and naturally-occurring non-proteinaceous entities. In certain embodiments the agent is a small molecule having a chemical moiety. Agents can be known to have a desired activity and/or property, or can be selected from a library of diverse compounds.

Cell-based assays for HTS can include such types as second messenger assays, reporter gene assays, and cell proliferation or cell differentiation assays.

| | |
|---|---|
| 2nd messenger | Detect ability of test agent to alter (increase or decrease) signal transduction pathways following activation of cell-surface receptors or other signaling pathways<br>Examples:<br>Using fluorescent molecules that respond to changes in intracellular Ca2+ concentration, membrane potential, pH, etc. to assay receptor stimulation and ion channel activation |
| Reporter gene | Detect ability of test agent to alter (increase or decrease) cellular responses at the transcription/translation level of one or more target genes.<br>Examples:<br>Coexpression of luciferase to catalyze the light-emitting luciferin reaction for detection of protein kinase C inhibitors<br>Quantification of G-protein coupled receptor (GPCR) internalization using a GPCR-green fluorescent protein hybrid |
| Cell proliferation/ differentiation cytotoxicity | Detect ability of test agent to alter (increase or decrease) the overall cell growth or death in response of IBD stem cells to external stimuli or stress.<br>Detect ability of test agent to alter (increase or decrease) differentiation of IBD stem cells, e.g., under air-liquid interface conditions, to produce diseased or normal epithelial cells/tissues |
| Epigenetic State | Detect ability of test agent to alter (increase or decrease) epigenetic state of IBD stem cell or differentiated epithelial cells/tissue derived from the IBD stem cell, such as for changes in chromatin structure (such as by chromatin immunoprecipitation), and/or DNA methylation (such as by bisulfite modification or CpG island microarray). |

The majority of cell-based HTS assays are carried out in multi-well plates as they can be easily miniaturized to increase the number of wells per plate for high throughput rates, on the order of 10,000 compounds per assay per day, and handled with a robotic system for automation. More recently, there are increasing interests in developing microfluidic devices for perfusion cultures that allow for the evaluation of long-term drug effects as well as studying interactions among different cell types in a biological system like the whole animal.

In general, cell culture modes include single cells, monolayer cells on a two-dimensional surface, multilayer cells or aggregate clusters in a 3D scaffold. 2D cell-based assays in multiwell plates together with automated operation are widely used in drug screening because of their low costs and easy operation. The third dimension in a 3D scaffold provides another direction for cell-cell interactions, cell migration, and cell morphogenesis, which may be critical in regulating cell cycle and tissue functions of the IBD stem cells or their differentiated progeny. In addition, 3D cell cultures provide not only the templates for cells to adhere and grow, but also the interconnectivity within the 3D constructs to allow nutrients and metabolites to be transported in and out of the engineered tissues. Consequently, 3D cell cultures may support a higher cell density than 2D cell cultures. In certain embodiments, such as differentiated tissues derived from the IBD stem cells, high specific surface areas offered by 3D also allow for a long-term cell culture in vitro.

Widely used HTS platforms (e.g. 96-, 384-, 1536-well plates) offer static microenvironments, with the medium supplied in a batch-wise manner. Although automation using robots allows the static cultures to be used as a feasible HTS platform for drug screening, in certain instances static cultures is not ideal for long-term cell culture due to the risk of contamination caused by repeated interventions. Modified multiwell plates with the integration of microfluidic systems, which has been reported with high throughput for drug screening (Kim et al. 2004 Breast Cancer Res Treat, 85:281-291) and cytotoxicity evaluation of anticancer drugs (Cukierman et al. 2001 Science 294:1708-1712) can therefore also be readily adapted for use in the drug screening embodiments of the present invention. Such systems, where a perfusion cell culture is achieved to compensate liquid evaporation, can maintain a cell culture for an extended period for testing long-term effects of drugs.

In addition to continuously providing nutrients and waste removal and thus keeping the cell culture system stable, perfusion can also be used to generate gradients of drug concentrations, creating a specific physical microenvironment (e.g. shear stress or interstitial fluid flow) and constructing a circulatory system to better mimic the in vivo conditions. See Heldin et al. 2004 Nat Rev Cancer 4:806-813. Compared to the static cell culture, perfusion can increase cell content and matrix synthesis in a 3D IBD tissue system derived by differentiation of IBD stem cells.

Cell-based assays are well established and widely used to analyze the effects of compounds on cellular activities, including nuclear size, mitochondrial membrane potential, intracellular calcium levels, membrane permeability, and cell number. The failure of early identification of toxic side effects of a compound has resulted in about 30% of the attrition of new drug candidates. Therefore, cytotoxicity testing, which generally relies on the quantification of cell number and viability, has become one of the most critical steps in early-phase drug discovery. Conventional methods for cell number counting use hemacytometer, Coulter counter or flow cytometry can be labor-intensive and time consuming, while Trypan blue exclusion and neutral red uptake methods for determining cell viability require the use of invasive chemicals. Furthermore, these methods have a relatively low throughput, and thus are not always good choices for HTS though can be used in the drug screening assays of the present invention. As off-line sampling during the cell culture process is limited by the small amount of medium used in HTS assays, from several μl to several ml, online detection is desired. Detection methods used in cell-based HTS assays can be divided mainly into two groups: electrochemical and optical techniques. In general, optical sensing is easier for miniaturization than electrochemical sensing.

(i) Electrochemical Methods

Various electrochemical biosensors, which integrate biological recognition elements and electrochemical transduction units, based on (a) cellular activity and function; (b) cellular barrier behavior; and (c) recording/stimulation of electric potential of electrogenic cells have been developed. These systems can generally adapted for use with the subject IBD stem cells and/or differentiated tissues derived therefrom, and be used to achieve noninvasive online monitoring of drug effects—such as cell killing/toxicity or alterations to proliferation rates or phenotypes/genotypes resulting from differentiation or epigenetic changes.

(ii) Electrochemical Method Based on Cellular Activity and Function

A living cell can be considered as an electrochemical system. Electron generation and charge transfer caused by redox reactions and the changes of ionic composition and concentration in living cells can be used to characterize cell viability in a homogenous solution. For example, when the IBD stem cells or their progeny are attached to a gold nanoparticle-modified carbon paste electrode, with platinum wire as auxiliary and saturated calomel electrode as reference electrodes, the cells can exhibit an irreversible voltammetric response which is related to the oxidation of guanine. The oxidation peak can be used to investigate the exogenous effect of a test agent on the oxidative state or resistant to oxidative damage to the IBD stem cell or IBD tissue, which provides an electrochemical approach for studying IBD stem cell drug sensitivity.

In addition, metabolism in cells leads to changes in metabolic products (e.g., lactic acid and carbon dioxide) or substrates (e.g., glucose and dissolved oxygen [DO]). A variety of electrochemical biosensors based on metabolic changes have been fabricated and can be used to test the ability of a test agent (or agents) to alter the metabolic state of an IBD stem cell or tissue derived therefrom. Electrochemical methods based on cellular activities include potentiometry and amperometry.

Conventional potentiometry cell-based sensors include an ion-selective electrode (ISE) or gas-sensing electrode (GSE) coated with a layer of cells. An ISE has been developed for screening of toxins by integrating cells with a K+ selective film. In such systems, a potential change caused by the ion accumulation or depletion on the electrode surface can be used to monitor metabolic products during cell growth.

Amperometric electrochemical methods using a specific enzyme electrode are widely used for the determination of pH, DO or glucose. The acidification rate in the vicinity of cells can be quantified using a microphysiometer. Cellular biochemical responses resulting from the accumulation of lactic acid and carbon dioxide can be approximately monitored using the pH value in pH-sensing chambers. Furthermore, heterogeneous pO2 distributions around tissues could be detected using a miniaturized system.

(iii) Electrochemical Method Based on Barrier Behavior

The local ionic environment at the electrode/solution interface changes in the presence of cells. In general, cells with insulating properties would significantly increase the electrode impedance. Thus, biological status of cells, including cellular viability, morphology, cell number, and cell apoptosis, and cell adhesion can be monitored using electrochemical impedance spectroscopic techniques. For example, an electrical impedance sensor array integrated into the bottom of a microtiter plate has been developed for the quantitative detection of living cells. Real-time assessment of cytotoxicity and acute toxicity can be achieved using this device. See Ku et al. 2008 Anal Chem 80:7543-7548.

(iv) Electrochemical Method Based on Cellular Electrical Potential

Electrogenic cells and tissues, such as heart muscle, pancreas beta and nerve cells, are able to generate bioelectrical signals resulting from the orchestrated activities of ion channels embedded within cell membrane. The normal epithelial lining of the gut, such as of the terminal ileum, undergo electrogenic sodium absorption that can create a signal for detection. These bioelectrical signals can be used to test drugs against critical diseases such as electrogenic secretion (Chlorine) and/or absorption (Sodium, Potassium) in tissue differentiated from normal versus IBD stem cells. For example, detection can make use of a nanoelectronic biosensor based on single-wall carbon nanotubes (SWCNTs). This method can be used to non-invasively detect cellular activities for electrogenic cells derived from the IBD stem cells with high throughput, high sensitivity, easy use, and the capacity of long-term cell culture.

(v) Optical Methods

Optical detection in cell-based HTS assays usually is carried out with colorimetric, luminescent, or fluorescent methods, examples of which are discussed below.

(vi) Colorimetric Method

Colorimetric methods are based on color change of the growth medium after cell metabolites react with chemical agents. Colorimetric assays using ruthenium dye and Alamar Blue, for example, have been developed and are readily adapted for use with the present invention. In addition, a spectrum of assays using tetrazolium salts such as MTT (3-(4,5-Dimethylthiazol-2-yl)-2,5-diphenyltetrazolium bromide), MTS (3-(4,5-dimethylthiazol-2-yl)-5-(3-carboxymethoxyphenyl)-2-(4-sulfophenyl)-2H-tetrazolium), and XTT (2,3-bis-(2-methoxy-4-nitro-5-sulfophenyl)-2H-tetrazolium-5-carboxanilide) are also commercially available. These methods are based on the reduction of a tetrazolium salt by actively growing cells to a colored formazan product that can be quantified with a spectrophotometer.

(vii) Luminescent Methods

Many organisms, including fireflies and some marine organisms, regulate their light production using luciferase in a variety of light-emitting reactions with emission color ranging from yellow-green to red. In luminescent assays, the oxidation of luciferin catalyzed by luciferase produces light that can be detected by a light sensitive apparatus such as an illuminometer or optical microscope, allowing observation of biological processes. Some luminescent reactions are mediated by ATP or calcium ions. Luciferase has been widely used as a reporter in cells expressing a luciferase gene under the control of a promoter of interest to assess its transcriptional activity. Many commercial cell-based kinase activity assays use luciferase as the reporter. Luciferase can also be used to detect the level of cellular ATP in cell viability assays. In addition, some enzymes, such as caspase and cytochrome P450, can convert proluminescent molecules to luciferin, and their activities can thus be detected in a coupled or two-step luciferase assay.

Although firefly luciferase is widely used in cell-based assays, its application in HTS is usually limited to endpoint assays because the requirements of cell lysis and addition of luciferase substrates. Unlike firefly luciferase, the luciferase (MetLuc) derived from the marine copepod *Metridia longa* is naturally secreted, which allows the development of live cell assays and multiple assays on the same cells using a no-lysis protocol.

(viii) Fluorescent Methods

Compared to luminescent methods, fluorescent methods have higher sensitivity and can be easier to be miniaturized for large-scale or high throughput measurements of cell activities, pathway activation, toxicity, and phenotypic cellular responses of exogenous stimuli. Fluorescent methods for cell-based assays were initially developed using small, highly-fluorescent, organic molecules, monitoring ion concentrations, membrane potential and as intracellular substrates for reporter genes. More recently, nanoparticles such as quantum dots (QDs) have been widely used as labels in cell-based assays and be adapted for use in the present invention. These semiconductor nanocrystals are photochemically stable, can provide a narrow and adjustable emission, and can be excited by light of any wavelength shorter than that of the emission peak. Thus, various emission colors can be simultaneously obtained using nanoparticles of different sizes excited with a single-wavelength light.

The development of reporter gene techniques using green fluorescent protein (GFP) has enabled online, non-invasive detection and quantification of cell proliferation and specific cellular functions. GFP, which was first discovered in the jellyfish, and its mutants have been developed with emission light colors ranging from blue to yellow. GFP is species-independent and generally non-toxic to cells. Its detection can be performed in living samples. Therefore, IBD stem cell-based assays using GFPs are amenable to real-time, automated, and non-invasive assessment of both chronic and acute cellular events. In addition, GFP can be coupled with Disco soma species red fluorescent protein (dsRed) for two-color or multiplex assays.

Cell-based assays using cDNA encoding a fluorescent protein provide an HT platform for non-invasive analysis of cell proliferation and death kinetics. Since a specific cellular event or function can be monitored based on the regulatory DNA sequence or promoter used in controlling the expression of the reporter gene, the assay is responsive to targeted effects, such as activation of signal transduction pathways, and is suitable for use in disease-relevant assays. In addition, two fluorescent proteins fused with a peptide linker comprising a caspase-3 cleavage site can be used to study the activation of caspase-3 or apoptosis in live cells based on changes in emission wavelength due to energy transfer between two close fluorophores, a phenomenon called fluorescence resonance energy transfer (FRET).

In general, whole-cell autofluorescence-based systems are non-invasive, fast, and simple for HTS applications. It can provide dynamic data and be used as high-content assays as well. Current commercial HTS systems use laser scanning imaging systems with fluorescence microscopy and quantitative image analysis to perform live-cell kinetic assays with high spatial and temporal resolution, and the various IBD stem cell and differentiated progeny thereof can be adapted for drug screening with these systems. They can be used to examine the context of living cells, quantify intracellular proteins, and monitor the trafficking of proteins fused with fluorescent reporters and some subcellular structures.

(ix) Microfluidic Cell-Based Assays

Microfluidics has emerged as a promising technology with widespread applications in engineering, biology and medicine. It has the potential to revolutionize the way we approach cell biology research. Microfluidics refers to the science and technology that allows one to manipulate tiny amounts (nanoliter to microliter) of fluids using microstructures with characteristic dimensions on the order of tens to hundreds of micometers. The controllable processing of microfluidic devices at dimensions close to cells and biomolecules enable their biological applications at the cellular level. In addition, the scale of microchannels corresponds well with the native cellular microenvironments, in which the ratio of cell volume to extracellular fluid volume can be greater than one.

Microfabricated cell culture devices have previously been demonstrated on silicon and polydimethylsiloxane (PDMS) substrates with other cells, and can be used with IBD stem cells and cells/tissues differentiated therefrom. Most of microfluidic platforms are fabricated using PDMS, which is optically transparent, gas permeable and biocompatible. The conventional format of microfluidics is not an ideal match for complete cell culture, because all of the reagents and cells are positioned in an interconnected network of enclosed microchannels, making it difficult to establish fresh, sterile sites for seeding new generations of cells. Recently, digital microfluidics (DMF) has emerged as an alternative to the conventional format of enclosed microchannels. DMF is a technique, in which nanoliter-sized droplets are manipulated on an open surface of an array of electrodes. For example, the lab-on-a-chip platforms are available which are capable of implementing all of the steps required for mammalian cell culture: cell seeding, growth, detachment, and re-seeding on a fresh surface for complete mammalian cell culture.

(x) Animal Models

The subject IBD stem cells or tissue derived therefrom can be used to generate non-human animals (preferably mammals) for in vivo evaluation of test agents. As shown in FIG. 22, IBD stem cells can be directed injected in sites within or outside of the gut, and the ability of a test agent to alter the growth, survival, differentiation of the IBD stem cells or tissue, and/or the recruitment of fibroblasts, immune cells or other cells to the site of the injection of the IBD stem cells or tissue can be evaluated.

In certain embodiments, the animal is a non-human primate. In other embodiments, the animal is a rodent, such as a mouse or rat. The animal may also be a rabbit, dog, cat, pig, cow, or other suitable non-human mammal for testing.

In certain embodiments, the IBD stem cells or derived tissue are of human origin, and the animal is immunosuppressed or immuno-incompetent, such as a SCID, NUDE or NIHIII mouse.

In certain embodiments, the IBD stem cells or derived tissue are introduced into the animal with a naturally occurring or artificial extracellular matrix (ECM). Examples of extracellular matrix-producing cells include chondrocytes that mainly produce collagen and proteoglycans; fibroblast cells that mainly produce type IV collagen, laminin, interstitial procollagens, and fibronectin; and colonic myofibroblasts that mainly produce collagens (type I, III, and V), chondroitin sulfate proteoglycan, hyaluronic acid, fibronectin, and tenascin-C. Alternatively, the ECM is a MATRIGEL basement membrane matrix.

(xi) Formulation and Use of Discovered Drug Agents

Subsequent to indentifying an agent that selectively effects the IBD stem cell or tissue derived from the IBD stem cell, relative to normal gut epithelial stem cells or tissue, the agent can be further optimized (such as by structure-activity alterations to the chemical structure, amino acid changes, truncations, fusions and other modifications in the case of protein or peptide therapeutics), subjected to animal toxicity and efficacy testing, utilized in human clinical trials, and ultimately, if approved for marketing, the resulting drug agent formulated for use in human patients and commercialized for use (administration) to human patients. That is, the present invention provides a method for providing a drug for treating inflammatory bowel disease, such as Crohn's disease or ulcerative colitis, comprising an overall discovery process for the drug which includes: contacting one or more test agents (e.g., in vitro) with IBD stem cells of the present invention or tissue derived therefrom, identifying a test agent, herein a "drug agent", that alters, for example, the proliferation, differentiation, epigenetic and/or genotypic state of the stem cell or tissue (preferably selectively relative to normal intestinal stem cells or tissue); optionally generating modifications to the structure of the drug agent to create an improved drug agent; establishing the safety and (optionally) efficacy of the drug agent (or improved drug agent) in non-human animals; formulating the drug agent or improved drug agent for use in human patients; conducting clinical trials in human subjects establishing the safety and efficacy of the drug agent or improved drug agent in human subjects; generating a packaged pharmaceutical preparation comprising the drug agent or improved drug agent formulated for use in human patients and a label providing instructions for administering and discontinuing use of the drug agent or improved drug agent in human patients.

In certain embodiments, the drug agent is selective for IBD stem cells or tissue derived from the IBD stem cell, relative to normal gut epithelial stem cells or tissue, by a factor of at least 2, more preferably at least 5, 10, 20, 30, 40, 50, 75, 100, 250, 500 or at least a 1000.

In certain embodiments, the drug agent is selective for IBD stem cells or tissue derived from the IBD stem cell, relative to normal gut epithelial stem cells or tissue, having an EC50 for the biological effect on IBD stem cells or tissue derived therefrom at least 2-fold less relative to EC50 for biological effect on normal gut epithelial stem cells or tissue, more preferably at least 5, 10, 20, 30, 40, 50, 75, 100, 250, 500 or at least a 1000 less.

In certain embodiments, the drug agent is selective for IBD stem cells or tissue derived from the IBD stem cell, relative to normal gut epithelial stem cells or tissue, having an IC50 for killing IBD stem cells or tissue derived therefrom at least 2-fold less relative to IC50 for killing on normal gut epithelial stem cells or tissue, more preferably at least 5, 10, 20, 30, 40, 50, 75, 100, 250, 500 or at least a 1000 less.

Pharmaceutical compositions of the present invention can be formulated to be administered orally, rectally, parentally, including, intravenously, mucosally, subcutaneously, intranasally, via inhalation (e.g., aerosol inhalation), locally, infusion, via a catheter, via a lavage, or by any other method or any combination of the foregoing as would be practiced by one of ordinary skill in the art.

In another embodiment, the invention provides a method for conducting a pharmaceutical business, comprising: (a) manufacturing the packaged pharmaceutical of the invention; and (b) marketing to healthcare providers the benefits of using the package or preparation to treat patients suffering from an inflammatory bowel disease such as Crohn's disease or ulcerative colitis.

In another embodiment, the invention provides a method for conducting a pharmaceutical business, comprising: (a) providing a distribution network for selling the packaged pharmaceutical of the invention; and (b) providing instruction material to patients or physicians for using the package or preparation to treat patients suffering from an inflammatory bowel disease such as Crohn's disease or ulcerative colitis.

In another embodiment, the invention provides a method for conducting a pharmaceutical business, comprising: (a) determining an appropriate dosage of an drug agent or improved drug agent identified by the methods of the present invention to treat patients suffering from an inflammatory bowel disease such as Crohn's disease or ulcerative colitis; (b) conducting therapeutic profiling of one or more formulations of the drug agent or improved drug agent identified in step (a), for efficacy and toxicity in animals; and (c) providing a distribution network for selling a the formulations identified in step (b) as having an acceptable therapeutic profile. The method may include an additional step of providing a sales group for marketing the preparation to healthcare providers.

In another embodiment, the invention provides a method for conducting a medical assistance reimbursement program, comprising: (a) providing a reimbursement program which permits, for prescription of a drug agent or improved drug agent of the invention for treating an inflammatory bowel disease, at least partial reimbursement to a healthcare provider or patient, or payment to a drug distributor; (b) processing one or more claims for prescription of a drug agent or improved drug agent of the invention for treating an inflammatory bowel disease; and (c) reimbursing the healthcare provider or patient, or paying a drug distributor, at least a portion of the cost of said prescription.

In another embodiment, the invention provides a method for treating an inflammatory bowel disease comprising administering to the patient a composition of a drug agent or improved drug agent of the invention in an amount sufficient to treat the disease in the animal as evaluated by a standardized test.

k. Transgenic Animals

Another aspect of the present invention relates to transgenic non-human animals having germline and/or somatic cells in which the biological activity of one or more of the IBD Genes Set, such as one or more of the pCD Gene Sequences, are altered by a chromosomally incorporated transgene. Such animals can be used as models for inflammatory bowel diseases or disorders, e.g., for understanding the pathology of disease and/or drug screening.

In one embodiment, the present invention provides a desired non-human animal or an animal (including human) cell which contains a predefined, specific and desired alteration rendering the non-human animal or animal cell predisposed to and inflammatory bowel disease.

In embodiments where the IBD gene is down-regulated in the disease state, the transgene may encode a mutant protein, such as dominant negative protein which antagonizes at least a portion of the biological function of a wild-type protein. Yet in other embodiments, the transgene can encode an antisense transcript which, when transcribed from the transgene, hybridizes with a gene or a mRNA transcript thereof, and inhibits expression of the gene. In still other embodiments, the transgene can, by such mechanisms as homologous recombination, knock-out the endogenous IBD gene.

A preferred transgenic non-human animal of the present invention has germline and/or somatic cells in which one or more alleles of a gene are disrupted by a chromosomally incorporated transgene, wherein the transgene includes a marker sequence providing a detectable signal for identifying the presence of the transgene in cells of the transgenic animal, and replaces at least a portion of the gene or is inserted into the gene or disrupts expression of a wild-type protein.

In embodiments where the IBD gene is up-regulated in the disease state, the transgene may encode a wild-type IBD gene product, and the transcriptionally regualtory sequences of the transgene can be used to cause overexpression of the IBD gene. Likewise, mutant IBD genes can be used which encode IBD proteins that are consitutitively or regulatively activated to mimic overexpression of the endogenous IBD gene.

Still another aspect of the present invention relates to methods for generating non-human animals and stem cells having a functionally disrupted endogenous gene. In a preferred embodiment, the method comprises the steps of:
(i) constructing a transgene construct including (a) a recombination region having at least a portion of an IBD gene, which recombination region directs recombination of the transgene with the gene, and (b) a marker sequence which provides a detectable signal for identifying the presence of the transgene in a cell;
(ii) transfering the transgene into stem cells of a non-human animal;
(iii) selecting stem cells having a correctly targeted homologous recombination between the transgene and the gene;
(iv) transfering cells identified in step (iii) into a non-human blastocyst and implanting the resulting chimeric blastocyst into a non-human female; and
(v) (v) collecting offspring harboring an endogenous gene allele having the correctly targeted recombination.

Yet another aspect of the invention provides a method for evaluating the potential of an agent to cause an IBD or to protect against development of an IBD by (i) contacting a transgenic animal of the present invention with a test agent, and (ii) ascertaining the presence, and more preferably the level, of onset or degree of severity of an inflammatory bowel disease or disorder, and comparing that with an untreated transgenic animal or transgenic animal treated with a control agent.

l. VSIG1 Agents

Given the pronounced overexpression of VSIG1 (V-set and immunoglobulin domain containing 1) in the isolated stem cells of pediatric Crohn's patients, another aspect of the invention relates to the use and pharmaceutical preparations of agents which reduce the expression of the VSIG1 gene or reduce or inhibit the biological activity of the VS1G1 protein, as as well as the detection of VSIG1 gene expression and VSIG1 protein levels as part of diagnostic assays and imaging protocols for identifying the presence of Crohn's stem cells or their progeny in patient samples or in in vivo imaging.

The VSIG1 gene encodes a member of the junctional adhesion molecule (JAM) family. A representative sequence for the human VSIG1 gene is provided in Gene ID: 340547 (see also Ensembl:ENSG00000101842, MIM:300620 and Vega:OTTHUMG00000022175). The members of immunoglobulin superfamily are transmembrane proteins and most of these proteins are involved in cell-cell adhesion. These proteins are highly glycosylated through N- and O-glycosylation. The encoded protein contains multiple glycosylation sites at the N-terminal region, and multiple phosphorylation sites and glutamic acid/proline (EP) repeats at the C-terminal region. The gene is expressed in normal stomach and testis, as well as in gastric, esophageal and ovarian cancers. Alternatively, spliced transcript variants encoding different isoforms have been found for this gene.

One aspect of the invention provides pharmaceutical preparations that inhibit or reduce the role in disease development or progression of IBD stem cells or their progeny that have upregulated expression of VSIG1, i.e., to be used as part of a treatment protocol for patients having or at risk of developing IBD, particularly Crohn's disease. These include, with limitation, nucleic acids, peptides and polypeptides (including antibodies), natural products, small molecules and carbohydrates. In certain embodiments, the therapeutic agent is locally delivered to the area of the gut afflicted by IBD, such as by oral delivery or local administered by injection or surgical placement.

In certain embodiments, the invention provides pharmaceutical preparations of nucleic acids that inhibit or reduce the expression of VSIG1 to be used as part of a treatment protocol for patients having or at risk of developing IBD, particularly Crohn's disease. These include, with limitation, antisense nucleic acids or RNA intereference nucleic acids (such as siRNA, miRNA and shRNA) or a sequence-directed ribozyme which include sequences that hybridize to a portion of the VSIG1 gene sequence or RNA transcript therefrom.

In certain embodiments, the invention provides pharmaceutical preparations of antibodies that selectively bind to and inhibit or reduce the biological function of VSIG1 to be used as part of a treatment protocol for patients having or at risk of developing IBD, particularly Crohn's disease.

In certain embodiments, the invention provides pharmaceutical preparations of antibody-drug conjugates (ADC) including antibodies that selectively bind to VSIG1 to be used as part of a treatment protocol for patients having or at risk of developing IBD, particularly Crohn's disease. The targeting of VSIG1 with the antibody portion of the ADC permits the delivery of a therapeutic agent to the diseased portion of the gut. In certain embodiments, the drug component of the ADC is cytotoxic or cytostatic to the cell expressing the VSIG1 protein to which the ADC binds. In other embodiments, the drug component of the ADC inhibits the differentiation and/or epigenetic traits of the the cell expressing the VSIG1 protein to which the ADC binds.

Another aspect of the invention provides diagnostic reagents for detecting the upregulated expression of VSIG1, for example, to identify the presence or absence of IBD stem cells in a biopsy or to image IBD impacted portions of the gut. These include, with limitation, nucleic acids and VSIG1 binding agents such as antibodies.

m. CLDN18 Agents

Given the pronounced overexpression of CLDN18 (Claudin-18) in the isolated stem cells of pediatric Crohn's patients, another aspect of the invention relates to the use and pharmaceutical preparations of agents which reduce the expression of the CLDN18 gene or reduce or inhibit the biological activity of the CLDN18 protein, as as well as the detection of CLDN18 gene expression and CLDN18 protein levels as part of diagnostic assays and imaging protocols for identifying the presence of Crohn's stem cells or their progeny in patient samples or in in vivo imaging.

The CLDN18 gene encodes a member of the claudins family, which are integral membrane proteins and components of tight junction strands. Tight junction strands serve as a physical barrier to prevent solutes and water from passing freely through the paracellular space between epithelial or endothelial cell sheets, and also play critical roles in maintaining cell polarity and signal transductions. PKC/MAPK/AP-1 (protein kinase C/mitogen-activated protein kinase/activator protein-1) dependent pathway regulates the expression of this gene in gastric cells. A representative sequence for the human CLDN18 gene is provided in Gene ID: 51208 (see also Ensembl:ENSG00000066405, MIM: 609210 and Vega:OTTHUMG00000159762).

One aspect of the invention provides pharmaceutical preparations that inhibit or reduce the role in disease development or progression of IBD stem cells or their progeny that have upregulated expression of CLDN18, i.e., to be used as part of a treatment protocol for patients having or at risk of developing IBD, particularly Crohn's disease. These include, with limitation, nucleic acids, peptides and polypeptides (including antibodies), natural products, small molecules and carbohydrates. In certain embodiments, the therapeutic agent is locally delivered to the area of the gut afflicted by IBD, such as by oral delivery or local administered by injection or surgical placement.

In certain embodiments, the invention provides pharmaceutical preparations of nucleic acids that inhibit or reduce the expression of CLDN18 to be used as part of a treatment protocol for patients having or at risk of developing IBD, particularly Crohn's disease. These include, with limitation, antisense nucleic acids or RNA intereference nucleic acids (such as siRNA, miRNA and shRNA) or a sequence-directed ribozyme which include sequences that hybridize to a portion of the CLDN18 gene sequence or RNA transcript therefrom.

In certain embodiments, the invention provides pharmaceutical preparations of antibodies that selectively bind to and inhibit or reduce the biological function of CLDN18 to be used as part of a treatment protocol for patients having or at risk of developing IBD, particularly Crohn's disease. An exemplary antibody for use as a therapeutic agent in the present invention is IMAB362 (Claudiximab), see PCT Publication WO2013174404.

In certain embodiments, the invention provides pharmaceutical preparations of antibody-drug conjugates (ADC) including antibodies that selectively bind to CLDN18 to be used as part of a treatment protocol for patients having or at risk of developing IBD, particularly Crohn's disease. The targeting of CLDN18 with the antibody portion of the ADC permits the delivery of a therapeutic agent to the diseased portion of the gut. In certain embodiments, the drug component of the ADC is cytotoxic or cytostatic to the cell expressing the CLDN18 protein to which the ADC binds. In other embodiments, the drug component of the ADC inhibits the differentiation and/or epigenetic traits of the the cell expressing the CLDN18 protein to which the ADC binds. An exemplary antibody for use in the antibody-drug conjugates of the present invention is IMAB362 (Claudiximab), see PCT Publication WO2013174404.

Another aspect of the invention provides diagnostic reagents for detecting the upregulated expression of CLDN18, for example, to identify the presence or absence of IBD stem cells in a biopsy or to image IBD impacted portions of the gut. These include, with limitation, nucleic acids and CLDN18 binding agents such as antibodies.

n. CD74 Agents

Given the pronounced overexpression of CD74 in the isolated stem cells of pediatric Crohn's patients, another aspect of the invention relates to the use and pharmaceutical preparations of agents which reduce the expression of the CD74 gene or reduce or inhibit the biological activity of the CD74 protein, as as well as the detection of CD74 gene expression and CD74 protein levels as part of diagnostic assays and imaging protocols for identifying the presence of Crohn's stem cells or their progeny in patient samples or in in vivo imaging.

The CD74 gene encodes a protein that associates with class II major histocompatibility complex (MHC) and is an important chaperone that regulates antigen presentation for immune response. It also serves as cell surface receptor for the cytokine macrophage migration inhibitory factor (MIF) which, when bound to the encoded protein, initiates survival pathways and cell proliferation. This protein also interacts with amyloid precursor protein (APP) and suppresses the production of amyloid beta (Abeta). Multiple alternatively spliced transcript variants encoding different isoforms have been identified. A representative sequence for the human CD74 gene is provided in Gene ID: 972 (see also sembl: ENSG00000019582, MIM:142790 and Vega: OTTHUMG00000163559).

One aspect of the invention provides pharmaceutical preparations that inhibit or reduce the role in disease development or progression of IBD stem cells or their progeny that have upregulated expression of CD74, i.e., to be used as part of a treatment protocol for patients having or at risk of developing IBD, particularly Crohn's disease. These include, with limitation, nucleic acids, peptides and polypeptides (including antibodies), natural products, small molecules and carbohydrates. In certain embodiments, the therapeutic agent is locally delivered to the area of the gut afflicted by IBD, such as by oral delivery or local administered by injection or surgical placement.

CD74 interacts with MHC class I and II proteins, contributing to antigen presentation. CD74 directs transport of MHC class II α and β chains from the endoplasmic reticulum (ER) or the cell surface to endosomes. As a chaperone, CD74 contributes to peptide editing in the MHC class II compartment. In endosomes, proteases degrade CD74, releasing MHC class II molecules. Prevention of CD74 degradation promotes the cell surface localization of MHC II. In certain embodiments, the invention targets the role of CD74 in MHC Class II trafficking and antigen presentation by IBD stem cells and IBD tissues by reducing the expression of the protein in IBD stem cells and their progeny and/or enhancing the degradation of CD74.

CD74 on the cell surface also serves as a receptor for macrophage migration inhibitory factor (MIF) and d-dopachrome tautomerase (d-DT/MIF-2). In certain embodiments, the invention targets the role of CD74 a cell surface receptor, such as by reducing the expression of the protein in IBD stem cells and their progeny, or inhibiting the interaction of CD74 with MIF and/or d-DT/MIF-2 such as through agents which bind the receptor and block either binding or signaling by MIF and/or d-DT/MIF-2 (such as antibodies and ligand antagonists) or receptor decoys or other agents which bind MIF and/or d-DT/MIF-2 and prevent their interaction with CD74.

In certain embodiments, the invention provides pharmaceutical preparations of nucleic acids that inhibit or reduce the expression of CD74 to be used as part of a treatment protocol for patients having or at risk of developing IBD, particularly Crohn's disease. These include, with limitation, antisense nucleic acids or RNA intereference nucleic acids (such as siRNA, miRNA and shRNA) or a sequence-directed ribozyme which include sequences that hybridize to a portion of the CD74 gene sequence or RNA transcript therefrom.

In certain embodiments, the invention provides pharmaceutical preparations of antibodies that selectively bind to and inhibit or reduce the biological function of CD74 to be used as part of a treatment protocol for patients having or at risk of developing IBD, particularly Crohn's disease.

In certain embodiments, the invention provides pharmaceutical preparations of antibody-drug conjugates (ADC) including antibodies that selectively bind to CD74 to be used as part of a treatment protocol for patients having or at risk of developing IBD, particularly Crohn's disease. The targeting of CD74 with the antibody portion of the ADC permits the delivery of a therapeutic agent to the diseased portion of the gut. In certain embodiments, the drug component of the ADC is cytotoxic or cytostatic to the cell expressing the CD74 protein to which the ADC binds. In other embodiments, the drug component of the ADC inhibits the differentiation and/or epigenetic traits of the the cell expressing the CD74 protein to which the ADC binds.

Another aspect of the invention provides diagnostic reagents for detecting the upregulated expression of CD74, for example, to identify the presence or absence of IBD stem cells in a biopsy or to image IBD impacted portions of the gut. These include, with limitation, nucleic acids and CD74 binding agents such as antibodies.

o. SERPINB2 Agents

Given the pronounced overexpression of SERPINB2 in the isolated stem cells of pediatric Crohn's patients, another aspect of the invention relates to the use and pharmaceutical preparations of agents which reduce the expression of the SERPINB2 gene or reduce or inhibit the biological activity of the SERPINB2 protein, as as well as the detection of SERPINB2 gene expression and SERPINB2 protein levels as part of diagnostic assays and imaging protocols for identifying the presence of Crohn's stem cells or their progeny in patient samples or in in vivo imaging.

The SERPINB2 gene is a memebr of the the serpin family of proteins characterized by a unique tertiary structure and, unlike standard mechanism inhibitors, employ a suicide-substrate-like mechanism to neutralize their target proteinases. SerpinB2 (also called plasminogen activator inhibitor 2; PAI-2), has been implicated in the negative regulation of caspase-1. In fact, expression of SerpinB2 in macrophages deficient in NF-κB signalling, blocked their spontaneous IL-1β secretion, indicating that this serpin might serve as a negative regulator of caspase-1 and its upregulation in IBD may be part of the mechanism underlying increased susceptibility to microbial infections in IBD patients. Indeed, the most highly expressed gene commonly elevated in both Crohn's and UC is SerpinB2. A representative sequence for the human SERPINB2 gene is provided in Gene ID: 5055 (see also Esembl:ENSG00000019582, MIM:142790 and Vega:OTTHUMG00000163559).

Native, metastable serpins such as serpinB2 inherently tend to undergo stabilizing conformational transitions. This intrinsic tendency is modifiable by ligand binding, thus structure-based drug design is an attractive strategy for developing inhibitors of SerpinB2 (i.e., an inhibitor that prevents the inhibitory activity of serpinB2) such as small molecules, aptamers, antibodies and the like.

One aspect of the invention provides pharmaceutical preparations that inhibit or reduce the role in disease development or progression of IBD stem cells or their progeny that have upregulated expression of SERPINB2, i.e., to be used as part of a treatment protocol for patients having or at risk of developing IBD, particularly Crohn's disease. These include, with limitation, nucleic acids, peptides and polypeptides (including antibodies), natural products, small molecules and carbohydrates. In certain embodiments, the therapeutic agent is locally delivered to the area of the gut afflicted by IBD, such as by oral delivery or local administered by injection or surgical placement.

In certain embodiments, the invention provides pharmaceutical preparations of nucleic acids that inhibit or reduce the expression of SERPINB2 to be used as part of a treatment protocol for patients having or at risk of developing IBD, particularly Crohn's disease. These include, with limitation, antisense nucleic acids or RNA intereference nucleic acids (such as siRNA, miRNA and shRNA) or a sequence-directed ribozyme which include sequences that hybridize to a portion of the SERPINB2 gene sequence or RNA transcript therefrom.

In certain embodiments, the invention provides pharmaceutical preparations of antibodies that selectively bind to and inhibit or reduce the biological function of SERPINB2 to be used as part of a treatment protocol for patients having or at risk of developing IBD, particularly Crohn's disease.

Another aspect of the invention provides diagnostic reagents for detecting the upregulated expression of SERPINB2, for example, to identify the presence or absence of IBD stem cells in a biopsy or to image IBD impacted portions of the gut. These include, with limitation, nucleic acids and SERPINB2 binding agents such as antibodies.

p. DPCR1 Agents

Given the pronounced overexpression of DPCR1 (diffuse panbronchiolitis critical region 1) in the isolated stem cells of pediatric Crohn's patients, another aspect of the invention relates to the use and pharmaceutical preparations of agents which reduce the expression of the DPCR1 gene or reduce or inhibit the biological activity of the DPCR1 protein, as as well as the detection of DPCR1 gene expression and DPCR1 protein levels as part of diagnostic assays and imaging protocols for identifying the presence of Crohn's stem cells or their progeny in patient samples or in in vivo imaging.

The DPCR1 gene is located between HLA-B and HLA-A on chromosome 6p21.33, is classified as one of the MHC class I molecules. The deduced 235-amino acid protein contains an N-terminal domain of about 164 amino acids that shares significant homology with the mucin-like repeat domain of zonadhesin (ZAN; 602372), followed by a transmembrane domain and an intracellular C-terminal domain of 48 amino acids. A representative sequence for the human DPCR1 gene is provided in Gene ID: 135656 (see also Ensembl:ENSG00000168631, MIM:613928 and Vega: OTTHUMG00000031104).

One aspect of the invention provides pharmaceutical preparations that inhibit or reduce the role in disease development or progression of IBD stem cells or their progeny that have upregulated expression of DPCR1, i.e., to be used as part of a treatment protocol for patients having or at risk of developing IBD, particularly Crohn's disease. These include, with limitation, nucleic acids, peptides and polypeptides (including antibodies), natural products, small molecules and carbohydrates. In certain embodiments, the therapeutic agent is locally delivered to the area of the gut afflicted by IBD, such as by oral delivery or local administered by injection or surgical placement.

In certain embodiments, the invention provides pharmaceutical preparations of nucleic acids that inhibit or reduce the expression of DPCR1 to be used as part of a treatment protocol for patients having or at risk of developing IBD, particularly Crohn's disease. These include, with limitation, antisense nucleic acids or RNA intereference nucleic acids (such as siRNA, miRNA and shRNA) or a sequence-directed ribozyme which include sequences that hybridize to a portion of the DPCR1 gene sequence or RNA transcript therefrom.

In certain embodiments, the invention provides pharmaceutical preparations of antibodies that selectively bind to and inhibit or reduce the biological function of DPCR1 to be used as part of a treatment protocol for patients having or at risk of developing IBD, particularly Crohn's disease.

Another aspect of the invention provides diagnostic reagents for detecting the upregulated expression of DPCR1, for example, to identify the presence or absence of IBD stem cells in a biopsy or to image IBD impacted portions of the gut. These include, with limitation, nucleic acids and DPCR1 binding agents such as antibodies.

Other features and advantages of the invention will be understood by reference to the detailed description and examples that follow.

IV. Examples

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

The present work sought to address mucosal barrier properties in Crohn's through the clonal analysis of mucosal stem cells derived from both pediatric cases and age-matched controls. Our findings reveal that unlike control cases, pediatric Crohn's patients harbor two separate and epigenetically stable populations of mucosal stem cells distinguished by an inflammatory gene signature. Superimposed on the inflammatory trait is a differentiation defect that severely alters the mucosal barrier properties of the terminal ileum. And while we trace the immediate basis of this differentiation defect to the repressed expression of Atonal BHLH transcription factor 1 (ATOH1), a gene required for secretory cell development in the colon[20], this repression is only emblematic of a more sweeping, homeotic conversion of terminal ileum stem cells to those of the proximal gastrointestinal tract that in turn dictates both the inflammatory and differentiation defects of these cells. Lastly, this coexistence of "Crohn's" and "normal" stem cells at the terminal ileum of these patients is likely of significance for the natural history of this disease as well as the rational basis of new therapeutic strategies.

Stable Inflammatory Gene Signature

Figure 2A:
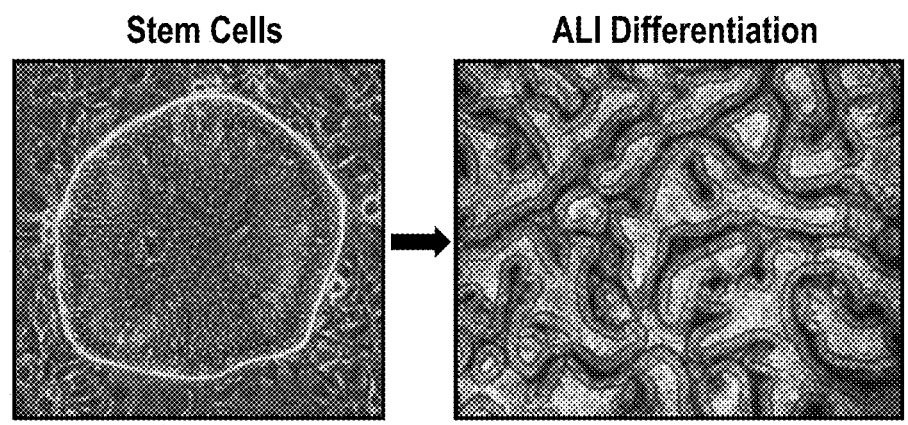
FIG. 2B. Expression heatmap comparing differentiated normal (FC1) and Crohn's (CD1, CD2) terminal ileum.
FIG. 2C. Principal component analysis of whole genome transcription profile of stem cells and differentiated epithelia from normal (FC1) and Crohn's (CD1, CD2). The Air-Liquid interface differentiation of stem cell pedigrees amplified the distinctions between the Normal and Crohn's clusters to with nearly 1,200 genes (>1.5-fold, $p<0.05$).
FIG. 2D. Most significant inflammatory pathways represented by genes differentially expressed in terminal ileum epithelia of Crohn's (CD1, CD2, CD3) relative to controls. For stem cells of the Crohn's cluster, gene expression profiling of ALI-differentiated terminal ileum stem cells reveals an enrichment of genes associated with inflammatory pathways involving antigen presentation, innate immune responses, cytokine signaling.
FIG. 2E. Overlap between genes differentially expressed (>2-fold, $p<0.05$) in both CD1 and CD2 and gene sets defined by replicated GWAS loci in Crohn's.
Figure 2B:
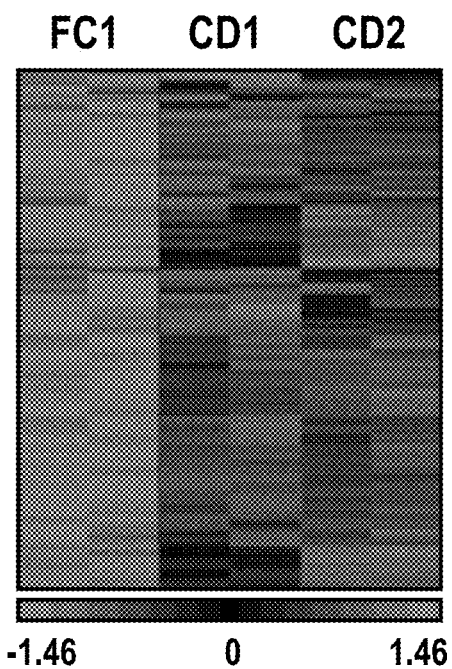
Figure 2D:
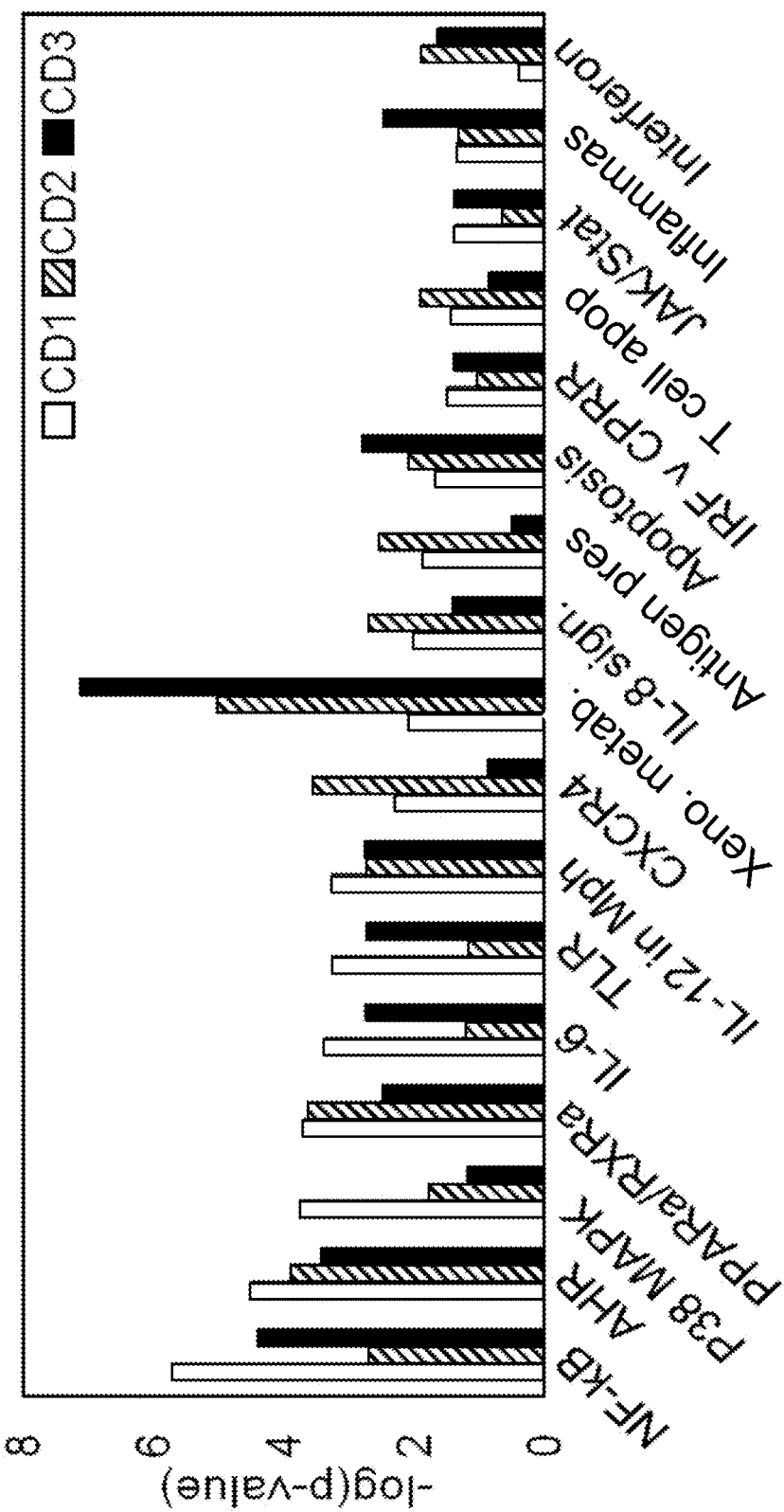
Figure 2E:
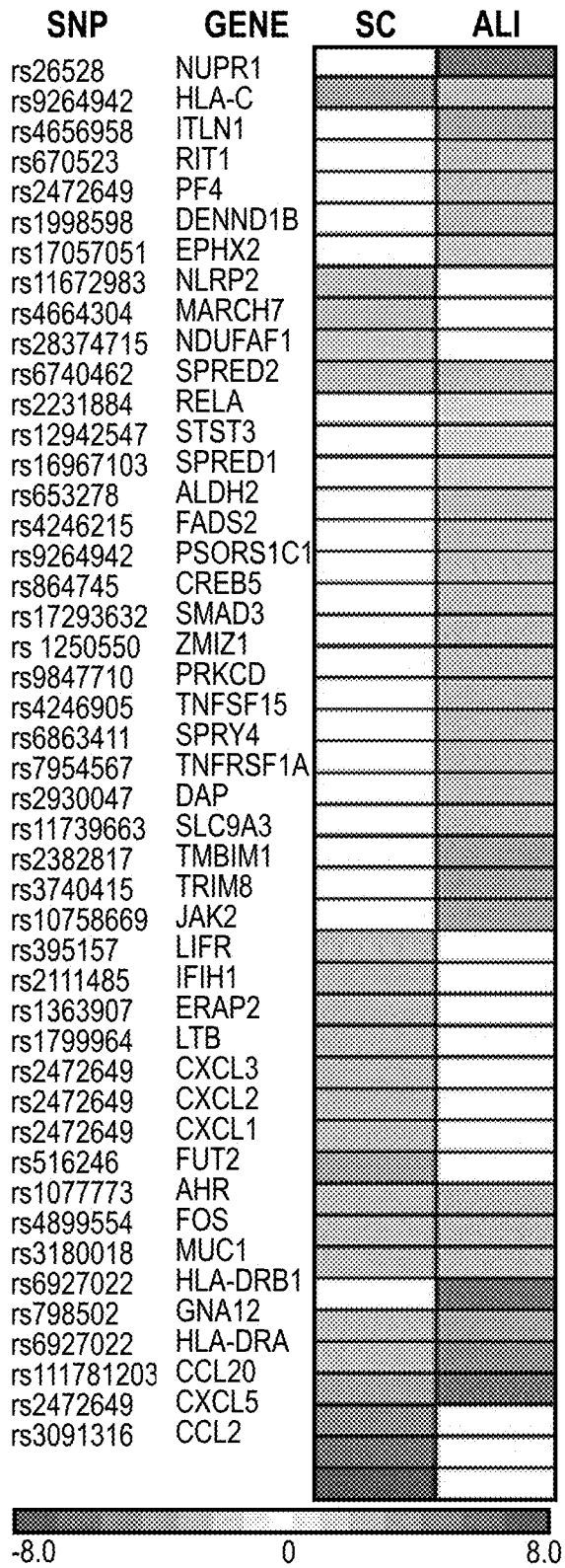

We cloned and propagated mucosal stem cells from endoscopic biopsies of children newly diagnosed with Crohn's disease and age-matched controls using recently developed technology that maintains columnar epithelial stem cells in a highly immature "ground state"[21,22]. In brief, approximately 150-200 independent stem cell colonies were derived from 1 millimeter (mm) biopsies of the terminal ileum and carried forward in sterile culture for minimum of eight weeks as either "pools" of clones or as subcloned "pedigrees" derived from single cells from these pools before analysis (FIG. 1a). These pedigrees consist of highly immature stem cells that can be differentiated to a 3-D intestinal mucosa by exposure to an air-liquid interface (ALI; FIG. 1a). Unsupervised clustering of whole genome expression profiles of terminal ileum stem cell pedigrees from three Crohn's cases (CD1, CD2, and CD3), an age-matched "functional" control lacking mucosal inflammation (FC1), and a 22-week fetal demise case (FT1) revealed a bimodal distribution of gene expression profiles with a Normal cluster dominated by control and fetal terminal ileum pedigrees, and a second, Crohn's cluster occupied by some or most of the stem cell pedigrees derived from Crohn's patients (FIG. 1b). However, we also noted that one or more of the stem cell pedigrees derived from the Crohn's cases appeared in the Normal cluster of the Principal Component Analysis (PCA) of whole genome expression profiles. The Crohn's cluster differentially expressed approximately 800 genes (>1.5-fold, p<0.05) compared to the Control cluster (FIG. 1c). Filtering these genes against known inflammatory gene sets yielded nearly 200 that populate innate immune and antigen presentation pathways previously linked to Crohn's (FIG. 1d; FIG. 7). The differentiation of stem cell pedigrees amplified the distinctions between the Normal and Crohn's clusters to with nearly 1,200 genes (>1.5-fold, p<0.05) evident by PCA of whole genome expression datasets (FIG. 2C). As seen in the stem cells of the Crohn's cluster, the gene expression profiling of the ALI-differentiated terminal ileum stem cells revealed an enrichment of genes associated with inflammatory pathways involving antigen presentation, innate immune responses, cytokine signaling (FIG. 2D).

Defective Secretory Cell Differentiation

Figures 3A, 3B:
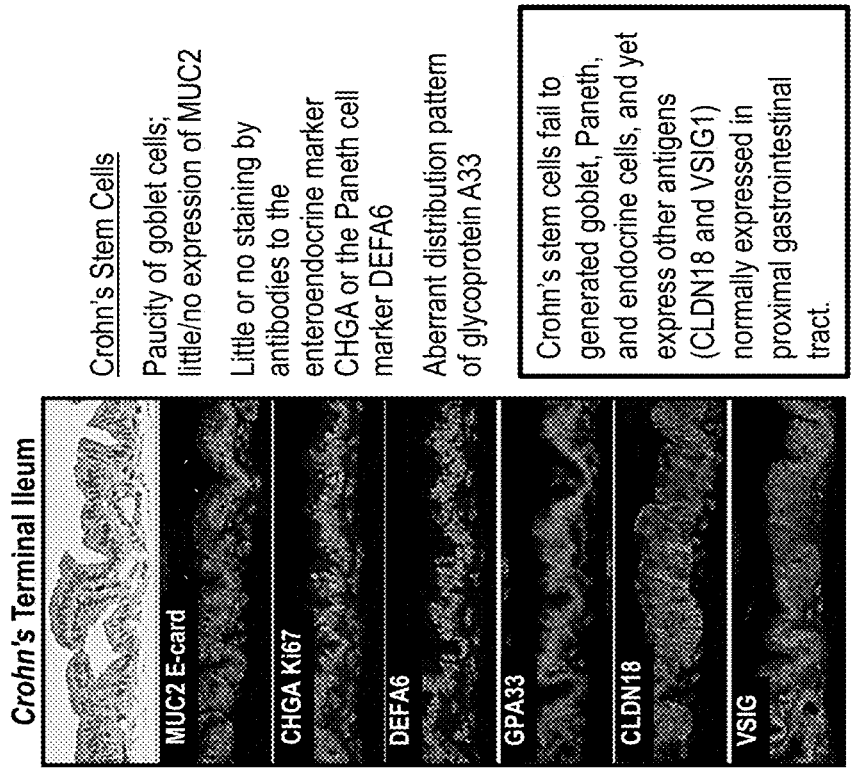
Figure 3C:
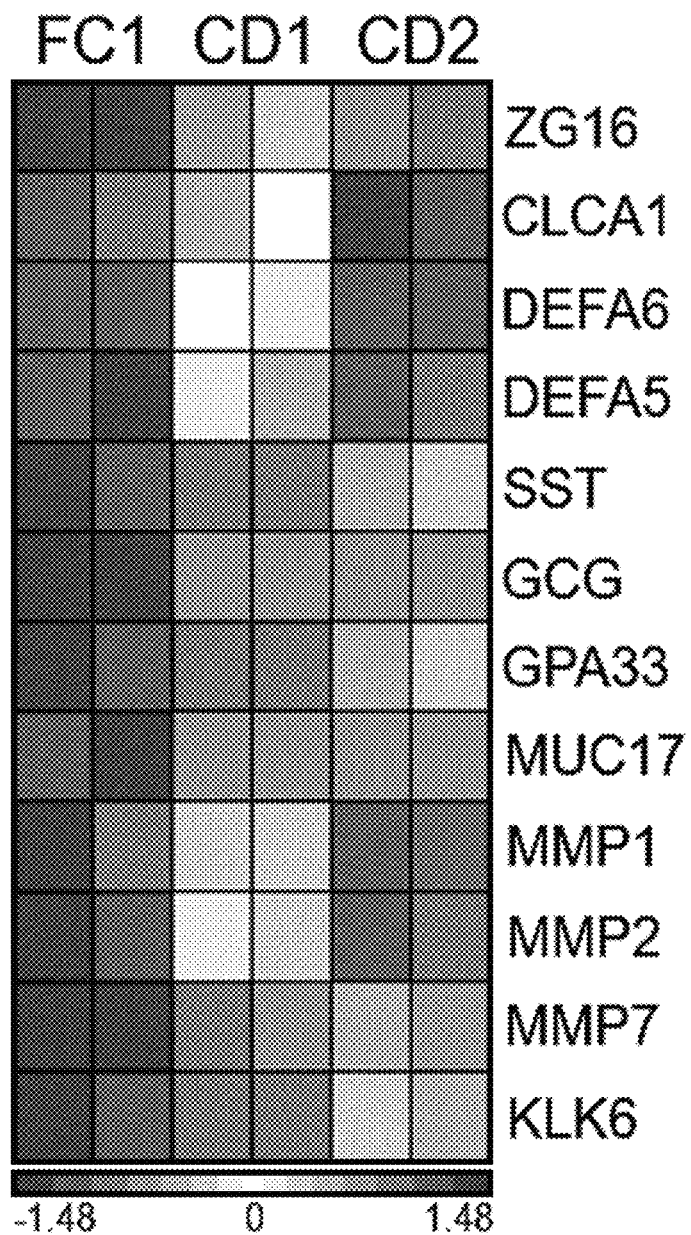
Figure 3F:
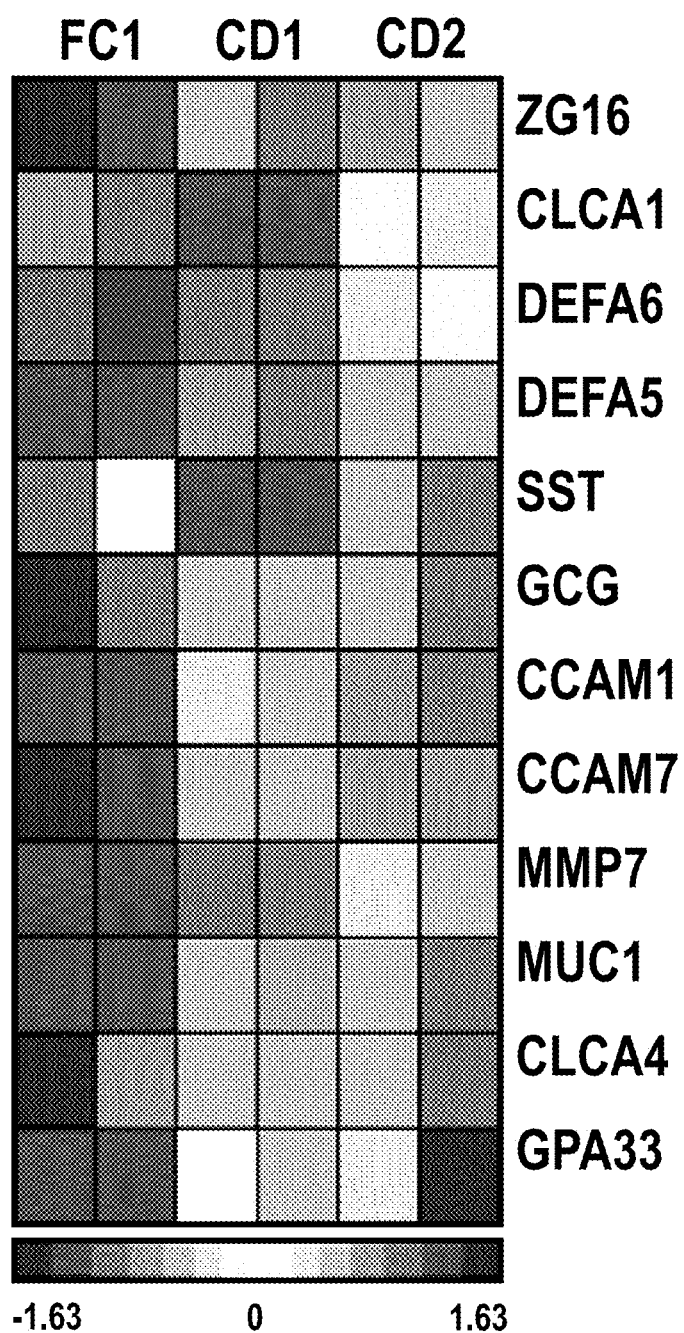
Figure 3G:
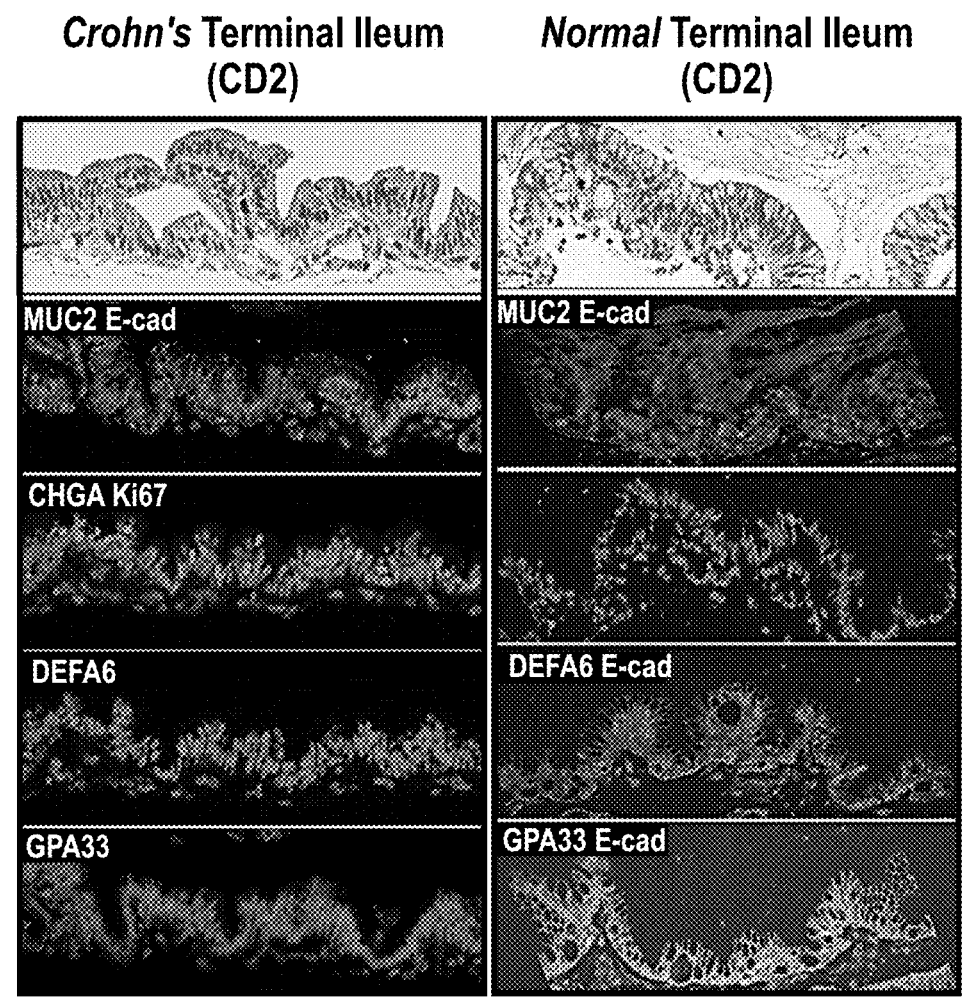
FIG. 3G. Stem cell pedigree from patient CD2 that binned with the Normal cluster differentiated to 3-D epithelial with the typical manifest of goblet cells, Paneth cells, and enteroendocrine cells produced by terminal ileum stem cells of control patients.

Terminal ileum stem cells from control patients differentiate in ALI cultures to yield a 3-D mucosa dominated by MUC2-expressing goblet cells (FIG. 3A). These control epithelia also displayed markers for enteroendocrine cells (chromogranin A; CHGA) and Paneth cells (defensin 6A; DEF6A); (FIG. 3A). In contrast, the majority of stem cell pedigrees derived from the terminal ileum of pediatric cases CD1, CD2, and CD3 yielded 3-D epithelia that lacked obvious goblet cells and correspondingly showed little or no expression of MUC2 (FIG. 3B). In addition, these in vitro-derived epithelia showed little or no staining by antibodies to the enteroendocrine marker CHGA or the Paneth cell marker DEFA6 (FIG. 3B). However, all of the stem cell pedigrees from patients CD1, CD2, or CD3 that binned with the Normal cluster differentiated to 3-D epithelial with the typical manifest of goblet cells, Paneth cells, and enteroendocrine cells produced by terminal ileum stem cells of control patients (FIG. 3G). In addition to the defects in secretory cell differentiation, these in vitro-generated Crohn's cluster epithelia also showed an aberrant distribution pattern of glycoprotein A33 (GPA33; FIG. 3B), a protein that forms an integral part of the tight junction in the colon and whose engineered deletion in mice yields a chronic inflammatory phenotype of the gastrointestinal tract[23]. At the same time, the 3-D Crohn's epithelia showed a high, ectopic expression of claudin 18 (CLDN18), a tight junction protein, and of V-set and immunoglobulin domain containing 1 (VSIG1), a junctional adhesion protein (FIG. 3B). These expression patterns in terminal ileum epithelial are supported by a broader comparison of expression profiles of particular genes associated with goblet, Paneth, and endocrine cells, all of which were low relative to control terminal ileum (FIG. 13). Thus Crohn's cluster stem cells of the terminal ileum from all three cases showed consistent abnormalities in both secretory cell differentiation and intercellular junctional assembly.

Homeotic Transformation of Crohn's Stem Cells

In addition to an extensive inflammatory gene signature and defective maturation of secretory cells, Crohn's cluster epithelia were distinguished by the ectopic expression of a host of metabolic enzymes that had no obvious links to either inflammation or secretory cell differentiation (FIG. 15A). We were struck by the fact that these enzymes, which function in the hydrolysis and transport of lipids, carbohydrates, and proteins, are normally expressed in proximal portions of gastrointestinal tract 12-14 feet anterior to the terminal ileum (FIG. 4A, FIG. 4B and FIG. 15A)[24]. To understand the scale and form of this ectopic gene expression, we mapped the gene expression profiles of the Crohn's cluster terminal ileum stem cells against those of each region of the gastrointestinal tract and their corresponding differentiated epithelia derived from a 22-week fetal demise case[21]. To do this we first identified and mapped all differentially expressed genes (1.8-fold, p<0.05) of normal fetal stem cells and their corresponding differentiated epithelia along the fetal gastrointestinal tract and then cross-indexed these datasets with all differentially expressed genes of the Crohn's and Normal clusters. This analysis yielded a set of 271 genes that were both differentially expressed between Crohn's and Normal epithelia and showed regional expression along the normal fetal gastrointestinal tract (FIG. 4B). Pathway analysis of these genes showed the most significant categories to be related to the metabolism and transport of nutrients (FIG. 4B). Mapping the genes over-represented in the Crohn's cluster terminal ileum epithelia to discrete regions of the fetal gastrointestinal tract revealed a shift in their distribution to one centered around gastric, duodenum and jejunum epithelia, whereas those over-represented in control terminal ileum generally mapped throughout the colon (FIG. 4C and FIG. 4D). The distribution patterns were highly similar across CD1, CD2, and CD3. Taken together, these data suggest that the terminal ileum stem cells of the Crohn's cluster displayed a switch in gene expression reminiscent of those driven by "homeotic" mutations in flies, which alter the developmental fate of segments along the Drosophila anterior-posterior body axis[26,26]. In particular, loss-of-function mutations in homeobox genes of the Bithorax complex (BX-C) result in a shift in the identity of posterior thoracic and abdominal segments (T3 to A8) to more that of the more anterior, mesothoracic (T2) segment[26-27]. Similarly, loss-of-function mutations of the Antennapedia complex (ANT-C) result in transformations of more anterior thoracic segments to the posterior T2 segment[26]. As homeobox-containing genes located within the four discrete HOX loci in humans play roles in tissue identity somewhat analogous to those of the Drosophila Bithorax and Antennapedia complexes[28-31], we asked whether the alterations apparent in Crohn's terminal ileum stem cells were accompanied by changes in the epigenetic profiles of these loci. Using whole-genome analyses of epigenetic histone marks, we identified multiple alterations in the epigenetic profiles of the HOX loci of stem cells of the Crohn's cluster compared to those of the Normal cluster (FIG. 16A). In particular, both the HOXA and HOXB loci in Crohn's cluster stem cells showed extensive regions of repressive histone 3 lysine 27 trimethylation (H3K27me3) at their 5' ends (FIG. 16A; FIG. 16C), a finding paralleled by the repression of HoxA13 and HoxA11 transcripts compared to normal terminal ileum stem cells (FIG. 16C). In contrast, the 3' portions of the HOXA, B, and C loci of Crohn's cluster stem cells showed a pattern of histone marks consistent with an overall potentiation or activation of 3' HOX genes relative to the Normal cluster stem cells (FIG. 16A; FIG. 16C). Interpreted in the context of prior studies of the patterning functions of the HOX loci[28-31], these data reveal a general epigenetic repression of genes situated at the 5'-ends of the HOXA and HOXB involved in posterior patterning, and a derepression of genes located at the 3'-ends of these loci generally linked to anterior fates. As such, these findings are consistent with the shift in gene expression profiles of Crohn's cluster stem cells derived from the terminal ileum to patterns of proximal gastrointestinal tract. In addition to epigenetic alterations to the HOX loci, we found that more than 50% of the differentially expressed genes between Crohn's and Normal cluster stem cells had histone modifications with a bias for H3K4 trimethylation and H3K27 demethylation for over-represented transcripts and a de-acetylation of H3K27 at genes of relatively low expression. Among these genes are a host of other transcription factors including CDX2 and GATA5, whose respective roles distal and proximal gastrointestinal tract differentiation are well established[32,33] (FIG. 16B).

Inflammatory Signature Driven by Homeotic Shift

Given the consistency of the traits of inflammation, secretory cell defects, and homeotic transformations of terminal ileum stem cells across the Crohn's cases examined, we wanted to determine whether they were somehow interdependent. We first asked whether the inflammatory gene signatures of Crohn's cluster stem cells followed the overall shift to proximal gastrointestinal tract gene expression seen in the Crohn's cluster stem cells. Our mapping of genes of the inflammatory signature across those differentially expressed in the fetal gastrointestinal tract revealed a similar shift in genes overexpressed in Crohn's disease to more anterior regions of the gastrointestinal tract whereas those under-expressed mapped to the fetal colon. In fact, approximately 80% of the genes over-represented in the inflammatory signature are normally expressed in proximal (gastric, duodenum, jejunum) portions of the fetal gastrointestinal tract but not in the colon. Conversely, 67% of genes under-represented in the inflammatory signature are normally expressed in the colon of the fetal gastrointestinal tract. A sampling of genes whose over- (e.g. AHR, URN, MGAT5, SMAD3, FUT2, and DUOX2) and under- (e.g. CLCA1, GUCY2C, IL37, and NOX1) representation might be a consequence of the homeotic transformation underscores the potential immunoregulatory impact of such a conversion (FIG. 19A). Consistent with the stability of the inflammatory signature in the Crohn's stem cells, 71% of the 180 genes showing enhanced expression in the inflammatory signature also had differential histone modifications marked by increased H3K4-trimethylation and a loss of H3K27-trimethylation typical of active or potentially active genes. Of down-regulated genes in the inflammatory gene signature, 48% had differential histone modifications and these were dominated by a loss of H3K27-acetylation and a gain of H3K27-trimethylation associated with gene repression (FIG. 17A). Examples of such over- and under-represented genes with histone modifications include the transcription factor aryl hydrocarbon receptor (AHR) and the enterotoxin receptor GUCY2C (FIG. 17B).

Our analysis of the inflammatory gene signatures of the Crohn's-derived stem cells revealed the differential expression of multiple genes (e.g. AHR, SMAD3, CCL2, FUT2) implicated by GWAS. To examine more broadly the relationship between the Crohn's cluster stem cells and the genetic architecture of Crohn's, we compared the set of genes linked by GWAS to Crohn's from multiple studies[7-1o] with those differentially expressed genes by Crohn's cluster stem cells and the epithelia generated from them and those predicted by disease association algorithms (e.g. GRAIL). A majority of the matches identified single genes among the multiple genes within a linkage disequilibrium (LD) block (e.g. NUPR1 at rs26526), and several highlight multiple genes coordinately upregulated within an LD block containing related genes such as CXCL1, 2, 3, and 5 at rs2472649[8], and class II MHC genes HLA-DRB1 and HLA-DRA at rs6927022[8]. We found an overlap of 28% of genes implicated by GRAIL and those differentially expressed by the Crohn's cluster cells (FIG. 19B), as will as another set of genes that were not captured by GRAIL and whose significance at this point is unclear. Regardless, the overlap between genes implicated by GWAS and those differentially expressed in Crohn's disease epithelia suggests broad links between these mucosal stem cells and the disease process.

Homeotic Shift Underlying Differentiation Defects

Figure 5L:
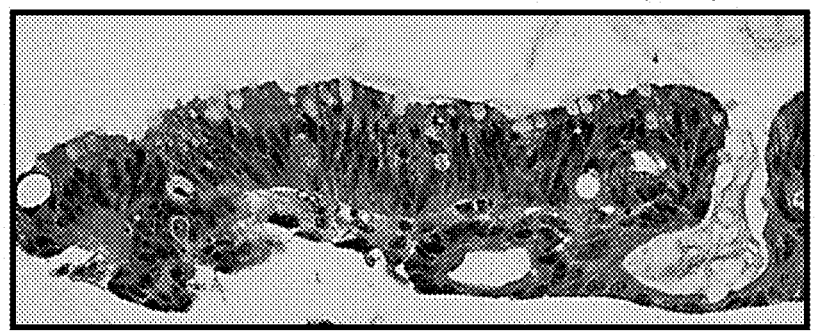

ATOH1 is known to regulate secretory cell differentiation in the airways and colon via its control of a network of downstream transcription factors that includes SPDEF, GFI1, and NEUROG3[20,34-37] (FIG. 4F). Given the impact of the homeotic shift of Crohn's cluster terminal ileum stem cells on inflammatory gene expression, we asked whether the transcription factors regulating secretory cell differentiation were similarly affected by this shift. Mapping the expression profiles of ATOH1, SPDEF, GFI1, and NEUROG3 onto the regiospecific expression patterns in the human fetal intestine showed that all are highly expressed in the distal gastrointestinal tract but much less so in proximal segments (FIG. 4F). Consistently, ATOH1 expression was differentially low in terminal ileum stem cells of the Crohn's cluster compared with those of the Normal cluster (FIG. 5A). We therefore asked if we could rescue the secretory cell phenotype of the Crohn's disease terminal ileum stem cells through supplementing ATOH1 expression via retroviral transduction. We transduced Crohn's cluster stem cells with a retrovirus driving ATOH1 and GFP expression and subsequently differentiated them in ALI cultures (FIG. 5B, FIG. 5E). This maturation of ATOH1-transduced cells yielded an epithelium replete with MUC2-expressing goblet cells. Expression profiling of goblet, Paneth, and endocrine cell markers showed that the virally-driven expression of ATOH1 resulted in a induction of genes associated with goblet cells and Paneth cells, though the impact on enteroendocrine cells was less obvious (FIG. 5F). Despite ATOH1's ability to complement the secretory cell defect in Crohn's cluster stem cells, these rescued cells showed only minor changes in gene expression generally involving a handful of secretory cell genes. Moreover, the rescue of this secretory cell defect did not appreciably alter the overall pattern of differential gene expression underlying the homeotic shift in the terminal ileum (FIG. 5H, FIG. 5I). We also performed the reverse experiment to assess the effect of the bi-allelic disruption[38] of ATOH1 in normal terminal ileum stem cells on their differentiation potential (FIG. 5J). Compared to the extreme differentiation defect seen in the Crohn's terminal ileum stem cells, the bi-allelic disruption of ATOH1 in normal cells showed a hypomorphic pattern of differentiation of secretory cells (FIG. 5L). Apart from this partial phenocopying of the Crohn's differentiation defect, our analysis of whole genome expression data from ATOH1-null normal terminal ileum stem cells showed no evidence for the induction of either an inflammatory gene signature or of the more general homeotic shift in gene expression.

Coexistence of Normal and Crohn's Stem Cells

The CD3 case was unusual in that the single terminal ileum biopsy yielded roughly equal numbers of stem cells in the Crohn's or Normal cluster whereas CD1 and CD2 were dominated by stem cells of the Crohn's cluster (c.f. FIG. 1). Using antibodies against cell surface markers expressed by Crohn's cluster stem cells such as VSIG1, we could readily identify and select stem cell colonies from the CD3 pool of clones that have the Crohn's or Normal traits (FIG. 6A and FIG. 6B). Pedigrees derived from VSIG1-negative colonies differentiated in ALI culture to terminal ileum with a normal complement of secretory cells, whereas those from VSIG1-positive pedigrees differentiated to epithelia with the typical secretory cell defects (FIG. 6B). The gene expression profiles of these two types of pedigrees also clustered by PCA and with their respective counterparts from CF1, CD1, and CD2 terminal ileum at both the stem cell and ALI differentiation levels (FIG. 6D). The characteristics of these two populations of stem cells from the CD3 terminal ileum seemed absolute in that those in the Crohn's cluster had the inflammatory gene signature, secretory cell defects, and the homeotic transformation whereas those of the Normal cluster had none of these features. Based on these findings, we screened larger numbers of colonies from the CD1 and CD2 terminal ileum biopsies and identified colonies equivalent to those of the Normal cluster in each of them. These findings provide strong evidence for the coexistence of normal and Crohn's disease stem cells in close proximity in the same patient and may underlie the observed, more macroscopic "skip-lesion" patterning that is a hallmark of Crohn's disease colonic mucosal. The binary properties of these stem cells might also explain the lack of established histopathology correlates in the terminal ileum of Crohn's disease patients that might be expected if all terminal ileum stem cells were uniform for the secretory cell differentiation defects observed in this study. Nevertheless, we asked whether antibodies specific to the epithelia generated in vitro from the Crohn's cluster stem cells could recognize discrete patterns in histological sections of Crohn's and normal biopsies. Our analysis reveal the co-mingling of normal epithelial glands dominated by MUC2-positive goblet cells and glands devoid of obvious goblet cells that reacted strongly with antibodies to VSIG1, PRSS2, and CLDN18, all gene products overexpressed by epithelia derived from cloned stem cells of the Crohn's cluster. None of these atypical foci were evident in control sections. We note that our findings are reminiscent of observations of 'pyloric gland" or "gastric" metaplasia in mucosal histological sections of Crohn's patients first described more than 60 years ago whose significance for the dynamics of Crohn's disease has remained unclear[39-41].

DISCUSSION

The key finding of this work is that the terminal ileum of pediatric patients with Crohn's disease harbors both normal and abnormal stem cells. The variant stem cells, as well as epithelia derived from them, show highly stable gene expression profiles tied to aberrant processes of inflammation, mucosal barrier formation, and metabolic processes more typical of epithelia found more in proximal portions of the gastrointestinal tract. About a third of these differentially expressed genes are linked to inflammatory pathways of the innate immune response, antigen presentation, and interferon signaling previously implicated in Crohn's disease. In addition, the overall gene expression profiles of these cells overlap with those found in 28% of GWAS loci described for Crohn's disease, suggesting a proximity between these stem cells and the pathology of Crohn's. While the relative contributions of mucosal stem cells and cells of the adaptive and innate immune system[18] to Crohn's disease pathogenesis remains unclear, the chronic nature of the inflammatory signaling in seen in this aberrant population of stem cells may impart to them disproportionate influence. If so, efforts to interfere with nodal aspects of their inflammatory gene signatures could do much to limit the morbidity of this disease.

Beyond their inflammatory character, the terminal ileum stem cells of all three cases showed a severe, cell-autonomous defect in secretory cell differentiation that underscores and extends the barrier defect hypothesis in this disorder[42]. Our findings confirm earlier genetic and pathophysiology data implicating mucosal and specifically Paneth cells defects[11,16,17], and expand the secretory cell phenotype in the terminal ileum to include defective differentiation of goblet and enteroendocrine cells. In light of their contributions to the mucus layer, enteric nervous system control[43], and anti-microbial factors, the combined loss of these secretory cells could render the terminal ileum particularly vulnerable to microbial challenge.

The most exotic and likely pathogenic feature of the terminal ileum stem cells of the Crohn's cluster is the shift in overall gene expression to that of an amalgam of proximal gastrointestinal epithelia including those of the stomach, duodenum and jejunum. As with the inflammatory gene signature and the defective secretory cell differentiation, this state of homeotic transformation was stable and stereotyped across cases and across at least six months of continuous growth in culture. And while the expression of metabolic enzymes typical of the proximal gastrointestinal tract was an initial hint of this homeotic transformation, our epistasis analyses support the notion that the homeotic transformation underlies both the inflammatory gene signature and the defective secretory differentiation of the Crohn's cluster stem cells. Thus the enhanced expression of genes such as AHR, MGAT5, SMAD3, DUOX2 and the loss of others such as GUCY2C, HLA-C, ALOX5, and NOX1 in Crohn's cluster stem cells is consistent with the shift in expression patterns of these genes between the terminal ileum and those of proximal gastrointestinal epithelia. Similarly, this homeotic transformation simultaneously represses ATOH1 and other transcription factors including SPDEF, GFI1, and NEUROG3 involved in secretory cell differentiation which likely explains why the differentiation defect is so much more extreme in the Crohn's cluster stem cells than those of the Normal cluster engineered for a biallelic disruption of ATOH1 alone. In a minimal sense the homeotically transformed terminal ileum would acquire barrier, immunological, and metabolic properties of proximal gastrointestinal tract devoted to nutrient processing and absorption in the near absence of gut microbes. Consequently, the transformed epithelial would be ill-suited to manage the 10,000-fold increase in intestinal microbes at the terminal ileum versus normal duodenum[44]. Experimentally, patterning defects due to homeotic transformations have been induced in flies or mammals by mutations of the Bithorax complex or homologous HOX loci, respectively[28-31]. It will be critical to understand how epigenetic mechanisms[45,46] might cooperate with environmental influences and genetic predisposition to bring about such transformations. Finally, the coexistence of two populations of stem cells in terminal ileum of pediatric Crohn's patients is physically manifested by the simultaneous presence of normal and metaplastic glands in the terminal ileum biopsies and resections examined here and in previous studies of Crohn's and inflammatory bowel disease in general[47-50]. If indeed these cells and their associated metaplasia contribute to Crohn's, their existence and specifically their coexistence with normal mucosal stem cells could inform new therapeutic strategies directed at neutralizing their pathogenic impact, reprogramming them to normalcy, or their selective eradication altogether.

CITED REFERENCES

1. Baumgart D C, and Sandborn W J. Crohn's disease. Lancet 380, 1590-1605 (2012).
2. Hyams J S. Standardized recording of parameters related to the natural history of inflammatory bowel disease: from Montreal to Paris. Dig Dis. 32, 337-344 (2014).

3. Regueiro M, Feagan B G, Zou B, Johanns J, Blank M A, Chevrier M, Plevy S, Popp J, Cornillie F J, Lukas M, Danese S, Gionchetti P, Hanauer S B, Reinisch W, Sandborn W J, Sorrentino D, Rutgeerts P; PREVENT Study Group. Infliximab reduces endoscopic, but not clinical, recurrence of Crohn's Disease after ileocolonic resection. Gastroenterology 150, 1568-1578 (2016).
4. Halfvarson J. Genetics in twins with Crohn's disease: less pronounced than previously believed? Inflamm Bowel Dis. 17, 6-12 (2011).
5. McGovern D P, Kugathasan S, and Cho J H. Genetics of Inflammatory Bowel Diseases. Gastroenterology 149, 1163-1176 (2015).
6. Jager S, Stange E F, Wehkamp J. Inflammatory bowel disease: an impaired barrier disease. Langenbecks Arch Surg. 398, 1-12 (2013).
7. Jostins L, Ripke S, Weersma R K, Duerr R H, McGovern D P, Hui K Y, Lee J C, Schumm L P, Sharma Y, Anderson C A, Essers J, Mitrovic M, Ning K, Cleynen I, Theatre E, Spain S L, Raychaudhuri S, Goyette P, Wei Z, Abraham C, Achkar J P, Ahmad T, Amininejad L, Ananthakrishnan A N, Andersen V, Andrews J M, Baidoo L, Balschun T, Bampton P A, Bitton A, Boucher G, Brand S, Burling C, Cohain A, Cichon S, D'Amato M, De Jong D, Devaney K L, Dubinsky M, Edwards C, Ellinghaus D, Ferguson L R, Franchimont D, Fransen K, Gearry R, Georges M, Gieger C, Glas J, Haritunians T, Hart A, Hawkey C, Hedl M, Hu X, Karlsen T H, Kupcinskas L, Kugathasan S, Latiano A, Laukens D, Lawrance I C, Lees C W, Louis E, Mahy G, Mansfield J, Morgan A R, Mowat C, Newman W, Palmieri O, Ponsioen C Y, Potocnik U, Prescott N J, Regueiro M, Rotter J I, Russell R K, Sanderson J D, Sans M, Satsangi J, Schreiber S, Simms L A, Sventoraityte J, Targan S R, Taylor K D, Tremelling M, Verspaget H W, De Vos M, Wijmenga C, Wilson D C, Winkelmann J, Xavier R J, Zeissig S, Zhang B, Zhang C K, Zhao H; International IBD Genetics Consortium (IIBDGC), Silverberg M S, Annese V, Hakonarson H, Brant S R, Radford-Smith G, Mathew C G, Rioux J D, Schadt E E, Daly M J, Franke A, Parkes M, Vermeire S, Barrett J C, Cho J H. Host-microbe interactions have shaped the genetic architecture of inflammatory bowel disease. Nature 491, 119-124 (2012).
8. Barrett J C, Hansoul S, Nicolae D L, et al. Genome-wide association defines more than 30 distinct susceptibility loci for Crohn's disease. Nat Genet. 40, 955-962 (2008).
9. Franke A, McGovern D P, Barrett J C, Wang K, Radford-Smith G L, Ahmad T, Lees C W, Balschun T, Lee J, Roberts R, Anderson C A, Bis J C, Bumpstead S, Ellinghaus D, Festen E M, Georges M, Green T, Haritunians T, Jostins L, Latiano A, Mathew C G, Montgomery G W, Prescott N J, Raychaudhuri S, Rotter J I, Schumm P, Sharma Y, Simms L A, Taylor K D, Whiteman D, Wijmenga C, Baldassano R N, Barclay M, Bayless T M, Brand S, Burling C, Cohen A, Colombel J F, Cottone M, Stronati L, Denson T, De Vos M, D'inca R, Dubinsky M, Edwards C, Florin T, Franchimont D, Gearry R, Glas J, Van Gossum A, Guthery S L, Halfvarson J, Verspaget H W, Hugot J P, Karban A, Laukens D, Lawrance I, Lemann M, Levine A, Libioulle C, Louis E, Mowat C, Newman W, Panes J, Phillips A, Proctor D D, Regueiro M, Russell R, Rutgeerts P, Sanderson J, Sans M, Seibold F, Steinhart A H, Stokkers P C, Torkvist L, Kullak-Ublick G, Wilson D, Walters T, Targan S R, Brant S R, Rioux J D, D'Amato M, Weersma R K, Kugathasan S, Griffiths A M, Mansfield J C, Vermeire S, Duerr R H, Silverberg M S, Satsangi J, Schreiber S, Cho J H, Annese V, Hakonarson H, Daly M J, Parkes M. Genome-wide meta-analysis increases to 71 the number of confirmed Crohn's disease susceptibility loci. Nat Genet. 42, 1118-1125 (2010).
10. Liu J Z, van Sommeren S, Huang H, Ng S C, Alberts R, Takahashi A, Ripke S, Lee J C, Jostins L, Shah T, Abedian S, Cheon J H, Cho J, Daryani N E, Franke L, Fuyuno Y, Hart A, Juyal R C, Juyal G, Kim W H, Morris A P, Poustchi H, Newman W G, Midha V, Orchard T R, Vahedi H, Sood A, Sung J J, Malekzadeh R, Westra H J, Yamazaki K, Yang S K; International Multiple Sclerosis Genetics Consortium; International IBD Genetics Consortium, Barrett J C, Franke A, Alizadeh B Z, Parkes M, B K T, Daly M J, Kubo M, Anderson C A, Weersma R K. Association analyses identify 38 susceptibility loci for inflammatory bowel disease and highlight shared genetic risk across populations. Nat Genet. 47, 979-986 (2015).
11. Wehkamp J, Salzman N H, Porter E, et al. Reduced Paneth cell alpha-defensins in ileal Crohn's disease. Proc Natl Acad Sci USA. 102, 18129-18134 (2005).
12. Hampe J, Franke A, Rosenstiel P, et al. A genome-wide association scan of non-synonymous SNPs identifies a susceptibility variant for Crohn disease in ATG16L1. Nat Genet. 39, 207-211 (2007).
13. Rioux J D, Xavier R J, Taylor K D, et al. Genome-wide association study identifies new susceptibility loci for Crohn disease and implicates autophagy in disease pathogenesis. Nat Genet. 39, 596-604 (2007).
14. Cadwell K, Liu J Y, Brown S L, et al. A key role for autophagy and the autophagy gene Atg16L1 in mouse and human intestinal Paneth cells. Nature 456, 259-263 (2008).
15. Saitoh T, Fujita N, Jang M H, Uematsu S, Yang B G, Satoh T, Omori H, Noda T, Yamamoto N, Komatsu M, Tanaka K, Kawai T, Tsujimura T, Takeuchi O, Yoshimori T, Akira S. Loss of the autophagy protein Atg16L1 enhances endotoxin-induced IL-1beta production. Nature 456, 264-268 (2008).
16. Adolph T E, Tomczak M F, Niederreiter L, Ko H J, Bock J, Martinez-Naves E, Glickman J N, Tschurtschenthaler M, Hartwig J, Hosomi S, Flak M B, Cusick J L, Kohno K, Iwawaki T, Billmann-Born S, Raine T, Bharti R, Lucius R, Kweon M N, Marciniak S J, Choi A, Hagen S J, Schreiber S, Rosenstiel P, Kaser A, Blumberg R S. Paneth cells as a site of origin for intestinal inflammation. Nature 503, 272-276 (2013).
17. Stappenbeck T S, and McGovern D P. Paneth Cell Alterations in the Development and Phenotype of Crohn's Disease. Gastroenterology 152, 322-326 (2017).
18. Abraham C, and Cho J H. Inflammatory bowel disease. N Engl J Med. 361, 2066-2078 (2009).
19. Cleynen I, Boucher G, Jostins L, Schumm L P, Zeissig S, Ahmad T, Andersen V, Andrews J M, Annese V, Brand S, Brant S R, Cho J H, Daly M J, Dubinsky M, Duerr R H, Ferguson L R, Franke A, Gearry R B, Goyette P, Hakonarson H, Halfvarson J, Hov J R, Huang H, Kennedy N A, Kupcinskas L, Lawrance I C, Lee J C, Satsangi J, Schreiber S, Theatre E, van der Meulen-de Jong A E, Weersma R K, Wilson D C; International Inflammatory Bowel Disease Genetics Consortium, Parkes M, Vermeire S, Rioux J D, Mansfield J, Silverberg M S, Radford-Smith G, McGovern D P, Barrett J C, Lees C W. Inherited determinants of Crohn's disease and ulcerative colitis phenotypes: a genetic association study. Lancet 387, 156-167 (2016).

20. Yang Q, Bermingham N A, Finegold M J, Zoghbi H Y. Requirement of Math1 for secretory cell lineage commitment in the mouse intestine. Science 294, 2155-2158 (2001).
21. Wang, X, Yamamoto, Y, Wilson, L H, Zhang, T., Howitt, B, Farrow, M A, Kern, F., Gang, N, Hong, Y, Khor, C C, Chevalier, B, Bertrand, D, Nagarjan, N, Sylvester, F A, Hyams, J S, Devers, T, Bronson, R, Lacy, D. B., Ho, K Y, Crum, C P, McKeon, F, and Xian, W. Cloning and variation of ground state intestinal stem cells. Nature 522, 173-178 (2015).
22. Yamamoto Y, Wang X, Bertrand D, Kern F, Zhang T, Hu Y Y, Deluba M, Srivastava S, Ming T, Khor C C, Wilson L, Blaszyk H, Rolshud D, Liu J J, Howitt B, Crum C P, Nagarajan N, Ho K Y, McKeon F, and Xian W. Mutational spectrum of Barrett's stem cells suggests paths to initiation and progression of a precancerous lesion. Nature Comm. 7:10380 (2016).
23. Williams B B, Tebbutt N C, Buchert M, Putoczki T L, Doggett K, Bao S, Johnstone C N, Masson F, Hollande F, Burgess A W, Scott A M, Ernst M, Heath J K. Glycoprotein A33 deficiency: a new mouse model of impaired intestinal epithelial barrier function and inflammatory disease. Dis Model Mech. 805-815 (2015).
24. Shimizu M. Interaction between food substances and the intestinal epithelium. Biosci Biotechnol Biochem. 74, 232-241 (2010).
25. Lewis, E. B. (1978). A gene complex controlling segmentation in *Drosophila*. Nature 276, 565-570.
26. Kaufman, T. C., Lewis, R., and Wakimoto, B. Cytogenetic analysis of chromosome 3 in *Drosophila melanogaster*: The homoeotic gene complex in polytene chromosome interval 84A-B. Genetics 94, 115-133 (1980).
27. McGinnis, W., Levine, M. S., Hafen, E., Kuroiwa, A., and Gehring, W. J. A conserved DNA sequence in homeotic genes of the *Drosophila* Antennapedia and bithorax complex. Nature 308, 428-433 (1984).
28. Tümpel S, Wiedemann L M, Krumlauf R. Hox genes and segmentation of the vertebrate hindbrain. Curr Top Dev Biol. 88, 103-137 (2009).
29. Mallo M, Wellik D M, Deschamps J. Hox genes and regional patterning of the vertebrate body plan. Dev Biol. 344, 7-15 (2010).
30. Wang K C, Yang Y W, Liu B, Sanyal A, Corces-Zimmerman R, Chen Y, Lajoie B R, Protacio A, Flynn R A, Gupta R A, Wysocka J, Lei M, Dekker J, Helms J A, Chang H Y. A long noncoding RNA maintains active chromatin to coordinate homeotic gene expression. Nature 472, 120-124 (2011).
31. Li L, Liu B, Wapinski O L, Tsai M C, Qu K, Zhang J, Carlson J C, Lin M, Fang F, Gupta R A, Helms J A, Chang H Y. Targeted disruption of Hotair leads to homeotic transformation and gene derepression. Cell Rep. 5, 3-12 (2013).
32. Chawengsaksophak K, James R, Hammond V E, Kontgen F, Beck F. Homeosis and intestinal tumours in Cdx2 mutant mice. Nature 386, 84-87 (1997).
33. Watanuki K, Yasugi S. Analysis of transcription regulatory regions of embryonic chicken pepsinogen (ECPg) gene. Dev Dyn. 228, 51-58 (2003).
34. Shroyer N F, Wallis D, Venken K J, Bellen H J, Zoghbi H Y. Gfi1 functions downstream of Math1 to control intestinal secretory cell subtype allocation and differentiation. Genes Dev. 19, 2412-2417 (2005).
35. Park K S, Korfhagen T R, Bruno M D, Kitzmiller J A, Wan H, Wert S E, Khurana Hershey G K, Chen G, Whitsett J A. SPDEF regulates goblet cell hyperplasia in the airway epithelium. J Clin Invest. 117, 978-988 (2007).
36. Noah T K, Kazanjian A, Whitsett J, Shroyer N F. SAM pointed domain ETS factor (SPDEF) regulates terminal differentiation and maturation of intestinal goblet cells. Exp Cell Res 316, 452-465 (2010).
37. Kim T H, Li F, Ferreiro-Neira I, Ho L L, Luyten A, Nalapareddy K, Long H, Verzi M, Shivdasani R A. Broadly permissive intestinal chromatin underlies lateral inhibition and cell plasticity. Nature 506, 511-515 (2014).
38. Jinek M, Chylinski K, Fonfara I, Hauer M, Doudna J A, Charpentier E. A programmable dual-RNA-guided DNA endonuclease in adaptive bacterial immunity. Science 337, 816-821 (2012).
39. Liber, A F. Aberrant pyloric glands in regional ileitis. AMA Arch Pathol. 51, 205-212 (1951).
40. Lee F D. Pyloric metaplasia in the small intestine. J Pathol Bacteriol. 87, 267-277 (1964).
41. Kushima R, Borchard F, Hattori T. A new aspect of gastric metaplasia in Crohn's disease: bidirectional (foveolar and pyloric) differentiation in so-called 'pyloric metaplasia' in the ileum. Pathol Int. 47, 416-419 (1997).
42. Jager S, Stange E F, Wehkamp J. Inflammatory bowel disease: an impaired barrier disease. Langenbecks Arch Surg. 398, 1-12 (2013).
43. Furness J B. Integrated neural and endocrine control of gastrointestinal function. Adv Exp Med Biol. 891, 159-173 (2016).
44. Canny G O, McCormick B A. Bacteria in the intestine, helpful residents or enemies from within? Infect Immun. 76, 3360-3373 (2008).
45. Ingham, P. W. Trithorax and the regulation of homeotic gene expression in *Drosophila*: A historical perspective. Int. J. Dev. Biol. 42, 423-429 (1998).
46. Geisler S J, Paro R. Trithorax and Polycomb group-dependent regulation: a tale of opposing activities. Development 142, 2876-2887 (2015).
47. Kariv R, Plesec T P, Gaffney K, Lian L, Fazio V W, Remzi F H, Lopez R, Goldblum J R, Shen B. Pyloric gland metaplasia and pouchitis in patients with ileal pouch-anal anastomoses. Aliment Pharmacol Ther. 31, 862-873 (2010).
48. Agarwal S, Stucchi A F, Dendrinos K, Cerda S, O'Brien M J, Becker J M, Heeren T, Farraye F A. Is pyloric gland metaplasia in ileal pouch biopsies a marker for Crohn's disease? Dig Dis Sci. 58, 2918-2925 (2013).
49. Neufert C, Agaimy A, Neurath M F, Mudter J. Confocal laser endomicroscopy for the in vivo detection of gastric foveolar metaplasia in long-standing ulcerative colitis. Inflamm Bowel Dis. 19, E77-78 (2013).
50. Dotti I, Mora-Buch R, Ferrer-PicOn E, Planell N, Jung P, Masamunt M C, Leal R F, Martin de Carpi J, Llach J, Ordas I, Bathe E, Panes J, Salas A. Alterations in the epithelial stem cell compartment could contribute to permanent changes in the mucosa of patients with ulcerative colitis. Gut (2016).
51. Haberman Y, Tickle T L, Dexheimer P J, Kim M O, Tang D, Karns R, Baldassano R N, Noe J D, Rosh J, Markowitz J, Heyman M B, Griffiths A M, Crandall W V, Mack D R, Baker S S, Huttenhower C, Keljo D J, Hyams J S, Kugathasan S, Walters T D, Aronow B, Xavier R J, Gevers D, Denson L A. Pediatric Crohn disease patients exhibit specific ileal transcriptome and microbiome signature. J Clin Invest. 124, 3617-3633 (2014).
52. Chen G B, Lee S H, Brion M J, Montgomery G W, Wray N R, Radford-Smith G L, Visscher P M; International IBD Genetics Consortium. (2014). Estimation and partitioning of (co)heritability of inflammatory bowel disease from GWAS and immunochip data. Hum Mol Genet. 23, 4710-4720.
53. Fransen K, Visschedijk M C, van Sommeren S, Fu J Y, Franke L, Festen E A, Stokkers P C, van Bodegraven A A, Crusius J B, Hommes D W, Zanen P, de Jong D J, Wijmenga C, van Diemen C C, Weersma R K. Analysis of SNPs with an effect on gene expression identifies UBE2L3 and BCL3 as potential new risk genes for Crohn's disease. Hum Mol Genet. 19, 3482-3488 (2010).
54. Gehring W J, Kloter U, Suga H. Evolution of the Hox gene complex from an evolutionary ground state. Curr Top Dev Biol.; 88, 35-61 (2009).
55. Holland P W, Booth H A, Bruford E A. Classification and nomenclature of all human homeobox genes. BMC Biol. 5, 47 (2007).
56. Wang K, Baldassano R, Zhang H, Qu H Q, Imielinski M, Kugathasan S, Annese V, Dubinsky M, Rotter J I, Russell R K, Bradfield J P, Sleiman P M, Glessner J T, Walters T, Hou C, Kim C, Frackelton E C, Garris M, Doran J, Romano C, Catassi C, Van Limbergen J, Guthery S L, Denson L, Piccoli D, Silverberg M S, Stanley C A, Monos D, Wilson D C, Griffiths A, Grant S F, Satsangi J, Polychronakos C, Hakonarson H. Comparative genetic analysis of inflammatory bowel disease and type 1 diabetes implicates multiple loci with opposite effects. Hum Mol Genet. 19, 2059-2067 (2010).
57. Puleston J, Cooper M, Murch S, Bid K, Makh S, Ashwood P, Bingham A H, Green H, Moss P, Dhillon A, Morris R, Strobel S, Gelinas R, Pounder R E, Platt A. A distinct subset of chemokines dominates the mucosal chemokine response in inflammatory bowel disease. Aliment Pharmacol Ther. 21, 109-120 (2005).
58. Okamoto R, Watanabe M. Role of epithelial cells in the pathogenesis and treatment of inflammatory bowel disease. J Gastroenterol. 51, 11-21 (2016).
59. Baumgart D C, and Sandborn W J. Crohn's disease. Lancet 380, 1590-1605 (2012).
60. Benchimol EI, Mack D R, Nguyen G C, Snapper S B, Li W, et al. 2014. Incidence, outcomes, and health services burden of very early onset inflammatory bowel disease. Gastroenterology 147:803-13.e7 (2014).
61. Peloquin J M, Goel G, Villablanca E J, and Xavier R J. Mechanisms of Pediatric Inflammatory Bowel Disease. Annu Rev Immunol. 34, 31-64 (2016).
62. Mekhjian H S, Switz D M, Melnyk C S, Rankin G B, Brooks R K. Clinical features and natural history of Crohn's disease. Gastroenterology 77, 898-906 (1979).
63. Rufo P A, Bousvaros A. Current therapy of inflammatory bowel disease in children. Paediatr Drugs. 8, 279-302 (2006).
64. Tysk C, Lindberg E, Jarnerot G, Floderus-Myrhed B. Ulcerative colitis and Crohn's disease in an unselected population of monozygotic and dizygotic twins. A study of heritability and the influence of smoking. Gut 29, 990-996 (1988).
65. Halfvarson J. Genetics in twins with Crohn's disease: less pronounced than previously believed? Inflamm Bowel Dis. 17, 6-12 (2011).
66. McGovern D P, Kugathasan S, and Cho J H. Genetics of Inflammatory Bowel Diseases. Gastroenterology 149, 1163-1176 (2015).
67. Jager S, Stange E F, Wehkamp J. Inflammatory bowel disease: an impaired barrier disease. Langenbecks Arch Surg. 398, 1-12 (2013).
68. Jostins L, Ripke S, Weersma R K, Duerr R H, McGovern D P, Hui K Y, Lee J C, Schumm L P, Sharma Y, Anderson C A, Essers J, Mitrovic M, Ning K, Cleynen I, Theatre E, Spain S L, Raychaudhuri S, Goyette P, Wei Z, Abraham C, Achkar J P, Ahmad T, Amininejad L, Ananthakrishnan A N, Andersen V, Andrews J M, Baidoo L, Balschun T, Bampton P A, Bitton A, Boucher G, Brand S, Buning C, Cohain A, Cichon S, D'Amato M, De Jong D, Devaney K L, Dubinsky M, Edwards C, Ellinghaus D, Ferguson L R, Franchimont D, Fransen K, Gearry R, Georges M, Gieger C, Glas J, Haritunians T, Hart A, Hawkey C, Hedl M, Hu X, Karlsen T H, Kupcinskas L, Kugathasan S, Latiano A, Laukens D, Lawrance I C, Lees C W, Louis E, Mahy G, Mansfield J, Morgan A R, Mowat C, Newman W, Palmieri O, Ponsioen C Y, Potocnik U, Prescott N J, Regueiro M, Rotter J I, Russell R K, Sanderson J D, Sans M, Satsangi J, Schreiber S, Simms L A, Sventoraityte J, Targan S R, Taylor K D, Tremelling M, Verspaget H W, De Vos M, Wijmenga C, Wilson D C, Winkelmann J, Xavier R J, Zeissig S, Zhang B, Zhang C K, Zhao H; International IBD Genetics Consortium (IIBDGC), Silverberg M S, Annese V, Hakonarson H, Brant S R, Radford-Smith G, Mathew C G, Rioux J D, Schadt E E, Daly M J, Franke A, Parkes M, Vermeire S, Barrett J C, Cho J H. Host-microbe interactions have shaped the genetic architecture of inflammatory bowel disease. Nature 491, 119-124 (2012).
69. Barrett J C, Hansoul S, Nicolae D L, et al. Genome-wide association defines more than 30 distinct susceptibility loci for Crohn's disease. Nat Genet. 40, 955-962 (2008).
70. Franke A, McGovern D P, Barrett J C, Wang K, Radford-Smith G L, Ahmad T, Lees C W, Balschun T, Lee J, Roberts R, Anderson C A, Bis J C, Bumpstead S, Ellinghaus D, Festen E M, Georges M, Green T, Haritunians T, Jostins L, Latiano A, Mathew C G, Montgomery G W, Prescott N J, Raychaudhuri S, Rotter J I, Schumm P, Sharma Y, Simms L A, Taylor K D, Whiteman D, Wijmenga C, Baldassano R N, Barclay M, Bayless T M, Brand S, Buning C, Cohen A, Colombel J F, Cottone M, Stronati L, Denson T, De Vos M, D'inca R, Dubinsky M, Edwards C, Florin T, Franchimont D, Gearry R, Glas J, Van Gossum A, Guthery S L, Halfvarson J, Verspaget H W, Hugot J P, Karban A, Laukens D, Lawrance I, Lemann M, Levine A, Libioulle C, Louis E, Mowat C, Newman W, Panes J, Phillips A, Proctor D D, Regueiro M, Russell R, Rutgeerts P, Sanderson J, Sans M, Seibold F, Steinhart A H, Stokkers P C, Torkvist L, Kullak-Ublick G, Wilson D, Walters T, Targan S R, Brant S R, Rioux J D, D'Amato M, Weersma R K, Kugathasan S, Griffiths A M, Mansfield J C, Vermeire S, Duerr R H, Silverberg M S, Satsangi J, Schreiber S, Cho J H, Annese V, Hakonarson H, Daly M J, Parkes M. Genome-wide meta-analysis increases to 71 the number of confirmed Crohn's disease susceptibility loci. Nat Genet. 42, 1118-1125 (2010).
71. Liu J Z, van Sommeren S, Huang H, Ng S C, Alberts R, Takahashi A, Ripke S, Lee J C, Jostins L, Shah T, Abedian S, Cheon J H, Cho J, Daryani N E, Franke L, Fuyuno Y, Hart A, Juyal R C, Juyal G, Kim W H, Morris A P, Poustchi H, Newman W G, Midha V, Orchard T R, Vahedi H, Sood A, Sung J J, Malekzadeh R, Westra H J, Yamazaki K, Yang S K; International Multiple Sclerosis Genetics Consortium; International IBD Genetics Consortium, Barrett J C, Franke A, Alizadeh B Z, Parkes M, B K T, Daly M J, Kubo M, Anderson C A, Weersma R K. Association analyses identify 38 susceptibility loci for inflammatory bowel disease and highlight shared genetic risk across populations. Nat Genet. 47, 979-986 (2015).

72. Wehkamp J, Salzman N H, Porter E, et al. Reduced Paneth cell alpha-defensins in ileal Crohn's disease. Proc Natl Acad Sci USA. 102, 18129-18134 (2005).
73. Hampe J, Franke A, Rosenstiel P, et al. A genome-wide association scan of non-synonymous SNPs identifies a susceptibility variant for Crohn disease in ATG16L1. Nat Genet. 39, 207-211 (2007).
74. Rioux J D, Xavier R J, Taylor K D, et al. Genome-wide association study identifies new susceptibility loci for Crohn disease and implicates autophagy in disease pathogenesis. Nat Genet. 39, 596-604 (2007).
75. Cadwell K, Liu J Y, Brown S L, et al. A key role for autophagy and the autophagy gene Atg16L1 in mouse and human intestinal Paneth cells. Nature 456, 259-263 (2008).
76. Saitoh T, Fujita N, Jang M H, Uematsu S, Yang B G, Satoh T, Omori H, Noda T, Yamamoto N, Komatsu M, Tanaka K, Kawai T, Tsujimura T, Takeuchi O, Yoshimori T, Akira S. Loss of the autophagy protein Atg16L1 enhances endotoxin-induced IL-1beta production. Nature 456, 264-268 (2008).
77. Adolph T E, Tomczak M F, Niederreiter L, Ko H J, Bock J, Martinez-Naves E, Glickman J N, Tschurtschenthaler M, Hartwig J, Hosomi S, Flak M B, Cusick J L, Kohno K, Iwawaki T, Billmann-Born S, Raine T, Bharti R, Lucius R, Kweon M N, Marciniak S J, Choi A, Hagen S J, Schreiber S, Rosenstiel P, Kaser A, Blumberg R S. Paneth cells as a site of origin for intestinal inflammation. Nature 503, 272-276 (2013).
78. Abraham C, and Cho J H. Inflammatory bowel disease. N Engl J Med. 361, 2066-2078 (2009).
79. Cleynen I, Boucher G, Jostins L, Schumm L P, Zeissig S, Ahmad T, Andersen V, Andrews J M, Annese V, Brand S, Brant S R, Cho J H, Daly M J, Dubinsky M, Duerr R H, Ferguson L R, Franke A, Gearry R B, Goyette P, Hakonarson H, Halfvarson J, Hov J R, Huang H, Kennedy N A, Kupcinskas L, Lawrance I C, Lee J C, Satsangi J, Schreiber S, Theatre E, van der Meulen-de Jong A E, Weersma R K, Wilson D C; International Inflammatory Bowel Disease Genetics Consortium, Parkes M, Vermeire S, Rioux J D, Mansfield J, Silverberg M S, Radford-Smith G, McGovern D P, Barrett J C, Lees C W. Inherited determinants of Crohn's disease and ulcerative colitis phenotypes: a genetic association study. Lancet 387, 156-167 (2016).
80. Rutgeerts P, Geboes K, Vantrappen G, Beyls J, Kerremans R, Hiele M. Predictability of the postoperative course of Crohn's disease. Gastroenterology 99, 956-963 (1990).
81. Yang Q, Bermingham N A, Finegold M J, Zoghbi H Y. Requirement of Math1 for secretory cell lineage commitment in the mouse intestine. Science 294, 2155-2158 (2001).
82. Wang, X, Yamamoto, Y, Wilson, L H, Zhang, T., Howitt, B, Farrow, M A, Kern, F., Gang, N, Hong, Y, Khor, C C, Chevalier, B, Bertrand, D, Nagarjan, N, Sylvester, F A, Hyams, J S, Devers, T, Bronson, R, Lacy, D. B., Ho, K Y, Crum, C P, McKeon, F, and Xian, W. Cloning and variation of ground state intestinal stem cells. Nature 522, 173-178 (2015).
83. Yamamoto Y, Wang X, Bertrand D, Kern F, Zhang T, Hu Y Y, Deluba M, Srivastava S, Ming T, Khor C C, Wilson L, Blaszyk H, Rolshud D, Liu J J, Howitt B, Crum C P, Nagarajan N, Ho K Y, McKeon F, and Xian W. Mutational spectrum of Barrett's stem cells suggests paths to initiation and progression of a precancerous lesion. Nature Comm. 7:10380 (2016).
84. Haberman Y, Tickle T L, Dexheimer P J, Kim M O, Tang D, Karns R, Baldassano R N, Noe J D, Rosh J, Markowitz J, Heyman M B, Griffiths A M, Crandall W V, Mack D R, Baker S S, Huttenhower C, Keljo D J, Hyams J S, Kugathasan S, Walters T D, Aronow B, Xavier R J, Gevers D, Denson L A. Pediatric Crohn disease patients exhibit specific ileal transcriptome and microbiome signature. J Clin Invest. 124, 3617-3633 (2014).
85. Chen G B, Lee S H, Brion M J, Montgomery G W, Wray N R, Radford-Smith G L, Visscher P M; International IBD Genetics Consortium. (2014). Estimation and partitioning of (co)heritability of inflammatory bowel disease from GWAS and immunochip data. Hum Mol Genet. 23, 4710-4720.
86. Fransen K, Visschedijk M C, van Sommeren S, Fu J Y, Franke L, Festen E A, Stokkers P C, van Bodegraven A A, Crusius J B, Hommes D W, Zanen P, de Jong D J, Wijmenga C, van Diemen C C, Weersma R K. Analysis of SNPs with an effect on gene expression identifies UBE2L3 and BCL3 as potential new risk genes for Crohn's disease. Hum Mol Genet. 19, 3482-3488 (2010).
87. Williams B B, Tebbutt N C, Buchert M, Putoczki T L, Doggett K, Bao S, Johnstone C N, Masson F, Hollande F, Burgess A W, Scott A M, Ernst M, Heath J K. Glycoprotein A33 deficiency: a new mouse model of impaired intestinal epithelial barrier function and inflammatory disease. Dis Model Mech. 805-815 (2015).
88. Shimizu M. Interaction between food substances and the intestinal epithelium. Biosci Biotechnol Biochem. 74, 232-241 (2010).
89. Lewis, E. B. (1978). A gene complex controlling segmentation in *Drosophila*. Nature 276, 565-570.
90. Kaufman, T. C., Lewis, R., and Wakimoto, B. Cytogenetic analysis of chromosome 3 in *Drosophila melanogaster*: The homoeotic gene complex in polytene chromosome interval 84A-B. Genetics 94, 115-133 (1980).
91. McGinnis, W., Levine, M. S., Hafen, E., Kuroiwa, A., and Gehring, W. J. A conserved DNA sequence in homeotic genes of the *Drosophila* Antennapedia and bithorax complex. Nature 308, 428-433 (1984).
92. Gehring W J, Kloter U, Suga H. Evolution of the Hox gene complex from an evolutionary ground state. Curr Top Dev Biol.; 88, 35-61 (2009).
93. Ingham, P. W. Trithorax and the regulation of homeotic gene expression in *Drosophila*: A historical perspective. Int. J. Dev. Biol. 42, 423-429 (1998).
94. Geisler S J, Paro R. Trithorax and Polycomb group-dependent regulation: a tale of opposing activities. Development 142, 2876-2887 (2015).
95. Holland P W, Booth H A, Bruford E A. Classification and nomenclature of all human homeobox genes. BMC Biol. 5, 47 (2007).
96. Shroyer N F, Wallis D, Venken K J, Bellen H J, Zoghbi H Y. Gfi1 functions downstream of Math1 to control intestinal secretory cell subtype allocation and differentiation. Genes Dev. 19, 2412-2417 (2005).
97. Park K S, Korfhagen T R, Bruno M D, Kitzmiller J A, Wan H, Wert S E, Khurana Hershey G K, Chen G, Whitsett J A. SPDEF regulates goblet cell hyperplasia in the airway epithelium. J Clin Invest. 117, 978-988 (2007).
98. Noah T K, Kazanjian A, Whitsett J, Shroyer N F. SAM pointed domain ETS factor (SPDEF) regulates terminal differentiation and maturation of intestinal goblet cells. Exp Cell Res 316, 452-465 (2010).
99. Kim T H, Li F, Ferreiro-Neira I, Ho L L, Luyten A, Nalapareddy K, Long H, Verzi M, Shivdasani R A.

Broadly permissive intestinal chromatin underlies lateral inhibition and cell plasticity. Nature 506, 511-515 (2014).
100. Jinek M, Chylinski K, Fonfara I, Hauer M, Doudna J A, Charpentier E. A programmable dual-RNA-guided DNA endonuclease in adaptive bacterial immunity. Science 337, 816-821 (2012).
101. Wang K, Baldassano R, Zhang H, Qu H Q, Imielinski M, Kugathasan S, Annese V, Dubinsky M, Rotter J I, Russell R K, Bradfield J P, Sleiman P M, Glessner J T, Walters T, Hou C, Kim C, Frackelton E C, Garris M, Doran J, Romano C, Catassi C, Van Limbergen J, Guthery S L, Denson L, Piccoli D, Silverberg M S, Stanley C A, Monos D, Wilson D C, Griffiths A, Grant S F, Satsangi J, Polychronakos C, Hakonarson H. Comparative genetic analysis of inflammatory bowel disease and type 1 diabetes implicates multiple loci with opposite effects. Hum Mol Genet. 19, 2059-2067 (2010).
102. Puleston J, Cooper M, Murch S, Bid K, Makh S, Ashwood P, Bingham A H, Green H, Moss P, Dhillon A, Morris R, Strobel S, Gelinas R, Pounder R E, Platt A. A distinct subset of chemokines dominates the mucosal chemokine response in inflammatory bowel disease. Aliment Pharmacol Ther. 21, 109-120 (2005).
103. Okamoto R, Watanabe M. Role of epithelial cells in the pathogenesis and treatment of inflammatory bowel disease. J Gastroenterol. 51, 11-21 (2016).
104. Jager S, Stange E F, Wehkamp J. Inflammatory bowel disease: an impaired barrier disease. Langenbecks Arch Surg. 398, 1-12 (2013).
105. Canny G O, McCormick B A. Bacteria in the intestine, helpful residents or enemies from within? Infect Immun. 76, 3360-3373 (2008). 106. Furness J B. Integrated neural and endocrine control of gastrointestinal function. Adv Exp Med Biol. 891, 159-173 (2016).
107. Mallo M, Wellik D M, Deschamps J. Hox genes and regional patterning of the vertebrate body plan. Dev Biol. 344, 7-15 (2010).
108. Tümpel S, Wiedemann L M, Krumlauf R. Hox genes and segmentation of the vertebrate hindbrain. Curr Top Dev Biol. 88, 103-137 (2009).

Methods

In Vitro Culture of Human Terminal Ileum and Colonic Epithelial Stem Cells

Terminal ileum and right colon endoscopic biopsies were obtained from newly diagnosed pediatric Crohn's patients and functional controls lacking mucosal inflammation under informed parental consent and institutional review board approval at the Connecticut Children's Medical Center, Hartford, CT USA and the University of North Carolina, Chapel Hill, Chapel Hill, NC, USA. 1 mm endoscopic biopsies were collected into cold F12 media (Gibco, USA) with 5% fetal bovine serum (Hyclone, USA), and then were minced by sterile scalpel into 0.2-0.5 mm³ sizes with a viscous and homogeneous appearance. The minced tissue was digested in 2 mg/ml collagenase type IV (Gibco, USA) at 37° C. for 30-60 min with agitation. Dissociated cells were passed through a 70 µm Nylon mesh (Falcon, USA) to remove masses and then were washed four times in cold F12 media, and seeded onto a feeder layer of lethally irradiated 3T3-J2 cells in cFAD media containing 125 ng/mL R-Spondin1 (R&D systems, USA), 1 µM Jagged-1 (AnaSpec Inc, USA), 100 ng/ml Human Noggin (Peprotech, USA), 2.5 µM Rock-inhibitor (Calbiochem, USA), 2 µM SB431542 (Cayman chemical, USA), 10 mM Nicotinamide (Sigma-Aldrich, USA). Cells were cultured at 37° C. in a 7.5% $CO_2$ incubator. The culture media was changed every two days. Colonies were digested by 0.25% trypsin-EDTA solution (Gibco, USA) for 5-8 min and passaged every 7 to 10 days. Colonies were trypsinized by TrypLE Express solution (Gibco, USA) for 8-15 min at 37° C. and cell suspensions were passed through 30 µm filters (Miltenyi Biotec, Germany). Approximately 20,000 epithelial cells were seeded to each well of 6-well plate. Cloning cylinder (Pyrex, USA) and high vacuum grease (Dow Corning, USA) were used to select single colonies for pedigrees. Gene expression analyses were performed on cells derived from passage 4-10 (P4-P10) cultures, at which the GI tract derived stem cells were observed to be both genetically and epigenetically stable and for all detectable purposes identical to the passage 1 stem cells from clone from which each was derived.

Histology and Immunostaining

Histology, hematoxylin and eosin (H&E) staining, immunohistochemistry, and immunofluorescence were performed using standard techniques. For immunofluorescence and immunohistochemistry, 4% paraformaldehyde-fixed, paraffin embedded tissue slides were subjected to antigen retrieval in citrate buffer (pH 6.0, Sigma-Aldrich, USA) at 120° C. for 20 min, and a blocking procedure was performed with 5% bovine serum albumin (BSA, Sigma-Aldrich, USA) and 0.05% Triton X-100 (Sigma-Aldrich, USA) in DPBS(−) (Gibco, USA) at room temperature for 1 hr. All images were captured by using the Inverted Eclipse Ti-Series (Nikon, Japan) microscope with Lumencor SOLA light engine and Andor Technology Clara Interline CCD camera and NIS-Elements Advanced Research v.4.13 software (Nikon, Japan) or LSM 780 confocal microscope (Carl Zeiss, Germany) with LSM software. Bright field cell culture images were obtained on an Eclipse TS100 microscope (Nikon, Japan) with Digital Sight DSFilcamera (Nikon, Japan) and NIS-Elements F3.0 software (Nikon, Japan).

Stem Cell Differentiation

Air-liquid interface (ALI) culture of terminal ileum and colonic epithelial cells was performed as described in the literature. Briefly, Transwell inserts (Corning Incorporated, USA) were coated with 20% Matrigel (BD biosciences, USA) and incubated at 37° C. for 30 min to polymerize. 200,000 irradiated 3T3-J2 cells were seeded to each Transwell insert and incubated at 37° C., 7.5% CO2 incubator overnight. QuadroMACS Starting Kit (LS) (Miltenyi Biotec, Germany) was used to purify the stem cells by removal of feeder cells. 200,000-300,000 stem cells were seeded into each Transwell insert and cultured with stem cell media. At confluency (3-7 days), the apical media on the inserts was removed through careful pipetting and the cultures were continued in differentiation media (stem cell media without nicotinamide) for an additional 6-12 days prior to harvesting. The differentiation media was changed every one or two days.

RNA Sample Preparation

For stem cell colonies, RNA was isolated using PicoPure RNA Isolation Kit (Life Technologies, USA). For ALI structure, RNA was isolated using Trizol RNA Isolation Kit (Life Technologies, USA). RNA quality (RNA integrity number, RIN) was measured by analysis Agilent 2100 Bioanalyzer and Agilent RNA 6000 Nano Kit (Agilent Technologies, USA). RNAs having a RIN>8 were used for microarray analysis.

Expression Microarray and Bioinformatics

Total RNAs obtained from immature colonies and ALI differentiated epithelia were used for microarray preparation with WT Pico RNA Amplification System V2 for amplification of DNA and Encore Biotin Module for fragmentation and biotin labeling (NuGEN Technologies, USA). All samples were prepared according to manufacturer's instructions and hybridized onto GeneChip Human Exon 1.0 ST or Human Transcriptome (HTA) Arrays (Affymetrix, USA). GeneChip operating software was used to process all the Cel files and calculate probe intensity values. To validate sample quality, quality checks were conducted using Affymetrix Expression Console software. The intensity values were log 2-transformed and imported into the Partek Genomics Suite 6.6 (Partek Incorporated, USA). Exons were summarized to genes and a 1-way ANOVA was performed to identify differentially expressed genes. For two sample statistics, p-values were calculated by student t-test for each analysis. Unsupervised clustering and heatmap generation were performed with sorted datasets by Euclidean distance based on average linkage clustering, and Principal Component Analysis (PCA) map was conducted using all or selected probe sets by Partek Genomics Suite 6.6. Pathway analysese were performed with Gene Set Enrichment Analysis (GSEA) and Ingenuity Pathway Analysis (IPA) software.

Antibodies:
  Mouse monoclonal Ki67 BD550609 (BD Pharmingen, USA)
  Goat polyclonal E-Cadherin AF648 (R&D Systems, USA)
  Goat polyclonal GFP ab5450 (Abcam, USA)
  Rabbit polyclonal SOX9 ab5535 (Abcam, USA)
  Rabbit polyclonal Chromogranin A (CHGA) ab15160 (Abcam, USA)
  Rabbit polyclonal Glycoprotein A33 (GPA33) ab108938 (Abcam, USA)
  Mouse monoclonal LI-Cadherin (Cdh17) sc-74209 (Santa Cruz, USA)
  Rabbit polyclonal Mucin 2 (MUC2) sc-15334 (Santa Cruz, USA)
  Rabbit polyclonal Claudin 18 (CLDN18) HPA018446 (Sigma-Aldrich, USA)
  Rabbit polyclonal Defensin 6 (DEFA6) HPA019462 (Sigma-Aldrich, USA)
  Rabbit polyclonal Mucin 17 (MUC17) HPA031634 (Sigma-Aldrich, USA)

Secondary Antibodies:
  Donkey anti-Rabbit IgG (H+L) AlexaFluor 594, A-21207 (ThermoFisher Scientific, USA)
  Donkey anti-Goat IgG (H+L) AlexaFluor 488, A-11055 (ThermoFisher Scientific, USA)
  Donkey anti-Mouse IgG (H+L) AlexaFluor 488, A-21202 (ThermoFisher Scientific, USA)

What is claimed is:

1. A purified population of stem cells derived from gastrointestinal biopsies from IBD patients, wherein the isolation, passaging and maintenance of the subject IBD stem cells was carried out using a culture media system comprising a basal media and (a) a ROCK (Rho Kinase) inhibitor; (b) a Wnt agonist; (c) a Bone Morphogenetic Protein (BMP) antagonist; (d) a Notched inhibitor; (e) a TGF β signaling pathway inhibitor selected from the group consisting of a TGF β inhibitor and a TGF β receptor inhibitor, wherein the population is characterized in that, when it is differentiated upon exposure to an air-liquid interface it produces epithelia tissue that expresses CLDN18 and VSIG1 at an elevated level relative to patient matched normal tissue, and is further characterized as lacking goblet, Paneth, and endocrine cells, and which cell culture conditions provide stable culture and passaging of the population of stem cells under conditions that maintain the genotype and epigenetics of the stem cell as it existed in the biopsy.

2. A cell culture comprising a purified population of stem cells according to claim 1.

3. The purified population of stem cells of claim 1, further comprising nicotinamide or an analog thereof.

4. The purified population of stem cells of claim 1, further comprising a mitogenic growth factor selected from the group consisting of EGF, KGF, TGFα, BDNF, HGF, and bFGF.

* * * * *